(12) United States Patent
Punt et al.

(10) Patent No.: US 9,885,066 B2
(45) Date of Patent: Feb. 6, 2018

(54) ORGANIC ACID PATHWAY

(71) Applicant: Dutch DNA Biotech B.V., Zeist (NL)

(72) Inventors: Peter Jan Punt, Zeist (NL); An Li, The Hague (NL); Martinus Petrus Maria Caspers, The Hague (NL)

(73) Assignee: DUTCH DNA BIOTECH B.V., Zeist (NL)

( * ) Notice: Subject to any disclaimer, the term of this patent is extended or adjusted under 35 U.S.C. 154(b) by 0 days.

(21) Appl. No.: 14/888,410

(22) PCT Filed: May 2, 2014

(86) PCT No.: PCT/NL2014/050284
§ 371 (c)(1),
(2) Date: Oct. 30, 2015

(87) PCT Pub. No.: WO2014/178717
PCT Pub. Date: Nov. 6, 2014

(65) Prior Publication Data
US 2016/0068873 A1   Mar. 10, 2016

(30) Foreign Application Priority Data

May 2, 2013  (EP) .................................... 13166305

(51) Int. Cl.
| | |
|---|---|
| *C12P 7/48* | (2006.01) |
| *C12N 1/20* | (2006.01) |
| *C12N 1/12* | (2006.01) |
| *C12N 1/00* | (2006.01) |
| *C12N 15/00* | (2006.01) |
| *C07H 21/04* | (2006.01) |
| *C12P 7/44* | (2006.01) |
| *C12N 9/10* | (2006.01) |

(52) U.S. Cl.
CPC .............. *C12P 7/48* (2013.01); *C12N 9/1025* (2013.01); *C12P 7/44* (2013.01); *C12Y 203/03001* (2013.01); *C12Y 401/01006* (2013.01)

(58) Field of Classification Search
None
See application file for complete search history.

(56) References Cited

U.S. PATENT DOCUMENTS

2010/0285546 A1* 11/2010 Liao .................. C12N 1/20
                                                          435/145

FOREIGN PATENT DOCUMENTS

| WO | WO-2007/063133 | 6/2007 |
|---|---|---|
| WO | WO-2009/014437 | 1/2009 |
| WO | WO-2009/104958 | 8/2009 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36)11643-50.*
Kisselev L., Polypeptide release factors in prokaryotes and eukaryotes: same function, different structure. Structure, 2002, vol. 10: 8-9.*
International Search Report for PCT/NL2014/050284, dated Jul. 24, 2014, 6 pages.
Li et al., "A clone-based transcriptomics approach for the identification of genes relevant for itaconic acid production in Aspergillus," Fungal Genetics and Biology (2011) 48:602-611.
Pel et al., "Genome sequencing and analysis of the versatile cell factory Aspergillus niger CBS 513.88," Nature Biotechnology (2007) 25(2):221-231 and database Uniprot, accession No. A2QSJ2.
Ruijter et al., "Properties of Aspergillus niger citrate synthase and effects of citA overexpression on citric acid production," FEMS Microbiology Letters (2000) 184:35-40.
Tevz et al., "Enhancing itaconic acid production by Aspergillus terreus," Appl. Microbiol. Biotechnol. (2010) 87:1657-1664.

* cited by examiner

*Primary Examiner* — Iqbal H Chowdhury
(74) *Attorney, Agent, or Firm* — Morrison & Foerster LLP

(57) ABSTRACT

The invention relates to the use of a cytosolic citric acid synthase for the heterologous production of citrate outside the mitochondrion of a micro-organism or algae, wherein the protein is selected from *A. niger* An08g10920, An01g09940, An09g03570, or an ortholog of these genes. Such production is achieved by introducing the nucleic acid encoding such a protein into a suitable host cell. Preferably the protein is *A. niger* An08g10920, An01g09940, An09g03570 or an ortholog thereof, more particularly, wherein such an ortholog is chosen from the group of proteins listed in FIG. 9 and proteins having a percentage identity of 70%, more preferably 75%, more preferably 80%, more preferably 85%, more preferably 90%, more preferably 95%, more preferably 98%, more preferably 99% with An08g10920, An01g09940 or An09g03570.

4 Claims, 22 Drawing Sheets

Figure 2:
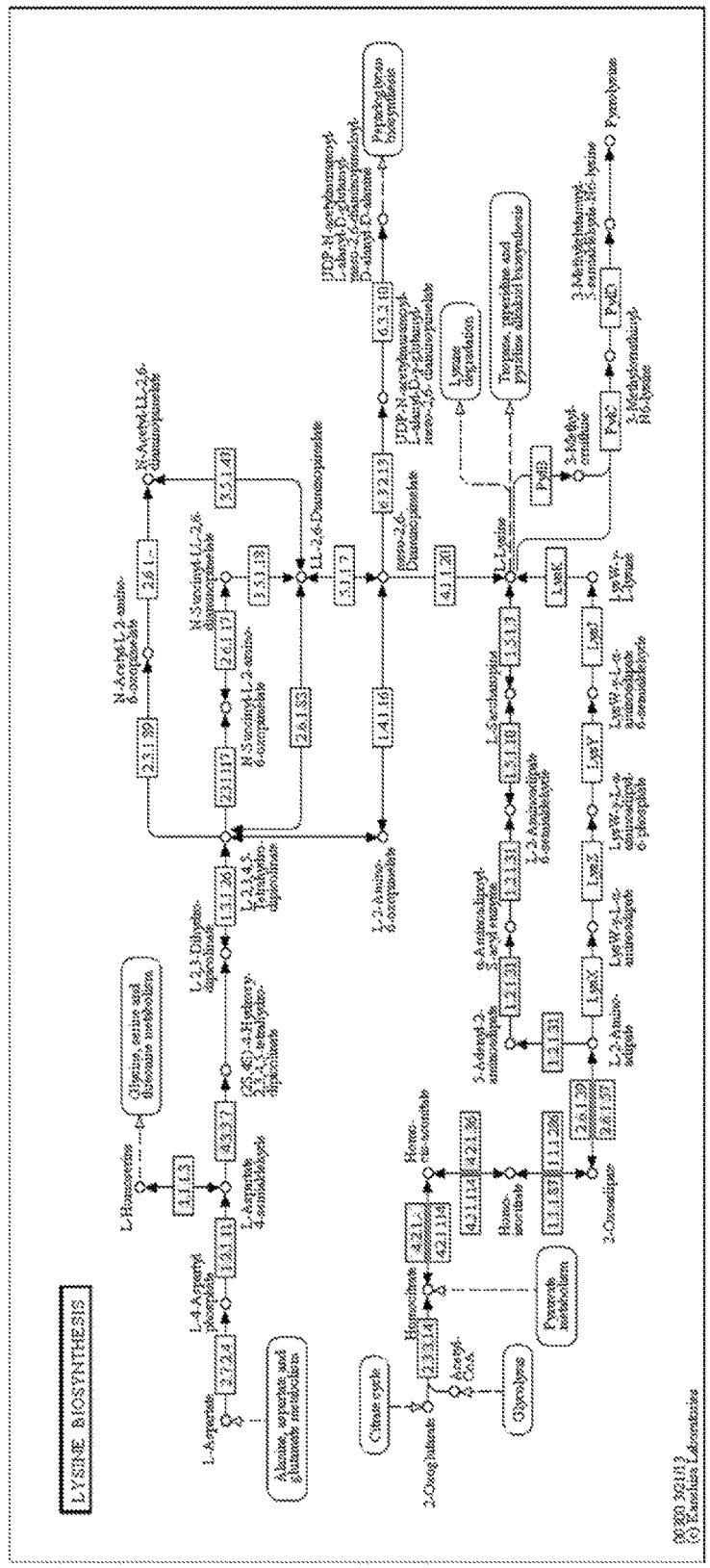

Figure 2 Lysine biosynthesis - Aspergillus niger (http://www.genome.jp/kegg-bin/show_pathway?org_name=ang&mapno=00300&mapscale=1.0&show_description=show)

FIG. 5A

Nucleotide sequence of the *Aspergillus* expression vector pABgpd-I.

4920 bp   DNA   circular   18-MAR-2011

```
   1 ctaaattgta agcgttaata ttttgttaaa attcgcgtta aattttttgtt aaatcagctc
  61 atttttaac caataggccg aaatcggcaa aatcccttat aaatcaaaag aatagaccga
 121 gataggttg agtggccgct acagggcgct cccattcgcc attcaggctg cgcaactgtt
 181 gggaagggcg tttcggtgcg ggcctcttcg ctattacgcc agctggcgaa aggggggatgt
 241 gctgcaaggc gattaagttg ggtaacgcca gggttttcc agtcacgacg ttgtaaaacg
 301 acggccagtg agcgcgacgt aatacgactc actatagggc gaattggcgg aaggccgtca
 361 aggccgcggc cgctcaggag gcgaatagat aattttgaaa tccctactga tacggcttcc
 421 caacgaggta ggagcggaaa ggatgatgag tggccaagta cctgccgatg ctttgttgtc
 481 tcacgacttg agtctcctga tataccaaca tcggtggccg gtgaagacaa tgaagacata
 541 tttctaagca atatgggctg tggccactcc gtgccacttg ctcgaagtaa cctgttgcat
 601 ttaccccatg taaggctgga ggctggatgg ggccactttg cagcagtatg tagaaagtac
 661 tagaaccatc ttccggtctc cgagacactg gtcaatattg acacggcagc atgatcatga
 721 aacccgagtc agaccagagc cgttcggatt gtgctatacc caagtcacg ttgtccataa
 781 ttgaataaat atgagcagtc ctttgtggcg tggaaacata cttagcatgt agagacaaac
 841 cttggtgcgc ggcttcaggc gggcatagtt agtatgctac ggtaccaccg atcttattgt
 901 accagaaaaa gtcccagcca gtccaatccc cattctaagc cacatgcatc cgttcgcatg
 961 catctgacat atcagattcg tccatctggt gcagtatcta acagaggcca gagcatcacc
1021 aacatgggta ccctcagcaa taatatgcat gcattgtgcc ccccctatgg agccgtagct
1081 ttcaagcaat tagacacgcg cccggccgaa tgagatgaac cgttggagcc atcatcccac
1141 tcatcccgct ccagaaagga gagaaagaaa aaaaaaaaat atgaccgagc gcgtgatgac
1201 cggtgaggac tccggtgaat tgatttgggt gacgggagag acccaagagg ggccagaata
1261 ataagaatgg ggaaggcgaa ggtaccgcct ttggggtcca gccacgcgac tccaacatgg
1321 aggggcactg gactaacatt attccagcac cgggatcacg ggccgaaagc ggcaaggccg
1381 cgcactgccc ctcttttttgg gtgaaagagc tggcagtaac ttaactgtac tttctggagt
1441 gaataatact actactatga aagaccgcga tgggccgata gtagtagtta cttccattac
1501 atcatctcat ccgcccggtt cctcgcctcc gcggcagtct acgggtagga tcgtagcaaa
1561 aacccggggg atagacccgt cgtcccgagc tggagttccg tataacctag gtagaaggta
1621 tcaattgaac ccgaacaact ggcaaaacat tctcgagatc gtaggagtga gtacccggcg
1681 tgatggaggg ggagcacgct cattggtccg tacggcagct gccgaggggg agcaggagat
1741 ccaaatatcg tgagtctcct gctttgcccg gtgtatgaaa ccggaaagga tccaaatatc
1801 gtgagtctcc tgctttgccc ggtgtatgaa accggaaagg actgctgggg aactggggag
1861 cggcgcaagc cgggaatccc agctgacaat tgacccatcc tcatgccgtg gcagagcttg
1921 aggtagcttt tgccccgtct gtctccccgg tgtgcgcatt cgactgggcg cggcatctgt
1981 gcctcctcca ggagcggagg acccagtagt aagtaggcct gacctggtcg ttgcgtcagt
2041 ccagaggttc cctcccctac ccttttttcta cttcccctcc ccgccgctc aacttttctt
2101 tccctttac tttctctctc tcttcctctt catccatcct ctcttcatca cttccctctt
2161 cccttcatcc aattcatctt ccaagtgagt cttcctcccc atctgtccct ccatctttcc
2221 catcatcatc tcccctccca gctcctcccc tcctctcgtc tcctcacgaa gcttgactaa
2281 ccattacccc gccacataga cacatctaaa ccatggacgt agttaattaa agatctaatc
2341 aggacggcaa actcaattca gaagtgtgct gtgagtgaga ctgattgccg agcgcagacg
2401 actctcgtgg aacccggctt gtggagaagc ttgagaaggt cttaactcct agcgtaaaag
2461 ctcatgatga cgtacaattt aatgaaatga tacaatgttc atatttcccg ttcaaatttc
2521 cggccttggt cagtgcgtaa gatgtccacg attgaatact aactcagtat gggtttggta
2581 gcattggcaa tgtagttata agcatgcacc ggttgaagac gtcggcccca gatgcaatgc
2641 tgcggtggtg actaagctct gcagtgaatg gaatgcgttt ctttgatcga cttcggcgtg
```

FIG. 5B

```
2701 ccgcgggatt ttctcggcgc ttctactggt gcagaaagga cgataccact ggctttcggt
2761 ccatgccaca tcccagtctc ccgggaaatt cattgcatac tttaagaaac aaactgatct
2821 ccataatttc cgtctttaga gttcacttgg tacttttggg tggatcgagg ggtgtccgcg
2881 gccatccaag tcacgtggag ggcagctaga ccacggattt tagagctaca ttgatccaag
2941 actcctggac cggcctcatg ggccttccgc tcactgcccg ctttccagtc gggaaacctg
3001 tcgtgccagc tgcattaaca tggtcatagc tgtttccttg cgtattgggc gctctccgct
3061 tcctcgctca ctgactcgct gcgctcggtc gttcgggtaa agcctggggt gcctaatgag
3121 caaaaggcca gcaaaaggcc aggaaccgta aaaaggccgc gttgctggcg ttttccata
3181 ggctccgccc ccctgacgag catcacaaaa atcgacgctc aagtcagagg tggcgaaacc
3241 cgacaggact ataaagatac caggcgtttc ccctggaag ctccctcgtg cgctctcctg
3301 ttccgaccct gccgcttacc ggatacctgt ccgcctttct cccttcggga agcgtggcgc
3361 tttctcatag ctcacgctgt aggtatctca gttcggtgta ggtcgttcgc tccaagctgg
3421 gctgtgtgca cgaaccccc gttcagcccg accgctgcgc cttatccggt aactatcgtc
3481 ttgagtccaa cccggtaaga cacgacttat cgccactggc agcagccact ggtaacagga
3541 ttagcagagc gaggtatgta ggcggtgcta cagagttctt gaagtggtgg cctaactacg
3601 gctacactag aagaacagta tttggtatct gcgctctgct gaagccagtt accttcggaa
3661 aaagagttgg tagctcttga tccggcaaac aaaccaccgc tggtagcggt ggttttttg
3721 tttgcaagca gcagattacg cgcagaaaaa aaggatctca agaagatcct ttgatctttt
3781 ctacggggtc tgacgctcag tggaacgaaa actcacgtta agggattttg gtcatgagat
3841 tatcaaaaag gatcttcacc tagatccttt taaattaaaa atgaagtttt aaatcaatct
3901 aaagtatata tgagtaaact tggtctgaca gttaccaatg cttaatcagt gaggcaccta
3961 tctcagcgat ctgtctattt cgttcatcca tagttgcctg actccccgtc gtgtagataa
4021 ctacgatacg ggagggctta ccatctggcc ccagtgctgc aatgataccg cgagaaccac
4081 gctcaccggc tccagattta tcagcaataa accagccagc cggaagggcc gagcgcagaa
4141 gtggtcctgc aactttatcc gcctccatcc agtctattaa ttgttgccgg gaagctagag
4201 taagtagttc gccagttaat agtttgcgca acgttgttgc cattgctaca ggcatcgtgg
4261 tgtcacgctc gtcgtttggt atggcttcat tcagctccgg ttcccaacga tcaaggcgag
4321 ttacatgatc ccccatgttg tgcaaaaaag cggttagctc cttcggtcct ccgatcgttg
4381 tcagaagtaa gttggccgca gtgttatcac tcatggttat ggcagcactg cataattctc
4441 ttactgtcat gccatccgta agatgctttt ctgtgactgg tgagtactca accaagtcat
4501 tctgagaata gtgtatgcgg cgaccgagtt gctcttgccc ggcgtcaata cgggataata
4561 ccgcgccaca tagcagaact ttaaaagtgc tcatcattgg aaaacgttct cggggcgaa
4621 aactctcaag gatcttaccg ctgttgagat ccagttcgat gtaacccact cgtgcaccca
4681 actgatcttc agcatctttt actttcacca gcgtttctgg gtgagcaaaa acaggaaggc
4741 aaaatgccgc aaaaaaggga ataagggcga cacggaaatg ttgaatactc atactcttcc
4801 tttttcaata ttattgaagc atttatcagg gttattgtct catgagcgga tacatatttg
4861 aatgtattta gaaaaataaa caaataggggg ttccgcgcac atttccccga aaagtgccac
```
//

FIG. 9A citrate synthase [Aspergillus niger CBS 513.88] NCBI Reference Sequence: XP_001393195.2

```
  1 mpdiasngar ngasqnaetk peppvlhvvd srtgkyfpip ivrnainase fkklkspedp
 61 ahpedqneqg irvfdpgysn tavsesqvty idglkgtiqy rgyniedivg kkkfidtahl
121 liwgewptpe qakslqekls svpvldesvf kviqafppns siigmmiaal savqstqmdr
181 ipahaaknly lgnpkavdde ivrlmgslsm itaavychht greftpprpe lsyienfllm
241 mghvesstgl pnpqyvdrie rlwvliadhe mtcstaaflq tasslpdvfs cmisalsaly
301 gplhggaiev ayknfeeigs venvaakier vkagkerlyg yghriyrvtd prfifirqil
361 delkeeiarn pllkvafevd rvasedeyfv trklrpnadl faalvysamg fptefilpls
421 llsrtqgfma hwkeamssta riwrpgqiyt ghlnrema
``` citrate synthase [Aspergillus niger ATCC 1015] GenBank: EHA18674.1

```
  1 mpdiasngar ngasqnaetk peppvlhvvd srtgkyfpip ivrnainase fkklkspedp
 61 ahpedqneqg irvfdpgysn tavsesqvty idglkgtiqy rgyniedivg kkkfidtahl
121 liwgewptpe qakslqekls svpvldesvf kviqafppns siigmmiaal savqstqmdr
181 ipahaaknly lgnpkavdde ivrlmgslsm itaavychht greftpprpe lsyienfllm
241 mghvesstgl pnpqyvdrie rlwvliadhe mtcstaaflq tasslpdvfs cmisalsaly
301 gplhggaiev ayknfeeigs venvaakier vkagkerlyg yghriyrvtd prfifirqil
361 delkeeiarn pllkvafevd rvasedeyfv trklrpnadl faalvysamg fptefilpls
421 llsrtqgfla hwkeamssta riwrpgqiyt ghlnrema
``` uncharacterized protein LOC100274406 [Zea mays] NCBI Reference Sequence: NP_001142237.1

```
MPDIAPNVARNGSSKHAETKPETPVLHVVDSRTGNYFPIPIVRNAINASEFKKLKSPEDPAHPEDQNEQG
IRVFDPGYSNTAVSESQVTYIDGLKGTIQYRGYNIEDIVGKKKFIDTAHLLIWGEWPTPEQAKSLQEKLS
SVPILDESVFKVIQAFPPNSSIIGMMIAALSAVQSSQMDRIPAHAAKNLYLGNPQAVDDEIVRLMGSLSM
ITAAVYCHHTGREFTPPRPELSYIENFLLMMGHVESSTGLPNPQYVDRIERLWVLIADHEMTCSTAAFLQ
TASSLPDVFSCMISALSALYGPLHGGAIEVAYKNFEEIGSVENVAAKIERVKAGKERLYGYGHRIYRVTD
PRFIFIRQILDELKEEIARNPLLKVAFEVDRVASEDEYFVTRKLRPNADLFAALVYSAMGFPTEFILPLS
LLSRTQGFMAHWKEAMSSTARIWRPGQIYTGHLNREMA
``` citrate synthase [Aspergillus kawachii IFO 4308] GenBank: GAA88109.1

```
  1 mpdiapnvar ngsaknaenk petpvlhvvd srtgnyfpip ivrnainase fkklkspedp
 61 ahpedqneqg irvfdpgysn tavsesqvty idglkgtiqy rgyniedivg kkkfidtahl
121 liwgewptpe qarslqekls svpildesvf kviqafppns siigmmiaal savqssqmdr
181 ipahaakly lgnpqavdde ivrlmgslsm itaavychht greftpprle lsyienfllm
241 mghvesstgl pnpqyvdrie rlwvliadhe mtcstaaflq tasslpdvfs cmisalsaly
301 gplhggaiev ayknfeeigs venvaakier vkagkerlyg yghriyrvtd prfifirqil
361 delkeeiarn pllkvafevd rvasedeyfv trklrpnadl faalvysamg fptefilpls
421 llsrtqgfma hwkeamssta riwrpgqiyt ghlsrema
``` citrate synthase [Aspergillus oryzae 3.042] GenBank: EIT75413.1

```
  1 mtvtqeaspk reslhiiddr tgsyysipiv nnainasdfk kvtapedkay panqtenglr
 61 vydpgysnta vshskityid glkgtiqyrg ysindivgrk tfidtahlli wghwpsaaea
121 etlqqrldqv pvpqdfvfnv iksfprdgsl mgmviaglsa lqssdmnaip ahvgktiyln
181 npeladqqii rvmanmsmlt aaaychhigr dftppragls yienfllmtg hveaatglpn
241 pryvnaierl wvliadhemt cstaallqta salpdviscm vsaisalygp lhggaievay
301 kniesigsis nvpakiarvk agkerlygyg hrvyrvtdpr fvfireilne lseevekdpl
361 lkvafevdrv asedeyftsr nlrpnadlfa afvykalgfp pefilplsil srtqgfmahw
421 reamgnppri wrpgqiytgd lnksmde
``` citrate synthase [Aspergillus oryzae RIB40] NCBI Reference Sequence: XP_001827205.1

FIG. 9B

```
  1 mtvtqeaspk reslhiiddr tgsyysipiv nnainasdfk kvtapedkay panqtenglr
 61 vydpgysnta vshskityid glkgtiqyrg ysindivgrk tfidtahlli wghwpstaea
121 etlqqrldqv pvpqdfvfnv iksfprdgsl mgmviaglsa lqssdmnaip ahvgktiyln
181 npeladqqii rvmanmsmlt aaaychhigr dftppragls yienfllmtg hveaatglpn
241 pryvnaierl wvliadhemt cstaallqta salpdviscm vsaisalygp lhggaievay
301 kniesigsis nvpakiarvk agkerlygyg hrvyrvtdpr fvfireilne lseevekdpl
361 lkvafevdrv asedeyftsr nlrpnadlfa afvykalgfp pefilplsil srtqgfmahw
421 reamgnppri wrpgqiytgd lnksmde
``` unnamed protein product [Aspergillus oryzae RIB40] GenBank: BAE66072.1 (AO090010000170)

```
  1 mtvtqeaspk reslhiiddr tgsyysipiv nnainasdfk kvtapedkay panqtenglr
 61 vydpgysnta vshskityid glkgtiqyrg ysindivgrk tfidtahlli wghwpstaea
121 etlqqrldqv pvpqdfvfnv iksfprdgsl mgmviaglsa lqssdmnaip ahvgktiyln
181 npeladqqii rvmanmsmlt aaaychhigr dftppragls yienfllmtg hveaatglpn
241 pryvnaierl wvliadhemt cstaallqta salpdviscm vsaisalygp lhggaievay
301 kniesigsis nvpakiarvk agkerlygyg hrvyrvtdpr fvfireilne lseevekdpl
361 lkvafevdrv asedeyftsr nlrpnadlfa afvykalgfp pefilplsil srtqgfmahw 421 reamgnppri wrpgqiytgd lnksmde
``` citrate synthase, putative [Aspergillus flavus NRRL3357] NCBI Reference Sequence: XP_002384448.1

```
  1 mtvtqeaspk reslhiiddr tgsyysipiv nnainasdfk kvtapedkay panqtenglr
 61 vydpgysnta vshskityid glkgtiqyrg ysindivgrk tfidtahlli wghwpstaea
121 etlqqrldqv pvpqdfvfnv iksfprdgsl mgmviaglsa lqssdmnaip ahvgktiyln
181 npeladqqii rvmanmsmlt aaaychhigr dftppragls yienfllmtg hveaatglpn
241 pryvnaierl wvliadhemt cstaallqta salpdviscm vsaisalygp lhggaievay
301 kniesigsis nvpakiarvk agkerlygyg hrvyrvtdpr fvfireilne lseevekdpl
361 lkvafevdrv asedeyftsr nlrpnadlfa afvykalgfp pefilplsil srtqgfmahw 421 reamgmpest lnssrsicpd tnignppriw rpgqiytgdl nksmde
```

AFL2G_11427 Aspergillus flavus

```
MTVTQEASPK RESLHIIDDR TGSYYSIPIV NNAINASDFK KVTAPEDKAY PANQTENGLR
VYDPGYSNTA VSHSKITYID GLKGTIQYRG YSINDIVGRK TFIDTAHLLI WGHWPSTAEA
ETLQQRLDQV PVPQDFVFNV IKSFPRDGSL MGMVIAGLSA LQSSDMNAIP AHVGKTIYLN
NPELADQQII RVMANMSMLT AAAYCHHIGR DFTPPRAGLS YIENFLLMTG HVEAATGLPN
PRYVNAIERL WVLIADHEMT CSTAALLQTA SALPDVISCM VSAISALYGP LHGGAIEVAY
KNIESIGSIS NVPAKIARVK AGKERLYGYG HRVYRVTDPR FVFIREILNE LSEEVEKDPL
LKVAFEVDRV ASEDEYFTSR NLRPNADLFA AFVYKALGFP PEFILPLSIL SRTQGFMAHW
REAMGNPPRI WRPGQIYTGD LNKSMDE
``` citrate synthase, putative [Talaromyces marneffei ATCC 18224] NCBI Reference Sequence: XP_002148678.1

```
  1 mspaaiissd daaksvdaka saktisrnfl hvidertgqy yqipihhnai sanefkkika
 61 pdseyyadqn engirvfdpg ftntavvesk vtyvdgkrgk iqyrgydlad vvannkkfid
121 tahlmvfgfw ptaeegagfq qklfdamhie qcvidtihaf prtasttlml taglaavqat
181 qmdripahma knlylgnptl vdeqivrlmg vlpivsavay chhtgrefks prsdltyien
241 flymcghvqe etglpnpryv qnferlwslv adhemtcsta avlltasslp dpisciisgi
301 gasygplhgg aiefaykdma digsvdncqt kidrvksgke rlfgyghrvy kvtdprsehi
361 qavletlkee idndpllkva felnriaqed eyfvsrglkp nadlfaafty gamgfppdfi
421 ltistisrtq glmahwkeam sgkpliwrpt qvytgkldlk mev
```

>Aspfo1_0085419 polypeptide
```
MPDIAPNVARNGSAKNAENKPETPVLHVVDSRTGNYFPIPIVRNAINASEFKKLKSPEDPAHPEDQNEQG
IRVFDPGYSNTAVSESQVTYIDGLKGTIQYRGYNIEDIVGKKKFIDTAHLLIWGEWPTPEQAKSLQEKLS
SVPILDESVFKVIQAFPPNSSIIGMMIAALSAVQSSQMDRIPAHAAKNLYLGNPQAVDDEIVRLMGSLSM
```

FIG. 9C

```
ITAAVYCHHTGREFTPPRLELSYIENFLLMMGHVESSTGLPNPQYVDRIERLWVLIADHEMTCSTAAFLQ
TASSLPDVFSCMISALSALYGPLHGGAIEVAYKNFEEIGSVENVAAKIERVKAGKERLYGYGHRIYRVTD
PRFIFIRQILDELKEEIARNPLLKVAFEVDRVASEDEYFVTRKLRPNADLFAALVYSAMGFPTEFILPLS
LLSRTQGFMAHWKEAMSSTARIWRPGQIYTGHLNREMA*

>Acar5010_212258 polypeptide
MPDIASNGARNGTSAHAEDKPDTPVLHVVDSRTGKYHSIPIVRNAINASEFKKLKTPEDPEHPEDQNEQG
IRVFDPGYSNTAVSESKVTYIDGLKGTIQYRGYRIEDIVGKKKFIDTAHLLIWGDWPTPEQAQTLHEKLA
SVPVINESVFKVIQAFPPNASIIGMMIAALSAVQSSQMDRIPAHAAKNLYLGVPKAVDDEIIRLMGTLSM
ITAAVYCHHIGREFTPPRPELSYIENFLLMMGHVDASTGLPNPQYVDRIERLWVLIADHEMTCSTAAFLQ
TASSLPDVFSCMISALSALYGPLHGGAIEVAYKNFEEIGTVENVAAKIERVKAGKERLYGYGHRIYRVTD
PRFTFISQILDELKEEIARNPILKVAFEVDRVASEDEYFVSRRLRPNADLFAALTYSAMGFPTEFILPLS
LLSRTQGFMAHWKEAMSGSARIWRPGQIYTGHLNREME*

Aspca3|171837|estExt_Genewise1Plus.C_100394 (Acar5010_171837)
MTTNGINGTNGVDAVPSLHVVDSRTGQYYEIPIVHNAIHASEFKRIKAPLNEDYYPDQTENGIRVFDPGF
SNTAVKESKITYIDGTKGIIQYRGYSIDDIIRQGKSFIDTVHLLIWGHWPSPIEAKKLQIRISDAMTLDG
SVYQVIRSFPPSGSIMGMIIAGLSALQSTQMHTVPAHAAKNLYLGNPEAVDEQIITVLAALPMISAIAYC
HHLNRPFTPPRRDLSYIENLFLMTGHVDPQTSLPNPRYVGYFERLWVLIADHEMTCSTAAMLQTASSLPD
AISSLISAISAMYGPLHGGAIEVAYRDIAAIGSIPACQEKIDRVKSGKERLYGYGHRVYRVTDPRAVHIQ
AVLAELQEEIAQDPLLKVAFELNRLAADDEYFVKRKLKPNADLFAAFTYGAMGFPEEFILPISIISRTQG
FLAHWKEAMGGTAKIWRPGQVYVGEVDRKFE*

Aspbr1_0068777 polypeptide
MPDIASNGARNGTSQHADKPEPPVLHVVDSRTGKYFPIPIVRNAINASEFKKLKSPEDPAHPEDQNEQGI
RVFDPGYSNTAVSESQITYIDGLKGTIQYRGYNIENIVGKKKFIDTAHLLIWGEWPTPEEAKSLQEKLSS
VPVLDESVFKVIQAFPLTAPSPNSSIIGMMIAALSAVQSSQMDRIPAHAAKNLYLGNPKAVDDEIIRLMG
SLSMITAAVYCHHTGREFTPPRPELSYIENFLLMMGHVESTTGLPNPQYVDRIERLWVLIADHEMTCSTA
AFLQTASSLPDVFSCMISALSALYGPLHGGAIEVAYKNFEEIGSVENVAAKIERVKAGKERLYGYGHRIY
RVTDPRFIFIRQILDELKEEIARNPLLKVAFEVDRVASEDEYFVSRKLRPNADLFAALVYSAMGFPTEFI
LPLSLLSRTQGFMAHWKEAMSSTARIWRPGQIYTGHLNREMA*

Asptu1_0164827 polypeptide
MPDIAPNVARNGSSKHAETKPETPVLHVVDSRTGNYFPIPIVRNAINASEFKKLKSPEDPAHPEDQNEQG
IRVFDPGYSNTAVSESQVTYIDGLKGTIQYRGYNIEDIVGKKKFIDTAHLLIWGEWPAPEQAKSLQEKLS
SVPILDESVFKVIQAFPPNSSIIGMMIAALSAVQSSQMDRIPAHAAKNLYLGNPQAVDDEIVRLMGSLSM
ITAAVYCHHTGREFTPPRPELSYIENFLLMMGHVESSTGLPNPQYVDRIERLWVLIADHEMTCSTAAFLQ
TASSLPDVFSCMISALSALYGPLHGGAIEVAYKNFEEIGSVENVAAKIERVKAGKERLYGYGHRIYRVTD
PRFIFIRQILDELKEEIARNPLLKVAFEVDRVASEDEYFVTRKLRPNADLFAALVYSAMGFPTEFILPLS
LLSRTQGFMAHWKEAMSSTARIWRPGQIYTGHLNREMA*
``` hypothetical protein PFICI_09705 [Pestalotiopsis fici W106-1] GenBank: ETS77643.1

```
  1 mspavisqtn gangtngaka qlgdvlhiid srtgqyhain ihqnainasd lkvlkapkda
 61 nhpeyqndqg irvydpgysn tlvseskity idglegtiqy rgysiddiig kkkfvdvshl
121 liwgkwpsad eaqtyqqrln dvplinetvf nvirsfpkdg silgmmiagl salqssdmsa
181 vpahaaknly lgqpknvddq iirvmaslsm itaaaychhs drtftpprkd fsyvgnfllm
241 tghveestgv pnpryvdaie rlwatvadhe mtcstaallq tasalpdvis slisalsasy
301 gplhggaiev ayknieeigt vedvpakier vkagkerlyg yghrvyrvtd prftyisdil
361 delsdeiekd pllrvafald raaaqdeyfi srklrpnadl faafaykaig fpanfilpis
421 avsrtqgfma hwkeamegap riwrpgqkyt gnlnqte
``` putative citrate synthase protein [Neofusicoccum parvum UCRNP2] GenBank: EOD45286.1

```
  1 matttitapa ngrvskdslt vtdnrtgstf tfpithnavn asnfkqikap edpdniadqn
 61 eqglrvfdpg fgntcvsesk itfidglkgi iqyrgydigd lieakkgfvd tahllwfgtl
121 pspkekqelq drlnavplid dhvfntirsf pkngspfgmi iaglmalqss emdlipahaa
181 kniylgnlsl vdsqlirvmq slsqicavay chqtgrtftp pradltfien fllmmghtea
241 atglpnpayv akferlwlli adhemtcsta amlqtasamp dalsclasat salygplhgg
```

FIG. 9D

```
301 aievayknia eigsvdnipp kiarvkagke rlygyghrvy rvpdpryrhi kevledltae
361 ieddpllkva feldrvartd eyftsrklnp nadlfaalay namgfepewi lpislmsrsq
421 gllahwkeam sgsariwrpg qiytgdlnkk ie
``` putative citrate synthase protein [Eutypa lata UCREL1] GenBank: EMR70107.1

```
  1 mataaptatk staannpmts sqseinvave krdvlhavdg rtglyysipi nknavnagdf
 61 kkikspadrk hpayqnelgl riydpgfsnt tvseskityi dgiegtiqyr gysihdifgk
121 kgwidvshll iwgnwpssae akeyqerlng vplldqhvld vihsfpkdgv itgmmiagls
181 alqscnldav payvgdnlyv ghpdrvdkqi ihllqsfami taacychsts reftqprqdf
241 syvenfllmv ghvdattglp sprhvdaler lwgvvadhem tcstaaflht asslpdiisc
301 fitaicaatg plhggaisva hkhikaigtv anvpakierv ksgkellygy ghrvyrttdp
361 rytyinqvld glteevardp llqvalaldk aasedeyfts rklfpnadlf aafayqalgf
421 ppdfvlpmsc lsrlqgfaah wkeglqgkpk iwrpgqiytg dlektmg
```

Aspergillus niger An09g03570

```
  1 MSKTRTPMRN MRSQFEERRS QPWTSRRSEP QEREPTAQIR SRVASGEIDL
 51 EDVLHRLVSG SYPTMPHMDG LSHKLTEAML AVPDDVQRTV WTHPHPDMIT
101 ASHDANMFRK SPEDTDRVMI RTVAAYAVVS GLANSHRKGL RFTPPTRGRS
151 YYEKSFVMAG LVPRTGRPGR VKLSCFRHQR VKQGRVKVFE YGHRSYKGIN
201 PRVPPIQSIL KNLDLSADNP LKLAEREFVQ LMPTSKSRGY ADTSNGFYPK
251 IISMAMLAQR IMGIMTHWRE YMLMRGKLLR PSHIYTGEAE GGVLPGIRTD
301 RASYVKVSLA SAVAADVLTS AERGPYMNIT SLGIMLVPSI GPLLGGLLSQ
351 QPG*
```

Aspergillus niger An01g09940

```
  1 MDQSLTVYLG VSIRPFELFR PRLHGLGQMA AAMPDKVQIC ASEPDKPQQN
 51 QDNSSDNPSQ THPIPFYNMA YTLASWLGRL FDAGKSLLPL QGNYINALLE
101 QELPGEREGT LTVRDNRTGS KYTIPIVRNS VPAMGFRQIC VDRAGKSPRQ
151 QFEDGLRLID PGYRNTAVKM SSITYINGNE GVILYRGHPL ASLIGKSYEE
201 ITHLLIWGSL PTPEQRLRFQ RRIAEAMMVV PENVKQLVAT FPRNTPPMVI
251 LCAVLTGYLA DQPELIPAHA GANLYNRRPE MVDEQIIRTL AVTAIAGSIA
301 HCHMKGEELR MADPNLSYIE NILWMGRYVD NNPAVTREKA AEILTKAWSL
351 YADHEMTNST SAFLHVSSSL ADPLSAMAAC CMSGYGLLHG GAIDAAYRGM
401 REIGGPQNVP KLIEKVINKE CRLSGYGHRI YKQVDPRAKY VREMLDELTR
451 DRDIREMDPV LQVAMEIDRI ASTHEYFVKR NLQANADLYG SFVYTALGID
501 SQFATVLAAT ARVSGVMAHW KEQTERAPDL WRPLQVYVPN *
``` citrate synthase [Aspergillus kawachii IFO 4308]

FIG. 9E

```
   1 mssgilyvkd srtdvqyeip irrnavsavd fkkikgpgtg adradqvagg lrvhdpglrn
  61 ttvvetaisf sdhersllf  rgysleqlwq sdfedvlhll vwgsyptvpq rnnlshrlte
 121 amlavpddvq rtiwglpgts splplivagl saclashpdm ipashdanmy rnnpedtdra
 181 iiqtvaayav vfglvnshrk glrfsppsrg rsyyenlfvm aglvdsrtgr pdrvklscfr
 241 rfsilnsdhg maltvfsala tsssltdpis clitaigsaw gplhfgates akrtleige
 301 aknipgyihn vkqghvkvfg yghrsykgid prvppirsil kdldmsadkl fklaeriesa
 361 csndayfter glyvngdfyg hfiftaigfd peiipaamla qrimgimahw reymltrgkl
 421 lrpshiytge aeerllpkfq qyqatlvaan qpategtpll aeqpakkpys iftpgqkrli
 481 ivtaalassf splsaniyyp alnsiaadlh vtssqinlti ttymlcqgla pafmgsfadq
 541 agrrpayilc favyitgnia lalqhsypal lilraiqscg ssgtvalasa vtadvitsae
 601 rgtymgitsl giilapsvgp lvggiltpai tstpgqkssr ialpnplttl sllshrptgl
 661 vllsngllfa syyavtagip sqfketyhln dsviglvfvp agvgsllstt fnglllldwny
 721 rrlreqfrsp ilqahhhgaf pierariqic lpltllaals ilsysalmsl atptlshalv
 781 lifaisfsit aaynimnili vdlyystpat amaannlvrc flgaaatglv hpamvrwgtg
 841 wttimnyhll islliplitt qiidplphyp qtlhlyypnt pwiqpgdtlq ildtkplpil
 901 stqhpplhqt ytilfldldv lynhttatvi lhwyqpdlip ypnntnillp npqvptrkpa
 961 pyiapqpptn shhrylylly tqppnytfpe cfehifppta earagfdmki ftdaaglgtp
1021 vagnwfyvrn evdlptgsgs gskggvatst smntattttt smrwvecdls sssssssssi
1081 stsvlttsta ivatttthr  ptdsptettl amsnnidesq vqaqarls
```

GenBank: GAA91575.1citrate synthase [Neosartorya fischeri NRRL 181]

```
   1 mssgtlyird srtnaeyeip irrnavsamd fkrikapaag adradqvasg lrvhdpglqn
  61 ttvvetrisf sdhekgllf  rgytleqlwd sdfedmlhll vwgsyptalq kkelsrklse
 121 emtmvpksvh rtietlprtt splplmlagl saclayapes ipastkpdly qsnsnvvdra
 181 iirtvaayav vfglvnchrr gipfaqpsrh ksylenlfqm aglvdqttgr pdptklscfr
 241 rfamlnadhg malsvfsalv ttssltdpis clitatgaaf gplhfgates anlalreigt
 301 pekvpkfiee vkqgkrrlfg yghrsykgld prvapirsil kdldtssnsl ikvaerieqv
 361 asadgyfrsr glypnadfyg nfvftgigfe pelipaamms qrimgvmahw reymckslqe
 421 svryrrvsdl kyv
```

NCBI Reference Sequence: XP_001260993.1citrate synthase [Aspergillus fumigatus Af293]

```
   1 msfgtlhird srtnaeyeip irrnavvamd fkrikapaag adradqvdsg lrvhdpglqn
  61 ttvveteisf sdhwkrllly rgytleqlwd sdfedmlhll vwgsyptalq kkelsrklse
 121 emtmvpksvh rtietlprtt splplmlvgl saclayvpes ipastkpdly qsnsnvldra
 181 iirtvaayav vfglvnchrr gipfaqpsrh tsylenlfhl aglvdqttgr pdptklscfq
 241 rfamlnadhg malsvfsalv tassltdpis clitatgaaf gplhfgates anlalrvigt
 301 penvpnfiee vkqgkqrlfg yghrsykgvd prvapirsil kdldmssnsl lkvaerieqv
 361 asaddyfrnr glypnadfyg nfvfteigfe pdmipaamma qrimgvmahw reymckplqq
 421 svryrrvshi dyi
```

NCBI Reference Sequence: XP_001481680.1citrate synthase, putative [Aspergillus flavus NRRL3357]

```
   1 myqksleppm ssgvlhivds rtkqkyeipi rrnvisaidl ksikapaagt dradhvadgl
  61 rvhdpglqnt tviesaisys dhergvllfh gytlsqlwds dfedmlhllv wgtyptmqqk
 121 kdlnrklteq mlavpdsvhr tirglprtts plplilagls aylacfpdti pasthaslyq
 181 gnlrnvdhav irtvaaygvi fglvnshrkg idfqppsqen sycanlfima glldrhssrp
 241 dptklscfrr famlnadhgm altvfsalvt assltdpisc lisavaaayg plhfgatvsa
 301 qrtlreigst dkvpefiegv knrrtklfgy ghrsykgldp rvrpiqsilk dldlskndyl
 361 kiterieeia saddyfrhrg lypnadfygn fvftaigfdp diipaamltq riigimahwr
 421 eymcmc
```

NCBI Reference Sequence: XP_002375601.1citrate synthase [Aspergillus oryzae RIB40]

```
   1 mssgvlhivd srtkqkyeip irrnvisaid lksikapaag tdradhvadg lrvhdpglqn
  61 ttviesaisy sdhergvllf hgytlsqlwd sdfedmlhll vwgtypsmqq kkdlnrklte
```

FIG. 9F

```
121 qmlavpdsvh rtirglprtt splplilagl saylacfpdt ipasthasly qgnlrnvdha
181 virtvaaygv ifglvnshrk gidfqppsqe nsycanlfim aglldrhssr pdptklscfr
241 rfamlnadhg maltvfsalv tassltdpis clisavaaay gplhfgatvs aqrtlreigs
301 tdkvpefieg vknrrtklfg yghrsykgld prvrpiqsil kdldlskndy lkiterieei
361 asaddyfrhr glypnadfyg nfvftaigfd pdiipaamlt qriigimahw reymcsdtid
421 lsdnwlqefi sgqpadltqd rnfldalgln sadstltaip sstndftgsa ktidvassel
481 qdqlplaayy ppasgfssyn ytffhgkrfc
```

NCBI Reference Sequence: XP_001727354.2TPA: citrate synthase, putative [Aspergillus nidulans FGSC A4]

```
  1 mssgtlyird srtdalyeip irrnsvsaad fkrikapgig anradqvsgg lrvhdpglln
 61 ttviesaisf sdherglllf rgysleelwk sdfedmlhll vwgsyptppq keqlrsklaa
121 qmlavpetvq tavqslpntt pplaliltgl stylscipet ipastdahqy ranrenvdna
181 vlrtvaayav vfgivashrk sipftppspd rtycenlftm aglvdpvagm pdpvklscfr
241 rfamlnadhg maltvfsalv tassltdpvs clitsvasaw gplhfgates aqraladigt
301 eagipaflde vkqgrkrlfg yghrsykrid prvrfvqsil hdlpstrllk laeaiecaas
361 addyfrsrgl ypnadfygnf vftgigfeve mipaamlaqr imgimahwre ymrefcahtt
421 ramqr
```

GenBank: CBF79704.1hypothetical protein AN7593.2 [Aspergillus nidulans FGSC A4] NCBI Reference Sequence: XP_680862.1

```
  1 mssgtlyird srtdalyeip irrnsvsaad fkrikapgig anradqvsgg lrvhdpglln
 61 ttviesaisf sdherglllf rgysleelwk sdfedmlhll vwgsyptppq keqlrsklaa
121 qmlavpetvq tavqslpntt pplaliltgl stylscipet ipastdahqy ranrenvdna
181 vlrtvaayav vfgivashrk sipftppspd rtycenlftm aglvdpvagm pdpvklscfr
241 rfamlnadhg maltvfsalv tassltdpvs clitsvasaw gplhfgates aqraladigt
301 eagipaflde vkqgrkrlfg yghrsykrid prvrfvqsil hdlpstrllk laeaiecaas
361 addyfrsrgl ypnadfygnf vftgigfeve mipaamlaqr imgimahwre ymhpiacptr
421 ksyvlpmrla trsssintsl lftsnhetsr rihdhahrnr nnpspltnch tritttantn
481 tiiialifel glkhspqiep ynhlkyllht fpkaahnthr ipcvhllppl vkhllsspkr
541 prggsarlli anqphnhyih glravqssgi sgtvalsaav aadivdsher gaymgltslg
601 nilapslgpv lgglitshcg wrgvfcflag ggvvvllvlg fflpetrkar vntlevgsve
661 rgqaegaapd nqqskrrkkp glpnpltplr llahfptslv llsnglvfas yyavtagips
721 qfariyglsd mevglvflpa gvgslvsatf ngalvdwnyr rvrkmyedtk vtaegdnevs
781 gaaegtqsdw efpverarlq vggpmtlfcs lvifiyglvl drhpplalsl amiflvsfsi
841 tasynvmnvl lvdlyystpa tvmatnnfvr cflgavstal vtpmierfgg grtygmvaal
901 ivgvccpvlg tvyvngvqwr vqreskfr
```

Citrate synthase-like [Penicillium roqueforti] GenBank: CDM33221.1

```
  1 mstgilfird srtnanyeip inrnavratd lqrirapsln snradqvahg lrvydpglqn
 61 tavtespisf sdhergllly rgytldqlwg cdfeemfhll lwgtyptasq feelrrqlaq
121 ymqvvpdivr qtivnlpket splplvlagl saylactpdv ipattnptiy qrdikradqi
181 ilrtvaayav vfgavrshrl gipwkspsih qtyyenlfam aglvdpktnr pdptrvscfr
241 rfgnlnaehg maltvfstvv tassltdpvs cliatvaaah gplhfgates aqlalrnige
301 pknvpafied iksgkqklfg yghrtykgmd prvrpiqsil kdmtdvnqpl lkvaeaieea
361 askdeffstr glypnadfyg nfvftgigfe pdmipaamla hriigimahw reymvnrgkl
421 frpihlytgh aeptsgprpk i
```

Pc12g00660 [Penicillium chrysogenum Wisconsin 54-1255] NCBI Reference Sequence: XP_002556968.1

```
  1 mclcrqvsge ttyfvpsgtl csrrillkms tgtlfirdsr tnvnyeipin rnavratdlq
 61 girasslnsn radqvahglr vydpglqnta vtqstisfsd hehglllyrg ytleqlwgce
121 feemfhlllr gtyptahqce elrqrlaqym qevpdivrqt ifnlprktsp lplilaglsa
181 ylacipdvip atanatiyqt hikradqvil qtvaayavvf gavrshrlgi pwrspslhqt
241 yyenlftmag lvdpetnrpd ptriscfrrf gnlnaehgma lsvfttlvta ssltdpvscl
```

FIG. 9G

```
301 issvaaahgp lhfgatesaq ralhnvgeps nvpafieeik agkqklfgyg hrtykgmdpr
361 vrpiqsilkd ltdvhqpllk vaeaieeaaa kdeyfstrgl ypnadfygnf vftgigfepe
421 mipaamlahr imgimahwre ymvtrgklfr pihlytgqae ptpgprpki
``` hypothetical protein COCCADRAFT_104929 [Bipolaris zeicola 26-R-13] GenBank: EUC30035.1

```
  1 msngfllvkd srttleyrvp iqrnsvlata fkdikapsss gnradkvgsg lrvhdpglln
 61 ttvvetgvsf adgerdlllf rgysleqlwq sdyedmlhlm vwakyptpvq keslrrllia
121 amlevpknvf eivsafpsss ppmpmvvagl aaylgsnpam ipassggniy qgniektdea
181 iintiaayav ivgmaachrk gieftapsld ysfvenlfhm sgmvddltgr pdamkvscfr
241 rfaalnmdhg malavfstmv tassltdpvs cliaslaaay gplhfgatea ahlslrsigd
301 kskvpefise vkqgkrklfg yghrtykgtd prvrpikeli edsgansdrl ieiareierl
361 asnddyftsr glhpnadfyg nfvftavgfq sdfipiamis qrligimahw reamvrgikl
421 frpshiytgd tepvytasak l
``` hypothetical protein COCMIDRAFT_107988 [Bipolaris oryzae ATCC 44560] GenBank: EUC40740.1

```
  1 msngfllvrd srttleyrvp iqrnsilata fkdikapsss asradkvgsg lrvhdpglln
 61 ttvvetgvsf adgerdlllf rgysleqlwq sdyedmlhlm vwdkyptpvq keslrralit
121 amlevpktvf eivstfpsas ppmpmvvagl aaylggnpdm ipassggniy qgniektdka
181 viktiaayav vvgmaachrk gieftapsld ynfienlfhm sgmvddltgr pdaikvscfr
241 rfaalnmdhg malavfstmv tassltdpis cliaslaaay gplhfgatea ahlnlrsigd
301 kskvpefise vkqgkrklfg yghrtykgtd prvkpikeli edsgansdpl ieiakeierl
361 asnddyftsr glhpnadfyg nfvftavgfq sdfipiamis qrligimahw reamvrgikl
421 frpshiytgd tepvytasak l
``` citrate synthase, putative [Aspergillus clavatus NRRL 1] NCBI Reference Sequence: XP_001275815.1

```
  1 myamillcya ifgvpqlpmd inraewlcnl lyqicpgfav ksctmssgvl fikdsrtniq
 61 yeipirrnai aavdfkrika psagtdradq vasglrvhdp gllnttvvet eisfsdherg
121 lllfrgytlq qlwdsefedm lhllvwgtyp tlrqrkelsr klvdcmlavp ktvhevirtl
181 psttsplpli maglsaylac ipgtipastn pdlyqgnmee vdraivrtva ayavvfglvn
241 chrkgipftp psheqlyfen lfsmaglvdp atnsadatkl scfrrfamln adhgmalsvf
301 salvtasslp dpisclitsi gaafgplhfa atesaqlalr eigtpdkvpe fieevkrgqr
361 rlfgyghrsy kgtdprvapi ksilkdldts dnpflkiaeq iervasaddf fskrglhpna
421 dfygnfvfta iddsrrddga adyrghgtle gvyv
``` hypothetical protein COCVIDRAFT_107070 [Bipolaris victoriae FI3] GenBank: EUN24125.1

```
  1 msngfllvkd srttleyrvp iqrnsvlata fkdikapsss gnradkvgsg lrvhdpglln
 61 ttvvetgvty rdgerdlllf rgysleqlwq sdyedmlhlm vwakyptpvq keslrrllia
121 amlevpknvf eivsafpsss ppmpmivagl aaylgsnpam ipassggniy qgniektdka
181 iintiaayav ivgmaachrk gieftapsld ysfvenlfhm sgmvddltgr pdamkvscfr
241 rfaalnmdhg malavfstmv tassltdpvs cliaslaaay gplhfgatea ahlslrsigd
301 kskvpefise vkqgkrklfg yghrtykgtd prvrpikeli edsgansdpl ieiareierl
361 asnddyftsr glhpnadfyg nfvftavgfh sdfipiamis qrligimahw reamvrgikl
421 frpshiytgd tepvytasak l
``` citrate synthase [Aspergillus ruber CBS 135680] GenBank: EYE90286.1

```
  1 magmlnitds rtnaqhqisi rhnailasdl kkttglrvhd pglqnttvve tgitvshhdt
 61 glllfrgykl qdlwdinsdf edilhllvwg vypsseqrkt lsrqlataml evpdvvfqti
121 ralpkttspl pllmaglsas lscrpemipa stnphlyrdp kiadhaiiyt iatyavafgi
181 irchrqgitf tspsvdnsyl enlfimaglv dpstgrpdpv rlscyrhfgi fnsdhgmals
241 vfsalvtass qtdpisclit atgaaygplh fgatesakra llhigtidnv psfiegvkqg
301 kqklfgyghr sykgmdprvq pmrklvcdlk ldsasnpllk iaerieqvas edewfarrgl
361 ypnadfyghf vlsgcgfetd iipaamlaqr vvgimahwre ymltggklfr pshiytgeee
```

FIG. 9H

```
421 gklklhlgqq vkmseenent plllpysvft psqkrllilt aalassfspf saniyypsln
481 siardlhvss sqinltitty micqglapaf mgsladqagr rpayllcfii yiagnialal
541 qhsypallil ravqscgssg tvalasavaa dvitsaergm ymgiaslgni lapslgpilg
601 gprrpkitfp nplgtlrllf hrptgfvlla ngiiyasyys vtaglpaqfh elynlqdlgi
661 glsfipaglg slfsatvngm lvdwnyhrvk mkmglpvtrd qkqdhgdfpi eqtrlqiglp
721 mmvflsffat vsltlvflis lfitaaynvl nvlivdlyyt tpatamaann lvrcflgaaa
781 tavvhplssq wgigwtysan immlstlllp lvsalhghly mrypdsrwit pgdtlpiaet
841 kpipilqttl pctspylllt idpdvqygtt stivlhwlqs lradcqtgfl yenpkseeta
901 vyippqppkr shhryifllf qqpedynlpe cyqhilpatk earvgfnpke fvevlglggp
961 lagnwfyven ggdarnel
``` hypothetical protein COCHEDRAFT_1118493 [Bipolaris maydis C5] GenBank: EMD85580.1

```
  1 msngflfvrd srttqeyrvp iqrnailata fkdikapsss gnradkldsg lrvhdpglln
 61 ttvvetgvsf adgerdlllf rgysleqlwq sdyedmlhll vwakyptpvq keslrralia
121 amlevpktvf evvsafpsas ppmpmvvagl aaylgsnpdm ipasnggniy qgdiektdka
181 ivktiaayav vvgmaachrk gieftaplld ynfienlfhm sgmvddltgr pdamkvscfr
241 rfaalnmdhg malavfstmv tassltdpis clvaslaaay gplhfgatea ahlnlrsigd
301 kskvpefise vkqgkrklfg yghrtykgtd prvrpikeli edsgansdpl ieiareverl
361 asnddyftsr glhpnadfyg nfvftavgfq sdfipiamis qrligimahw reamgessdt
``` citrate synthase, putative [Talaromyces stipitatus ATCC 10500] NCBI Reference Sequence: XP_002482831.1

```
  1 msdgtlfved srsgkkyeip irhntvlatd lkrikassta anradkvadg lrlydpglen
 61 ttvvetsmty adadrgllmf rgyaleqlwe sefedmlhlm vwgkyptpsq saslrkdlas
121 lmgdipktvf eviekfprdc ppmpmlvagl aaylsddlds iptfnggnif hgnvektdea
181 ilktvaafas vvgiagshrr giaftppsld kgyldnlfkm mgivdpttnk pspekldcfr
241 rftiintdhg malsafahlv atsaladpis gligslvaay gplhfgapea ayktiksigg
301 pqnvpsflde vksgkrrlfg yghrtyrtvd prlapiksal qtlnvetdip letayeidrl
361 asnddyflkr glhanadfyt pycfikigfh peefpiamfa qriigimahw reamlrkvkl
421 frpthiytge tepvehikip skl
``` citrate synthase, putative [Talaromyces stipitatus ATCC 10500] NCBI Reference Sequence: XP_002485362.1

```
  1 msdgtlfiqd srtskqytis vtsdtitavd fqkitsptgk lalydpglqn tiikktqitg
 61 rdpvtgitlf rglsakeiwn rhadfedhfh llvfgkypsp eesealrrrl avqmtvvpet
121 vikavqafpr tshplpmiia glaafisadp sslpairggn iyhgnralcd egvirataay
181 avvmglinsh rkqlpyvpad pqksfyenvf ammrcpvhhn ylvtfregmv lnsdngmtqs
241 svvllstass lpdpisclis aitaaygplh ygaqeagstt lksigsldkv pefleqvkrr
301 errlfgfghr lhkredprla svkrwlkmmd ytpdqeplle laqeidrlas sdeyfikrnl
361 ranadfythf lfkawgfdwd mlcaanmfhr iiglmahwre amdqpikifr atdlyvgpvv
421 iqednrtvle epkiqsrl
``` conserved hypothetical protein [Aspergillus terreus NIH2624] NCBI Reference Sequence: XP_001216503.1

```
  1 magllnqpsa tpdgvkiscf rrfallnadh gmalsvfsal vtasslpdpl ssvlsavaaa
 61 ygplhfgate tahrtlreig spdnvpsfie evkngrrklf gyghraykgv dprvqpiqsi
121 lkdldmssng llkiaerieq tastddyflk rglypnadfy gnfvftgigf epdmipaaml
181 aqriigimah wreymlnrgk llrpshiytg dvkaaeissk l
```

Citrate synthase [Penicillium digitatum PHI26] GenBank: EKV06554.1

```
  1 mcskatsplp lilaglsahl aclpdvipat tnptiyqtdi kradqiilqt vagyavvfga
 61 vrshrlglpw rspslhqtyy enlftmaglv dpetnypdlr giscfrrfgn lnaehgmalt
121 afssivtass ltdpvsclis alaaahgplh fgatesaqra lrdigepknv pafieevkag
181 kqklfgyghr tykgmdprvr piqsilkdli hinqpllkva eaiedaaakd dyfvsrglyp
```

FIG. 9I

```
    241 nadfygnfvf tgm
``` citrate synthase [Colletotrichum graminicola M1.001] GenBank: EFQ27732.1

```
      1 mgvifyglkh lrpffsllgl vkrsmvmvnk aiqksprivh wvlgrhdids pcstltvldn
     61 rtkrryeipi rrnavsalef qkittahcgi esvgqvdfgl rvldpgyrnt acvesnitfv
    121 dgkrgyiqlr gypieylven hdyeevihli iwgrlpdave kkelqrriaa gcappehvvq
    181 vitsfprdsl tstmvmagma ayascdegav stlqsgcpay lgqpdkvdaa listisalat
    241 vvaltychkr gkrlapvdpe asftanvlgm mgfqegmsgk pdaemvqcfe klwilyadqe
    301 mlnslsaflh aastlvdpls cclsgivsgy gplhggaldl aykafqdvkl penvpallad
    361 vkakkqrlfg yghrvykvvd prakfirami nqyrdkvesn pllsvameid rvastdeyft
    421 srslkanadl ygcflytafg fepdiivama slsripgvla hwreamlekg pllwrpqqvf
    481 tgaladeyyc atr
``` citrate synthase [Auricularia delicata TFB-10046 SS5] NCBI Reference Sequence: XP_007347043.1

```
      1 mgrwalnkag atslgessgs ltvidnrtqr tyeveikhna ikatdlrrit aagvaadpvd
     61 qvesglrvld kgylnlacme ssvtllidgkr gyiqyrdksi delvrnndye evahlliwgr
    121 lpsleektrl rrglaaamvp pqsvidviqa fprdsltfpm llaglsafaa vdkgtqqvhe
    181 sgrpvylgnt pavdaaivrs laalattval vhchkrgiaf tpadpegtli gnlllmmgfk
    241 kdgrpdpkie kcleklwily adhemtnsta sflhaastlt dpiscliagv vsgygplhgg
    301 aldlaykgfe evgtpervpe liadvkakkq rlfgyghrvy ktvdprlryi rdmmddhwae
    361 msanpllrva leidrvagqd pyftsrnlkv nadlygcfly tafgfdtdii tavaavsria
    421 gvlahwream hqqpmlwrpm qvftgsmaqa
``` citrate synthase [Aspergillus oryzae RIB40] NCBI Reference Sequence: XP_001827205.1

```
      1 mtvtqeaspk reslhliddr tgsyysipiv nnainasdfk kvtapedkay panqtenglr
     61 vydpgysnta vshskityid glkgtiqyrg ysindivgrk tfidtahlli wghwpstaea
    121 etlqqrldqv pvpqdfvfnv iksfprdgsl mgmviaglsa lqssdmnaip ahvgktiyln
    181 npeladqqil rvmanmsmlt aaaychhigr dftppragls yienfllmtg hveaatglpn
    241 pryvnaieri wvliadhemt cstaallqta salpdvlscm vsalsalygp lhggaievay
    301 kniesigsis nvpakiarvk agkerlygyg hrvyrvtdpr fvfireilne lseevekdpl
    361 lkvafevdrv asedeyftsr nlrpnadlfa afvykalgfp pefllplsil srtqgfmahw
    421 reamgnppri wrpgqiytgd lnksmde
``` citrate synthase [Aspergillus oryzae 3.042] GenBank: EIT75413.1

```
      1 mtvtqeaspk reslhliddr tgsyysipiv nnainasdfk kvtapedkay panqtenglr
     61 vydpgysnta vshskityid glkgtiqyrg ysindivgrk tfidtahlli wghwpsaaea
    121 etlqqrldqv pvpqdfvfnv iksfprdgsl mgmviaglsa lqssdmnaip ahvgktiyln
    181 npeladqqil rvmanmsmlt aaaychhigr dftppragls yienfllmtg hveaatglpn
    241 pryvnaieri wvliadhemt cstaallqta salpdvlscm vsalsalygp lhggaievay
    301 kniesigsis nvpakiarvk agkerlygyg hrvyrvtdpr fvfireilne lseevekdpl
    361 lkvafevdrv asedeyftsr nlrpnadlfa afvykalgfp pefllplsil srtqgfmahw
    421 reamgnppri wrpgqiytgd lnksmde
``` citrate synthase [Aspergillus kawachii IFO 4308] GenBank: GAA88109.1

```
      1 mpdiapnvar ngsaknaenk petpvlhvvd srtgnyfpip ivrnainase fkklkspedp
     61 ahpedqneqg irvfdpgysn tavsesqvty idglkgtiqy rgyniedivg kkkfidtahl
    121 liwgewptpe qarslqekls svpildesvf kviqafppns siigmmiaal savqssqndr
    181 ipahaaknly lgnpqavdde ivrlmgslsm itaavychht greftpprle lsyienfllm
    241 mghvesstgl pnpqyvdrie rlwvliadhe mtcstaaflq lasslpdvfs cmisalsaly
    301 gplhggaiev ayknfeeigs venvaakier vkagkerlyg yghriyrvtd prfifirqil
    361 delkeeiarn pllkvafevd rvasedeyfv trklrpnadl faalvysamg fptefilpls
    421 llsrtqgfma hwkeamssta riwrpgqiyt ghlsrema
```

FIG. 9J uncharacterized protein LOC100274406 [Zea mays] NCBI Reference Sequence: NP_001142237.1

```
  1 mpdiapnvar ngsskhaetk petpvlhvvd srtgnyfpip ivrnainase fkklkspedp
 61 ahpedqneqg irvfdpgysn tavsesqvty idglkgtiqy rgyniedivg kkkfidtahl
121 liwgewptpe qakslqekls svpildesvf kviqafppns siigmmiaal savqssqmdr
181 ipahaaknly lgnpqavdde ivrlmgslsm itaavychht greftpprpe lsyienfllm
241 mghvesstgl pnpqyvdrie rlwvliadhe mtcstaaflq tasslpdvfs cmisalsaly
301 gplhggaiev ayknfeeigs venvaakier vkagkerlyg yghriyrvtd prfifirqil
361 delkeeiarn pllkvafevd rvasedeyfv trklrpnadl faalvysamg fptefilpls
421 llsrtqgfma hwkeamssta riwrpgqiyt ghlnrema
``` citrate synthase [Aspergillus niger CBS 513.88] NCBI Reference Sequence: XP_001393195.2

```
  1 mpdiasngar ngasqnaetk peppvlhvvd srtgkyfpip ivrnainase fkklkspedp
 61 ahpedqneqg irvfdpgysn tavsesqvty idglkgtiqy rgyniedivg kkkfidtahl
121 liwgewptpe qakslqekls svpvldesvf kviqafppns siigmmiaal savqstqmdr
181 ipahaaknly lgnpkavdde ivrlmgslsm itaavychht greftpprpe lsyienfllm
241 mghvesstgl pnpqyvdrie rlwvliadhe mtcstaaflq tasslpdvfs cmisalsaly
301 gplhggaiev ayknfeeigs venvaakier vkagkerlyg yghriyrvtd prfifirqil
361 delkeeiarn pllkvafevd rvasedeyfv trklrpnadl faalvysamg fptefilpls
421 llsrtqgfma hwkeamssta riwrpgqiyt ghlnrema
``` unnamed protein product [Aspergillus niger] GenBank: CAK45764.1

```
  1 mpdiasngar ngasqnaetk peppvlhvvd srtgkyfpip ivrnainase fkklkspedp
 61 ahpedqneqg irvfdpgysn tavsesqvty idglkgtiqy rgyniedivg kkkfidtahl
121 liwgewptpe qakslqekls svpvldesvf kviqafppns siigmmiaal savqstqmdr
181 ipahaaknly lgnpkavdde ivrlmgslsm itaavychht greftpprpe lsyienfllm
241 mghvesstgl pnpqyvdrie rlwvliadhe mtcstaaflq tasslpdvfs cmisalsaly
301 gplhggaiev ayknfeeigs venvaakier vkagkerlyg yghriyrvtd prfifirqil
361 delkeeiarn pllkvafevd rvasedeyfv trklrpnadl faalvysamg fptefilpls
421 llsrtqgfma hwkeamssta riwrpgqiyt ghlnremais kartkthasr qttwarrrnv
481 sglrlmkian rmang
``` citrate synthase [Aspergillus niger ATCC 1015] GenBank: EHA18674.1

```
  1 mpdiasngar ngasqnaetk peppvlhvvd srtgkyfpip ivrnainase fkklkspedp
 61 ahpedqneqg irvfdpgysn tavsesqvty idglkgtiqy rgyniedivg kkkfidtahl
121 liwgewptpe qakslqekls svpvldesvf kviqafppns siigmmiaal savqstqmdr
181 ipahaaknly lgnpkavdde ivrlmgslsm itaavychht greftpprpe lsyienfllm
241 mghvesstgl pnpqyvdrie rlwvliadhe mtcstaaflq tasslpdvfs cmisalsaly
301 gplhggaiev ayknfeeigs venvaakier vkagkerlyg yghriyrvtd prfifirqil
361 delkeeiarn pllkvafevd rvasedeyfv trklrpnadl faalvysamg fptefilpls
421 llsrtqgfla hwkeamssta riwrpgqiyt ghlnrema
``` citrate synthase, putative [Talaromyces marneffei ATCC 18224] NCBI Reference Sequence: XP_002148678.1

```
  1 mspaaiissd daaksvdaka saktisrnfl hvidertgqy yqipihhnai sanefkkika
 61 pdseyyadqn engirvfdpg ftntavvesk vtyvdgkrgk iqyrgydlad vvannkkfid
121 tahlmvfgfw ptaeegagfq qklfdamhie qcvidtihaf prtasttlml taglaavqat
181 qmdripahma knlylgnptl vdeqivrlmg vlpivsavay chhtgrefks prsdltyien
241 flymcghvqe etglpnpryv qnferlwslv adhemtcsta avlltasslp dpisciisgi
301 gasygplhgg aiefaykdma digsvdncqt kidrvksgke rlfgyghrvy kvtdprsehi
361 qavletlkee idndpllkva felnriaqed eyfvsrglkp nadlfaafty gamgfppdfi
421 ltistisrtq glmahwkeam sgkpliwrpt qvytgkldlk mev
``` citrate synthase, putative [Aspergillus flavus NRRL3357] NCBI Reference Sequence: XP_002384448.1

FIG. 9K

```
  1 mtvtqeaspk reslhiiddr tgsyysipiv nnainasdfk kvtapedkay panqtenglr
 61 vydpgysnta vshskityid glkgtiqyrg ysindivgrk tfidtahlli wghwpstaea
121 etlqqrldqv pvpqdfvfnv iksfprdgsl mgmviaglsa lqssdmnaip ahvgktiyln
181 npeladqqii rvmanmsmlt aaaychhigr dftppragls yienflllmtg hveaatglpn
241 pryvnaierl wvliadhemt cstaallqta salpdviscm vsaisalygp lhggaievay
301 kniesigsis nvpakiarvk agkerlygyg hrvyrvtdpr fvfireilne lseevekdpl
361 lkvafevdrv asedeyftsr nlrpnadlfa afvykalgfp pefilplsil srtqgfmahw
421 reamgmpest lnssrsicpd tnignppriw rpgqiytgdl nksmde
``` putative citrate synthase protein [Eutypa lata UCREL1] GenBank: EMR66249.1

```
  1 mggswtqmls ptflvhmvak llgqtqmgea dgsltitdnr tgrqytipin rntvkatdfr
 61 ritaaglgad paemvesglk vfdrgylnta cmesnitfid gkrgyiqyrd ysidhlfrnn
121 dfeevahlvm fgklpspsek mtfrralakg meapqnvinv irafpkdslt fpmilaglsa
181 yagvdpgtek thhegrayyl gnmkevdaai irtlsalatv iaitychkrg reftpadpng
241 sfvantllmm gftkdgkadp eveacferlw ilyadhemtn staavlhaas tltdpisslv
301 sgivsaygpl hggaidlayk gfeevgtvdn vsqlitdvkg kkqrlfgygh riyktvdprs
361 kfiremiaek qelvdsnpll riafeidria nedpyftsrn lkanadlygc flytalgfet
421 diiiamacls rtpgamahwr esmqqgpmlw rplqvftgnv tapsars
``` putative citrate synthase protein [Eutypa lata UCREL1] GenBank: EMR70107.1

```
  1 mataaptatk staannpmts sqseinvave krdvlhavdg rtglyysipi nknavnagdf
 61 kkikspadrk hpayqnelgl riydpgfsnt tvseskityi dgiegtiqyr gysihdifgk
121 kgwidvshll iwgnwpssae akeyqerlng vplldqhvld vihsfpkdgv itgmmiagls
181 alqscnldav payvgdnlyv ghpdrvdkqi ihllqsfami taacychsts reftqprqdf
241 syvenfllmv ghvdattglp sprhvdaler lwgvvadhem tcstaaflht asslpdiisc
301 fitaicaatg plhggaisva hkhikaigtv anvpakierv ksgkellygy ghrvyrttdp
361 rytyinqvld glteevardp llqvalaldk aasedeyfts rklfpnadlf aafayqalgf
421 ppdfvlpmsc lsrlqgfaah wkeglqgkpk iwrpgqiytg dlektmg
``` putative citrate synthase protein [Neofusicoccum parvum UCRNP2] GenBank: EOD45286.1

```
  1 matttitapa ngrvskdslt vtdnrtgstf tfpithnavn asnfkqikap edpdniadqn
 61 eqglrvfdpg fgntcvsesk itfidglkgi iqyrgydigd lieakkgfvd tahllwfgtl
121 pspkekqelq drlnavplid dhvfntirsf pkngspfgmi iaglmalqss emdlipahaa
181 kniylgnlsl vdsqlirvmq slsqicavay chqtgrtftp pradltfien fllmmghtea
241 atglpnpayv akferlwlli adhemtcsta amlqtasamp dalsclasat salygplhgg
301 aievayknia eigsvdnipp kiarvkagke rlygyghrvy rvpdpryrhi kevledltae
361 ieddpllkva feldrvartd eyftsrklnp nadlfaalay namgfepewi lpislmsrsq
421 gllahwkeam sgsariwrpg qiytgdlnkk ie
``` unnamed protein product [Aspergillus niger] GenBank: CAK37177.1

```
  1 maytlaswlg rlfdagksll plqgnyinal leqelpgere gtltvrdnrt gskytipivr
 61 nsvpamgfrq icvdragksp rqqfedglrl idpgyrntav kmssitying negvilyrgh
121 plasligksy eeithlliwg slptpeqrlr fqrriaeamm vvpenvkqlv atfprntppm
181 vilcavltgy ladqpelipa haganlynrr pemvdeqiir tlavtaiags iahchmkgee
241 lrmadpnlsy ienilwmgry vdnnpavtre kaaeiltkaw slyadhemtn stsaflhvss
301 sladplsama accmsgygll hggaidaayr gmreiggpqn vpkliekvin kecrlsgygh
361 riykqvdpra kyvremldel trdrdiremd pvlqvameid riastheyfv krnlqanadl
421 ygsfvytalg idsqfatvla atarvsgvma hwkeqterap dlwrplqvyv pn
``` citrate synthase [Aspergillus kawachii IFO 4308] GenBank: GAA82055.1

```
  1 maytlaswlg rlfdagksll plqgnyinal leqelpgere gtltvrdnrt gskytipivr
 61 nsvpamgfrq icvdragksp rqqfedglrl idpgyrntav kmssitying negvilyrgh
```

FIG. 9L

```
121 plasligksy eeithlliwg slptpeerlr fqrriaeamm vvpenvkqlv atfprntppm
181 vilcavltgy ladqpelipa haganlynrr pemvdeqiir tlavtaiags iahchmkgee
241 lraadpnlsy ienilwmgry vdnnaaitre kaaeiltkaw slyadhemtn stsaflhvss
301 sladplsama accmsgygll hggaidaayr gmreiggpen vpkliekvin kecrlsgygh
361 riykqvdpra kyvremldel trdrdiremd pvlqvameid riastheyfv krnlqanadl
421 ygsfvytalg idsqfatvla atarvsgvma hwkeqterap dlwrplqvyv pn
``` hypothetical protein ASPNIDRAFT_126525 [Aspergillus niger ATCC 1015] GenBank: EHA28368.1

```
  1 mphmdglshk lteamlavpd dvqrtvwthp icqenfersw ksgnipgysq rvkqgrvkvf
 61 eyghrsykgi nprvppiqsi lknldlsadn plklaerler vcptdayfke qglyvndadt
121 sngfypkiis mamlaqrimg imthwreymc kq
```

ORGANIC ACID PATHWAY

CROSS-REFERENCE TO RELATED APPLICATIONS

This application is the national phase of PCT application PCT/NL2014/050284 having an international filing date of 2 May 2014, which claims benefit of European patent application No. 13166305.6 filed 2 May 2013. The contents of the above patent applications are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 313632019900_SeqList.txt, date recorded: Oct. 30, 2015, size: 284,842 KB).

The invention relates to the field of microbial production, more specifically production of organic acids, such as citric acid and its derivatives, such as oxaloacetic acid, itaconic acid (itaconate) and metacrylic acid, more specifically the production thereof in micro-organisms.

One of the most fundamental and ubiquitous metabolic pathways in living organisms is the citric acid cycle, or Krebs cycle, named after the discoverer. In eukaryotes this process takes place in the mitochondrion and is fed mainly by pyruvate and acetyl-CoA that are transported from the cytoplasm into the mitochondrion. Some of the constituents of the Krebs cycle or derivatives thereof may be transported back to the cytoplasm by active transport mechanisms, in general by tricarboxylic acid transporters. This basically means that cytoplasmatic metabolic routes that are dependent on, or starting from organic acids such as citric acid (citrate), malic acid (malate) oxaloacetic acid (oxaloacetate) heavily depend, and in general are limited by the activity within the Krebs cycle and the availability of the tricarboxylic acid transporters.

Hitherto no specific metabolic route for the production of extramitochondrial citric acid was elucidated. Yet, the availability of citric acid in the cytoplasm is extremely useful for the production of this acid itself and, even more importantly, for the production of derivatives and metabolites of citric acid. Citric acid is the starting point for many metabolic routes. One important metabolic route is the production of itaconic acid.

Production and metabolism of itaconic acid in microbial cells has been studied extensively for several decades (Calam, C. T. et al., 1939, Thom. J. Biochem., 33:1488-1495; Bentley, R. and Thiessen, C. P., 1956, J. Biol. Chem. 226:673-720; Cooper, R. A. and Kornberg, H. L., 1964, Biochem. J., 91:82-91; Bonnarme, P. et al., 1995, J. Bacteriol. 117:3573-3578; Dwiarti, L. et al., 2002, J. Biosci. Bioeng. 1:29-33), but the metabolic pathway for itaconic acid has not been unequivocally established (Wilke, Th. and Vorlop, K.-D., 2001, Appl. Microbiol. Biotechnol. 56:289-295; Bonnarme, P. et al., 1995, J. Bacteriol. 177:3573-3578). Two complicating factors in this respect are that the biosynthesis route for itaconic acid is thought to occur both in the cytosol and the mitochondria (Jaklitsch, W. M. et al., 1991, J. Gen. Microbiol. Appl. 6:51-61) and that aconitase, the enzyme that interconverts citric acid into cis-aconitate, and vice versa, and other enzymes in the metabolic pathway have been found to be present in many isoforms in microbial cells.

Figure 1:
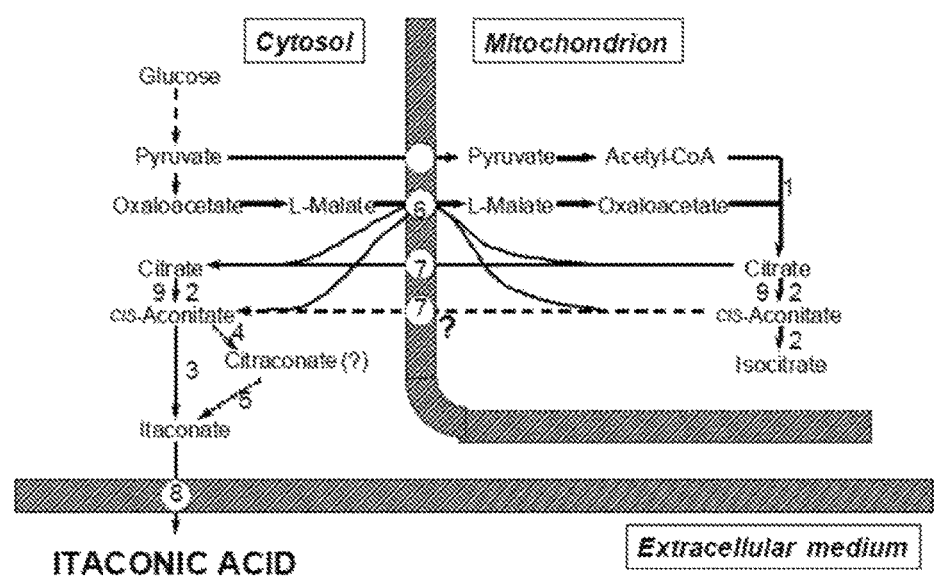

The general scheme currently envisioned for itaconic acid biosynthesis is given in FIG. 1, wherein clearly the existence of the biosynthetic route both in the cytosol and the mitochondria is depicted and the putative connection between these two compartments. At several point of this scheme possibilities exist to try to improve the existing commercial production of itaconic acid in micro-organisms.

The production of itaconic acid from citrate has been achieved in *Aspergillus* (and also other micro-organisms) with technology as described in WO 2009/014437, WO 2009/104958 and WO 2009/110796.

However, next to itaconate, citrate can also be used as a starting point for the production of malate, succinate, glutamate and metacrylic acid.

Further, citric acid can also lead to a metabolic route for lysine and from there to penicillin and similar compounds. Alternatively, citric acid can lead to the synthesis of fatty acids and thus be a source for biodiesel production. Moreover metabolites of citric acid, in particular acetyl-CoA, form the basis of biosynthetic routes towards fatty acids, polyketides and the mevalonate pathway towards terpenoids and other compounds Yet, however, there is still need for an enzyme capable of production or overproduction of citric acid.

SUMMARY OF THE INVENTION

The present inventors now have elucidated a gene coding for an enzyme that is able to catalyze the reaction from oxaloacetate to citric acid, a so-called citrate synthase enzyme, which is present and functional outside the mitochondrion (and probably in the cytoplasm) of eukaryotic organisms.

The invention therefore comprises the use of a protein having cytosolic citric acid synthase activity for the heterologous production of citrate in the cytosol of a micro-organism or algae, preferably wherein said micro-organism is a fungus or a yeast or a plant or algal cell, more preferably when said micro-organism is selected from the group of *Aspergillus* spp., more particularly, *A. niger, A. nidulans, A. terreus, A. clavatus, A. oryzae* or *A. flavus, Neurospora* spp., more particularly *N. crassa* or *N. tetrasperma, Sclerotina, Gibberella, Coniothyrium, Psiticum, Magnaporthe, Podospora, Chaetomium, Phaeosphaeria, Botryotinia, Neosartorya, Pyrenophora, Panicum, Aureococcus, Penicillium, Trichoderma, Sordaria, Colleotrichum, Verticillium, Arthrobotrys, Nectria, Leptosphaeria, Fusarium, Glomerella, Geomyces, Myceliophthora, Pichia, Saccharomyces* spp., such as *S. pastorianus, S. cerevisiae, S. boulardii, S. carlsbergensis, S. kudriavzevii,* and *S. paradoxus, Zygosaccharomyces, Schizosaccharomyces pombe, Kluyveromyces* spp., *Yarrowia lipolytica, Monascus* spp. (such as *M. rubber, M. purpureus, M. pilosus, M. vitreus* and *M. pubigerus*), *Penicillium* spp. (such as *P. citrinum, P. chrysogenum*), *Hansenula* spp., *Torulaspora delbrueckii, Hypomyces* spp., *Dotatomyces* spp. (such as *D. stemonitis*), *Issatchenko orientalis, Phoma* spp., *Eupenicillium* spp., *Gymnoascus* spp., *Pichia labacensis, Pichia anomala, Wickerhamomyces anomalus, Candida cariosilognicola, Paecilomyces virioti, Scopulariopsis brevicaulis, Brettanomyces* spp., such as *B. bruxellensis, B. anomalus, B. custersianus, B. naardenensis* and *Brettanomyces nanus, Dekkera bruxellensis, Dekkera anoma* and *Trichoderma* spp. (such as *T. viride*).

Preferably in said use the protein is derived from *A. niger*. It is also preferred when the protein is *A. niger* An08g10920 or an ortholog thereof, more particularly, wherein such an ortholog is chosen from the group of CAK45764.1/

An08g10920, XP001393195.2/ANI1_1474074, EHA18674.1/Aspni5_176409, NP_001142237.1, GAA88109.1/AKAW_06223, EIT75413.1/Ao3042_08560, XP_001827205.1/AOR_1_298024, AO090010000170, XP_002384448.1/AFLA_117410, AFL2G_11427, XP_002148678.1/PMAA_091390, Aspfo1_0085419, Acar5010_212258, Acar5010_171837, Aspbr1_0068777, Asptu1_0164827, and proteins having a percentage identity of 70%, more preferably 75%, more preferably 80%, more preferably 85%, more preferably 90%, more preferably 95%, more preferably 98%, more preferably 99% with An08g10920.

Further part of the invention is a vector for transforming a micro-organism comprising a nucleic acid sequence coding for a protein as defined above. Also part of the invention is a transgenic organism transformed with such a vector or comprising a heterologous citric acid synthase as defined above.

The invention also comprises a method for the production of citric acid comprising overexpression of a gene coding for a citric acid synthase as defined above.

In a further preferred embodiment, the invention comprises a method for the production of itaconic acid comprising overexpression of a gene coding for a citric acid synthase as defined above and overexpression of a gene coding for the enzyme cis-aconitic acid decarboxylase (CAD) in a suitable host cell.

In an also preferred embodiment of the present invention, the invention also comprises a method for the production of a derivative of citric acid comprising overexpression of a gene coding for a citric acid synthase as defined in any of claim 1, 2 or 3 and overexpression of one or more genes that encode enzymes that are capable of converting citric acid into said derivative of citric acid in a suitable host cell. Preferably in such a method said one or more genes are selected from the group comprising An08g10860 (fatty acid synthase subunit beta), An08g10870 (2-methylcitrate dehydratase, prpD)( ); An08g10880 (GAL4; GAL4-like Zn2Cys6 binuclear), An08g10930 (3-oxoacyl-[acyl-carrier-protein] synthase); An08g10970 (MFS multidrug transporter); An08g10980 (transcription factor acetate regulatory DNA binding protein facB), An01g09950, An09g06220, An15g01780, An02g14730 (cytosolic prpD family), An05g02230 and An08g10530 (cytosolic aconitases) An02g12430, (non-mitochondrial isocitrate dehydrogenase) An04g06210 (homocitrate synthase), An11g00510 and An11g00530 (citrate lyase). Further preferred in such a method said suitable host cell is a micro-organism or algae, more preferably a fungus or a yeast or a plant or algal cell, preferably selected from the group of Aspergillus spp., more particularly, A. niger, A. nidulans, A. terreus, A. clavatus, A. oryzae or A. flavus, Neurospora spp., more particularly N. crassa or N. tetrasperma, Sclerotina, Gibberella, Coniothyrium, Psiticum, Magnaporthe, Podospora, Chaetomium, Phaeosphaeria, Botryotinia, Neosartorya, Pyrenophora, Panicum, Aureococcus, Penicillium, Trichoderma, Sordaria, Colleotrichum, Verticillium, Arthrobotrys, Nectria, Leptosphaeria, Fusarium, Glomerella, Geomyces, Myceliophthora, Pichia, Saccharomyces spp., such as S. pastorianus, S. cerevisiae, S. boulardii, S. carlsbergensis, S. kudriavzevii, and S. paradoxus, Zygosaccharomyces, Schizosaccharomyces pombe, Kluyveromyces spp., Yarrowia lipolytica, Monascus spp. (such as M. rubber, M. purpureus, M. pilosus, M. vitreus and M. pubigerus), Penicillium spp. (such as P. citrinum, P. chrysogenum), Hansenula spp., Torulaspora delbrueckii, Hypomyces spp., Dotatomyces spp. (such as D. stemonitis), Issatchenko orientalis, Phoma spp., Eupenicillium spp., Gymnoascus spp., Pichia labacensis, Pichia anomala, Wickerhamomyces anomalus, Candida cariosilognicola, Paecilomyces virioti, Scopulariopsis brevicaulis, Brettanomyces spp., such as B. bruxellensis, B. anomalus, B. custersianus, B. naardenensis and Brettanomyces nanus, Dekkera bruxellensis, Dekkera anoma and Trichoderma spp. (such as T. viride), most preferably wherein said micro-organism is chosen from the group consisting of Aspergillus niger, A. acidus, A. tubigensis, A. oryzae, A. kawachii, A. flavus, A. acidus, A. carbonarius, A. brasiliensis, S. cerevisiae, Talaromyces marneffei, Zea mays, Pichia anomala and Dekkera bruxellensis.

The invention also comprises a method for the production of a derivative of citric acid, preferably wherein said derivative is itaconic acid comprising overexpression of a gene coding for a citric acid synthase as defined in any of claims 1, 2 or 3 and a gene encoding for protein that is involved in the production or transport of itaconate or any precursor thereof, preferably wherein the gene is selected from the group of cis-aconitic acid decarboxylase (CAD), ATEG_09969.1, ATEG_09970.1 and ATEG_09972.1.

In a further preferred embodiment the invention comprises a method as defined above, wherein said host cell is cultured under anaerobic conditions. Alternatively or additionally, the invention comprises a method as defined above, wherein said host cell is cultured under anaerobic conditions in the presence of nitrate as N-source.

LEGENDS TO THE FIGURES

FIG. 1: Postulated biosynthesis route(s) for itaconic acid in *A. terreus*. 1, Citrate synthase; 2, Aconitase; 3, cis-aconitic acid decarboxylase (itaconate-forming); 4, cis-aconitic acid decarboxylase (citraconate-forming); 5, citraconate isomerase; 6, mitochondrial dicarboxylate-tricarboxylate antiporter; 7, mitochondrial tricarboxylate transporter; 8, dicarboxylate transporter; 9, 2-methylcitrate dehydratase.

FIG. 2. Schematic projection of the lysine biosynthetic pathway.

Figure 3:
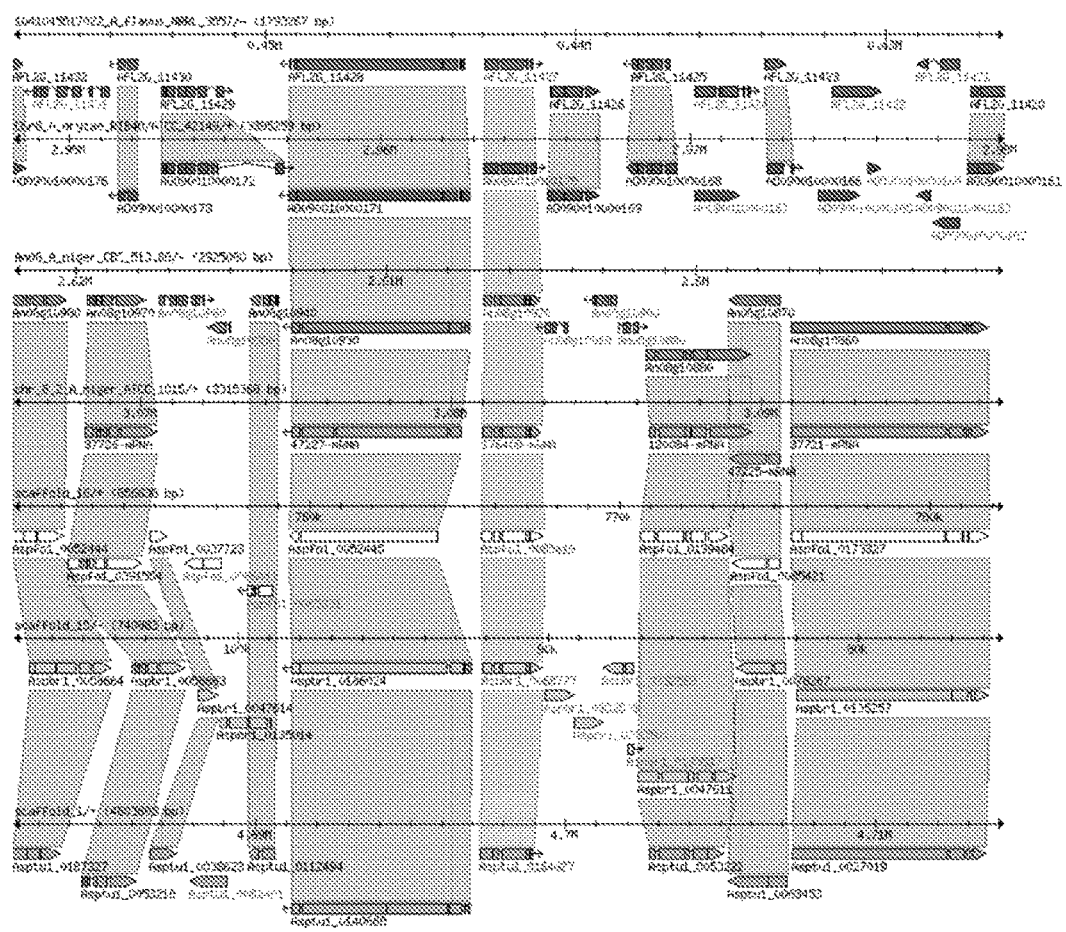

FIG. 3: CitB cluster analysis of five *Aspergillus* species (citB gene indicated in the fifth column from the left and as identified as AFL2G_11427, AO090010000170, An08g10920, 176409-mRNA, Aspfo1_0085419, Aspbr1_10068777 and Asptu1_0164827). From top to bottom *A. flavus* NRRL 3357, *A. oryzae* RIB40/ATCC 42149, *A. niger* CBS 51388, *A. niger* ATCC 1015, *A. acidus*, *A. carbonarius* ITEM 5010. The "black *Aspergilli*", *A. niger*, *A. acidus* and *A. carbonarius*, show similar clustering of the genes surrounding the citB gene, whereas the genomic region in *A. oryzae* and *A. flavus* only contains the citB (An08g10920) ortholog and the orthologs of An08g10880 and An08g10930. For *A. terreus* (not depicted) no corresponding gene cluster was found at all.

Figure 4:
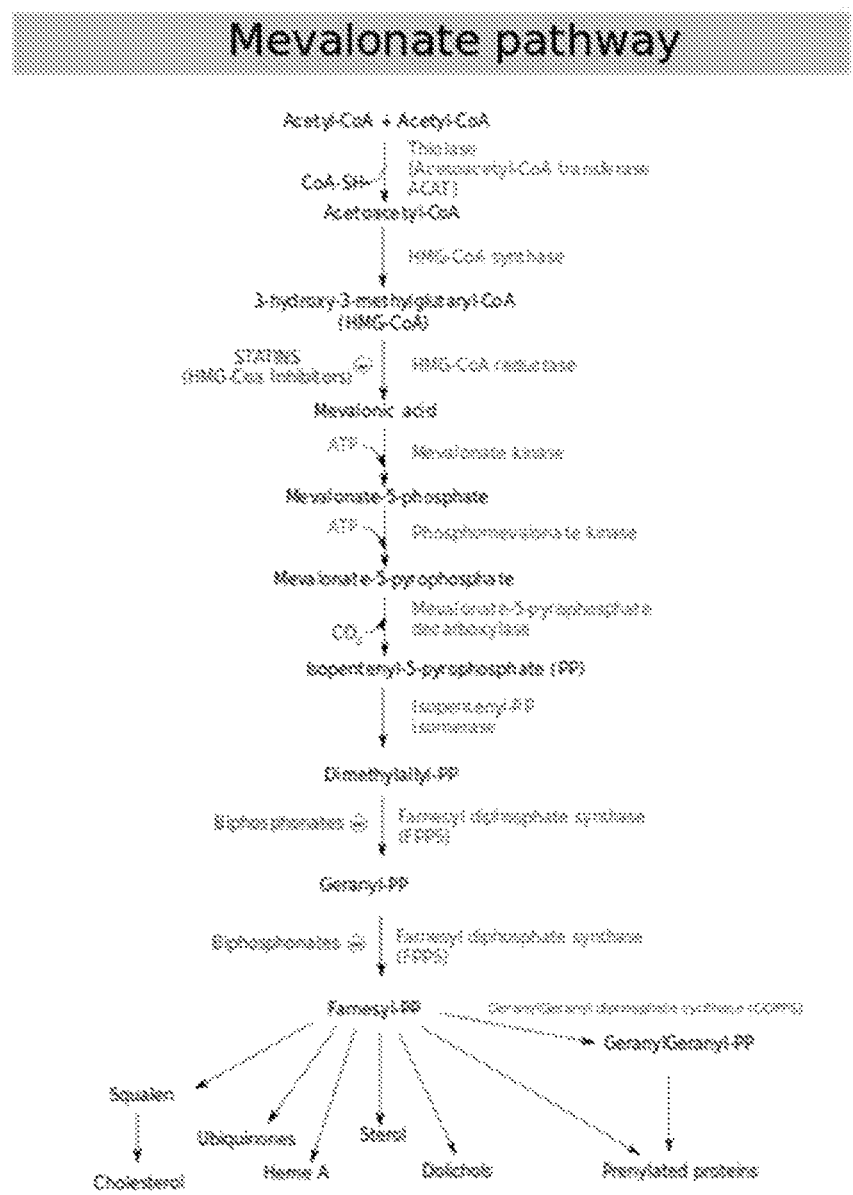

FIG. 4 Mevalonate pathway.

FIG. 5A-B. Nucleotide sequence of the *Aspergillus* expression vector pABgpd-I.

Figure 6:
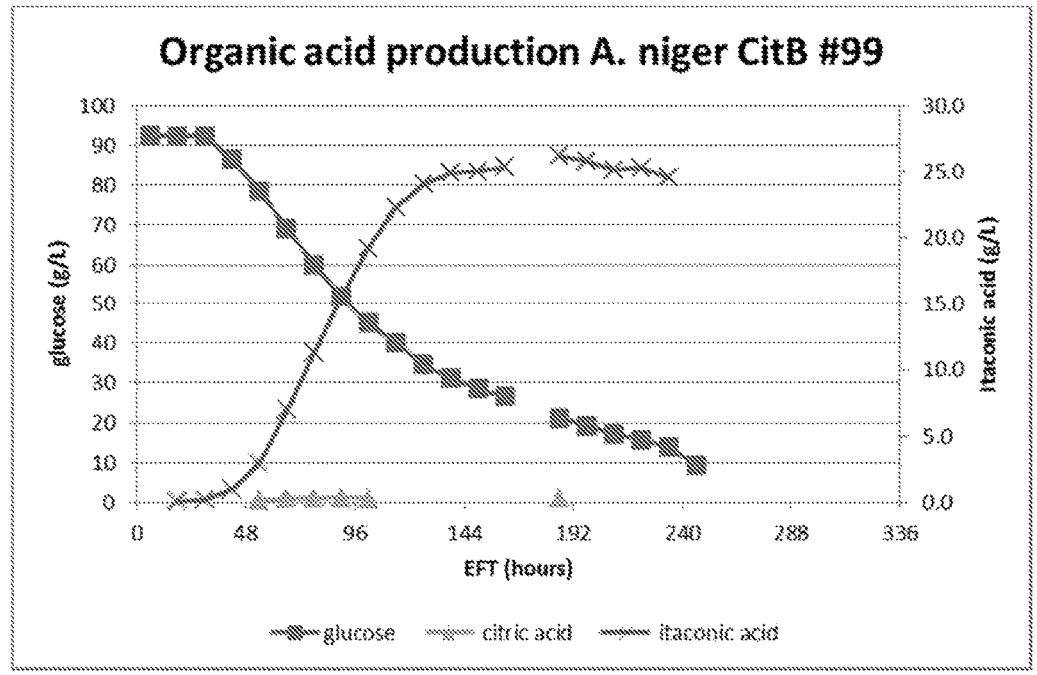

FIG. 6. Glucose consumption and organic acid production of *A. niger* CitB #99.

Figure 7:
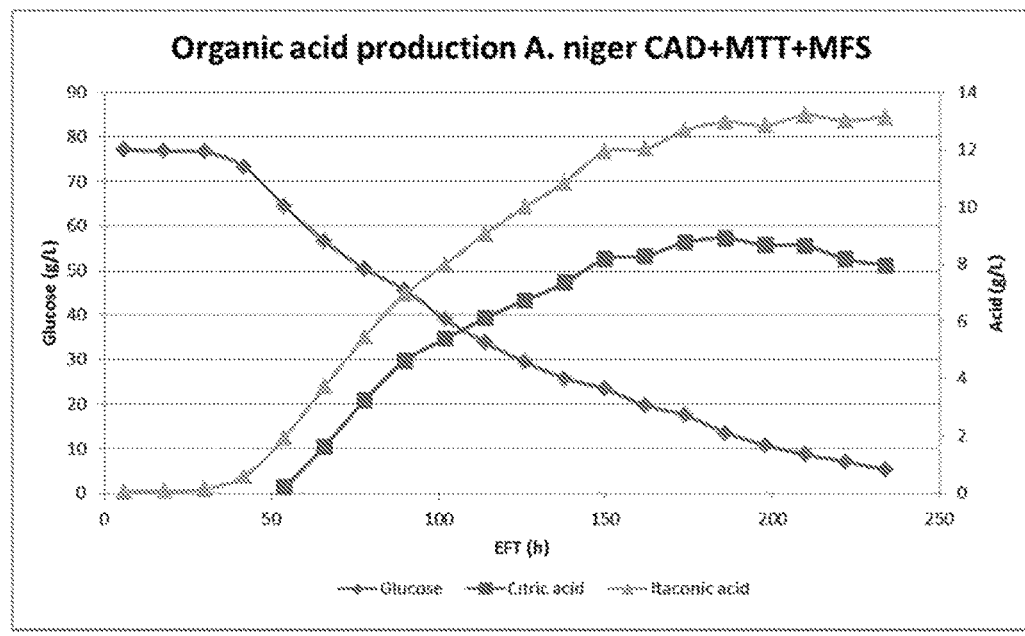

FIG. 7. Glucose consumption and organic acid production of *A. niger* CAD+MTT+MFS.

Figure 8:
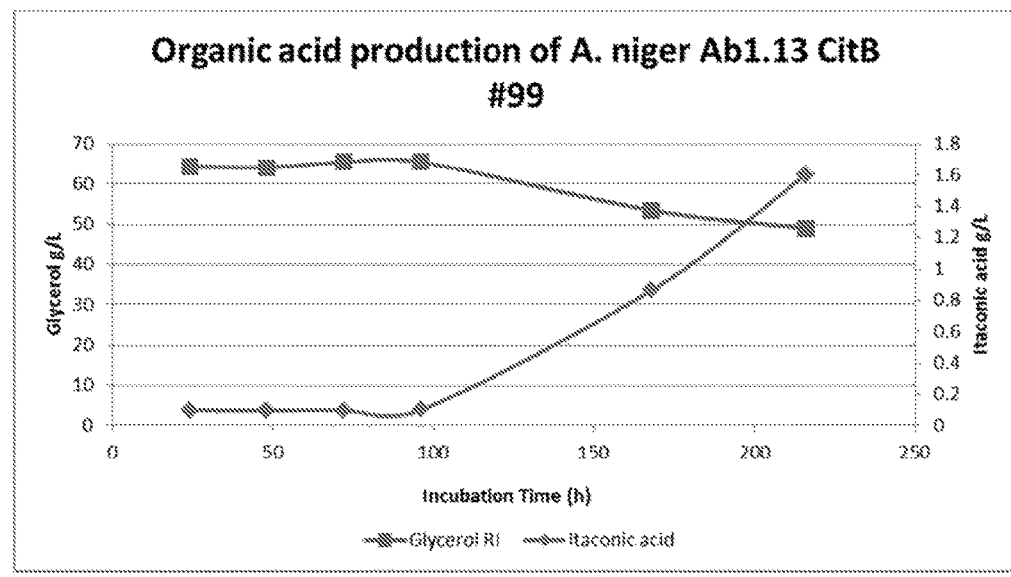

FIG. 8. Growth and itaconic acid production of *A. niger* AB1.13 CitB #99 on glycerol.

FIG. 9A-L. Amino acid sequences of orthologous citB citrate synthase like proteins.

Figure 10:
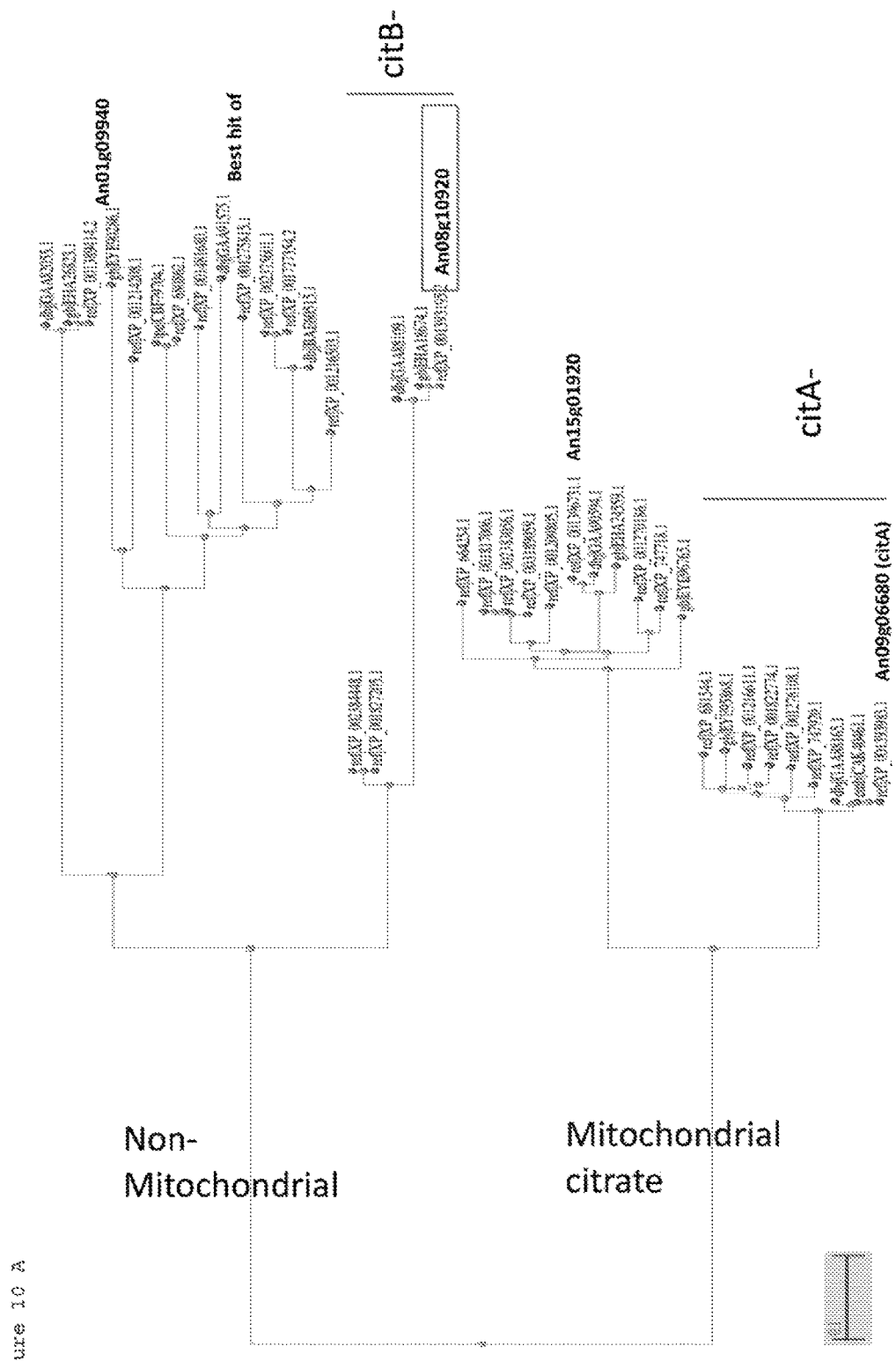
Figure 10:
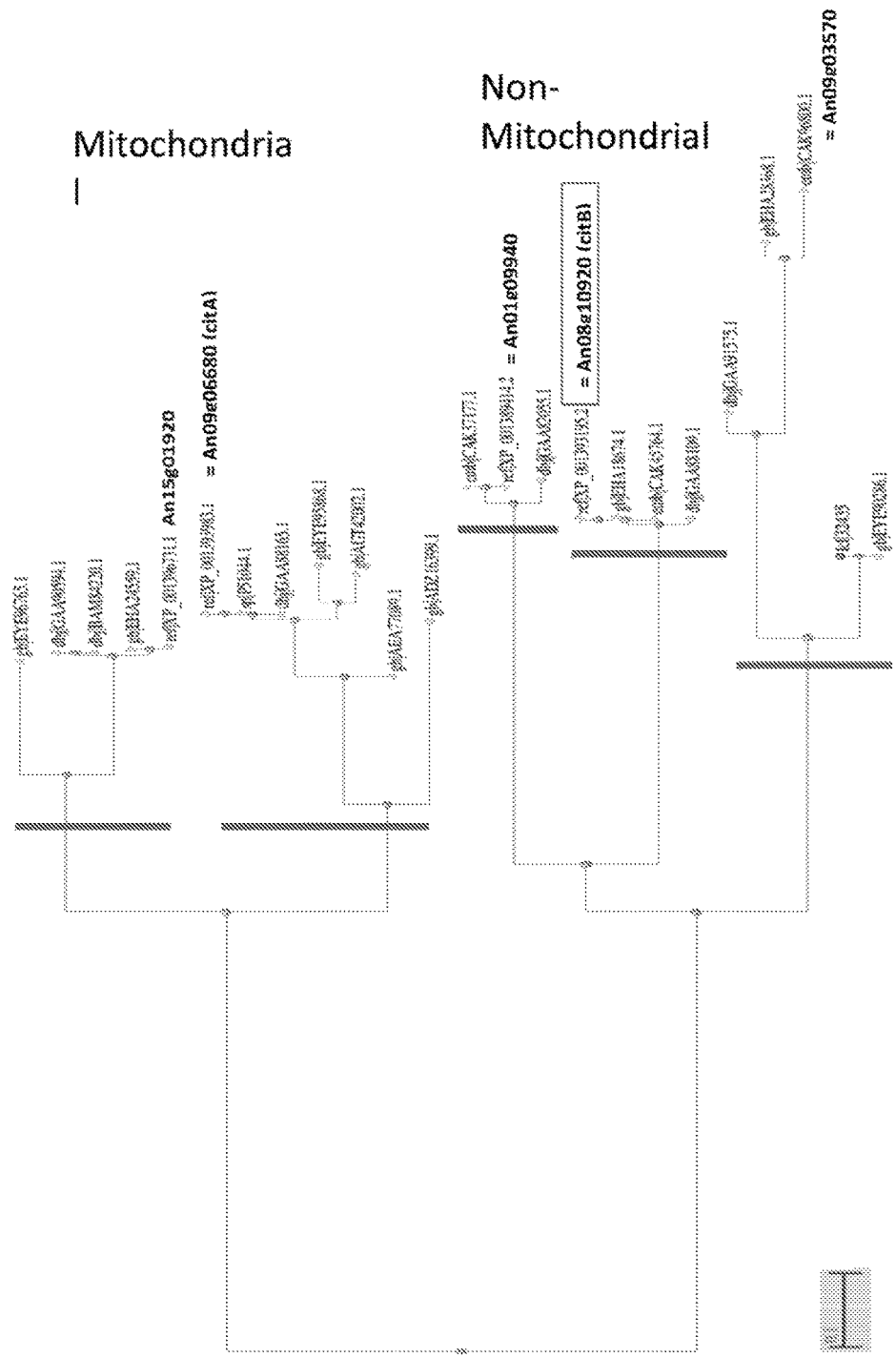

FIG. 10. A. Homology tree of *Aspergillus* citrate synthase like proteins; B. Homology tree of *Aspergillus niger, A. kawachii, A. ruber* citrate synthase like proteins.

DETAILED DESCRIPTION OF THE INVENTION

"Fungi" are herein defined as eukaryotic microorganisms and include all species of the subdivision Eumycotina (Alexopoulos, C. J., 1962, In: Introductory Mycology, John Wiley & Sons, Inc., New York). The term fungus thus includes both filamentous fungi and yeast. "Filamentous fungi" are herein defined as eukaryotic microorganisms that include all filamentous forms of the subdivision Eumycotina. These fungi are characterized by a vegetative mycelium composed of chitin, cellulose, and other complex polysaccharides. The filamentous fungi used in the present invention are morphologically, physiologically, and genetically distinct from yeasts. Vegetative growth by filamentous fungi is by hyphal elongation and carbon catabolism of most filamentous fungi are obligately aerobic. "Yeasts" are herein defined as eukaryotic microorganisms and include all species of the subdivision Eumycotina that predominantly grow in unicellular form. Yeasts may either grow by budding of a unicellular thallus or may grow by fission of the organism.

The term "fungal", when referring to a protein or nucleic acid molecule thus means a protein or nucleic acid whose amino acid or nucleotide sequence, respectively, naturally occurs in a fungus.

The core of the invention resides in the discovery of a new, alternative parallel pathway for the production of citric acid from oxaloacetic acid. Most surprisingly, said production takes place outside of the mitochondrion, and probably in the cytoplasm. Accordingly, this route is active even under conditions where the mitochondrial citric acid cycle is inactive, which means that production of citric acid can advantageously take place in the absence of an active TCA cycle under anaerobic or low oxygen conditions. Further, it has appeared that the enzyme is expressed during the stationary phase, which means that an overexpression of citric acid can be achieved without any biomass growth of the producing organism. Moreover, previous research (Rafledge C., 2000, FEMS Microbiol. Lett. 189(2):317-319; Ruijter G. et al., 2000, FEMS Microbiol. Lett. 184(1): 35-40; Murray, S. and Hynes, M. 2010, Eukaryotic Cell 9(4):656-666) has shown that improvement of product fluxes through rational manipulation of the central metabolism (citrate synthase) has not been successful, which is in contrast to the results obtained in the present invention For sake of easy reference, the enzyme will be addressed in this specification as the citrate synthase B or citB-enzyme, or just citB.

The citB gene as originally isolated was derived from *Aspergillus niger*. However, also comprised in the invention are homologous proteins that are derived from other micro-organisms (also called orthologs) and the nucleotide sequences coding for these. It will be clear for a person skilled in the art that on basis of the nucleotide sequences coding for the CitB enzyme of *A. niger* orthologs from other micro-organism species can be easily found through database searching in the NCBI GenBank based on sequence similarity and alignment analysis using minimal gap size in the alignment. A list of these orthologs is presented in Table 1a.

TABLE 1a

List of citB orthologs found in the NCBI GenBank database and orthologous genes in *Aspergillus* species (AspGD database, Broad institute). The sequences of these genes are given in FIG. 9.

| Accession | Species |
|---|---|
| CAK45764.1/An08g10920 | *Aspergillus niger* |
| XP001393195.2/ANI1_1474074 | *Aspergillus niger* |
| EHA18674.1/Aspni5_176409 | *Aspergillus niger* |
| NP_001142237.1 | *Zea mays* |
| GAA88109.1/AKAW_06223 | *Aspergillus kawachii* |
| EIT75413.1/Ao3042_08560 | *Aspergillus oryzae* |
| XP_001827205.1/AOR_1_298024 | *Aspergillus oryzae* |
| AO090010000170 | *A. oryzae* |
| XP_002384448.1/AFLA_117410 | *Aspergillus flavus* |
| AFL2G_11427 | *Aspergillus flavus* |
| XP_002148678.1/PMAA_091390 | *Talaromyces marneffei* |
| Aspfo1_0085419 | *A. acidus* |
| Acar5010_212258 | *A. carbonarius_* |
| Acar5010_171837 | *A. carbonarius* |
| Aspbr1_0068777 | *A. brasiliensis* |
| Asptu1_0164827 | *A. tubingensis* |
| ETS77643.1 | *Pestalotiopsis fici* |
| EOD45286.1 | *Neofusicoccum parvum* |
| EMR70107.1 | *Eutypa lata* |

Also part of the invention are nucleotide sequences which are conservatively modified variants of the above mentioned sequences or polymorphic variants thereof. Those of skill in the art will recognize that the degeneracy of the genetic code allows for a plurality of polynucleotides to encode the identical amino acid. Such "silent variations" can be used, for example, to selectively hybridize and detect allelic variants of the nucleotide sequences of the present invention. Additionally, the present invention provides isolated nucleotide sequences comprising one or more polymorphic (allelic) variants of the above nucleotide sequences. Further part of the invention are polynucleotides still coding for a protein which has a biological function identical to the function of the CitB enzyme, which are the product of amplification from a nucleotide library using primer pairs which selectively hybridize under stringent conditions to loci within the above mentioned nucleotide sequences. The primer length in nucleotides is selected from the group of integers consisting of from at least 15 to 50. Those of skill in the art will recognize that a lengthened primer sequence can be employed to increase specificity of binding (i.e. annealing) to a target sequence. Stringent conditions in this respect means a reaction at a temperature of between 60° C. and 65° C. in 0.3 strength citrate buffered saline containing 0.1% SDS followed by rinsing at the same temperature with 0.3 strength citrate buffered saline containing 0.1% SDS.

Thus, also part of the invention are polynucleotides which selectively hybridize, under selective hybridization conditions, to one or more of the above discussed nucleotide sequences, and which code for an amino acid sequence which has a biological function similar to the function of the CitB enzyme disclosed in the present invention. With "a biological function similar to the function of CitB" it is meant the ability to convert oxaloacetate into citrate and to perform this conversion outside the mitochondrion, in the cytoplasm.

Another way to indicate hybridization potential is on sequence identity. In this sense, the present invention provides also for nucleotide sequences which have a percentage of identity related to the above mentioned sequences of 65% to 95%. Thus, for example, the percentage of identity can be at least, 65%, 70%, 75%, 80%, 85%, 90%, or 95%.

Sequence identity on nucleotide sequences can be calculated by using the BLASTN computer program (which is publicly available, for instance through the National Center for Biotechnological Information, accessible via the internet on http://www.ncbi.nlm.nih.gov/) using the default settings of 11 for wordlength (W), 10 for expectation (E), 5 as reward score for a pair of matching residues (M), −4 as penalty score for mismatches (N) and a cutoff of 100.

Similarly, the homology can be calculated on basis of the amino acid sequence of the enzyme encoded by said nucleotide sequences. For amino acids, the sequence identity can be calculated through the BLASTP computer program (also available through http://www.ncbi.nlm.nih.gov/). On the amino acid level homologues or orthologs are defined as amino acid sequences having a biological function similar to the CitB enzyme and having a sequence identity of at least 50%, preferably at least 55%, preferably at least 60%, more preferably at least 70%, more preferably at least 80%, more preferably at least 90%, more preferably at least 95% to the amino acid sequence of the *A. niger* CitB enzyme as depicted in FIG. 3.

Further included in the invention are enzymes, and nucleotide sequences coding for such enzymes, with a functional citrate synthase activity, but which lack the signal sequence that normally would cause them to be expressed or to be functional in the mitochondrion. Further included in the present invention and within the definition of citB according to the invention are mitochondrial citrate synthase enzymes in which the signal sequence has been replaced with the signal sequences of the *A. niger* citB enzyme (An08g10920).

As is shown in the Examples, also the enzymes with annotation An01 g09940 and An09g03570 lack the mitochondrial signal protein part. It is thus envisaged that these proteins and orthologs of these proteins would also qualify as citB enzymes according to the invention. These enzymes and their orthologs, listed in the Table 1 b below, are also depicted in FIG. 9.

TABLE 1b

Protein sequences of predicted non-mitochondrial citrate synthases homologous to An09g03570 and An01g09940 (these also consists of several citB homologues)

|  | Homology to GAA91575 (besthit of An09g03570) |  |
| --- | --- | --- |
| citrate synthase [*Aspergillus kawachii* IFO 4308] An09g03570 BEST hit | 100% | GAA91575.1 |
| citrate synthase [*Neosartorya fischeri* NRRL 181] >gb|EAW19096.1| citrate synthase [*Neosartorya fischeri* NRRL 181] | 71% | XP_001260993.1 |
| citrate synthase [*Aspergillus fumigatus* Af293] >gb|EBA27504.1| citrate synthase, putative [*Aspergillus fumigatus* Af293] >gb|EDP55036.1| citrate synthase [*Aspergillus fumigatus* A1163] | 69% | XP_001481680.1 |
| citrate synthase, putative [*Aspergillus flavus* NRRL3357] >gb|EED54329.1| citrate synthase, putative [*Aspergillus flavus* NRRL3357] | 68% | XP_002375601.1 |
| citrate synthase [*Aspergillus oryzae* RIB40] | 68% | XP_001727354.2 |
| TPA: citrate synthase, putative (AFU orthologue; AFUA 2G15312) [*Aspergillus nidulans* FGSC A4] | 69% | CBF79704.1 |
| hypothetical protein AN7593.2 [*Aspergillus nidulaus* FGSC A4] >gb|EAA62173.1| hypothetical protein AN7593.2 [*Aspergillus nidulaus* FGSC A4] | 69% | XP_680862.1 |
| Citrate synthase-like [*Penicillium roqueforti*] | 61% | CMD33221.1 |
| Pc12g00660 [*Penicillium chrysogenum* Wisconsin 54-1255] >emb|CAP79693.1| Pc12g00660 [*Penicillium chrysogenum* Wisconsin 54-1255] | 61% | XP_002556968.1 |
| hypothetical protein COCCADRAFT 104929 [*Bipolaris zeicola* 26-R-13] | 59% | EUC30035.1 |
| hypothetical protein COCMIDRAFT 107988 [*Bipolaris oryzae* ATCC 44560] | 59% | EUC40740.1 |
| citrate synthase, putative [*Aspergillus clavatus* NRRL 1] >gb|EAW14389.1| citrate synthase, putative [*Aspergillus clavatus* NRRL 1] | 67% | XP_001275815.1 |
| hypothetical protein COCVIDRAFT 107070 [*Bipolaris victoriae* FI3] | 59% | EUN24125.1 |
| citrate synthase [*Aspergillus ruber* CBS 135680] | 59% | EYE90286.1 |
| hypothetical protein COCHEDRAFT 1118493 [*Bipolaris maydis* C5] >gb|ENH9968.1| hypothetical protein COCC4DRAFT 151813 [*Bipolaris maydis* ATCC 48331] | 58% | EMD85580.1 |
| citrate synthase, putative [*Talaromyces stipitatus* ATCC 10500] >gb| EED18839.1| citrate synthase, putative [*Talaromyces stipitatus* ATCC 10500] | 52% | XP_002482831.1 |
| citrate synthase, putative [*Talaromyces stipitatus* ATCC 10500] >gb| EED15409.1| citrate synthase, putative [*Talaromyces stipitatus* ATCC 10500] | 42% | XP_002485362.1 |
| conserved hypothetical protein [*Aspergillus terreus* NIH2624] >gb|EAU32144.1| conserved hypothetical protein [*Aspergillus terreus* NIH2624] | 68% | XP_001216503.1 |
| Citrate synthase [*Penicillium digitatum* PHI26] >gb|EKV21626.1| Citrate synthase [*Penicillium digitatum* Pd1] | 61% | EKV06554.1 |
| citrate synthase [*Colletotrichum graminicola* M1.001] | 39% | EFQ27732.1 |
| citrate synthase [*Auricularia delicata* TFB-10046 SS5] >gb|EJD44900.1| citrate synthase [*Auricularia delicata* TFB-10046 SS5] | 39% | XP_007347043.1 |
| citrate synthase [*Aspergillus oryzae* RIB40] >dbj|BAE66072.1| unnamed protein product [*Aspergillus oryzae* RIB40] | 38% | XP_001827205.1 |
| citrate synthase [*Aspergillus oryzae* 3.042] | 38% | EIT75413.1 |
| citrate synthase [*Aspergillus kawachii* IFO 4308] | 38% | GAA88109.1 |
| uncharacterized protein LOC100274406 [*Zea mays*] >gb|ACF87962.1| unnamed [*Zea mays*] | 38% | NP_001142237.1 |

TABLE 1b-continued

Protein sequences of predicted non-mitochondrial citrate
synthases homologous to An09g03570 and An01g09940 (these also
consists of several citB homologues)

| | Homology to GAA91575 (besthit of An09g03570 | |
|---|---|---|
| citrate synthase [*Aspergillus niger* CBS 513.88] An08g10920 = citB | 37% | XP_001393195.2 |
| unnamed protein product [*Aspergillus niger*] An08g10920 = citB | 37% | CAK45764.1 |
| citrate synthase [*Aspergillus niger* ATCC 1015] | 37% | EHA18674.1 |
| citrate synthase, putative [*Talaromyces marneffei* ATCC 18224] >gb|EEA22411.1| citrate synthase, putative [*Talaromyces marneffei* ATCC 18224] | 38% | XP_002148678.1 |
| citrate synthase, putative [*Aspergillus flavus* NRRL3357] >gb|EED45512.1| citrate synthase, putative [*Aspergillus flavus* NRRL3357] | 37% | XP_002384448.1 |
| putative citrate synthase protein [*Eutypa lata* UCREL1] | 38% | EMR66249.1 |
| putative citrate synthase protein [*Neofusicoccum paryum* UCRNP2] | 36% | EOD45286.1 |
| putative citrate synthase protein [*Eutypa lata* UCREL1] | 38% | EMR70107.1 |
| unnamed protein product [*Aspergillus niger*] >gb|EHA26823.1| citrate synthase [*Aspergillus niger* ATCC 1015] | 36% | CAK37177.1 |
| citrate synthase [*Aspergillus kawachii* IFO 4308] | 35% | GAA82055.1 |
| citrate synthase [*Aspergillus niger* CBS 513.88] An01g09940 | 36% | XP_001389414.2 |

All of these proteins, and orthologs and homologs as defined, are deemed to be encompassed in the term "citB protein" or "citB enzyme" as used herein.

It is further contemplated that overexpression of the gene in a heterologous organism, which in nature does not or hardly produce extramitochondrial citric acid, is able to provide such an organism with a functional pathway for expression of citric acid outside the mitochondrion, and preferably in the cytoplasm. Preferably such overexpression is accomplished in filamentous fungi, yeasts and/or bacteria, such as, but not limited to, *Aspergillus* sp., such as the fungi *A. terreus, A. itaconicus, A. oryzae* and *A niger, Ustilago zeae, Ustilago maydis, Ustilago* sp., *Candida* sp., *Mortierella* sp., *Yarrowia* sp., *Rgizopus* sp. *Yarrowia lipolytica, Rhodotorula* sp. and *Pseudozyma Antarctica*, the bacterium *E. coli* and the yeast *Saccharomyces* sp, e.g. *S. cerevisiae, Pichia* sp, e.g. *P. pastoris* or *P. anomala*. Also plant cells and algal cells and cell cultures may be used as host. Especially preferred are heterologous organisms in which the substrate oxaloacetate is abundantly available in the host organism. Also applicable in the present invention are hosts that may grow anaerobically while using $NO_3$ as source of nitrogen, such as the yeasts *P. anomala* and *Dekkera bruxellensis*. In such a case the acceptor nitrate can yield reductive compounds in the same was as oxygen produces reductive compounds in aerobic fermentation. Similarly also *Aspergillus* species, such as *A. terreus* can grow at very low oxygen levels using dissimilatory nitrate reduction (Stief, P., Fuchs-Ocklenhurg, S., Kamp, A., Manohar, C.-S., Houbraken, J., Boekhout, T., De Beer, D., Stoeck, T. Dissimilatory nitrate reduction by *Aspergillus terreus* isolated from the seasonal oxygen minimum zone in the Arabian Sea (2014) BMC Microbiology, 14 (1), art. no. 35) allowing the production of organic acids as described in the present invention under these conditions.

Further preferred are host organisms which next to the heterologous citB enzyme further contain enzymes that specifically metabolize citric acid further. One of the pathways which is very suitable for this is the pathway to form itaconic acid, wherein from citric acid cis-aconitate is formed by the enzyme aconitase or the enzyme (2-methyl) citrate dehydratase, which enzymes are considered to be functional in the cytosol (see FIG. 1). The production of itaconic acid the can be achieved by the enzyme CAD, which provides cis-aconitic acid decarboxylase activity, thereby converting cis-aconitate into itaconic acid. An advantageous method of producing itaconic acid, the enzymes used therein and the sequences thereof and/or hosts for performing this metabolic pathway have been described in WO 2009/014437. Further optimisation of the present invention in the aspect of the invention dealing with the production of itaconic acid can be achieved by modulating the activity of the regulator protein that comprises a zinc finger and a fungal specific transcription factor domain as can be found on the gene cluster that also comprises ATEG_09970, wherein this regulator protein is indicated as ATEG_09969.1 Further, overexpression of a nucleic acid sequence encoding an itaconate transporting Major Facilitator Superfamily Transporter (MFST) gene sequence (hereinafter "the itaconate transporter") enhances the production/transport of itaconate as described herein as described in WO 2009/104958 and WO 2009/110796. Also the sequences of these enzymes may be found in these references. Preferably said nucleic acid comprises the ATEG_09972.1 sequence of *Aspergillus terreus* or a nucleic acid that shares more than about 70%, preferably more than about 80%, preferably more than about 90% sequence identity with the sequence of ATEG_09972.1. This process can be even further optimised by combining the overexpression of a CAD gene as described in WO 2009/014437, with overexpression of di/tricarboxylate transporters, capable of transporting, among others, cis-aconitate, citrate or isocitrate from the mitochondrion to the cytosol, preferably the gene encoded by the nucleic acid sequence of ATEG_09970.1. Overexpression of this transporter will lead to an increase in cis-aconitate in the cytosol, which can be further converted to itaconic acid (see also WO 2009/104958). Accordingly, the combination of an heterologous citB gene and a gene selected from the group of di/tricarboxylate transporters is not only advantageous for the production of itaconate, but it may also cause an increase in the expression of other citrate derivatives as discussed above.

Of course, ideally, combinations of citB with one or more and preferably all of the genes that have been specified above as enhancing the production of itaconic acid maybe applied to act in concert to boost the production and transport of itaconic acid and/or its derivatives.

Recombinant host cells can be obtained using methods known in the art for providing cells with recombinant nucleic acids. These include transformation, transconjugation, transfection or electroporation of a host cell with a suitable plasmid (also referred to as vector) comprising the nucleic acid construct of interest operationally coupled to a promoter sequence to drive expression. Host cells of the invention are preferably transformed with a nucleic acid construct as further defined below and may comprise a single but preferably comprises multiple copies of the nucleic acid construct. The nucleic acid construct may be maintained episomally and thus comprise a sequence for autonomous replication, such as an ARS sequence. Suitable episomal nucleic acid constructs may e.g. be based on the yeast 2µ or pKD1 (Fleer et al., 1991, Biotechnology 9: 968-975) plasmids. Preferably, however, the nucleic acid construct is integrated in one or more copies into the genome of the host cell. Integration into the host cell's genome may occur at random by illegitimate recombination but preferably the nucleic acid construct is integrated into the host cell's genome by homologous recombination as is well known in the art of fungal molecular genetics (see e.g. WO 90/14423, EP-A-0 481 008, EP-A-0 635 574 and U.S. Pat. No. 6,265,186).

Transformation of host cells with the nucleic acid constructs of the invention and additional genetic modification of the fungal host cells of the invention as described above may be carried out by methods well known in the art. Such methods are e.g. known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation and genetic modification of fungal host cells are known from e.g. EP-A-0 635 574, WO 98/46772, WO 99/60102 and WO 00/37671.

In another aspect the invention relates to a nucleic acid construct comprising a nucleotide sequence encoding a CitB enzyme or homolog or ortholog thereof as defined above and used for transformation of a host cell as defined above. In the nucleic acid construct, the nucleotide sequence encoding the CitB protein preferably is operably linked to a promoter for control and initiation of transcription of the nucleotide sequence in a host cell as defined below. The promoter preferably is capable of causing sufficient expression of the CitB enzyme in the host cell. Promoters useful in the nucleic acid constructs of the invention include the promoter that in nature provides for expression of the CitB gene. Further, both constitutive and inducible natural promoters as well as engineered promoters can be used. Promoters suitable to drive expression of the CitB gene in the hosts of the invention include e.g. GAL7, GAL10, or GAL 1, CYC1, HIS3, PGL, PH05, ADC1, TRP1, URA3, LEU2, ENO, TPI, and A0X1. Other suitable promoters include PDC, GPD1, PGK1, TEF, TDH, promoters from glycolytic genes (e.g. from a glyceraldehyde-3-phosphate dehydrogenase gene), ribosomal protein encoding gene promoters, alcohol dehydrogenase promoters (ADH1, ADH4, and the like), promoters from genes encoding amylo- or cellulolytic enzymes (glucoamylase, TAKA-amylase and cellobiohydrolase). Other promoters, both constitutive and inducible and enhancers or upstream activating sequences will be known to those of skill in the art. The promoters used in the nucleic acid constructs of the present invention may be modified, if desired, to affect their control characteristics. Preferably, the promoter used in the nucleic acid construct for expression of the CitB gene is homologous to the host cell in which the CitB protein is expressed.

In the nucleic acid construct, the 3'-end of the nucleotide acid sequence encoding the CitB enzyme preferably is operably linked to a transcription terminator sequence. Preferably the terminator sequence is operable in a host cell of choice. In any case the choice of the terminator is not critical; it may e.g. be from any fungal gene, although terminators may sometimes work if from a non-fungal, eukaryotic, gene. The transcription termination sequence further preferably comprises a polyadenylation signal.

Optionally, a selectable marker may be present in the nucleic acid construct. As used herein, the term "marker" refers to a gene encoding a trait or a phenotype which permits the selection of, or the screening for, a host cell containing the marker. A variety of selectable marker genes are available for use in the transformation of fungi. Suitable markers include auxotrophic marker genes involved in amino acid or nucleotide metabolism, such as e.g. genes encoding ornithine-transcarbamylases (argB), orotidine-5'-decaboxylases (pyrG, URA3) or glutamine-amido-transferase indoleglycerol-phosphate-synthase phosphoribosyl-anthranilate isomerases (trpC), or involved in carbon or nitrogen metabolism, such e.g. niaD or facA, and antibiotic resistance markers such as genes providing resistance against phleomycin, bleomycin or neomycin (G418). Preferably, bidirectional selection markers are used for which both a positive and a negative genetic selection is possible. Examples of such bidirectional markers are the pyrG (URA3), facA and amdS genes. Due to their bidirectionality these markers can be deleted from transformed filamentous fungus while leaving the introduced recombinant DNA molecule in place, in order to obtain fungi that do not contain selectable markers. This essence of this MARKER GENE FREE™ transformation technology is disclosed in EP-A-0 635 574, which is herein incorporated by reference. Of these selectable markers the use of dominant and bidirectional selectable markers such as acetamidase genes like the amdS genes of *A. nidulans, A. niger* and *P. chrysogenum* is most preferred. In addition to their bidirectionality these markers provide the advantage that they are dominant selectable markers that, the use of which does not require mutant (auxotrophic) strains, but which can be used directly in wild type strains.

Optional further elements that may be present in the nucleic acid constructs of the invention include, but are not limited to, one or more leader sequences, enhancers, integration factors, and/or reporter genes, intron sequences, centromers, telomers and/or matrix attachment (MAR) sequences. The nucleic acid constructs of the invention may further comprise a sequence for autonomous replication, such as an ARS sequence. Suitable episomal nucleic acid constructs may e.g. be based on the yeast 2µ or pKD1 (Fleer et al., 1991, Biotechnology 9: 968-975) plasmids. Alternatively the nucleic acid construct may comprise sequences for integration, preferably by homologous recombination (see e.g. WO98/46772). Such sequences may thus be sequences homologous to the target site for integration in the host cell's genome. The nucleic acid constructs of the invention can be provided in a manner known per se, which generally involves techniques such as restricting and linking nucleic acids/nucleic acid sequences, for which reference is made to the standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987).

In a further aspect the invention relates to fermentation processes in which the transformed host cells of the invention are used for the production of citric acid and products that can be derived from further metabolic routes from citric acid. Such a fermentation process may be an aerobic fermentation process, but since the location of the enzyme is outside the mitochondrion advantageously an oxygen-limited or anaerobic fermentation process may be applied. This enables a lot of possible circumstances or conditions under which production of the citric acid can still occur. In particular circumstances with an inactive TCA cycle which are normally believed to be incompatible with citric acid production. In particular various yeast species are able to grow anaerobically by fermentation. For pertaining a suitable cofactor balance in particular yeast strains able to use $NO_3$ such as Dekkera bruxellensis and Pichia anomola are preferred. The fermentation process may either be a submerged or a solid state fermentation process.

In a solid state fermentation process (sometimes referred to as semi-solid state fermentation) the transformed host cells are fermenting on a solid medium that provides anchorage points for the fungus in the absence of any freely flowing substance. The amount of water in the solid medium can be any amount of water. For example, the solid medium could be almost dry, or it could be slushy. A person skilled in the art knows that the terms "solid state fermentation" and "semi-solid state fermentation" are interchangeable. A wide variety of solid state fermentation devices have previously been described (for review see, Larroche et al., "Special Transformation Processes Using Fungal Spores and Immobilized Cells", Adv. Biochem. Eng. Biotech., (1997), Vol 55, pp. 179; Roussos et al., "Zymotis: A large Scale Solid State Fermenter", Applied Biochemistry and Biotechnology, (1993), Vol. 42, pp. 37-52; Smits et al., "Solid-State Fermentation-A Mini Review, 1998), Agro-Food-Industry Hi-Tech, March/April, pp. 29-36). These devices fall within two categories, those categories being static systems and agitated systems. In static systems, the solid media is stationary throughout the fermentation process. Examples of static systems used for solid state fermentation include flasks, petri dishes, trays, fixed bed columns, and ovens. Agitated systems provide a means for mixing the solid media during the fermentation process. One example of an agitated system is a rotating drum (Larroche et al., supra). In a submerged fermentation process on the other hand, the transformed fungal host cells are fermenting while being submerged in a liquid medium, usually in a stirred tank fermenter as are well known in the art, although also other types of fermenters such as e.g. airlift-type fermenters may also be applied (see e.g. U.S. Pat. No. 6,746,862).

Preferred in the invention is a submerged fermentation process, which is performed in batch or fed-batch. This means that there is a continuous input of feed containing a carbon source and/or other relevant nutrients in order to improve citric acid yields. The input of the feed can, for example, be at a constant rate or when the concentration of a specific substrate or fermentation parameter falls below some set point.

There are also fermentation processes where a fungus grows on a solid support in an aqueous phase in so-called biofilm processes. In those conditions there will be an oxygen limitation meaning that the metabolism in such a case at least partially will be anaerobically. Biofilms have been used for a long time in water treatment facilities where they were called slime, mats or sludge, but no other practical use was seen until recently. This has brought that most of the available information is on bacterial and, in recent years, on yeast biofilms. Filamentous fungi are naturally adapted to growth on surfaces and in these conditions they show a particular physiological behaviour which it is different to that in a submerged culture; thus, they can be considered as biofilm forming organisms according to the above concept. Differential physiological behaviour of most attached fungi corresponds principally to a higher production and secretion of enzymes and also to a morphological differentiation which is absent in submerged cultures (Akao, T. et al., Curr. Genet. 41:275-281, 2002; Biesebeke, R. et al., FEMS Yeast Res. 2:245-248, 2002). The advantages of this form of growth have been industrially exploited by two culture systems: SSF and cell immobilization (Gutierrez-Correa, M. and Villena, G., Rev. peru. Boil. 10(2):113-124, 2003). Once citric acid is produced in the host cell this citric acid can be used as a substrate for further metabolic processes. One of these metabolic processes is the production of itaconic acid. For this a conversion from citric acid via cis-aconitate to itaconic acid has to be performed via the enzymes aconitase and CAD (cis-aconitate decarboxylase). Such a conversion and further methods of additionally increasing the production of itaconic acid from cis-aconitate has been described in WO 2009/014437, WO 2009/104958 and WO 2009/110796.

Next to a pathway to itaconic acid, citric acid can also be used as a starting point for other metabolic routes. One of the most commercially interesting routes is the production of methacrylic acid. Methacrylic acid can be produced directly by decarboxylation of itaconic acid, but it can also be produced through other metabolic routes (see Carlsson, M. et al., Ind. Eng. Chem. Res. 33:1989-1996, 1994). Citric acid is also one of the basic building blocks in the biosynthesis of fatty acids and triglycerides. Fatty acids form important storage molecules for energy, which energy later can be used, e.g. when fatty acids have been used as a source of biodiesel. The exact nature of the fatty acid is—for use as biofuel—less relevant, since all types of plant fatty acids may be used as such. Fatty acids can, of course, also be used as such, e.g. as food additives. This is especially important in the case of the essential fatty acids, like linoleic acid and α-linolenic acid. for the production of other compounds, such as biodegradable plastics.

Further, citric acid can be used to be a starting point for the biosynthesis of lysine (via homocitrate and homo-cis-aconitate). FIG. 2 gives an overview of the chemical reactions and pathways that can be used to convert citrate into lysine.

This pathway is also required for the biosynthetic production of aminoadipate which is an intermediate for penicillin and other antibiotic compounds. Lysine, in turn, may be used as a starting point for the production of caprolactam (see US 2009/005532, and from there be used for the production of plastics (such as nylon-6, a polyamide).

Further, citrate can also be used as a precursor for the mevalonate pathway (see FIG. 4). This can lead to the production of terpenoids. Lastly, citrate (and acetyl CoA) may function as precursor for a polyketide pathway, resembling fatty acid biosynthesis. Polyketide antibiotics, antifungals, cytostatics, anticholesteremic, antiparasitics, coccidiostats, animal growth promoters and natural insecticides that may be produced following such a pathway are commercially important compounds.

It has further been found that the cluster in which the citB gene is residing contains other genes that have a relation with the pathways in which citrate is involved. In the citB (An08g10920) cluster that is present in a particular A. niger strain the following genes can be found: An08g10860 (fatty acid synthase) An08g10870 (2-methylcitrate dehydratase (prpD)),); An08g10880 (GAL4; GAL4-like Zn2Cys6 binuclear), An08g10930 (3-oxoacyl-[acyl-carrier-protein] synthase, fatty acid synthase); An08g10970 (MFS multidrug transporter); An08g10980 (transcription factor acetate regulatory DNA binding protein facB). (Over)expression of any of these genes, next to the expression of citB is thought to be especially favorable to increase the production and usurpation of intracellular citrate.

in the CAD-expressing strain. BG=expression values are at background levels, thus calculation of ratio value (R; expressed as 2 Log R) is not relevant

TABLE 2

Citrate synthase, aconitase and cis-aconitate decarboxylase (prpD) genes in *A. niger*.

| Gene_ID | Protein | Subcell. Loc. WolfPsort | RNAseq results CAD | WT | 2LogR |
|---|---|---|---|---|---|
| An09g06680/ANI_1_876084 | citrate synthase citA | mito: 19.0 | 9501 | 8977 | −0.02 |
| An15g01920/ANI_1_1226134 | citrate synthase | mito: 22.0 | 345 | 616 | −0.87 |
| An09g03570 | citrate synthase | unknown0 | 4 | BG | |
| An08g10920/ANI_1_1474074 | citrate synthase citB | cyto: 10.0 | 9515 | 917 | 3.34 |
| An01g09940/ANI_1_2950014 | citrate synthase | cysk: 11, cyto: 8 | 11 | 62 | BG |
| An02g11040/ANI_1_3018024 | aconitase | mito: 20.5 | 0 | 0 | BG |
| An08g10530/ANI_1_1410074 | aconitase | cyto: 19.0 | 11203 | 5897 | 0.89 |
| An09g03870/ANI_1_470084 | aconitase | mito: 26.5 | 571 | 1254 | −1.17 |
| An16g05760/ANI_1_1808144 | aconitase | mito: 24.0 | 22 | 16 | BG |
| An05g02230/ANI_1_578044 | aconitase | cyto: 12.5 | 234 | 89 | 1.36 |
| An01g09950/ANI_1_2952014 | prpD | cyto: 13.0 | 50 | 59 | BG |
| An09g06220/ANI_1_1536084 | prpD | cyto: 12.5 | 67 | 318 | −2.28 |
| An15g01780/ANI_1_306134 | prpD | cyto: 13.5 | 1565 | 1632 | −0.1 |
| An08g10870/ANI_1_2490074 | prpD | cyto: 16.5 | 6099 | 570 | 3.38 |
| An02g14730/ANI_1_3352024 | prpD | cyto: 13.5 | 48 | 47 | BG |
| An01g09930/ANI_1_29480 | prpD | mito: 10.0 | 12 | 45 | BG |

In bold the genes induced in the CAD-expressing strain.
BG = expression values are at background levels, thus calculation of ratio value (R; expressed as 2LogR) is not relevant

EXAMPLES

Example 1 Enzyme Analysis in Itaconic Acid Producing Strain

The table 2 below gives an overview of proteins/genes in *Aspergillus niger* and *S. cerevisiae* belonging to the enzyme classes citrate synthase, aconitase and cis-aconitase decarboxylase. For all members in *A. niger* the results of expression analysis is given by RNA sequencing results in the WT strain and an itaconic acid producing strain (transgenic for CAD by carrying extra gene copies of the cis-aconitate decarboxylase from *A. terreus* as described in WO 2009/014437). This shows that An08g10920, tentatively called citB, encoding a citrate synthase without a predicted mitochondrial localization, is highly induced in the itaconic acid production strain. This gene has no homologue in *S. cerevisiae*. Only in closely related black *Aspergilli* homologues are present (see below under genome mining citB gene cluster). Also one of the predicted cytosolic cis-aconitase decarboxylase (prpD) genes from *A. niger*, An08g10870 which is clustered with citB is highly induced. Also the canonical cytosolic aconitase An08g10530 more distantly linked is induced in the CAD strain.

In *S. cerevisiae* all three citrate synthase proteins and the single prpD gene are mitochondrial, while both aconitases are cytosolic as predicted for the common metabolic pathways.
Table 2 Citrate synthase, aconitase and cis-aconitate decarboxylase (prpD) genes in *A. niger*. In hold the genes induced From this Table it appears that two of the *A. niger* proteins are clearly located in the mitochondrion (An09g09980 and An15g01920), while two *A. niger* genes are located outside the mitochondrion (An01g09940 and An08g10920), while the location of one protein is undecided (An09g03570). In a homology tree (see FIG. 10) it appears that a distinction can also be made between mitochondrial and non-mitochondrial citrate synthase enzymes on basis of homology.

Example 2 RNA Sequence Analysis of *A. niger* CAD Transformant in Comparison to the Wildtype Strain RNAseq is a new transcriptomics platform which allows direct sequencing of mRNAs. This means that no arrays are required and all expressed RNA is measured (non-coding, non annotated). Shake flask cultures in fermentation medium described below were grown for 46 hours at 33° C. from which biomass samples were harvested. Total RNA was isolated from biomass samples using Trizol (Invitrogen). The total RNA was send to BaseClear (The Netherlands). Before random mRNA sequencing could be performed, mRNA purification was performed via oligo-dT beads (Illumina TruSeq RNA samp.prep), followed by first-strand cDNA synthesis with random primers. Adaptor ligation, adding 120 bp, was carried out, followed by ~270 bp gel-isolation (cDNA inserts ~150 bp). Subsequently, paired-end sequencing was performed, resulting in Illumina HiSeq data (28-29 M reads/sample). Data analysis was performed to obtain output files of RNA-Seq alignments (*.clc, *,sam) and RNA-Seq expression tables (*.csv, *.cic, *.xlsx). Sample-normalised expression values were expressed as RKPM/sample (=Reads per Kilobase of exon model per Million mapped reads (Mortazavi et. al 2008)). The data analysis performed at TNO comprised of defining the "Floor" of RPKM values (Excel) (S<1 was defined as S=1). After introducing the "Floor" the differentials of the expression values of the CAD transformant and wildtype were calculated in Excel (R=Sx/Sref; 2 log R ratios). Below table 2 provides the RNAseq data (counts and 2 log R ratios) of the genes directly surrounding the citrate synthase genes which might belong to the putative citrate synthase/prpD gene clusters. AB1.13 data refer to the WT *A. niger* host strain, while AB1.13CAD refer to the itaconic acid producing strain (CAD) carrying extra gene copies of the cis-aconitate decarboxylase from *A. terreus* as described in WO 2009/014437. Note that RNAseq values lower than 100-200 represent very low expression. Of the related genes/gene clusters only the citB cluster (An08g10860-An08g1011030, in bold and italics) shows significantly induced expression in the AB1.13CAD strain (Table 3) The other gene regions containing citrate synthase, aconitase and cis-aconitate decarboxylase genes (underlined) show no induction (Table 3)

TABLE 3

RNAseq analysis

| value AB1.13CAD (Sx) count | value AB1.13 (Sref) count | value 2log(Sx/Sref) | gene name CBS 513.88 code | ATCC 1015 code | Protein |
|---|---|---|---|---|---|
| 60113 | 12 | 12.26 | — | — | ATEG_09971_*A. terreus* cad gene |
| 0 | 0 | 0.00 | An08g10760 | ANI_1_2472074 | hypothetical protein |
| 574 | 1409 | −1.33 | An08g10780 | ANI_1_2476074 | glycosyl hydrolase family 43 protein |
| 0 | 3 | 0.00 | An08g10800 | ANI_1_2480074 | L-amino acid oxidase LaoA |
| 26 | 34 | −0.42 | An08g10810 | ANI_1_2482074 | appr-1-p processing enzyme family protein |
| 126 | 146 | −0.25 | An08g10820 | ANI_1_2484074 | aldehyde dehydrogenase |
| 19 | 135 | −2.86 | An08g10830 | ANI_1_2486074 | geranylgeranyl pyrophosphate synthase |
| 17445 | 1403 | 3.60 | An08g10860 | ANI_1_2488074 | sterigmatocystin biosynthesis fatty acid synthase subunit beta |
| 6099 | 570 | 3.38 | An08g10870 | ANI_1_2490074 | 2-methylcitrate dehydratase (prpD) |
| 2893 | 141 | 4.32 | An08g10880 | ANI_1_2492074 | GAL4; GAL4-like Zn2Cys6 binuclear cluster DNA-binding domain; found in transcription regulators like GAL4 |
| 9515 | 917 | 3.34 | An08g10920 | ANI_1_1474074 | citrate synthase citB |
| 21473 | 1212 | 4.11 | An08g10930 | ANI_1_2494074 | 3-oxoacyl-[acyl-carrier-protein] synthase |
| 11804 | 2195 | 2.39 | An08g10970 | ANI_1_2500074 | MFS multidrug transporter |
| 1850 | 1490 | 0.28 | An08g10980 | ANI_1_2502074 | acetate regulatory DNA binding protein facB |
| 57671 | 15873 | 1.83 | An08g10990 | ANI_1_1484074 | dienelactone hydrolase family protein |
| 956 | 377 | 1.31 | An08g11000 | — | GAL4-like Zn2Cys6 binuclear cluster DNA-binding domain; similarity to the A. niger xlnR gene |
| 776 | 473 | 0.68 | An08g11010 | ANI_1_2504074 | hypothetical protein |
| 140252 | 64632 | 1.08 | An08g11030 | ANI_1_1486074 | 3-phytase B |
| 287 | 408 | −0.54 | An08g11040 | ANI_1_1488074 | zinc finger protein ZPR1 |
| 157 | 330 | −1.11 | An08g11060 | ANI_1_2506074 | hypothetical protein |
| 6 | 11 | 0.00 | An08g11070 | ANI_1_2508074 | extracellular invertase |
| 1386 | 1163 | 0.22 | An01g09730 | ANI_1_2924014 | choline transport protein |
| 2 | 1 | 0.00 | An01g09740 | ANI_1_2926014 | 3-hydroxyacyl-CoA dehydrogenase |
| 1 | 7 | 0.00 | An01g09750 | ANI_1_1318014 | cytochrome B5 |
| 31 | 30 | 0.01 | An01g09760 | ANI_1_1320014 | cytochrome P450 monooxygenase |
| 37 | 55 | −0.61 | An01g09770 | ANI_1_2928014 ANI_1_2930014 | Zn(II)2Cys6 transcription factor calcium/calmodulin dependent protein kinase |
| 434 | 1331 | −1.65 | An01g09780 | ANI_1_2932014 | D-lactate dehydrogenase |
| 356 | 597 | −0.78 | An01g09800 | ANI_1_1328014 | acylamide-delta3(E)-desaturase |
| 342 | 226 | 0.56 | An01g09810 | ANI_1_2934014 | glycosyl transferase |
| 595 | 313 | 0.89 | An01g09820 | ANI_1_2936014 | udp-glucose 6-dehydrogenase |
| 267 | 304 | −0.22 | An01g09830 | ANI_1_1332014 | glutathione S-transferase |
| 634 | 677 | −0.13 | An01g09840 | ANI_1_1334014 | NADH:ubiquinone oxidoreductase 6.6kD subunit |
| 90 | 84 | 0.06 | An01g09850 | ANI_1_2938014 | sin3-associated polypeptide Sap18 |
| 155 | 137 | 0.14 | An01g09860 | ANI_1_1338014 | mRNA splicing factor (Prp18) |
| 0 | 1 | 0.00 | An01g09870 | ANI_1_2940014 | hypothetical protein |
| 303 | 168 | 0.82 | An01g09880 | ANI_1_2942014 | hypothetical protein |
| 248 | 182 | 0.41 | An01g09890 | ANI_1_1344014 | ADP-ribosylation factor family protein |
| 63 | 73 | −0.25 | An01g09900 | ANI_1_2944014 | hypothetical protein |
| 236 | 215 | 0.10 | An01g09910 | ANI_1_2946014 | phosphatidylinositol N-acetylglucosaminyltransferase gpi3 subunit |
| 169 | 138 | 0.26 | An01g09920 | ANI_1_1350014 | ATP-dependent RNA helicase dbp6 |
| 12 | 45 | −1.94 | An01g09930 | ANI_1_948014 | 2-methylcitrate dehydratase (prpD) |
| 11 | 62 | −2.53 | An01g09940 | ANI_1_2950014 | citrate synthase |
| 50 | 59 | −0.27 | An01g09950 | ANI_1_2952014 | immune-responsive protein (prpD) |
| 11 | 18 | −0.01 | An01g09960 | ANI_1_1358014 | exo-1,4-beta-xylosidase xlnD |
| 12 | 62 | −2.40 | An01g09970 | ANI_1_2954014 | hypothetical protein |
| 7 | 57 | −3.06 | An01g09980 | ANI_1_1362014 | Asp-hemolysin |
| 1106 | 845 | 0.35 | An01g10000 | ANI_1_2956014 | ABC multidrug transporter |
| 123 | 359 | −1.58 | An01g10010 | ANI_1_2958014 | cystathionine gamma-synthase |
| 1237 | 3533 | −1.55 | An01g10030 | ANI_1_1368014 | sphinganine hydroxylase BasA |
| 4824 | 4664 | 0.01 | An01g10050 | ANI_1_1370014 | hypothetical protein |
| 229 | 170 | 0.39 | An01g10060 | ANI_1_2962014 | Zn(II)2Cys6 transcription factor |
| 94 | 109 | −0.25 | An01gl0070 | ANI_1_1374014 | signal recognition particle protein |
| 3 | 6 | 0.00 | An15g01770 | ANI_1_1208134 | C-5 cytosine methyltransferase DmtA |
| 1565 | 1632 | −0.10 | An15g01780 | ANI_1_306134 | 2-methylcitrate dehydratase (prpD) |

TABLE 3-continued

RNAseq analysis

| value AB1.13CAD (Sx) count | value AB1.13 (Sref) count | value 2log(Sx/Sref) | gene name CBS 513.88 code | ATCC 1015 code | Protein |
|---|---|---|---|---|---|
| 0 | 7 | 0.00 | An15g01790 | ANI_1_1210134 | pantothenate transporter |
| 5 | 12 | −0.41 | An15g01800 | ANI_1_1212134 | amidohydrolase |
| 144 | 86 | 0.71 | An15g01810 | ANI_1_1214134 | C6 zinc finger domain protein |
| 19 | 18 | 0.00 | An15g01830 | ANI_1_1216134 | sodium transport ATPase 5 |
| 222 | 186 | 0.22 | An15g01840 | ANI_1_1218134 | short-chain dehydrogenase/reductase family |
| 398 | 460 | −0.24 | An15g01850 | ANI_1_318134 | glutamine synthetase |
| 455 | 1272 | −1.52 | An15g01860 | ANI_1_320134 | malate synthase, glyoxysornal |
| 19 | 14 | 0.41 | An15g01870 | ANI_1_1220134 | hypothetical protein |
| 1 | 0 | 0.00 | An15g01880 | ANI_1_1222134 | hypothetical protein |
| 1283 | 808 | 0.63 | An15g01890 | ANI_1_1224134 | beta-glucosidase E |
| 51 | 117 | −1.23 | An15g01900 | ANI_1_326134 | choline transport protein |
| 1392 | 1000 | 0.44 | An15g01910 | ANI_1_328134 | [NU]+ prion formation protein 1 |
| 345 | 616 | −0.87 | An15g01920 | ANI_1_1226134 | citrate synthase |
| 2 | 65 | −2.57 | An15g01930 | ANI_1_1228134 | hypothetical protein |
| 68 | 75 | −0.18 | An15g01940 | ANI_1_1230134 | FAD binding domain protein |
| 50 | 31 | 0.65 | An15g01950 | ANI_1_1232134 | very-long-chain acyl-CoA synthetase family protein (CefD1) |
| 174 | 250 | −0.56 | An15g01960 | ANI_1_1234134 | sarcosine oxidase |
| 236 | 357 | −0.63 | An15g01970 | ANI_1_340134 | hypothetical protein |
| 116 | 153 | −0.43 | An15g01980 | ANI_1_342134 | 8-amino-7-oxononanoate synthase |
| 461 | 509 | −0.18 | An15g01990 | ANI_1_344134 | onanonoxo-7-onima-8-eninoihtemlysoneda |
| 1537 | 1798 | −0.26 | An15g02000 | ANI_1_1238134 | biotin synthase |
| 0 | 4 | 0.00 | An09g03570 | — | similarity to citrate synthase citA |
| 67 | 318 | −2.28 | An09g06220 | ANI_1_1536084 | immune-responsive protein (prpD) |
| 295 | 853 | −1.57 | An09g06460 | ANI_1_842084 | hypothetical protein |
| 2156 | 2686 | −0.35 | An09g06480 | ANI_1_844084 | phosphatidylinositol transfer protein sfh5 |
| 756 | 652 | 0.18 | An09g06490 | ANI_1_846084 | lanosterol synthase |
| 328 | 574 | −0.84 | An09g06500 | ANI_1_1562084 | SGT1 and CS domain protein |
| 151 | 210 | −0.51 | An09g06510 | ANI_1_1564084 | PQ loop repeat protein |
| 287 | 286 | −0.03 | An09g06520 | ANI_1_852084 | sir2 family transcriptional regulator |
| 657 | 500 | 0.36 | An09g06530 | ANI_1_1566084 | negative regulator of the PHO system |
| 48 | 70 | −0.58 | An09g06540 | ANI_1_856084 | spindle pole protein Nnf1 |
| 344 | 278 | 0.27 | An09g06550 | ANI_1_858084 | hypothetical protein |
| 1482 | 877 | 0.72 | An09g06570 | ANI_1_862084 | hypothetical protein |
| 403 | 513 | −0.38 | An09g06580 | ANI_1_864084 | NTF2 and RRM domain protein |
| 10266 | 15839 | −0.66 | An09g06590 | ANI_1_860084 | heat shock protein 90 |
| 594 | 1492 | −1.36 | An09g06610 | ANI_1_866084 | hypothetical protein |
| 1424 | 1100 | 0.34 | An09g06630 | ANI_1_868084 | HLH transcription factor (PalcA) |
| 289 | 325 | −0.20 | An09g06640 | ANI_1_870084 | DNA-directed RNA polymerase III subunit RPC-3 |
| 3021 | 3534 | −0.26 | An09g06650 | ANI_1_872084 | ubiquinol-cytochrome C reductase complex core protein 2 |
| 2866 | 3756 | −0.43 | An09g06670 | ANI_1_874084 | DNA replication protein YHM2 |
| 9051 | 8977 | −0.02 | An09206680 | ANI_1_876084 | citrate synthase citA |
| 833 | 715 | 0.19 | An09g06700 | ANI_1_878084 | RNA binding protein Nrd1 |
| 345 | 1089 | −1.69 | An09g06710 | ANI_1_1568084 | O-acetylhomoserine (thiol)-lyase |
| 187 | 463 | −1.34 | An09g06720 | ANI_1_1568084 | hypothetical protein |
| 283 | 3532 | −3.68 | An09g06730 | ANI_1_882084 | arginine permease |
| 609 | 607 | −0.03 | An09g06740 | ANI_1_886084 | AMP-binding enzyme |
| 460 | 470 | −0.07 | An09g06750 | ANI_1_1570084 | hypothetical protein |
| 1035 | 698 | 0.53 | An09g06760 | ANI_1_1572084 | WW domain protein |
| 288 | 315 | −0.16 | An09g06770 | ANI_1_1574084 | WD repeat protein |
| 391 | 624 | −0.71 | An09g06780 | ANI_1_894084 | peruxisomal membrane protein Pmp47 |
| 3632 | 3045 | 0.22 | An09g06790 | ANI_1_896084 | GIP-binding protein ypt1 |
| 751 | 1026 | −0.49 | An09g06800 | ANI_1_898084 | aminopeptidase |
| 375 | 296 | 0.31 | An09g06810 | ANI_1_1576084 | TFIIH basal transcription factor complex p47 subunit |
| 290 | 214 | 0.40 | An09g06820 | ANI_1_902084 | hypothetical protein |
| 6 | 7 | 0.00 | An09g06830 | ANI_1_1578084 | pumilio-family RNA binding repeat protein |
| 1396 | 963 | 0.50 | An09g06840 | ANI_1_906084 | hypothetical protein |
| 3021 | 2861 | 0.04 | An09g06850 | ANI_1_908084 | NADH-ubiquinone oxidoreductase subunit |
| 255 | 244 | 0.03 | An09g06860 | ANI_1_1580084 | hypothetical protein |
| 964 | 796 | 0.24 | An09g06870 | ANI_1_1582084 | cytokinesis regulator (Byr4) |
| 2 | 11 | −1.76 | An09g06890 | ANI_1_1584084 | hypothetical protein |

Example 3 Isolation of RNA from Fermentation Samples and Shake Flask Samples

*A. niger* strains were cultured under different fermentation conditions (see table 4). Five-Liter controlled batch fermentations were performed in New Brunswick Scientific Bioflow 3000 fermenters.

The following conditions were used unless stated otherwise:

Temp. 37° C.

pH start 3.5 set point 2.3

DO set points Day 1: 75%

Day 2, 3, 4: 50%

Subsequent days: 25%

Preculture: 100 ml of the same medium as used in the fermentation medium ($10^7$ spores/ml) in 500 ml baffled Erlenmeyer flasks, overnight, 37° C., 150 rpm.
pH control: 4M KOH (Base), 1.5M $H_3PO_4$ (Acid)
Antifoam: Struktol (Schill & Seilacher)
Fermentation Medium Compositions:
Per liter: 2.36 g of $NH_4SO_4$, 0.11 g of $KH_2PO_4$, 2.08 g of $MgSO_4*7H_2O$, 0.13 g of $CaCl_2*2H_2O$, 0.074 of NaCl, 0.2 mg of $CuSO_4*5H_2O$, 5.5 mg of $Fe(III)SO_4*7H_2O$, 0.7 mg of $MnCl_2*4H_2O$ and 1.3 mg of $ZnSO_4*7H_2O$ and 100 g of glucose as a carbon source.
All media were prepared in demineralized water.

TABLE 4 fermentation conditions of *A. niger* strains

| Biomass sample | Strain | medium | fermentation condition | glucose | biomass | ita/DWT |
|---|---|---|---|---|---|---|
| 1 2010 exp2 F12 T3 (70 h) | N201 | M12 | 100-25% DO, pH start 3.5 control 2.3 | 60.0 | 12,460 | — |
| 2 2011 exp2 F8 T6 (88.5 h) | N201 CAD02 | M12 + Cu | 100-25% DO, pH start 3.5 control 2.3 | 204 | 16,930 | 0.052 |
| 3 2011 exp2 F9 T6 (88.5 h) | N201 CAD02 | M12 + Cu | 25% DO, pH start 3.5 control 2.3 | 204 | 17,970 | 0.101 |
| 4 2011 exp4 F9 T2 (27 h) | N201 CAD02 | M12 + Cu | 10% DO, pH start 3.5 control 2.3 | 201 | 20,790 | 0.102 |
| 5 2011 exp7 F8 T5 (68 h) | N201 CAD02 | M12 + Cu | 15% DO, pH start 3.5 control 2.3 | 213 | 18,670 | 0.100 |
| 6 2011 exp4 F8 T2 (27 h) | N201 CAD02 | M12 + Cu | 20% DO, pH start 3.5 control 2.3 | 201 | 18,250 | 0.137 |
| 7 2010 exp2 F11 T3 (70 h) | AB1.13 wt pyr+ (Cora) | M12 | 100-25% DO, pH start 3.5 control 2.3 | 60.0 | 11,600 | — |
| 8 2010 exp2 F13 T3 (70 h) | AB1.13 ΔoahA#76 | M12 | 100-25% DO, pH start 3.5 control 2.3 | 60.0 | 8,880 | — |
| 9 2011 exp2 F10 T6 (88.5 h) | AB1.13 ΔoahA#76 CAD 05 | M12 + Cu | 100-25% DO, pH start 3.5 control 2.3 | 204 | 15,070 | 0.110 |
| 10 2011 exp1 F8 T5 (49 h) | AB1.13 CAD pyr+ | M12 − Cu | 100-25% DO, pH start 3.5 control 2.3 | 210 | 14,937 | 0.152 |
| 11 2011 exp1 F9 T5 (49 h) | AB1.13 CAD pyr+ | M12 | 100-25% DO, pH start 3.5 control 2.3 | 210 | 17,339 | 0.106 |
| 12 2011 exp1 F10 T5 (49 h) | AB1.13 CAD pyr+ | M12 + Cu | 100-25% DO, pH start 3.5 control 2.3 | 210 | 27,350 | 0.081 |
| 13 2011 exp4 F10 T2 (27 h) | AB 1.13 CAD + FHB 2,5 | M12 + Cu | 10% DO, pH start 3.5 control 2.3 | 201 | 15,200 | 0.205 |
| 14 2011 exp7 F10 T5 (68 h) | AB 1.13 CAD + FHB 2,5 | M12 + Cu | 20% DO, pH start 3.5 control 2.3 | 213 | 16,780 | 0.153 |
| 15 2011 exp6 F10 T3 (27 h) | AB 1.13 CAD + FHB 2,5 | M12 + Cu | 5% DO, pH start 3.5 control 2.3 | 210 | 12,026 | 0.191 |

For the shake flask cultures the fermentation medium described above was used. The cultures were grown for 46 hours at 33° C. from which biomass samples were harvested.

RNA was isolated from biomass samples using Trizol from Invitrogen. Equal amounts of RNA (8 micrograms) were loaded on a RNA gel and blotted on Hybond N+ membrane from GE Healthcare.

Example 4 Northern Analysis

From the RNAseq data it was shown that several genes in a gene cluster, including the citB gene, were upregulated in the TNO-CAD strain compared to the TNO-WT strain.

To confirm the RNAseq results and to analyze different strains and different fermentation conditions, Northern analysis was carried out.

Primers were designed to amplify gene fragments by PCR of four upregulated genes from the gene cluster (citB, MFS, citR and prpD, seeTable 5) and other interesting genes (gpdA, citA, CAD). The labeling of the gene fragments was carried out using the PCR DIG Probe Synthesis Kit (Roche).

Hybridization was performed using the DIG-High Prime DNA Labeling and Detection Starter Kit II (Roche).

TABLE 5

Primers for Northern analysis

| o5886-CitA forward | TGTTGTCGCCGTAGCCGAGC |
| o5887-CitA reverse | AGCTCCTCCCCAAGGCTCCC |

TABLE 5-continued

| Primers for Northern analysis | |
|---|---|
| o5888-CitB forward | GCGACGCGGTCCACCTCAAA |
| o5889-CitB reverse | GCACAGGACTGCCCAACCCC |
| o5890-An08g10880 forward | GCTTCGCGGCCCATACTGCT |
| o5891-An08g10880 reverse | TGAAGCTGCCAACACCCCGC |
| o5892-An08g10870 forward | GATGGACGGCCACCCACTGC |
| o5893-An08g10870 reverse | TGCGCTCCCTTCAGCAGCAC |
| o5894-An08g10970 forward | GCAAAGGGTGCCAGGCCGAT |
| o5895-An08g10970 reverse | CTGGGTGCTGGTCATCGCGG |
| cadA forward | GGTCTTAGCCGAGCAAGGC |
| cadA reverse | GCGACACTCATCTGCCCTG |
| gpdA forward | ATCGAGACCTACGAGGAGGG |
| gpdA reverse | CCGGGAGTTCCTGCGAAGG |

The results of the Northern analysis of the fermentation samples are shown in the table 6 below.

TABLE 6

Results Northern analysis

| Strain | gpdA | cadA | citA (An09g06680) | citB (An08g10920) | citB (RT-qPCR citB/g pdA ratio) | An08g10880 | An08g10870 | An08g10970 |
|---|---|---|---|---|---|---|---|---|
| Shake flask culture | | | | | | | | |
| AB1.13pyr+ | NA | NA | NA | NA | 0.2 | NA | NA | NA |
| AB1.13 CAD pyr+ | NA | NA | NA | NA | 5.0 | NA | NA | NA |
| Controlled fermentation | | | | | | | | |
| AB1.13 CAD pyr+ | +++ | +++ | + | − | 0.2-0.5 | − | − | − |
| AB1.13.CAD/MTT/MFS#3 | NA | NA | NA | NA | 0.8 | NA | NA | NA |
| AB1.13 CAD+ FHB 2,5 | +++ | +++ | + | −/+ | 0.8 | − | − | + |
| N201 | +++ | − | + | − | 0.2 | − | − | −/+ |
| N201 CAD02 | ++++ | +++ | + | − | 1.0 | − | − | − |

From the Northern analysis it was concluded that the expression of the geners from the gene cluster showed low expression levels, or no expression was detected, or were below detection limits.

Example 5 Quantitative RT-PCR

Northern analysis revealed very low expression levels, most likely below the detection limit of the method. Therefore, quantitative RT-PCR was carried out using the Superscript III platinum One Step Quantitative RT-PCR kit (Life Technologies) to analyze the expression of the citB gene (see Table 6). A primer-probe combination for the citB gene was designed using the software Primer Express 2.0 (Applied Biosystems). To compare the expression level of citB with a highly expressed gene, also gpdA primers were designed. For the normalization of the citB and gpdA data, also a quantitative RT-PCR was carried out using 18S primers. The quantitative PCR was performed on the 7500 Fast Real time PCR system (Applied Biosystems). The total RNA isolated from biomass of fermentation experiments, which was used in the Northern analysis, was analyzed in this method. Also the total RNA used for the RNAseq experiment was analyzed and total RNA isolated from *A. niger* strains grown in a new shakeflask culture experiment was analyzed. In the normalized RT-qPCR results can been seen that the citB gene is induced in certain conditions. For the samples used for RNAseq RT-qPCR confirmed the RNAseq results.

Example 6 Genome Mining citB Gene Cluster

In table 7 the results of a genome mining effort of the citB gene cluster is given.
Sequences were obtained from NCBI. Alignments were performed using
BLASTX with a BLOSUM62 matrix and the default settings for BLASTX (http://www.ncbi.nlm.nih.gov/blast/bl2seq/wblast2.cgi).

TABLE 7

Blast results of genes from the CitB genome cluster

| Query | | | BLASTX best hits | | |
|---|---|---|---|---|---|
| Gene | Accession nr. | Description | Accession nr. | Strain | E value |
| An08g10860 | ang: ANI_1_24880 74 | sterigmatocystin biosynthesis fatty acid synthase subunit beta | GAA88112.1 | *Aspergillus kawachii* | 0 |
| | | | XP_002149767.1 | *Penicillium marneffei* | 0 |
| | | | XP_002340041.1 | *Talaromyces stipitatus* | 0 |
| | | | XP_002384436.1 | *Aspergillus flavus* | 0 |
| | | | XP_001827193.1 | *Aspergillus oryzae* | 0 |

TABLE 7-continued

Blast results of genes from the CitB genome cluster

| Query | | | BLASTX best hits | | |
|---|---|---|---|---|---|
| Gene | Accession nr. | Description | Accession nr. | Strain | E value |
| An08g10870 | ang: ANI_1_2490074 | 2-methylcitrate dehydratase | GAA88111.1 | Aspergillus kawachii | 0 |
| | | | XP_002384435.1 | Aspergillus flavus | 0 |
| | | | XP_001827192.1 | Aspergillus oryzae | 0 |
| An08g10880 | ang: ANI_1_2492074 | GAL4; GAL4-like Zn2Cys6 binuclear cluster DNA-binding domain; found in transcription regulators like GAL4 | GAA88110.1 | Aspergillus kawachii | 0 |
| | | | EDP52162.1 | Aspergillus fumigatus | E−127 |
| | | | XP_001259243.1 | Neosartorya fischeri | E−124 |
| | | | XP_001274697.1 | Aspergillus clavatus | E−122 |
| | | | AAD34561.1 | Aspergillus terreus | E−50 |
| An08g10920 | ang: ANI_1_1474074 | citrate synthase | NP_001142237.1 | Zea mays | 0 |
| | | | GAA88109.1 | Aspergillus kawachii | 0 |
| | | | XP_002384448.1 | Aspergillus flavus | E−164 |
| | | | XP_001827205.1 | Aspergillus oryzae | E−164 |
| | | | XP_002148678.1 | Penicillium marneffei | E−137 |
| An08g10930 | ang: ANI_1_2494074 | 3-oxoacyl-[acyl-carrier-protein] synthase | GAA88108.1 | Aspergillus kawachii | 0 |
| | | | XP_001827206.1 | Aspergillus oryzae | 0 |
| | | | XP_002384449.1 | Aspergillus flavus | 0 |
| | | | EFQ31023.1 | Glomerella graminicola | 0 |
| | | | XP_002836001.1 | Tuber melanosporum | 0 |
| An08g10970 | ang: ANI_1_2500074 | MFS multidrug transporter | GAA88107.1 | Aspergillus kawachii | 0 |
| | | | EHK20962.1 | Trichoderma virens | E−171 |
| | | | EGR44089.1 | Trichoderma reesei | E−168 |
| | | | EHK50986.1 | Trichoderma atroviride | E−167 |
| | | | XP_002376688.1 | Aspergillus flavus | E−166 |
| | | | XP_001820954.1 | Aspergillus oryzae | E−166 |
| An08g10980 | ang: ANI_1_2502074 | similarity to acetate regulatory DNA binding protein facB | GAA88106.1 | Aspergillus kawachii | 0 |
| | | | XP_001820955.2 | Aspergillus oryzae | E−132 |
| | | | XP_002376689.1 | Aspergillus flavus | E−123 |
| An08g10990 | ang: ANI_1_1484074 | dienelactone hydrolase family protein | GAA88105.1 | Aspergillus kawachii | E−109 |
| | | | EHY59914.1 | Exophiala dermatitidis | E−77 |
| | | | XP_002481994.1 | Talaromyces stipitatus | E−64 |
| | | | XP_002150690.1 | Penicillium marneffei | E−61 |

It appears that the genes as depicted in NP_001142237.1, GAA88109.1, XP_002384448.1, XP_001827205.1 and XP_002148678.1 can be considered to be orthologs of the *Aspergillus niger* citrate synthase.

Using the search tool Sybil on the AspGD website (Broad Institute) (http://aspgd.broadinstitute.org/cgi-bin/asp2_v3/shared/show_protein_cluster.cgi?site=asp2_v8) orthologous clusters from multiple genomes can be depicted as shown in FIG. 3.

The citrate synthase gene (An08g10920) was further used to search for the ortholog clusters in other *Aspergillus* genomes. As can be seen in FIG. 3, the "black *Aspergilli*", *A. niger* (2 genomes) *A. acidus*, *A. tubigensis* and *A. brasiliensis*, show similar clustering of the genes surrounding the citB gene, whereas the genomic region in *A. oryzae* and *A. flavus* only contain the citB (An08g10920) ortholog and the orthologs of An08g10880 and An08g10930. For *A. terreus* no corresponding gene cluster was found at all.

Example 7A Overexpression of the *A. niger* citB Gene in *Aspergillus niger*

To establish the overexpression of the citB gene in *A. niger*, a PCR generated copy of the gene was generated. For this purpose two sets of primers were generated as shown below. PCR amplification based on *A. niger* genomic DNA resulted in the isolation of PCR fragments from which the complete coding region of the citB gene could be isolated as a BsmBI-NcoI fragment.

```
Translation of citB genomic seq (1-1874)
Universal code
       BsmBI             citB-F3-ATG+BsmBI
5'-CGTCTCCCATGCCCGACATCGCATCCAAC-3'
      citB-F1-6
      5'-ATCACTATGCCCGACATCGC-3
    1        ATGCCCGACATCGCATCCAACGGTGCCCGCAACGGCGCCTCCCAGAATGCAGAGACCAAG
    1          M  P  D  I  A  S  N  G  A  R  N  G  A  S  Q  N  A  E  T  K 61        CCAGAACCCCCCGTTCTCCATGTGGTAGACAGCCGCACGGGGAAGTACTTCCCCATCCCT
   21          P  E  P  P  V  L  H  V  V  D  S  R  T  G  K  Y  F  P  I  P
```

```
121       ATCGTGCGCAACGCCATCAACGCAAGCGAATTCAAGAAACTCAAGTCCCCCGAGGATCCC
41           I  V  R  N  A  I  N  A  S  E  F  K  K  L  K  S  P  E  D  P

181       GCACATCCTGAAGATCAGAACGAGCAGGGCATCCGGGTGTTGACCCCGGATACTCCAAC
61           A  H  P  E  D  Q  N  E  Q  G  I  R  V  F  D  P  G  Y  S  N

241       ACGGCTGTTAGTGAGAGCCAGGTTACCTACATgtgcgttttctctgctgcataggattga
81           T  A  V  S  E  S  Q  V  T  Y  I 301       tcatggcgaagagtaactgataacggggcgcagCGATGGCCTGAAGGGAACCATCCAGTA
                                            D  G  L  K  G  T  I  Q  Y 361       CCGTGGTTACAACATCGAGGATATTGTGGGCAAGAAGAAGTTTATTGACACGGCACACCT
121          R  G  Y  N  I  E  D  I  V  G  K  K  K  F  I  D  T  A  H  L 421       GCTCATTTGGGAGAATGGCCGACGCCGGAACAGGCCAAATCTCTGCAGGAGAAGCTCTC
141          L  I  W  G  E  N  P  T  P  E  Q  A  K  S  L  Q  E  K  L  S 481       CAGCGTACCTGTCCTGGATGAATCCGTCTTCAAAGTCATTCAGGCATTCCCgtaagtttc
161          S  V  P  V  L  D  E  S  V  F  K  V  I  Q  A  F  P 541       accctagttttagcctctagtcctttcccccacggtctaacggctccagTCCCAACTCGT
                                                                P  N  S 601       CCATTATCGGCATGATGATCGCCGCTCTGTCAGCTGTCCAGAGTACCCAGATGGATCGCA
200          S  I  I  G  M  M  I  A  A  L  S  A  V  Q  S  T  Q  M  D  R 661       TCCCCGCCCATGCGGCCAAGAACCTCTACTTGGGCAATCCTAAGGCCGTCGATGATGAGA
220          I  P  A  H  A  A  K  N  L  Y  L  G  N  P  K  A  V  D  D  E 721       TCGTCCGTCTGATGGGCTCGCTGTCCATGATCACCGCTGCTGTCTACTGCCACCATACCG
240          I  V  R  L  M  G  S  L  S  M  I  T  A  A  V  Y  C  H  H  T 781       GACGGGAATTTACCCCGCCACGTCCGGAACTTTCCTACATCGAGAACTTCCTGTTGATGA
260          G  R  E  F  T  P  P  R  P  E  L  S  Y  I  E  N  F  L  L  M 841       TGGGCCACGTCGAGTCTAGCACAGGACTGCCCAACCCCCAGTACGTCGACCGCATTGAGC
280          M  G  H  V  E  S  S  T  G  L  P  N  P  Q  Y  V  D  R  I  E 901       GTCTCTGGGTCCTCATTGCCGATCACGAGATGACCTGCTCGACTGCCGCGTTCTTGCAGA
300          R  L  W  V  L  I  A  D  H  E  M  T  C  S  T  A  A  F  L  Q 961       CAGCCTCCTCCCTGCCGGATGTATTCTCCTGTATGATCTCCGCACTGTCGGCGCTCTATG
320          T  A  S  S  L  P  D  V  F  S  G  M  T  S  A  L  S  A  L  Y 1021      GTCCGCTGCATGGTGGGGCCATTGAGGTAGCTTACAAAAATTTCGAGGAGATTGGCTCGG
340          G  P  L  H  G  G  A  I  E  V  A  Y  K  N  F  E  E  I  G  S 1081      TTGAGAACGTCGCGGCCAAGATAGAACGTGTCAAGGCCGGTAAGGAGCGTCTGTACGGCT
360          V  E  N  V  A  A  K  I  E  R  V  K  A  G  K  E  R  L  Y  G 1141      ACGGTCACCGCATCTACCGCGTCACAGACCCGCGCTTCATCTTCATCCGCCAGATCTTAG
380          Y  G  H  R  I  Y  R  V  T  D  P  R  F  I  F  I  R  Q  I  L 1201      ACGAGTTGAAGGAAGAGATCGCCCGGAACCCGCTGCTGAAGGTGGCGTTTGAGGTGGACC
400          D  E  L  K  E  E  I  A  R  N  P  L  L  K  V  A  F  E  V  D 1261      GCGTCGCCTCGGAGGATGAATACTTTGTCACCCGGAAGCTACGGCCCAACGCCGATCTCT
420          R  V  A  S  E  D  E  Y  F  V  T  R  K  L  R  P  N  A  D  L 1321      TTGCGGCGCTTGTGTATAGTGCCATgtaggccttccgtgaagtagtggtttcagacatca
440          F  A  A  L  V  Y  S  A  M 1381      gacccgctaacgcattgggaatagGGGCTTCCCGACTGAGTTTATTCTACCGTTGTCGCT
                                      G  F  P  T  E  F  I  L  P  L  S  L 1441      GTTGTCCCGCACGCAGGGATTCATGGCCCACTGGAAAGAAGCCATGTgtaagtggcccat
                L  S  R  T  Q  G  F  M  A  H  W  K  E  A  M 1501      tttgccactgcgtgtcccactotgagactaacgatgtgacagCGAGCACGGCACGTATCT
                                                      S  S  T  A  R  I 3'-ATCCGTC
                                                              3'-ATCCGTC
1561      GGCGGCCCGGCCAGATCTACACCGGACACTTGAACCGCGAGATGGCGTAGgtctaggag
520          W  R  P  G  Q  I  Y  T  G  H  L  N  R  E  M  A  *
```

-continued

```
                    NcoI              citB-R1 + NcoI
              AAAGCGAGAGTGGTACC-5'
                  citB-R1 + 1631
              AAAGCGAGAT-5'
1621          tttcgctctcatcggtg Overview primers
citB-F1-6          ATCACTATGCCCGACATCGC 50.6° C.

citB-F3-ATG + BsmBI    CGTCTCCCATGCCCGACATCGCATCCAAC 63.3° C.

citB-R1 + 1631     TGAGAGCGAAACTGCCTA 54.1° C.

citB-R1 + NcoI     CCATGGTGAGAGCGAAACTGCCTA 54.1° C.

citB-F3-ATG + BsmBI; 29-mer; 63.3° C.
5'-CGTCTCCCATGCCCGACATCGCATCCAAC-3' Primer
         ||||||  |||||||||||||||
3'-       TACGGGCTGTAGCGTAGGTTG-5' (21) Strand - citB-F1-6; 20-mer; 50.6° C.
5'-ATCACTATGCCCGACATCGC-3' Primer
           |||||||||  |||||
3'-        TACGGGCTGTAGCG-5' (14) Strand - citB-R1 + NcoI; 24-mer; 54.1° C.
5'-CCATGGTGAGAGCGAAACTGCCTA-3' Primer
     |  || ||||||  ||||||||||
3'-GTGGCTACTCTCGCTTTGACGGAT-5' (1614) Strand + citB-R1 + 1631; 18-mer; 54.1° C.
5'-TGAGAGCGAAACTGCCTA-3' Primer
   |||||||||  |||||  |||
3'-ACTCTCGCTTTGACGGAT-5' (1614) Strand +
```

The resulting BsmBI-NcoI fragment was cloned in the NcoI site of the *Aspergillus* expression vector pABgpd-I (FIG. 5). In a derivative of this vector also the *Aspergillus* auxotrophic selection marker pyrG was cloned.

Subsequently, an itaconic acid producing *Aspergillus niger* strain (Li, A. et al., Appl. Microbial. Biotechnol. 1-11, 2013; Li, A. et al. Fungal Genet. Biol. 48:602-611, 2011) was transformed with the citB overexpression vector. PyrG+ transformants were purified by single colony purification and retested for their PyrG+ phenotype. Several PyrG+ transformants were subsequently cultured in shake flask cultures from which the expression of the introduced citB expression cassette was analyzed using quantitative RT-PCR. In addition Southern analysis was carried out to confirm the presence of intact copies of the expression cassette in the transformants.

The transformants with the highest copy number and/or highest citB expression level were cultured in batch fermentations. Following up, the media samples were analyzed by HPLC for the amount of itaconic acid produced by the *A. niger* transformants. Besides this, other organic acids like citric acid and oxalic acid were also analyzed due to their relevance in the assumed itaconate production pathway in *Aspergillus niger*.

Cultivation Conditions

For the screening and selection of *A. niger* transformants, our previously developed screening assay was used (Li et al. 2012). After seeding, all plates were directly sealed with an oxygen permeable film (Sealing film sterile, breathable M20193, Dispolab the Netherlands), placed in a plastic air bag and cultivated in a 33° C., 850 rpm incubator (Microtron, Infos-ht) for 60 h. In the end of the cultivation, culture medium was harvested and used for HPLC analysis.

For shakeflask and controlled batch fermentations, the production medium (M12) described in our previous study (Li et al. 2012) with the following composition was used (per liter): 100 g glucose, 2.36 g $(NH_4)_2SO_4$, 0.11 g $KH_2PO_4$, 0.5 g $MgSO_4.7H_2O$, 0.6 mg $FeSO_4.7H_2O$, 2.5 mg $CuSO_4.5H_2O$, 0.6 mg $ZnSO_4.7H_2O$, 0.074 g NaCl, and 0.13 g $CaCl_2.2H_2O$. This medium was prepared in demineralised water. The production medium M12+Cu has an extra addition of 2.5 mg $CuSO_4.5H_2O$ (0.01 mM). For controlled fermentation pre-cultures were prepared by inoculation of 106 spores per milliliter in 2×100-mL production medium in two 500 mL baffled Erlenmeyer flasks. After 64 h at 33° C. and shaking at 125 rpm, the pre-cultures were used for inoculation of the fermenters. Fermentations were performed in 5-L Benchtop Fermentors (BioFlo 3000, New Brunswick Scientific Co., Inc.) at 33° C. The basic pH regime was initiated at 3.5 and subsequently regulated at 2.3, by addition of 4 M KOH (base). Struktol was applied as antifoam agent (Schill & Seilacher) in all cultures throughout the fermentation. Air was used for sparging the bioreactor at a constant flow of 0.25 vvm [(vol.liquid)$^{-1}$ min$^{-1}$]. The solubility of oxygen in the medium is around 225 µMol at 33° C. Pure air sparging was calibrated as 100% D.O., whereas pure nitrogen sparging was calibrated as 0% D.O. In the basic D.O. regime, D.O. was set at 100% from the start of the fermentation. As soon as due to mycelial growth D.O. levels dropped below 25%, stirrer agitation was increased automatically to maintain D.O. at 25%. For studying the influence of oxygen availability on itaconic acid production, D.O was fixed throughout the whole fermentation at 10, 15, 20, and 25% for strain N201 CAD and at 5, 10, and 20% for strain HBD 2.5. The different percentage of D.O. was obtained by varying the mixture of air/nitrogen in the inlet gas.

The cultured transformants were analysed for the presence of citric acid and derivatives in microplate cultures.

Based on these cultures several transformants producing increased itaconic acid levels were selected for further research.

Based on the results obtained in microplate screening a selection of transformants was grown in shakeflask cultures as described by Li et al., 2012, 2013 and analysed for itaconic acid productivity and yield

| Strain | Itaconic acid Productivity (mg/L/hr) | Itaconic acid Yield (mg/g Glucose) Shake flask |
|---|---|---|
| culture | | |
| CAD | 7.8 | |
| CAD + citB#49 | 8.8 | |
| CAD + citB#53 | 11.4 | |
| CAD + citB#71 | 10.4 | |
| CAD + citB#84A | 8.7 | |
| CAD MFS/MTT#48 | 17.9 | |
| CAD MFS/MTT#49 | 31.2 | |
| CAD MFS/MTT#63 | 26.7 | |
| Controlled fermentation | | |
| CAD | 8.9 | 30 |
| CAD | 11.2 | |
| CAD + citB#53 | 15.4 | 42 |
| CAD MFS/MTT#8 | 20.9 | |
| CAD MFS/MTT#63 | 50.2 | |

As shown the introduction of the citB gene into an *A. niger* strain already expressing cadA resulted in increased productivity and yields of secreted itaconic acid.

Introduction of two previously identified organic acid transporters (MTT/MFS) as described in WO 2009/104958 and WO 2009/110796 in a single host strain also resulted in increased productivity of itaconic acid.

Example 7B. Overexpression of *A. niger* citB in a Host Strain Expressing all Three Genes of the Itaconic Acid Gene Cluster Strain Construction In a strain already simultaneously expressing the *A. terreus* cadA, mfsA and mttA genes, which genes and strains have been described in WO 2009/014437, WO 2009/104958 and WO 2009/110796 as shown in the table in Example 7A, above, (strains CADMFSMTT#63 or #49), the *A. niger* citB expression vector was introduced by cotransformation using the phleomycin resistance marker for transformant selection. From the resulting tranosformants strain CitB#99 was selected for further analysis Fermentation Conditions Controlled batch cultivations were performed in 5 liter batch fermentors (BioFlo 3000, New Brunswick Scientific Co., Inc.). The production medium, as published earlier by An Li et al., 2012, consists of the following (per liter): 100 g glucose, 2.36 g $(NH_4)_2SO_4$, 0.11 g $KH_2PO_4$, 0.5 g $MgSO_4.7H_2O$, 0.6 g $FeSO_4.7H_2O$, 2.5 mg $CuSO_4.5H_2O$, 0.6 mg $ZnSO_4.7H_2O$, 0.074 g NaCl and 0.13 g $CaCl_2.2H_2O$. This medium was prepared in demineralized water. Inoculum was prepared with $1.0·10^6$ spores/mL in 100 mL production medium in 500 mL baffled Erlenmeyer flasks. Inoculum was then incubated at 33° C. for 72 hours and shaking at 125 rpm. Temperature was kept stable at 33° C. throughout the fermentation. The fermentation starts with a pH of 3.5 and afterwards is kept stable at 2.3 by addition of 4M KOH. The bioreactor was sparged with a constant flow of 1.25 vvm [(vol.liquid)$^{-1}$ min$^{-1}$] air. The system was calibrated as 100% D. O. by sparging the bioreactor with pure air whereas pure nitrogen sparging was calibrated as 0% D. O. Throughout the course of the fermentation the D. O. was kept at 20%, which is achieved by applying various mixtures of air and nitrogen in the inlet gas. Struktol (Schill & Seilacher) was used as antifoaming agent. Autosamples were taken every six hours using a 0.22 µM filter (Applikon Biotechnology, USA).

HPLC Analysis

Filter-sterilized fermentation samples were analyzed by high-performance liquid chromatography (HPLC) to quantify metabolites and assess organic acid production. Samples were loaded on a WATERS e2695 Separations Module outfitted with an Aminex HPX-87H column (Bio-Rad) and 5 mM $H_2SO_4$ as eluent. Metabolites were detected by a refractive index detector (WATERS 2414) and a dual-wavelength detector (WATERS UV/Vis 2489) simultaneously. Empower Pro was used as software for the processing of data (Empower 2 Software, copyright 2005-2008, Waters Corporation, Milford, Mass., USA).

Results

In order to compare the organic acid production capacity of the CitB #99 strain with the AB1.13 CAD+MTT+MFS strain, controlled batch fermentations were performed. The glucose consumption and organic acid production capacity of the two strains is depicted in FIG. 6 (CitB #99) and FIG. 7 (AB1.13 CAD+MTT+MFS). As can be seen in FIG. 6 and FIG. 7, CitB #99 produces more itaconic acid (higher yield) and has a higher production rate. CitB #99 produces itaconic acid up to 25 grams per liter and, unexpectedly, no citric acid. This shows that the conversion of citric acid to itaconic acid is very efficient in our transformed strain. Furthermore, the improved production rate of itaconic acid is a major step forwards; maximum yield is achieved after 5 days of fermentation, whereas the AB1.13 CAD+MTT+MFS strain needs 7 days to achieve maximum yield of around 12 grams per liter.

Example 7C Itaconic Acid Production on Crude Second Generation Feedstocks

Shakeflask Cultures

Cultivations in shakeflasks were performed in order to assess if the CitB #99 strain can grow on second generation feedstocks e.g. glycerol. For this experiment crude waste glycerol was acquired from a biodiesel production plant. In the biodiesel process a waste product containing glycerol as mayor carbon source is produced as waste product. The experiment was performed in 500 mL baffled Erlenmeyer shakeflasks with a volume of 100 mL. Medium was prepared by adding 10 mL of crude glycerol from the company to 90 mL demineralized water. Preculture was prepared by inoculating $1.0·10^6$ spores/mL in 100 mL production medium in 500 mL baffled Erlenmeyer flasks and grown overnight at 33° C. and shaking at 125 rpm. From this preculture 2 mL was used as inoculum.

Results

In order to assess if the CitB #99 strain can grow on second-generation feedstock, shakeflask cultivations were performed with glycerol as C-source (FIG. 8). The flasks were incubated at 33° C. for 216 hours. In FIG. 8 it can be seen that glycerol consumption starts after 96 hours together with the production of itaconic acid. The first 96 hours of incubation appear to be necessary for the organism to adapt to the environment. This phenomenon may partly be caused due to the fact that the preculture was grown on production medium, which has glucose as C-source, rather than glycerol. Production level of itaconic acid leads up to approximately 1.5 grams per liter indicating that this strain can produce itaconic acid when grown on a second generation feedstocks, such as crude glycerol. For future purposes the CitB #99 strain can be cultivated in controlled batch fermentations to achieve optimal itaconic acid production.

Example 8 Overexpression of the *A. niger* citB Gene and *A. terreus* cadA Gene in *Saccharomyces cerevisiae*

For the overexpression of *A. niger* citB and *A. terreus* cadA in *Saccharomyces cerevisiae* an expression vector was synthesized at Geneart (Life technologies Europe, Bleiswijk, The Netherlands) containing two expression cassettes. The *Saccharomyces* codon optimized gene encoding the *A. niger* CitB protein was inserted between the gpd promotor and CYC1 terminator of *Saccharomyces*. The *Saccharomyces* codon optimized gene encoding the *A. terreus* CAD protein was inserted between the tef promotor and ADH1 terminator of *Saccharomyces*. In between both expression cassettes the URA3 marker was placed in antisense. The complete fragment was surrounded with URA3 flanking regions for integration at the URA3 locus in *Saccharomyces cerevisiae*.

```
5' URA3 flank-GPD promoter-citB gene (codon optimized for Saccharomyces
cerevisiae)-CYC1 terminator-URA3 marker-TEF promoter-CAD gene (codon
optimized for Saccharomyces cerevisiae)-ADH1 terminator-3' URA3 flank
        NotI
    1   GCGGCCGCGATAAGTTTTGACCATCAAAGAAGGTTAATGTGGCTGTGGTTTCAGGGTCCA

61   TAAAGCTTTCAGTTTATCATTATCAATACTCGCCATTTCAAAGAATACGTAAATAATTAA

121   TAGTAGTGATTTTCCTAACTTTATTTAGTCAAAAAATTAGCCTTTTAATTCTGCTGTAAC

181   CCGTACATGCCCAAAATAGGGGGCGGGTTACACAGAATATATAACATCGTAGGTGTCTGG

241   GTGAACAGTTTATTCCTGGCATCCACTAAATATAATGGAGCCCGCTTTTTAAGCTGGCAT

301   CCAGAAAAAAAAAGAATCCCAGCACCAAAATATTGTTTTCTTCACCAACCATCAGTTCAT

361   AGGTCCATTCTCTTAGCGCAACTACAGAGAACAGGGGCACAAACAGGCAAAAAACGGGCA

421   CAACCTCAATGGAGTGATGCAACCTGCCTGGAGTAAATGATGACACAAGGCAATTGACCC

481   ACGCATGTATCTATCTCATTTTCTTACACCTTCTATTACCTTCTGCTCTCTCTGATTTGG

541   AAAAAGCTGAAAAAAAAGGTTGAAACCAGTTCCCTGAAATTATTCCCCTACTTGACTAAT

601   AAGTATATAAAGACGGTAGGTATTGATTGTAATTCTGTAAATCTATTTCTTAAACTTCTT

661   AAATTCTACTTTTATAGTTAGTCTTTTTTTAGTTTTAAAACACCAGAACTTAGTTTCGA

XbaI
  721   CGGATTCTAGAATGCCAGATATTGCTTCTAATGGTGCTAGAAATGGTGCTTCTCAAACG
                     M  P  D  I  A  S  N  G  A  R  N  G  A  S  Q  N

781   CTGAAACAAAACCAGAACCACCAGTTTTACACGTTGTTGATTCAAGAACTGGTAAGTACT
  260    A  E  T  K  P  E  P  P  V  L  H  V  V  C  S  R  T  G  K  Y

841   TCCCAATCCCAATCGTTAGAAATGCTATTAACGCCTCCGAGTTCAAGAAGTTGAAATCTC
  280    F  P  I  P  I  V  R  N  A  I  N  A  S  E  F  K  K  L  K  S

901   CAGAAGATCCAGCTCATCCAGAAGATCAAAACGAACAAGGTATCAGAGTTTTCGATCCAG
  300    P  E  D  P  A  H  P  E  D  Q  N  E  Q  G  I  R  V  F  D  P

961   GTTACTCTAATACCGCTGTTTCTGAATCTCAAGTTACCTACATTGATGGTTTGAAGGGTA
  320    G  Y  S  N  T  A  V  S  E  S  Q  V  T  Y  I  D  G  L  K  G

1021   CTATCCAATACAGAGGTTACAACATCGAAGATATCGTCGGTAAGAAGAAGTTCATTGATA
  340    T  I  Q  Y  R  G  Y  N  I  E  D  I  V  G  K  K  K  F  I  D

1081   CCGCCCATTTGTTGATTTGGGGTGAATGGCCAACTCCAGAACAAGCTAAATCATTGCAAG
  360    T  A  H  L  L  I  W  G  E  W  P  T  P  E  Q  A  K  S  L  Q

1141   AAAAGTTGTCCTCCGTTCCAGTTTTGGATGAATCTGTTTTCAAGGTTATTCAAGCCTTCC
  380    E  K  L  S  S  V  P  V  L  D  E  S  V  F  K  V  I  Q  A  F

1201   CACCAAACTCCTCTATTATTGGTATGATGATTGCTGCTTTGTCCGCTGTTCAATCTACTC
  400    P  P  N  S  S  I  I  G  M  M  I  A  A  L  S  A  V  Q  S  T

1261   AAATGGATAGAATACCAGCTCATGCTGCTAAGAACTTGTATTTGGGTAATCCAAAAGCCG
  420    Q  M  D  R  I  P  A  H  A  A  K  N  L  Y  L  G  N  P  K  A

1321   TTGATGACGAAATCGTTAGATTGATGGGTTCCTTGTCTATGATTACTGCTGCTGTTTACT
  440    V  D  D  E  I  V  R  L  M  G  S  L  S  M  I  T  A  A  V  Y

1381   GTCATCATACCGGTAGAGAATTTACTCCACCAAGACCAGAATTGTCCTACATCGAAAATT
  460    C  H  H  T  G  R  E  F  T  P  P  R  P  E  L  S  Y  I  E  N
```

```
                                                              -continued
1441 TCTTGTTGATGATGGGTCACGTCGAATCTTCTACTGGTTTGCCAAATCCACAATACGTTG
 480 F  L  L  M  M  G  H  V  E  S  S  T  G  L  P  N  P  Q  Y  V 1501 ACAGAATTGAAAGATTGTGGGTTTTGATTGCCGATCACGAAATGACTTGTTCTACTGCTG
 500 D  R  I  E  R  L  W  V  L  I  A  D  H  E  M  T  C  S  T  A 1561 CTTTCTTGCAAACTGCTTCTTCATTGCCAGATGITTTCTCTTGTATGATCTCTGCTTTGT
 520 A  F  L  Q  T  A  S  S  L  P  D  V  F  S  C  M  I  S  A  L 1621 CTGCATTATACGGTCCATTGCATGGTGGTGCTATTGAAGTTGCTTACAAGAACTTCGAAG
 540 S  A  L  Y  G  P  L  H  G  G  A  I  E  V  A  Y  K  N  F  E 1681 AAATCGGTTCCGTTGAAAATGTTGCTGCCAAAATCGAAAGAGTTAAGGCCGGTAAAGAAA
 560 E  I  G  S  V  E  N  V  A  A  K  T  E  R  V  K  A  G  K  E 1741 GATTATACGGTTACGGTCATAGAATCTACAGAGTTACTGATCCAAGATTCATCTTCATCA
 580 R  L  Y  G  Y  G  H  R  I  Y  R  V  T  D  P  R  F  I  F  I 1801 GACAAATCTTGGATGAATTGAAAGAAGAAATCGCCAGAAACCCTTTGTTGAAGGTTGCTT
 600 R  Q  I  L  D  E  L  K  E  E  I  A  R  N  P  L  L  K  V  A 1861 TTGAAGTTGATAGAGTCGCCTCTGAAGATGAATACTTCGTTACCAGAAAGTTAAGACCAA
 620 F  E  V  D  R  V  A  S  E  D  E  Y  F  V  T  R  K  L  R  P 1921 ACGCTGATTTGTTTGCTGCCTTGGTTTATTCTGCTATGGGTTTTCCAACCGAGTTCATCT
 610 N  A  D  L  F  A  A  L  V  Y  S  A  M  G  F  P  T  E  F  I 1981 TGCCATTGTCTTTGTTGTCAAGAACCCAAGGTTTTATGGCCCATTGGAAAGAAGCTATGT
 660 L  P  L  S  L  L  S  R  T  Q  G  F  M  A  H  W  K  E  A  M 2041 CATCTACTGCTAGAATTTGGAGACCTGGTCAAATCTATACTGGTCACTTGAATAGAGAAA
 680 S  S  T  A  R  I  W  R  P  G  Q  I  Y  T  G  H  L  N  R  E XhoI
2101 TGGCTTAACTCGAGTCATGTAATTAGTTATGTCACGCTTACATTCACGCCCTCCCCCCAC
 700 M  A  *

2161 ATCCGCTCTAACCGAAAAGGAAGGAGTTAGACAACCTGAAGTCTAGGTCCCTATTTATTT

2221 TTTTATAGTTATGTTAGTATTAAGAACGTTATTTATATTTCAAATTTTTCTTTTTTTTCT

2281 GTACAGACGCGTGTACGCATGTAACATTATACTGAAAACCTTGCTTGAGAAGGTTTTGGG

BamHI
2341 ACGCTCGAAGGCTTTAATTTGCGGCCGGTGGATCCTTTTCTTTCCAATTTTTTTTTTTTC

2401 GTCATTATAAAAATCATTACGACCGAGATTCCCGGGTAATAACTGATATAATTAAATTGA

*  N  Q
     TCGAGATTAAACACTCAAATCATATGTACGTAAATGAATATTATGTCAAAAAATCAAAAC
2461 AGCTCTAATTTGTGAGTTTAGTATACATGCATTTACTTATAATACAGTTTTTTAGTTTTG

Q  G  C  R  R  L  Y  A  E  W  G  A  K  R  Y  R  E  G  E  V
     GACCGGCGTAGAAGAGTTTATACGAAGGGTCGGACGAAAAGACATTGCAAGTGGGAGATG
2521 CTGGCCGCATCTTCTCAAATATGCTTCCCAGCCTGCTTTTCTGTAACGTICACCCTCTAC

K  A  D  R  G  K  A  F  L  G  R  G  V  I  I  I  D  S  G  T
     GAATCGTAGGGAAGGGAAACGTTTATCAGGAGAAGGTTGTTATTATTACAGTCTAGGACA
2581 CTTAGCATCCCTTCCCTTTGCAAATAGTCCTCTICCAACAATAATAATGICAGATCCTGT

S  V  V  D  D  V  T  R  Y  Q  Q  G  L  A  D  G  K  D  D  L
     TCTCTGGTGTAGTAGGTGCCAAGATATGACAACTGGGTACGCAGAGGGAACAGTAGATT
2641 AGAGACCACATCATCCACGGTTCTATACTGTTGACCCAATGCGTCTCCCTTGTCATCTAA

G  V  G  P  T  M  I  L  W  D  Y  G  E  D  R  G  G  M  D  R
     TGGGTGTGGCCCACAGTATTAGTTGGTTAGCATTGGAAGTAGAGAAGGTGGGTACAGAGA
2701 ACCCACACCGGGTGTCATAATCAACCAATCGTAACCTTCATCTCTTCCACCCATGTCTCT

Q  A  I  F  G  I  V  F  D  K  D  S  K  A  I  D  V  T  G  K
     AACTCGTTATTTCGGCTATTGTTTTAGAAACAGCGAGAAGCGTTACAGTTGTCATGGGAA
2761 TTGAGCAATAAAGCCGATAACAAAATCTTTGTCGCTCTTCGCAATGTCAACAGTACCCTT

T  Y  E  G  T  S  L  S  G  K  C  S  L  E  A  L  M  L  L  G
     TCATATAAGAGGTCATCTATCCCTCGGGAACGTACTGTTAAGACGATTGTAGTTTTCCGG
2821 AGTATATTCTCCAGTAGATAGGGAGCCCTTGCATGACAATTCTGCTAACATCAAAAGGCC

R  P  E  K  T  V  E  E  A  A  Q  K  L  G  S  V  I  G  P  G
     AGATCCAAGGAAACAATGAAGAAGACGGCGGACGAAGTTTGGCGATTGTTATGGACCCGG
```

```
                                        -continued
2881 TCTAGGTTCCTTTGTTACTTCTTCTGCCGCCTGCTTCAAACCGCTAACAATACCTGGGCC V   V   G   H   A   N   T   I   D   A   W   E   A   I   R   Y   V   G   A   S
     GTGGTGTGGCACACGTAAGCATTACAGACGGGTAAGACGATAAGACATATGTGGGCGTCT
2941 CACCACACCGTGTGCATTCGTAATGTCTGCCCATTCTGCTATTCTGTATACACCCGCAGA Y   Q   L   K   V   T   N   G   I   D   A   F   K   R   D   E   F   L   L   F
     CATGACGTTAAACTGACATAATGGTTACAGTCGTTTAAAAGACAGAAGCTTCTCATTTTT
3001 GTACTGCAATTTGACTGTATTACCAATGTCAGCAAATTTTCTGTCTTCGAAGAGTAAAAA N   Y   K   A   S   L   A   K   L   P   K   V   T   G   E   M   S   F   D   T
     TAACATGAACCGCCTATTACGGAAATCGCCGAATTGACACGGGAGGTACCTTTTTACTCA
3061 ATTGTACTTGGCGGATAATGCCTTTAGCGGCTTAACTGTGCCCTCCATGGAAAAATCAGT L   I   D   V   H   T   K   L   L   C   I   K   P   G   L   A   E   V   L   E
     GTTCTATAGGTGTACACAAAATCATTTGTTTAAAACCCTGGATTACGAAGTTGATTGAG
3121 CAAGATATCCACATGTGTTTTAGTAAACAAATTTTGGGACCTAATGCTTCAACTAACTC L   L   E   K   T   T   R   V   D   L   S   A   C   L   N   T   Q   K   E   H
     GTCATTAAGGAACCACCATGCTTGTAGGTTACTTCGTGTGTTCAAACAAACGAAAAGCAC
3181 CAGTAATTCCTTGGTGGTACGAACATCCAATGAAGCACACAAGTTTGTTTGCTTTTCGTG M   I   N   F   L   K   A   A   V   P   S   P   H   T   A   A   R   E   K   Y
     GTACTATAATTTATCGAACCGTCGTTGTCCTGATCCTACTCATCGTCGTGCAAGGAATAT
3241 CATGATATTAAATAGCTTGGCAGCAACAGGACTAGGATGAGTAGCAGCACGTTCCTTATA T   A   K   S   M
     ACATCGAAAGCTGTA
3301 TGTAGCTTTCGACATGATTTATCTTCGTTTCCTGCAGGTTTTTGTTCTGTGCAGTTGGGT

3361 TAAGAATACTGGGCAATTTCATGTTTCTTCAACACTACATATGCGTATATATACCAATCT

3421 AAGTCTGTGCTCCTTCCTTCGTTCTTCCTTCTGTTCGGAGATTACCGAATCAAAAAAATT

EcoRI
3481 TCAAAGAAACCGAAATCAAAAAAAGAATAAAAAAAAAATGATGAATTGAAGAATTCTTA

3541 CCCATAAGGTTGTTTGTGACGGCGTCGTACAAGAGAACGTGGGAACTTTTTAGGCTCACC

3601 AAAAAAGAAAGAAAAAATACGAGTTGCTGACAGAAGCCTCAAGAAAAAAAAAATTCTTCT

3661 TCGACTATGCTGGAGGCAGAGATGATCGAGCCGGTAGTTAACTATATATAGCTAAATTGG

3721 TTCCATCACCTTCTTTTCTGGTGTCGCTCCTTCTAGTGCTATTTCTGGCTTTTCCTATTT

3781 TTTTTTTTCCATTTTTCTTTCTCTCTTTCTAATATATAAATTCTCTTGCATTTTCTATTT

3841 TTCTCTCTATCTATTCTACTTGTTTATTCCCTTCAAGGTTTTTTTTAAGGAGTACTTGT

XbaI
3901 TTTTAGAATATACGGTCAACGAACTATAATTAACTAAACTCTAGAATGACCAAGCAATCC
                                                       M   T   K   Q   S

3961 GCTGATTCTAATGCTAAATCTGGTGTTACCGCTGAAATTTGTCATTGGGCTTCTAATTTG
1321  A   D   S   N   A   K   S   G   V   T   A   E   I   C   H   W   A   S   N   L

4021 GCCACCGATGATATTCCATCTGATGTTTTGGAAAGAGCCAAGTACTTGATCTTGGATGGT
1341  A   T   D   D   I   P   S   D   V   L   E   R   A   K   Y   L   I   L   D   G

4081 ATTGCTTGTGCTTGGGTTGGTGCTAGAGTTCCATGGTCTGAAAAGTATGTTCAAGCTACC
1361  I   A   C   A   W   V   G   A   R   V   P   W   S   E   K   Y   V   Q   A   T

4141 ATGTCTTTTGAACCACCAGGTGCTTGTAGAGTTATTGGTTATGGTCAAAAATTGGGTCCA
1381  M   S   F   E   P   P   G   A   C   R   V   I   G   Y   G   Q   K   L   G   P

4201 GTTGCTGCTGCTATGACTAATTCTGCTTTTATTCAAGCCACCGAATTGGATGATTACCAT
1401  V   A   A   A   M   T   N   S   A   F   I   Q   A   T   E   L   D   D   Y   H

4261 TCTGAAGCTCCATTGCATTCTGCTTCTATAGTTTTGCCAGCTGTTTTTGCTGCTTCTGAA
1421  S   E   A   P   L   H   S   A   S   I   V   L   P   A   V   F   A   A   S   E

4321 GTTTTGGCTGAACAAGGTAAAACCATCTCCGGTATTGATGTTATTTTGGCTGCTATCGTT
1441  V   L   A   E   Q   G   K   T   I   S   G   I   D   V   I   L   A   A   I   V

4381 GGTTTCGAATCTGGTCCAAGAATTGGTAAAGCTATCTACGGTTCTGACTTGTTGAACAAT
1461  G   F   E   S   G   P   R   I   G   K   A   I   Y   G   S   D   L   L   N   N
```

```
4491 GGTTGGCATTGTGGTGCTGTTTATGGTGCTCCAGCTGGTGCTTTGGCTACTGGTAAGTTG
1481  G   W   H   C   G   A   V   Y   G   A   P   A   G   A   L   A   T   G   K   L

4501 TTGGGTTTGACTCCAGATTCTATGGAAGATGCTTTGGGTATTGCATGTACTCAAGCTTGT
1501  L   G   L   T   P   D   S   M   E   D   A   L   G   I   A   C   T   Q   A   C

4561 GGTTTGATGTCTGCTCAATATGGTGGTATGGTTAAGAGAGTTCAACACGGTTTTGCTGCA
1521  G   L   M   S   A   Q   Y   G   G   M   V   K   R   V   Q   H   G   F   A   A

4621 AGAAATGGTTTGTTGGGTGGTTTGTTGGCTTATGGTGGTTATGAAGCTATGAAGGGTGTA
1541  R   N   G   L   L   G   G   L   L   A   Y   G   G   Y   E   A   M   K   G   V

4681 TTGGAAAGATCTTACGGTGGTTTCTTGAAGATGTTCACTAAGGGTAATGGTAGAGAACCA
1561  L   E   R   S   Y   G   G   F   L   K   M   F   T   K   G   N   G   R   E   P

4741 CCATACAAAGAAGAAGAAGTTGTTGCTGGTTTGGGTTCTTTTTGGCATACTTTCACCATC
1581  P   Y   K   E   E   E   V   V   A   G   L   G   S   F   W   H   T   F   T   I

4801 AGAATCAAGTTGTATGCTTGTGCGGTTTGGTTCATGGTCCAGTTGAAGCTATTGAAAAG
1601  R   I   K   L   Y   A   C   C   G   L   V   H   G   P   V   E   A   I   E   K

4861 TTGCAAAGAAGATACCCAGAATTATTGAACAGAGCCAACTTGTCCAACATCAGACATGTT
1621  L   Q   R   R   Y   P   E   L   L   N   R   A   N   L   S   N   I   R   H   V

4921 TACGTTCAATTGTCTACCGCCTCTAATTCTCATTGTGGTTGGATTCCAGAAGAAAGACCA
1641  Y   V   Q   L   S   T   A   S   N   S   H   C   G   W   I   P   E   E   R   P

4981 ATTTCTTCTATTGCCGGTCAAATGTCCGTTGCTTACATTTTGGCTGTTCAATTGGTTGAC
1661  I   S   S   I   A   G   Q   M   S   V   A   Y   I   L   A   V   Q   L   V   D

5041 CAACAATGTTTGTTGGCCCAATTCTCCGAATTTGATGACAATTTGGAAAGACCAGAAGTT
1681  Q   Q   C   L   L   A   Q   F   S   E   F   D   D   N   L   E   R   P   E   V

5101 TGGGATTTGGCTAGAAAAGTTACTCCATCCCACTCCGAAGAATTTGATCAAGATGGTAAC
1701  W   D   L   A   R   K   V   T   P   S   H   S   E   E   F   D   Q   D   G   N

5161 TGTTTGTCCGCTGGTAGAGTTAGAATTGAGTTCAACGATGGTTCCTCTGTTACCGAAACT
1721  C   L   S   A   G   R   V   R   I   E   F   N   D   G   S   S   V   T   E   T

5221 GTTGAAAAACCATTGGGTGTCAAAGAACCTATGCCAAACGAAAGAATCTTGCACAAGTAT
1741  V   E   K   P   L   G   V   K   E   P   M   P   N   E   R   I   L   H   K   Y

5281 AGAACTTTGGCTGGTTCTGTTACCGATGAATCAAGAGTCAAAGAAATCGAAGATTTGGTC
1761  R   T   L   A   G   S   V   T   D   E   S   R   V   K   E   T   E   D   L   V

5341 TTGTCCTTGGATAGATTGACTGATATTACCCCTTTGTTGGAATTATTGAATTGCCCAGTT
1781  L   S   L   D   R   L   T   D   I   T   P   L   L   E   L   L   N   C   P   V

XhoI
5401 AAGTCCCCATTGGTCTAACTCGAGGCGAATTTCTTATGATTTATGATTTTTATTATTAAA
1801  K   S   P   L   V   *

5461 TAAGTTATAAAAAAAATAAGTGTATACAAATTTTAAAGTGACTCTTAGGTTTTAAAACGA

5521 AAATTCTTATTCTTGAGTAACTCTTTCCTGTAGGTCAGGTTGCTTTCTCAGGTATAGCAT

5581 GAGGTCGCTCTTATTGACCACACCTCTACCGGCATGCCGAGCAAATGCCTGCAAATCGCT

5641 CCCCATTTCACCCAATTGTAGATATGCTAACTCCAGCAATGAGTTGATGAATCTCGGTGT

5701 GTATTTTATGTCCTCAGAGGACAACACCTGTTGTAATCGTTCTTCCACACTCATGGCCTT

NotI
5761 TATAAAAAGGAACTATCCAATACCTCGCCAGAACCAAGTAACAGTATTTTGCGGCCGC
```

The citB expression fragment was isolated from the synthesized vector using BamHI-SstI and cloned into the pFL61 yeast expression vector (ATCC77215; http://www.l-gcstandards-atcc.org/Products/All/77215.aspx; Minet M. et al. Complementaton of Saccharomyces cerevisiae auxotrophic mutants by Arabidopsis thaliana cDNA. Plant J. 2: 417-422, 1992), which was digested with BamHI and SstI. The cadA expression fragment was isolated using Acc651-EcoRI and cloned into the pFL61 yeast expression vector. The resulting citB and cadA expression vectors were transformed to the Saccharomyces cerevisiae strain CEN.PK113-5D using the electroporation protocol as described in (Transformation of commercial baker's yeast strains by electroporation., Gysler et al., Biotechnology Techniques Vol 4 No 4 285-290 (1990)) The yeast transformants were purified by single colony purification and analyzed with PCR for the presence of the expression vector. Subsequently, the transformants carrying citB or cadA genecopies were cultured in microtitreplate cultures under aerobic and anaerobic conditions and analyzed for the organic acid production using HPLC. In cadA expressing strains under both anaerobic and aerobic conditions itaconic acid production was detected in the culture medium.

The invention claimed is:

1. A method for producing itaconic acid which method comprises modifying a eukaryotic host cell wherein said modifying consists of providing said host cell with both a nucleic acid that expresses a gene encoding a citric acid synthase that lacks a signal for expression in the mitochondrion, wherein the citric acid synthase is that encoded by an *A. niger* gene designated An08g10920 (SEQ ID NO: 18), or An01g09940 (SEQ ID NO: 50), or An09g03570 (SEQ ID NO: 49), or is an ortholog thereof, wherein the ortholog is a protein that has citric acid synthase activity and a percentage identity of at least 95% with that encoded by An08g10920 (SEQ ID NO: 18), or An01g09940 (SEQ ID NO: 50) or An09g03570 (SEQ ID NO: 49); and with a nucleic acid that expresses a gene encoding cis-aconitic acid decarboxylase (CAD); and culturing said eukaryotic host cell.

2. The method of claim 1, wherein said modifying is effected by transforming the host cell with a vector comprising said nucleic acid that expresses sequence encoding said citric acid synthase and a vector comprising said nucleic acid that expresses sequence encoding CAD.

3. The method of claim 1, wherein said host cell is a fungus or a yeast or a plant or algal cell.

4. The method of claim 1, wherein said host cell is selected from the group of *Aspergillus* spp., *Neurospora* spp., *Sclerotina, Gibberella, Coniothyrium, Psiticum, Magnaporthe, Podospora, Chaetomium, Phaeosphaeria, Botryotinia, Neosartorya, Pyrenophora, Panicum, Aureococcus, Penicillium, Trichoderma, Sordaria, Colleotrichum, Verticillium, Arthrobotrys, Nectria, Leptosphaeria, Fusarium, Glomerella, Geomyces, Myceliophthora, Pichia, Saccharomyces* spp., *Zygosaccharomyces, Schizosaccharomyces pombe, Kluyveromyces* spp., *Yarrowia lipolytica, Monascus* spp., *Penicillium* spp., *Hansenula* spp., *Torulaspora delbrueckii, Hypomyces* spp., *Dotatomyces* spp., *Issatchenko orientalis, Phoma* spp., *Eupenicillium* spp., *Gymnoascus* spp., *Pichia labacensis, Pichia anomala, Wickerhamomyces anomalus, Candida cariosilognicola, Paecilomyces virioti, Scopulariopsis brevicaulis, Brettanomyces* spp., *Dekkera bruxellensis, Dekkera anoma* and *Trichoderma* spp.

* * * * *

SEQUENCE LISTING

<160> NUMBER OF SEQ ID NOS: 86

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
tgttgtcgcc gtagccgagc                                               20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
agctcctccc caaggctccc                                               20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gcgacgcggt ccacctcaaa                                               20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gcacaggact gcccaacccc                                               20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gcttcgcggc ccatactgct                                               20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
tgaagctgcc aacaccccgc                                               20

<210> SEQ ID NO 7
<211> LENGTH: 20
<212> TYPE: DNA
<213> ORGANISM: Artificial Sequence -continued

```
<220> FEATURE:
<223> OTHER INFORMATION: primer

<400> SEQUENCE: 7
gatggacggc cacccactgc                                               20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
tgcgctccct tcagcagcac                                               20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
gcaaagggtg ccaggccgat                                               20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ctgggtgctg gtcatcgcgg                                               20

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
ggtcttagcc gagcaaggc                                                19

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
gcgacactca tctgccctg                                                19

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
atcgagacct acgaggaggg                                               20
```

-continued

```
<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
ccgggagttc ctgcgaagg                                                    19

<210> SEQ ID NO 15
<211> LENGTH: 29
<212> TYPE: DNA
<213> ORGANISM: Artificial Sequence
<220> FEATURE:
<223> OTHER INFORMATION: citB-F3-ATG+BsmBI primer

<400> SEQUENCE: 15
cgtctcccat gcccgacatc gcatccaac                                         29

<210> SEQ ID NO 16
<211> LENGTH: 20
<212> TYPE: DNA
<213> ORGANISM: Artificial Sequence
<220> FEATURE:
<223> OTHER INFORMATION: citB-F1-6 primer

<400> SEQUENCE: 16
atcactatgc ccgacatcgc                                                   20

<210> SEQ ID NO 17
<211> LENGTH: 1620
<212> TYPE: DNA
<213> ORGANISM: Aspergillus niger
<220> FEATURE:
<221> NAME/KEY: CDS
<222> LOCATION: (1)..(272)
<220> FEATURE:
<221> NAME/KEY: CDS
<222> LOCATION: (334)..(531)
<220> FEATURE:
<221> NAME/KEY: CDS
<222> LOCATION: (590)..(1346)
<220> FEATURE:
<221> NAME/KEY: CDS
<222> LOCATION: (1406)..(1487)
<220> FEATURE:
<221> NAME/KEY: CDS
<222> LOCATION: (1543)..(1607)

<400> SEQUENCE: 17 atg ccc gac atc gca tcc aac ggt gcc cgc aac ggc gcc tcc cag aat        48
Met Pro Asp Ile Ala Ser Asn Gly Ala Arg Asn Gly Ala Ser Gln Asn
1               5                   10                  15 gca gag acc aag cca gaa ccc ccc gtt ctc cat gtg gta gac agc cgc        96
Ala Glu Thr Lys Pro Glu Pro Pro Val Leu His Val Val Asp Ser Arg
                20                  25                  30 acg ggg aag tac ttc ccc atc cct atc gtg cgc aac gcc atc aac gca       144
Thr Gly Lys Tyr Phe Pro Ile Pro Ile Val Arg Asn Ala Ile Asn Ala
            35                  40                  45 agc gaa ttc aag aaa ctc aag tcc ccc gag gat ccc gca cat cct gaa       192
Ser Glu Phe Lys Lys Leu Lys Ser Pro Glu Asp Pro Ala His Pro Glu
        50                  55                  60 gat cag aac gag cag ggc atc cgg gtg ttt gac ccc gga tac tcc aac       240
Asp Gln Asn Glu Gln Gly Ile Arg Val Phe Asp Pro Gly Tyr Ser Asn
65                  70                  75                  80
```

-continued

| | |
|---|---|
| acg gct gtt agt gag agc cag gtt acc tac at gtgcgttttc tctgctgcat<br>Thr Ala Val Ser Glu Ser Gln Val Thr Tyr Ile<br>                          85                          90 | 292 |
| aggattgatc atggcgaaga gtaactgata acggggcgca g c gat ggc ctg aag<br>                                                          Asp Gly Leu Lys<br>                                                                              95 | 346 |
| gga acc atc cag tac cgt ggt tac aac atc gag gat att gtg ggc aag<br>Gly Thr Ile Gln Tyr Arg Gly Tyr Asn Ile Glu Asp Ile Val Gly Lys<br>                    100                        105                        110 | 394 |
| aag aag ttt att gac acg gca cac ctg ctc att tgg gga gaa tgg ccg<br>Lys Lys Phe Ile Asp Thr Ala His Leu Leu Ile Trp Gly Glu Trp Pro<br>                    115                        120                        125 | 442 |
| acg ccg gaa cag gcc aaa tct ctg cag gag aag ctc tcc agc gta cct<br>Thr Pro Glu Gln Ala Lys Ser Leu Gln Glu Lys Leu Ser Ser Val Pro<br>                    130                        135                        140 | 490 |
| gtc ctg gat gaa tcc gtc ttc aaa gtc att cag gca ttc cc<br>Val Leu Asp Glu Ser Val Phe Lys Val Ile Gln Ala Phe Pro<br>                    145                        150                        155 | 531 |
| gtaagtttca ccctagtttt agcctctagt cctttccccc acggtctaac ggctccag t | 590 |
| ccc aac tcg tcc att atc ggc atg atg atc gcc gct ctg tca gct gtc<br>Pro Asn Ser Ser Ile Ile Gly Met Met Ile Ala Ala Leu Ser Ala Val<br>                    160                        165                        170 | 638 |
| cag agt acc cag atg gat cgc atc ccc gcc cat gcg gcc aag aac ctc<br>Gln Ser Thr Gln Met Asp Arg Ile Pro Ala His Ala Ala Lys Asn Leu<br>                    175                        180                        185 | 686 |
| tac ttg ggc aat cct aag gcc gtc gat gat gag atc gtc cgt ctg atg<br>Tyr Leu Gly Asn Pro Lys Ala Val Asp Asp Glu Ile Val Arg Leu Met<br>190                        195                        200                        205 | 734 |
| ggc tcg ctg tcc atg atc acc gct gct gtc tac tgc cac cat acc gga<br>Gly Ser Leu Ser Met Ile Thr Ala Ala Val Tyr Cys His His Thr Gly<br>                    210                        215                        220 | 782 |
| cgg gaa ttt acc ccg cca cgt ccg gaa ctt tcc tac atc gag aac ttc<br>Arg Glu Phe Thr Pro Pro Arg Pro Glu Leu Ser Tyr Ile Glu Asn Phe<br>                    225                        230                        235 | 830 |
| ctg ttg atg atg ggc cac gtc gag tct agc aca gga ctg ccc aac ccc<br>Leu Leu Met Met Gly His Val Glu Ser Ser Thr Gly Leu Pro Asn Pro<br>                    240                        245                        250 | 878 |
| cag tac gtc gac cgc att gag cgt ctc tgg gtc ctc att gcc gat cac<br>Gln Tyr Val Asp Arg Ile Glu Arg Leu Trp Val Leu Ile Ala Asp His<br>                    255                        260                        265 | 926 |
| gag atg acc tgc tcg act gcc gcg ttc ttg cag aca gcc tcc tcc ctg<br>Glu Met Thr Cys Ser Thr Ala Ala Phe Leu Gln Thr Ala Ser Ser Leu<br>270                        275                        280                        285 | 974 |
| ccg gat gta ttc tcc tgt atg atc tcc gca ctg tcg gcg ctc tat ggt<br>Pro Asp Val Phe Ser Cys Met Ile Ser Ala Leu Ser Ala Leu Tyr Gly<br>                    290                        295                        300 | 1022 |
| ccg ctg cat ggt ggg gcc att gag gta gct tac aaa aat ttc gag gag<br>Pro Leu His Gly Gly Ala Ile Glu Val Ala Tyr Lys Asn Phe Glu Glu<br>                    305                        310                        315 | 1070 |
| att ggc tcg gtt gag aac gtc gcg gcc aag ata gaa cgt gtc aag gcc<br>Ile Gly Ser Val Glu Asn Val Ala Ala Lys Ile Glu Arg Val Lys Ala<br>                    320                        325                        330 | 1118 |
| ggt aag gag cgt ctg tac ggc tac ggt cac cgc atc tac cgc gtc aca<br>Gly Lys Glu Arg Leu Tyr Gly Tyr Gly His Arg Ile Tyr Arg Val Thr<br>                    335                        340                        345 | 1166 |
| gac ccg cgc ttc atc ttc atc cgc cag atc tta gac gag ttg aag gaa<br>Asp Pro Arg Phe Ile Phe Ile Arg Gln Ile Leu Asp Glu Leu Lys Glu<br>350                        355                        360                        365 | 1214 |
| gag atc gcc cgg aac ccg ctg ctg aag gtg gcg ttt gag gtg gac cgc | 1262 |

```
Glu Ile Ala Arg Asn Pro Leu Leu Lys Val Ala Phe Glu Val Asp Arg
            370                 375                 380 gtc gcc tcg gag gat gaa tac ttt gtc acc cgg aag cta cgg ccc aac      1310
Val Ala Ser Glu Asp Glu Tyr Phe Val Thr Arg Lys Leu Arg Pro Asn
        385                 390                 395 gcc gat ctc ttt gcg gcg ctt gtg tat agt gcc atg taggcttcc            1356
Ala Asp Leu Phe Ala Ala Leu Val Tyr Ser Ala Met
            400                 405 gtgaagtagt ggtttcagac atcagacccg ctaacgcatt gggaatagg ggc ttc ccg    1414
                                                      Gly Phe Pro
                                                              410 act gag ttt att cta ccg ttg tcg ctg ttg tcc cgc acg cag gga ttc      1462
Thr Glu Phe Ile Leu Pro Leu Ser Leu Leu Ser Arg Thr Gln Gly Phe
            415                 420                 425 atg gcc cac tgg aaa gaa gcc atg t gtaagtggcc cattttgcca              1507
Met Ala His Trp Lys Glu Ala Met
430                 435 ctgcgtgtcc cactctgaga ctaacgatgt gacag cg  agc acg gca cgt atc       1559
                                          Ser Ser Thr Ala Arg Ile
                                                          440 tgg cgg ccc ggc cag atc tac acc gga cac ttg aac cgc gag atg gcg      1607
Trp Arg Pro Gly Gln Ile Tyr Thr Gly His Leu Asn Arg Glu Met Ala
        445                 450                 455 taggtctagg cag                                                        1620

<210> SEQ ID NO 18
<211> LENGTH: 458
<212> TYPE: PRT
<213> ORGANISM: Aspergillus niger

<400> SEQUENCE: 18

Met Pro Asp Ile Ala Ser Asn Gly Ala Arg Asn Gly Ala Ser Gln Asn
1               5                   10                  15

Ala Glu Thr Lys Pro Glu Pro Val Leu His Val Val Asp Ser Arg
            20                  25                  30

Thr Gly Lys Tyr Phe Pro Ile Pro Ile Val Arg Asn Ala Ile Asn Ala
            35                  40                  45

Ser Glu Phe Lys Lys Leu Lys Ser Pro Glu Asp Pro Ala His Pro Glu
    50                  55                  60

Asp Gln Asn Glu Gln Gly Ile Arg Val Phe Asp Pro Gly Tyr Ser Asn
65                  70                  75                  80

Thr Ala Val Ser Glu Ser Gln Val Thr Tyr Ile Asp Gly Leu Lys Gly
                85                  90                  95

Thr Ile Gln Tyr Arg Gly Tyr Asn Ile Glu Asp Ile Val Gly Lys Lys
            100                 105                 110

Lys Phe Ile Asp Thr Ala His Leu Leu Ile Trp Gly Glu Trp Pro Thr
            115                 120                 125

Pro Glu Gln Ala Lys Ser Leu Gln Glu Lys Leu Ser Ser Val Pro Val
            130                 135                 140

Leu Asp Glu Ser Val Phe Lys Val Ile Gln Ala Phe Pro Pro Asn Ser
145                 150                 155                 160

Ser Ile Ile Gly Met Met Ile Ala Ala Leu Ser Ala Val Gln Ser Thr
                165                 170                 175

Gln Met Asp Arg Ile Pro Ala His Ala Ala Lys Asn Leu Tyr Leu Gly
            180                 185                 190

Asn Pro Lys Ala Val Asp Asp Glu Ile Val Arg Leu Met Gly Ser Leu
            195                 200                 205
```

Ser Met Ile Thr Ala Ala Val Tyr Cys His His Thr Gly Arg Glu Phe
210                 215                 220

Thr Pro Pro Arg Pro Glu Leu Ser Tyr Ile Glu Asn Phe Leu Leu Met
225                 230                 235                 240

Met Gly His Val Glu Ser Ser Thr Gly Leu Pro Asn Pro Gln Tyr Val
            245                 250                 255

Asp Arg Ile Glu Arg Leu Trp Val Leu Ile Ala Asp His Glu Met Thr
        260                 265                 270

Cys Ser Thr Ala Ala Phe Leu Gln Thr Ala Ser Ser Leu Pro Asp Val
    275                 280                 285

Phe Ser Cys Met Ile Ser Ala Leu Ser Ala Leu Tyr Gly Pro Leu His
290                 295                 300

Gly Gly Ala Ile Glu Val Ala Tyr Lys Asn Phe Glu Glu Ile Gly Ser
305                 310                 315                 320

Val Glu Asn Val Ala Ala Lys Ile Glu Arg Val Lys Ala Gly Lys Glu
                325                 330                 335

Arg Leu Tyr Gly Tyr Gly His Arg Ile Tyr Arg Val Thr Asp Pro Arg
            340                 345                 350

Phe Ile Phe Ile Arg Gln Ile Leu Asp Glu Leu Lys Glu Glu Ile Ala
        355                 360                 365

Arg Asn Pro Leu Leu Lys Val Ala Phe Glu Val Asp Arg Val Ala Ser
370                 375                 380

Glu Asp Glu Tyr Phe Val Thr Arg Lys Leu Arg Pro Asn Ala Asp Leu
385                 390                 395                 400

Phe Ala Ala Leu Val Tyr Ser Ala Met Gly Phe Pro Thr Glu Phe Ile
                405                 410                 415

Leu Pro Leu Ser Leu Leu Ser Arg Thr Gln Gly Phe Met Ala His Trp
            420                 425                 430

Lys Glu Ala Met Ser Ser Thr Ala Arg Ile Trp Arg Pro Gly Gln Ile
        435                 440                 445

Tyr Thr Gly His Leu Asn Arg Glu Met Ala
    450                 455

<210> SEQ ID NO 19
<211> LENGTH: 24
<212> TYPE: DNA
<213> ORGANISM: Artificial Sequence
<220> FEATURE:
<223> OTHER INFORMATION: citB-R1+NcoI primer

<400> SEQUENCE: 19
ccatggtgag agcgaaactg ccta                                          24

<210> SEQ ID NO 20
<211> LENGTH: 18
<212> TYPE: DNA
<213> ORGANISM: Artificial Sequence
<220> FEATURE:
<223> OTHER INFORMATION: citB-R1+1631 primer

<400> SEQUENCE: 20
tgagagcgaa actgccta                                                 18

<210> SEQ ID NO 21
<211> LENGTH: 21
<212> TYPE: DNA
<213> ORGANISM: Artificial Sequence
<220> FEATURE:

-continued

```
<223> OTHER INFORMATION: overlap with primer

<400> SEQUENCE: 21
gttggatgcg atgtcgggca t                                      21

<210> SEQ ID NO 22
<211> LENGTH: 14
<212> TYPE: DNA
<213> ORGANISM: Artificial Sequence
<220> FEATURE:
<223> OTHER INFORMATION: overlap with primer

<400> SEQUENCE: 22
gcgatgtcgg gcat                                              14

<210> SEQ ID NO 23
<211> LENGTH: 24
<212> TYPE: DNA
<213> ORGANISM: Artificial Sequence
<220> FEATURE:
<223> OTHER INFORMATION: overlap with primer

<400> SEQUENCE: 23
taggcagttt cgctctcatc ggtg                                   24

<210> SEQ ID NO 24
<211> LENGTH: 18
<212> TYPE: DNA
<213> ORGANISM: Artificial Sequence
<220> FEATURE:
<223> OTHER INFORMATION: overlap withprimer

<400> SEQUENCE: 24
taggcagttt cgctctca                                          18

<210> SEQ ID NO 25
<211> LENGTH: 5818
<212> TYPE: DNA
<213> ORGANISM: Artificial Sequence
<220> FEATURE:
<223> OTHER INFORMATION: S. cerevisiae expression construct: 5' URA3
      flank- GPD promoter-citB gene (codon optimized for Saccharomyces
      cerevisiae)-CYC1 terminator - URA3 marker - TEF promoter-CAD gene
      (codon optimized for Saccharomyces cerevisiae)-ADH1 terminator -
<220> FEATURE:
<221> NAME/KEY: CDS
<222> LOCATION: (732)..(2105)
<223> OTHER INFORMATION: citB gene codon optimised
<220> FEATURE:
<221> NAME/KEY: misc_feature
<222> LOCATION: (2455)..(3315)
<223> OTHER INFORMATION: URA3 marker (coded on complimentary strand)
<220> FEATURE:
<221> NAME/KEY: CDS
<222> LOCATION: (3946)..(5415)
<223> OTHER INFORMATION: CAD gene codon optimised

<400> SEQUENCE: 25
gcggccgcga taagttttga ccatcaaaga aggttaatgt ggctgtggtt tcagggtcca    60
taaagctttc agtttatcat tatcaatact cgccatttca aagaatacgt aaataattaa   120
tagtagtgat tttcctaact ttatttagtc aaaaaattag ccttttaatt ctgctgtaac   180
ccgtacatgc ccaaaatagg gggcgggtta cacagaatat ataacatcgt aggtgtctgg   240
gtgaacagtt tattcctggc atccactaaa tataatggag cccgcttttt aagctggcat   300
ccagaaaaaa aaagaatccc agcaccaaaa tattgttttc ttcaccaacc atcagttcat   360
```

```
aggtccattc tcttagcgca actacagaga acaggggcac aaacaggcaa aaacgggca      420 caacctcaat ggagtgatgc aacctgcctg gagtaaatga tgacacaagg caattgaccc      480
acgcatgtat ctatctcatt ttcttacacc ttctattacc ttctgctctc tctgatttgg      540
aaaaagctga aaaaaaaggt tgaaaccagt tccctgaaat tattcccta cttgactaat       600 aagtatataa agacggtagg tattgattgt aattctgtaa atctatttct taaacttctt      660
aaattctact tttatagtta gtcttttttt tagttttaaa acaccagaac ttagtttcga      720
cggattctag a atg cca gat att gct tct aat ggt gct aga aat ggt gct      770
            Met Pro Asp Ile Ala Ser Asn Gly Ala Arg Asn Gly Ala
              1               5                  10 tct caa aac gct gaa aca aaa cca gaa cca cca gtt tta cac gtt gtt      818
Ser Gln Asn Ala Glu Thr Lys Pro Glu Pro Pro Val Leu His Val Val
 15              20                  25 gat tca aga act ggt aag tac ttc cca atc cca atc gtt aga aat gct      866
Asp Ser Arg Thr Gly Lys Tyr Phe Pro Ile Pro Ile Val Arg Asn Ala
30              35                  40                  45 att aac gcc tcc gag ttc aag aag ttg aaa tct cca gaa gat cca gct      914
Ile Asn Ala Ser Glu Phe Lys Lys Leu Lys Ser Pro Glu Asp Pro Ala
                50                  55                  60 cat cca gaa gat caa aac gaa caa ggt atc aga gtt ttc gat cca ggt      962
His Pro Glu Asp Gln Asn Glu Gln Gly Ile Arg Val Phe Asp Pro Gly
            65                  70                  75 tac tct aat acc gct gtt tct gaa tct caa gtt acc tac att gat ggt     1010
Tyr Ser Asn Thr Ala Val Ser Glu Ser Gln Val Thr Tyr Ile Asp Gly
        80                  85                  90 ttg aag ggt act atc caa tac aga ggt tac aac atc gaa gat atc gtc     1058
Leu Lys Gly Thr Ile Gln Tyr Arg Gly Tyr Asn Ile Glu Asp Ile Val
    95                  100                 105 ggt aag aag aag ttc att gat acc gcc cat ttg ttg att tgg ggt gaa     1106
Gly Lys Lys Lys Phe Ile Asp Thr Ala His Leu Leu Ile Trp Gly Glu
110             115                 120                 125 tgg cca act cca gaa caa gct aaa tca ttg caa gaa aag ttg tcc tcc     1154
Trp Pro Thr Pro Glu Gln Ala Lys Ser Leu Gln Glu Lys Leu Ser Ser
                130                 135                 140 gtt cca gtt ttg gat gaa tct gtt ttc aag gtt att caa gcc ttc cca     1202
Val Pro Val Leu Asp Glu Ser Val Phe Lys Val Ile Gln Ala Phe Pro
            145                 150                 155 cca aac tcc tct att att ggt atg atg att gct gct ttg tcc gct gtt     1250
Pro Asn Ser Ser Ile Ile Gly Met Met Ile Ala Ala Leu Ser Ala Val
        160                 165                 170 caa tct act caa atg gat aga ata cca gct cat gct gct aag aac ttg     1298
Gln Ser Thr Gln Met Asp Arg Ile Pro Ala His Ala Ala Lys Asn Leu
    175                 180                 185 tat ttg ggt aat cca aaa gcc gtt gat gac gaa atc gtt aga ttg atg     1346
Tyr Leu Gly Asn Pro Lys Ala Val Asp Asp Glu Ile Val Arg Leu Met
190                 195                 200                 205 ggt tcc ttg tct atg att act gct gct gtt tac tgt cat cat acc ggt     1394
Gly Ser Leu Ser Met Ile Thr Ala Ala Val Tyr Cys His His Thr Gly
                210                 215                 220 aga gaa ttt act cca cca aga cca gaa ttg tcc tac atc gaa aat ttc     1442
Arg Glu Phe Thr Pro Pro Arg Pro Glu Leu Ser Tyr Ile Glu Asn Phe
            225                 230                 235 ttg ttg atg atg ggt cac gtc gaa tct tct act ggt ttg cca aat cca     1490
Leu Leu Met Met Gly His Val Glu Ser Ser Thr Gly Leu Pro Asn Pro
        240                 245                 250 caa tac gtt gac aga att gaa aga ttg tgg gtt ttg att gcc gat cac     1538
Gln Tyr Val Asp Arg Ile Glu Arg Leu Trp Val Leu Ile Ala Asp His
```

```
                   255                 260                 265
gaa atg act tgt tct act gct gct ttc ttg caa act gct tct tca ttg      1586
Glu Met Thr Cys Ser Thr Ala Ala Phe Leu Gln Thr Ala Ser Ser Leu
270                 275                 280                 285 cca gat gtt ttc tct tgt atg atc tct gct ttg tct gca tta tac ggt      1634
Pro Asp Val Phe Ser Cys Met Ile Ser Ala Leu Ser Ala Leu Tyr Gly
                290                 295                 300 cca ttg cat ggt ggt gct att gaa gtt gct tac aag aac ttc gaa gaa      1682
Pro Leu His Gly Gly Ala Ile Glu Val Ala Tyr Lys Asn Phe Glu Glu
            305                 310                 315 atc ggt tcc gtt gaa aat gtt gct gcc aaa atc gaa aga gtt aag gcc      1730
Ile Gly Ser Val Glu Asn Val Ala Ala Lys Ile Glu Arg Val Lys Ala
        320                 325                 330 ggt aaa gaa aga tta tac ggt tac ggt cat aga atc tac aga gtt act      1778
Gly Lys Glu Arg Leu Tyr Gly Tyr Gly His Arg Ile Tyr Arg Val Thr
    335                 340                 345 gat cca aga ttc atc ttc atc aga caa atc ttg gat gaa ttg aaa gaa      1826
Asp Pro Arg Phe Ile Phe Ile Arg Gln Ile Leu Asp Glu Leu Lys Glu
350                 355                 360                 365 gaa atc gcc aga aac cct ttg ttg aag gtt gct ttt gaa gtt gat aga      1874
Glu Ile Ala Arg Asn Pro Leu Leu Lys Val Ala Phe Glu Val Asp Arg
                370                 375                 380 gtc gcc tct gaa gat gaa tac ttc gtt acc aga aag tta aga cca aac      1922
Val Ala Ser Glu Asp Glu Tyr Phe Val Thr Arg Lys Leu Arg Pro Asn
            385                 390                 395 gct gat ttg ttt gct gcc ttg gtt tat tct gct atg ggt ttt cca acc      1970
Ala Asp Leu Phe Ala Ala Leu Val Tyr Ser Ala Met Gly Phe Pro Thr
        400                 405                 410 gag ttc atc ttg cca ttg tct ttg ttg tca aga acc caa ggt ttt atg      2018
Glu Phe Ile Leu Pro Leu Ser Leu Leu Ser Arg Thr Gln Gly Phe Met
    415                 420                 425 gcc cat tgg aaa gaa gct atg tca tct act gct aga att tgg aga cct      2066
Ala His Trp Lys Glu Ala Met Ser Ser Thr Ala Arg Ile Trp Arg Pro
430                 435                 440                 445 ggt caa atc tat act ggt cac ttg aat aga gaa atg gct taactcgagt       2115
Gly Gln Ile Tyr Thr Gly His Leu Asn Arg Glu Met Ala
                450                 455 catgtaatta gttatgtcac gcttacattc acgccctccc cccacatccg ctctaaccga   2175
aaaggaagga gttagacaac ctgaagtcta ggtccctatt tatttttta tagttatgtt    2235 agtattaaga acgttattta tatttcaaat ttttctttt tttctgtaca dacgcgtgta    2295
cgcatgtaac attatactga aaaccttgct tgagaaggtt ttgggacgct cgaaggcttt   2355
aatttgcggc cggtggatcc ttttctttcc aatttttttt ttttcgtcat tataaaaatc   2415
attacgaccg agattcccgg gtaataactg atataattaa attgaagctc taatttgtga   2475
gtttagtata catgcattta cttataatac agttttttag ttttgctggc cgcatcttct   2535
caaatatgct tcccagcctg cttttctgta acgttcaccc tctaccttag catcccttcc   2595
ctttgcaaat agtcctcttc caacaataat aatgtcagat cctgtagaga ccacatcatc   2655
cacggttcta tactgttgac ccaatgcgtc tcccttgtca tctaaaccca caccgggtgt   2715
cataatcaac caatcgtaac cttcatctct tccacccatg tctctttgag caataaagcc   2775
gataacaaaa tctttgtcgc tcttcgcaat gtcaacagta cccttagtat attctccagt   2835
agatagggag cccttgcatg acaattctgc taacatcaaa aggcctctag gttcctttgt   2895
tacttcttct gccgctgct tcaaaccgct aacaatacct gggcccacca caccgtgtgc    2955
attcgtaatg tctgcccatt ctgctattct gtatacaccc gcagagtact gcaatttgac   3015
```

-continued

```
tgtattacca atgtcagcaa attttctgtc ttcgaagagt aaaaaattgt acttggcgga       3075
taatgccttt agcggcttaa ctgtgccctc catggaaaaa tcagtcaaga tatccacatg       3135 tgttttagt aaacaaattt tgggacctaa tgcttcaact aactccagta attccttggt        3195
ggtacgaaca tccaatgaag cacacaagtt tgtttgcttt cgtgcatga tattaaatag        3255 cttggcagca acaggactag gatgagtagc agcacgttcc ttatatgtag ctttcgacat      3315
gatttatctt cgtttcctgc aggttttgt tctgtgcagt tgggtaaga atactgggca         3375 atttcatgtt tcttcaacac tacatatgcg tatatatacc aatctaagtc tgtgctcctt      3435
ccttcgttct tccttctgtt cggagattac cgaatcaaaa aaatttcaaa gaaaccgaaa       3495
tcaaaaaaaa gaataaaaaa aaaatgatga attgaagaat tcttacccat aaggttgttt      3555
gtgacggcgt cgtacaagag aacgtgggaa cttttaggc tcaccaaaaa agaaagaaaa        3615
aatacgagtt gctgacagaa gcctcaagaa aaaaaaatt cttcttcgac tatgctggag       3675
gcagagatga tcgagccggt agttaactat atatagctaa attggttcca tcaccttctt      3735
ttctggtgtc gctccttcta gtgctatttc tggcttttcc tattttttt tttccatttt       3795 tctttctctc tttctaatat ataaattctc ttgcattttc tatttttctc tctatctatt      3855
ctacttgttt attcccttca aggttttttt ttaaggagta cttgttttta gaatatacgg      3915
tcaacgaact ataattaact aaactctaga atg acc aag caa tcc gct gat tct       3969
                                    Met Thr Lys Gln Ser Ala Asp Ser
                                    460                 465 aat gct aaa tct ggt gtt acc gct gaa att tgt cat tgg gct tct aat       4017
Asn Ala Lys Ser Gly Val Thr Ala Glu Ile Cys His Trp Ala Ser Asn
        470                 475                 480 ttg gcc acc gat gat att cca tct gat gtt ttg gaa aga gcc aag tac       4065
Leu Ala Thr Asp Asp Ile Pro Ser Asp Val Leu Glu Arg Ala Lys Tyr
    485                 490                 495 ttg atc ttg gat ggt att gct tgt gct tgg gtt ggt gct aga gtt cca       4113
Leu Ile Leu Asp Gly Ile Ala Cys Ala Trp Val Gly Ala Arg Val Pro
500                 505                 510 tgg tct gaa aag tat gtt caa gct acc atg tct ttt gaa cca cca ggt       4161
Trp Ser Glu Lys Tyr Val Gln Ala Thr Met Ser Phe Glu Pro Pro Gly
515                 520                 525                 530 gct tgt aga gtt att ggt tat ggt caa aaa ttg ggt cca gtt gct gct       4209
Ala Cys Arg Val Ile Gly Tyr Gly Gln Lys Leu Gly Pro Val Ala Ala
                535                 540                 545 gct atg act aat tct gct ttt att caa gcc acc gaa ttg gat gat tac       4257
Ala Met Thr Asn Ser Ala Phe Ile Gln Ala Thr Glu Leu Asp Asp Tyr
            550                 555                 560 cat tct gaa gct cca ttg cat tct gct tct ata gtt ttg cca gct gtt       4305
His Ser Glu Ala Pro Leu His Ser Ala Ser Ile Val Leu Pro Ala Val
        565                 570                 575 ttt gct gct tct gaa gtt ttg gct gaa caa ggt aaa acc atc tcc ggt       4353
Phe Ala Ala Ser Glu Val Leu Ala Glu Gln Gly Lys Thr Ile Ser Gly
    580                 585                 590 att gat gtt att ttg gct gct atc gtt ggt ttc gaa tct ggt cca aga       4401
Ile Asp Val Ile Leu Ala Ala Ile Val Gly Phe Glu Ser Gly Pro Arg
595                 600                 605                 610 att ggt aaa gct atc tac ggt tct gac ttg ttg aac aat ggt tgg cat       4449
Ile Gly Lys Ala Ile Tyr Gly Ser Asp Leu Leu Asn Asn Gly Trp His
                615                 620                 625 tgt ggt gct gtt tat ggt gct cca gct ggt gct ttg gct act ggt aag       4497
Cys Gly Ala Val Tyr Gly Ala Pro Ala Gly Ala Leu Ala Thr Gly Lys
            630                 635                 640
```

```
ttg ttg ggt ttg act cca gat tct atg gaa gat gct ttg ggt att gca      4545
Leu Leu Gly Leu Thr Pro Asp Ser Met Glu Asp Ala Leu Gly Ile Ala
            645                 650                 655 tgt act caa gct tgt ggt ttg atg tct gct caa tat ggt ggt atg gtt      4593
Cys Thr Gln Ala Cys Gly Leu Met Ser Ala Gln Tyr Gly Gly Met Val
660                 665                 670 aag aga gtt caa cac ggt ttt gct gca aga aat ggt ttg ttg ggt ggt      4641
Lys Arg Val Gln His Gly Phe Ala Ala Arg Asn Gly Leu Leu Gly Gly
675                 680                 685                 690 ttg ttg gct tat ggt ggt tat gaa gct atg aag ggt gta ttg gaa aga      4689
Leu Leu Ala Tyr Gly Gly Tyr Glu Ala Met Lys Gly Val Leu Glu Arg
                695                 700                 705 tct tac ggt ggt ttc ttg aag atg ttc act aag ggt aat ggt aga gaa      4737
Ser Tyr Gly Gly Phe Leu Lys Met Phe Thr Lys Gly Asn Gly Arg Glu
            710                 715                 720 cca cca tac aaa gaa gaa gaa gtt gtt gct ggt ttg ggt tct ttt tgg      4785
Pro Pro Tyr Lys Glu Glu Glu Val Val Ala Gly Leu Gly Ser Phe Trp
                725                 730                 735 cat act ttc acc atc aga atc aag ttg tat gct tgt tgc ggt ttg gtt      4833
His Thr Phe Thr Ile Arg Ile Lys Leu Tyr Ala Cys Cys Gly Leu Val
740                 745                 750 cat ggt cca gtt gaa gct att gaa aag ttg caa aga aga tac cca gaa      4881
His Gly Pro Val Glu Ala Ile Glu Lys Leu Gln Arg Arg Tyr Pro Glu
755                 760                 765                 770 tta ttg aac aga gcc aac ttg tcc aac atc aga cat gtt tac gtt caa      4929
Leu Leu Asn Arg Ala Asn Leu Ser Asn Ile Arg His Val Tyr Val Gln
                775                 780                 785 ttg tct acc gcc tct aat tct cat tgt ggt tgg att cca gaa gaa aga      4977
Leu Ser Thr Ala Ser Asn Ser His Cys Gly Trp Ile Pro Glu Glu Arg
            790                 795                 800 cca att tct tct att gcc ggt caa atg tcc gtt gct tac att ttg gct      5025
Pro Ile Ser Ser Ile Ala Gly Gln Met Ser Val Ala Tyr Ile Leu Ala
                805                 810                 815 gtt caa ttg gtt gac caa caa tgt ttg ttg gcc caa ttc tcc gaa ttt      5073
Val Gln Leu Val Asp Gln Gln Cys Leu Leu Ala Gln Phe Ser Glu Phe
        820                 825                 830 gat gac aat ttg gaa aga cca gaa gtt tgg gat ttg gct aga aaa gtt      5121
Asp Asp Asn Leu Glu Arg Pro Glu Val Trp Asp Leu Ala Arg Lys Val
835                 840                 845                 850 act cca tcc cac tcc gaa gaa ttt gat caa gat ggt aac tgt ttg tcc      5169
Thr Pro Ser His Ser Glu Glu Phe Asp Gln Asp Gly Asn Cys Leu Ser
                855                 860                 865 gct ggt aga gtt aga att gag ttc aac gat ggt tcc tct gtt acc gaa      5217
Ala Gly Arg Val Arg Ile Glu Phe Asn Asp Gly Ser Ser Val Thr Glu
            870                 875                 880 act gtt gaa aaa cca ttg ggt gtc aaa gaa cct atg cca aac gaa aga      5265
Thr Val Glu Lys Pro Leu Gly Val Lys Glu Pro Met Pro Asn Glu Arg
                885                 890                 895 atc ttg cac aag tat aga act ttg gct ggt tct gtt acc gat gaa tca      5313
Ile Leu His Lys Tyr Arg Thr Leu Ala Gly Ser Val Thr Asp Glu Ser
900                 905                 910 aga gtc aaa gaa atc gaa gat ttg gtc ttg tcc ttg gat aga ttg act      5361
Arg Val Lys Glu Ile Glu Asp Leu Val Leu Ser Leu Asp Arg Leu Thr
915                 920                 925                 930 gat att acc cct ttg ttg gaa tta ttg aat tgc cca gtt aag tcc cca      5409
Asp Ile Thr Pro Leu Leu Glu Leu Leu Asn Cys Pro Val Lys Ser Pro
            935                 940                 945 ttg gtc taactcgagg cgaatttctt atgatttatg attttatta ttaaataagt       5465
Leu Val
```

```
tataaaaaaa ataagtgtat acaaatttta aagtgactct taggttttaa aacgaaaatt    5525
cttattcttg agtaactctt tcctgtaggt caggttgctt tctcaggtat agcatgaggt    5585
cgctcttatt gaccacacct ctaccggcat gccgagcaaa tgcctgcaaa tcgctcccca    5645
tttcacccaa ttgtagatat gctaactcca gcaatgagtt gatgaatctc ggtgtgtatt    5705
ttatgtcctc agaggacaac acctgttgta atcgttcttc cacactcatg gcctttataa    5765
aaaggaacta tccaatacct cgccagaacc aagtaacagt attttgcggc cgc           5818
```

<210> SEQ ID NO 26
<211> LENGTH: 458
<212> TYPE: PRT
<213> ORGANISM: Artificial Sequence
<220> FEATURE:
<223> OTHER INFORMATION: Synthetic Construct

<400> SEQUENCE: 26

```
Met Pro Asp Ile Ala Ser Asn Gly Ala Arg Asn Gly Ala Ser Gln Asn
1               5                   10                  15

Ala Glu Thr Lys Pro Glu Pro Pro Val Leu His Val Val Asp Ser Arg
                20                  25                  30

Thr Gly Lys Tyr Phe Pro Ile Pro Ile Val Arg Asn Ala Ile Asn Ala
            35                  40                  45

Ser Glu Phe Lys Lys Leu Lys Ser Pro Glu Asp Pro Ala His Pro Glu
        50                  55                  60

Asp Gln Asn Glu Gln Gly Ile Arg Val Phe Asp Pro Gly Tyr Ser Asn
65                  70                  75                  80

Thr Ala Val Ser Glu Ser Gln Val Thr Tyr Ile Asp Gly Leu Lys Gly
                85                  90                  95

Thr Ile Gln Tyr Arg Gly Tyr Asn Ile Glu Asp Ile Val Gly Lys Lys
            100                 105                 110

Lys Phe Ile Asp Thr Ala His Leu Leu Ile Trp Gly Glu Trp Pro Thr
        115                 120                 125

Pro Glu Gln Ala Lys Ser Leu Gln Glu Lys Leu Ser Ser Val Pro Val
    130                 135                 140

Leu Asp Glu Ser Val Phe Lys Val Ile Gln Ala Phe Pro Pro Asn Ser
145                 150                 155                 160

Ser Ile Ile Gly Met Met Ile Ala Ala Leu Ser Ala Val Gln Ser Thr
                165                 170                 175

Gln Met Asp Arg Ile Pro Ala His Ala Ala Lys Asn Leu Tyr Leu Gly
            180                 185                 190

Asn Pro Lys Ala Val Asp Asp Glu Ile Val Arg Leu Met Gly Ser Leu
        195                 200                 205

Ser Met Ile Thr Ala Ala Val Tyr Cys His His Thr Gly Arg Glu Phe
    210                 215                 220

Thr Pro Pro Arg Pro Glu Leu Ser Tyr Ile Glu Asn Phe Leu Leu Met
225                 230                 235                 240

Met Gly His Val Glu Ser Ser Thr Gly Leu Pro Asn Pro Gln Tyr Val
                245                 250                 255

Asp Arg Ile Glu Arg Leu Trp Val Leu Ile Ala Asp His Glu Met Thr
            260                 265                 270

Cys Ser Thr Ala Ala Phe Leu Gln Thr Ala Ser Ser Leu Pro Asp Val
        275                 280                 285

Phe Ser Cys Met Ile Ser Ala Leu Ser Ala Leu Tyr Gly Pro Leu His
    290                 295                 300
```

Gly Gly Ala Ile Glu Val Ala Tyr Lys Asn Phe Glu Glu Ile Gly Ser
305                 310                 315                 320

Val Glu Asn Val Ala Ala Lys Ile Glu Arg Val Lys Ala Gly Lys Glu
            325                 330                 335

Arg Leu Tyr Gly Tyr Gly His Arg Ile Tyr Arg Val Thr Asp Pro Arg
        340                 345                 350

Phe Ile Phe Ile Arg Gln Ile Leu Asp Glu Leu Lys Glu Glu Ile Ala
    355                 360                 365

Arg Asn Pro Leu Leu Lys Val Ala Phe Glu Val Asp Arg Val Ala Ser
370                 375                 380

Glu Asp Glu Tyr Phe Val Thr Arg Lys Leu Arg Pro Asn Ala Asp Leu
385                 390                 395                 400

Phe Ala Ala Leu Val Tyr Ser Ala Met Gly Phe Pro Thr Glu Phe Ile
                405                 410                 415

Leu Pro Leu Ser Leu Leu Ser Arg Thr Gln Gly Phe Met Ala His Trp
            420                 425                 430

Lys Glu Ala Met Ser Ser Thr Ala Arg Ile Trp Arg Pro Gly Gln Ile
        435                 440                 445

Tyr Thr Gly His Leu Asn Arg Glu Met Ala
    450                 455

<210> SEQ ID NO 27
<211> LENGTH: 490
<212> TYPE: PRT
<213> ORGANISM: Artificial Sequence
<220> FEATURE:
<223> OTHER INFORMATION: Synthetic Construct

<400> SEQUENCE: 27

Met Thr Lys Gln Ser Ala Asp Ser Asn Ala Lys Ser Gly Val Thr Ala
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
                85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205

```
Ser Ala Gln Tyr Gly Gly Met Val Lys Arg Val Gln His Gly Phe Ala
210                 215                 220

Ala Arg Asn Gly Leu Leu Gly Gly Leu Ala Tyr Gly Gly Tyr Glu
225                 230                 235                 240

Ala Met Lys Gly Val Leu Glu Arg Ser Tyr Gly Gly Phe Leu Lys Met
            245                 250                 255

Phe Thr Lys Gly Asn Gly Arg Glu Pro Pro Tyr Lys Glu Glu Val
            260                 265                 270

Val Ala Gly Leu Gly Ser Phe Trp His Thr Phe Thr Ile Arg Ile Lys
            275                 280                 285

Leu Tyr Ala Cys Cys Gly Leu Val His Gly Pro Val Glu Ala Ile Glu
290                 295                 300

Lys Leu Gln Arg Arg Tyr Pro Glu Leu Leu Asn Arg Ala Asn Leu Ser
305                 310                 315                 320

Asn Ile Arg His Val Tyr Val Gln Leu Ser Thr Ala Ser Asn Ser His
                325                 330                 335

Cys Gly Trp Ile Pro Glu Glu Arg Pro Ile Ser Ser Ile Ala Gly Gln
            340                 345                 350

Met Ser Val Ala Tyr Ile Leu Ala Val Gln Leu Val Asp Gln Gln Cys
            355                 360                 365

Leu Leu Ala Gln Phe Ser Glu Phe Asp Asp Asn Leu Glu Arg Pro Glu
370                 375                 380

Val Trp Asp Leu Ala Arg Lys Val Thr Pro Ser His Ser Glu Glu Phe
385                 390                 395                 400

Asp Gln Asp Gly Asn Cys Leu Ser Ala Gly Arg Val Arg Ile Glu Phe
            405                 410                 415

Asn Asp Gly Ser Ser Val Thr Glu Thr Val Glu Lys Pro Leu Gly Val
            420                 425                 430

Lys Glu Pro Met Pro Asn Glu Arg Ile Leu His Lys Tyr Arg Thr Leu
            435                 440                 445

Ala Gly Ser Val Thr Asp Glu Ser Arg Val Lys Glu Ile Glu Asp Leu
450                 455                 460

Val Leu Ser Leu Asp Arg Leu Thr Asp Ile Thr Pro Leu Leu Glu Leu
465                 470                 475                 480

Leu Asn Cys Pro Val Lys Ser Pro Leu Val
                485                 490

<210> SEQ ID NO 28
<211> LENGTH: 804
<212> TYPE: DNA
<213> ORGANISM: Saccharomyces cerevisiae
<220> FEATURE:
<221> NAME/KEY: CDS
<222> LOCATION: (1)..(804)
<223> OTHER INFORMATION: URA3

<400> SEQUENCE: 28 atg tcg aaa gct aca tat aag gaa cgt gct gct act cat cct agt cct    48
Met Ser Lys Ala Thr Tyr Lys Glu Arg Ala Ala Thr His Pro Ser Pro
1               5                   10                  15 gtt gct gcc aag cta ttt aat atc atg cac gaa aag caa aca aac ttg    96
Val Ala Ala Lys Leu Phe Asn Ile Met His Glu Lys Gln Thr Asn Leu
                20                  25                  30 tgt gct tca ttg gat gtt cgt acc acc aag gaa tta ctg gag tta gtt   144
Cys Ala Ser Leu Asp Val Arg Thr Thr Lys Glu Leu Leu Glu Leu Val
            35                  40                  45 gaa gca tta ggt ccc aaa att tgt tta cta aaa aca cat gtg gat atc   192
```

```
Glu Ala Leu Gly Pro Lys Ile Cys Leu Leu Lys Thr His Val Asp Ile
         50                  55                  60 ttg act gat ttt tcc atg gag ggc aca gtt aag ccg cta aag gca tta      240
Leu Thr Asp Phe Ser Met Glu Gly Thr Val Lys Pro Leu Lys Ala Leu
 65                  70                  75                  80 tcc gcc aag tac aat ttt tta ctc ttc gaa gac aga aaa ttt gct gac      288
Ser Ala Lys Tyr Asn Phe Leu Leu Phe Glu Asp Arg Lys Phe Ala Asp
                 85                  90                  95 att ggt aat aca gtc aaa ttg cag tac tct gcg ggt gta tac aga ata      336
Ile Gly Asn Thr Val Lys Leu Gln Tyr Ser Ala Gly Val Tyr Arg Ile
            100                 105                 110 gca gaa tgg gca gac att acg aat gca cac ggt gtg gtg ggc cca ggt      384
Ala Glu Trp Ala Asp Ile Thr Asn Ala His Gly Val Val Gly Pro Gly
        115                 120                 125 att gtt agc ggt ttg aag cag gcg gca gaa gaa gta aca aag gaa cct      432
Ile Val Ser Gly Leu Lys Gln Ala Ala Glu Glu Val Thr Lys Glu Pro
130                 135                 140 aga ggc ctt ttg atg tta gca gaa ttg tca tgc aag ggc tcc cta tct      480
Arg Gly Leu Leu Met Leu Ala Glu Leu Ser Cys Lys Gly Ser Leu Ser
145                 150                 155                 160 act gga gaa tat act aag ggt act gtt gac att gcg aag agc gac aaa      528
Thr Gly Glu Tyr Thr Lys Gly Thr Val Asp Ile Ala Lys Ser Asp Lys
                165                 170                 175 gat ttt gtt atc ggc ttt att gct caa aga gac atg ggt gga aga gat      576
Asp Phe Val Ile Gly Phe Ile Ala Gln Arg Asp Met Gly Gly Arg Asp
            180                 185                 190 gaa ggt tac gat tgg ttg att atg aca ccc ggt gtg ggt tta gat gac      624
Glu Gly Tyr Asp Trp Leu Ile Met Thr Pro Gly Val Gly Leu Asp Asp
        195                 200                 205 aag gga gac gca ttg ggt caa cag tat aga acc gtg gat gat gtg gtc      672
Lys Gly Asp Ala Leu Gly Gln Gln Tyr Arg Thr Val Asp Asp Val Val
210                 215                 220 tct aca gga tct gac att att att gtt gga aga gga cta ttt gca aag      720
Ser Thr Gly Ser Asp Ile Ile Ile Val Gly Arg Gly Leu Phe Ala Lys
225                 230                 235                 240 gga agg gat gct aag gta gag ggt gaa cgt tac aga aaa gca ggc tgg      768
Gly Arg Asp Ala Lys Val Glu Gly Glu Arg Tyr Arg Lys Ala Gly Trp
                245                 250                 255 gaa gca tat ttg aga aga tgc ggc cag caa aac taa                      804
Glu Ala Tyr Leu Arg Arg Cys Gly Gln Gln Asn
        260                 265

<210> SEQ ID NO 29
<211> LENGTH: 267
<212> TYPE: PRT
<213> ORGANISM: Saccharomyces cerevisiae

<400> SEQUENCE: 29

Met Ser Lys Ala Thr Tyr Lys Glu Arg Ala Ala Thr His Pro Ser Pro
 1               5                  10                  15

Val Ala Ala Lys Leu Phe Asn Ile Met His Glu Lys Gln Thr Asn Leu
                20                  25                  30

Cys Ala Ser Leu Asp Val Arg Thr Thr Lys Glu Leu Leu Glu Leu Val
            35                  40                  45

Glu Ala Leu Gly Pro Lys Ile Cys Leu Leu Lys Thr His Val Asp Ile
         50                  55                  60

Leu Thr Asp Phe Ser Met Glu Gly Thr Val Lys Pro Leu Lys Ala Leu
 65                  70                  75                  80

Ser Ala Lys Tyr Asn Phe Leu Leu Phe Glu Asp Arg Lys Phe Ala Asp
```

85                  90                  95
Ile Gly Asn Thr Val Lys Leu Gln Tyr Ser Ala Gly Val Tyr Arg Ile
                100                 105                 110

Ala Glu Trp Ala Asp Ile Thr Asn Ala His Gly Val Val Gly Pro Gly
            115                 120                 125

Ile Val Ser Gly Leu Lys Gln Ala Ala Glu Glu Val Thr Lys Glu Pro
        130                 135                 140

Arg Gly Leu Leu Met Leu Ala Glu Leu Ser Cys Lys Gly Ser Leu Ser
145                 150                 155                 160

Thr Gly Glu Tyr Thr Lys Gly Thr Val Asp Ile Ala Lys Ser Asp Lys
                165                 170                 175

Asp Phe Val Ile Gly Phe Ile Ala Gln Arg Asp Met Gly Arg Asp
            180                 185                 190

Glu Gly Tyr Asp Trp Leu Ile Met Thr Pro Gly Val Gly Leu Asp Asp
        195                 200                 205

Lys Gly Asp Ala Leu Gly Gln Gln Tyr Arg Thr Val Asp Asp Val Val
    210                 215                 220

Ser Thr Gly Ser Asp Ile Ile Val Gly Arg Gly Leu Phe Ala Lys
225                 230                 235                 240

Gly Arg Asp Ala Lys Val Glu Gly Glu Arg Tyr Arg Lys Ala Gly Trp
                245                 250                 255

Glu Ala Tyr Leu Arg Arg Cys Gly Gln Gln Asn
            260                 265

<210> SEQ ID NO 30
<211> LENGTH: 4920
<212> TYPE: DNA
<213> ORGANISM: Artificial Sequence
<220> FEATURE:
<223> OTHER INFORMATION: Aspergillus expression vector pABgpd-I

<400> SEQUENCE: 30
ctaaattgta agcgttaata ttttgttaaa attcgcgtta aatttttgtt aaatcagctc      60
attttttaac caataggccg aaatcggcaa atcccttat aaatcaaaag aatagaccga     120
gatagggttg agtggccgct acagggcgct cccattcgcc attcaggctg cgcaactgtt    180
gggaagggcg tttcggtgcg ggcctcttcg ctattacgcc agctggcgaa aggggatgt     240 gctgcaaggc gattaagttg ggtaacgcca gggttttccc agtcacgacg ttgtaaaacg    300
acggccagtg agcgcgacgt aatacgactc actatagggc gaattggcgg aaggccgtca   360
aggccgcggc cgctcaggag gcgaatagat aattttgaaa tccctactga tacggcttcc    420
caacgaggta ggagcggaaa ggatgatgag tggccaagta cctgccgatg ctttgttgtc    480
tcacgacttg agtctcctga tataccaaca tcggtggccg gtgaagacaa tgaagacata    540
tttctaagca atatgggctg tggccactcc gtgccacttg ctcgaagtaa cctgttgcat    600 ttacccccatg taaggctgga ggctggatgg gccactttg cagcagtatg tagaaagtac    660
tagaaccatc ttccggtctc cgagacactg gtcaatattg acacggcagc atgatcatga    720
aacccgagtc agaccagagc cgttcggatt gtgctatacc ccaagtcacg ttgtccataa    780
ttgaataaat atgagcagtc ctttgtggcg tggaaacata cttagcatgt agagacaaac    840
cttggtgcgc ggcttcaggc gggcatagtt agtatgctac ggtaccaccg atcttattgt    900
accagaaaaa gtcccagcca gtccaatccc cattctaagc cacatgcatc cgttcgcatg    960
catctgacat atcagattcg tccatctggt gcagtatcta acagaggcca gagcatcacc   1020

```
aacatgggta ccctcagcaa taatatgcat gcattgtgcc cccccctatgg agccgtagct    1080 ttcaagcaat tagacacgcg cccggccgaa tgagatgaac cgttggagcc atcatcccac    1140
tcatcccgct ccagaaagga gagaaagaaa aaaaaaaaat atgaccgagc gcgtgatgac    1200
cggtgaggac tccggtgaat tgatttgggt gacgggagag acccaagagg ggccagaata    1260
ataagaatgg ggaaggcgaa ggtaccgcct ttggggtcca gccacgcgac tccaacatgg    1320
aggggcactg gactaacatt attccagcac cgggatcacg ggccgaaagc ggcaaggccg    1380
cgcactgccc ctcttttttgg gtgaaagagc tggcagtaac ttaactgtac tttctggagt    1440
gaataatact actactatga aagaccgcga tgggccgata gtagtagtta cttccattac    1500
atcatctcat ccgcccggtt cctcgcctcc gcggcagtct acgggtagga tcgtagcaaa    1560
aacccggggg atagaccccgt cgtcccgagc tggagttccg tataacctag gtagaaggta    1620
tcaattgaac ccgaacaact ggcaaaacat tctcgagatc gtaggagtga gtacccggcg    1680
tgatggaggg ggagcacgct cattggtccg tacggcagct gccgaggggg agcaggagat    1740
ccaaatatcg tgagtctcct gctttgcccg gtgtatgaaa ccggaaagga tccaaatatc    1800
gtgagtctcc tgctttgccc ggtgtatgaa accggaaagg actgctgggg aactggggag    1860
cggcgcaagc cgggaatccc agctgacaat tgacccatcc tcatgccgtg gcagagcttg    1920
aggtagcttt tgccccgtct gtctccccgg tgtgcgcatt cgactgggcg cggcatctgt    1980
gcctcctcca ggagcggagg acccagtagt aagtaggcct gacctggtcg ttgcgtcagt    2040
ccagaggttc cctcccctac cctttttcta cttcccctcc ccgccgctc aacttttctt    2100 tccctttttac tttctctctc tcttcctctt catccatcct ctcttcatca cttccctctt    2160
cccttcatcc aattcatctt ccaagtgagt cttcctcccc atctgtccct ccatctttcc    2220
catcatcatc tcccctccca gctcctcccc tcctctcgtc tcctcacgaa gcttgactaa    2280
ccattacccc gccacataga cacatctaaa ccatggacgt agttaattaa agatctaatc    2340
aggacggcaa actcaattca gaagtgtgct gtgagtgaga ctgattgccg agcgcagacg    2400
actctcgtgg aacccggctt gtggagaagc ttgagaaggt cttaactcct agcgtaaaag    2460
ctcatgatga cgtacaattt aatgaaatga tacaatgttc atatttcccg ttcaaatttc    2520
cggccttggt cagtgcgtaa gatgtccacg attgaatact aactcagtat gggtttggta    2580
gcattggcaa tgtagttata agcatgcacc ggttgaagac gtcggcccca gatgcaatgc    2640
tgcggtggtg actaagctct gcagtgaatg gaatgcgttt ctttgatcga cttcggcgtg    2700
ccgcgggatt ttctcggcgc ttctactggt gcagaaagga cgataccact ggctttcggt    2760
ccatgccaca tcccagtctc ccgggaaatt cattgcatac tttaagaaac aaactgatct    2820 ccataattc cgtctttaga gttcacttgg tacttttggg tggatcgagg ggtgtccgcg    2880
gccatccaag tcacgtggag ggcagctaga ccacggattt tagagctaca ttgatccaag    2940
actcctggac cggcctcatg ggccttccgc tcactgcccg ctttccagtc gggaaacctg    3000
tcgtgccagc tgcattaaca tggtcatagc tgtttccttg cgtattgggc gctctccgct    3060
tcctcgctca ctgactcgct gcgctcggtc gttcgggtaa agcctggggt gcctaatgag    3120
caaaaggcca gcaaaggcc aggaaccgta aaaaggccgc gttgctggcg ttttccata    3180 ggctccgccc cctgacgag catcacaaaa atcgacgctc aagtcagagg tggcgaaacc    3240
cgacaggact ataaagatac caggcgtttc ccctggaag ctccctcgtg cgctctcctg    3300
ttccgaccct gccgcttacc ggataccgt ccgcctttct cccttcggga agcgtggcgc    3360
tttctcatag ctcacgctgt aggtatctca gttcggtgta ggtcgttcgc tccaagctgg    3420
```

```
gctgtgtgca cgaaccccc gttcagcccg accgctgcgc cttatccggt aactatcgtc    3480
ttgagtccaa cccggtaaga cacgacttat cgccactggc agcagccact ggtaacagga    3540
ttagcagagc gaggtatgta ggcggtgcta cagagttctt gaagtggtgg cctaactacg    3600
gctacactag aagaacagta tttggtatct gcgctctgct gaagccagtt accttcggaa    3660
aaagagttgg tagctcttga tccggcaaac aaaccaccgc tggtagcggt ggttttttg     3720
tttgcaagca gcagattacg cgcagaaaaa aaggatctca agaagatcct ttgatctttt    3780
ctacggggtc tgacgctcag tggaacgaaa actcacgtta agggattttg gtcatgagat    3840
tatcaaaaag gatcttcacc tagatccttt taaattaaaa atgaagtttt aaatcaatct    3900
aaagtatata tgagtaaact tggtctgaca gttaccaatg cttaatcagt gaggcaccta    3960
tctcagcgat ctgtctattt cgttcatcca tagttgcctg actccccgtc gtgtagataa    4020
ctacgatacg ggagggctta ccatctggcc ccagtgctgc aatgataccg cgagaaccac    4080
gctcaccggc tccagattta tcagcaataa accagccagc cggaagggcc gagcgcagaa    4140
gtggtcctgc aactttatcc gcctccatcc agtctattaa ttgttgccgg gaagctagag    4200
taagtagttc gccagttaat agtttgcgca acgttgttgc cattgctaca ggcatcgtgg    4260
tgtcacgctc gtcgtttggt atggcttcat tcagctccgg ttcccaacga tcaaggcgag    4320
ttacatgatc ccccatgttg tgcaaaaaag cggttagctc cttcggtcct ccgatcgttg    4380
tcagaagtaa gttggccgca gtgttatcac tcatggttat ggcagcactg cataattctc    4440
ttactgtcat gccatccgta agatgctttt ctgtgactgg tgagtactca accaagtcat    4500
tctgagaata gtgtatgcgg cgaccgagtt gctcttgccc ggcgtcaata cgggataata    4560
ccgcgccaca tagcagaact ttaaaagtgc tcatcattgg aaaacgttct tcggggcgaa    4620
aactctcaag gatcttaccg ctgttgagat ccagttcgat gtaacccact cgtgcaccca    4680
actgatcttc agcatctttt actttcacca gcgtttctgg gtgagcaaaa acaggaaggc    4740
aaaatgccgc aaaaaaggga ataagggcga cacggaaatg ttgaatactc atactcttcc    4800
tttttcaata ttattgaagc atttatcagg gttattgtct catgagcgga tacatatttg    4860
aatgtattta gaaaaataaa caaatagggg ttccgcgcac atttccccga aaagtgccac    4920
```

<210> SEQ ID NO 31
<211> LENGTH: 458
<212> TYPE: PRT
<213> ORGANISM: Aspergillus niger

<400> SEQUENCE: 31

Met Pro Asp Ile Ala Ser Asn Gly Ala Arg Asn Gly Ala Ser Gln Asn
1               5                   10                  15

Ala Glu Thr Lys Pro Glu Pro Val Leu His Val Val Asp Ser Arg
            20                  25                  30

Thr Gly Lys Tyr Phe Pro Ile Pro Ile Val Arg Asn Ala Ile Asn Ala
        35                  40                  45

Ser Glu Phe Lys Lys Leu Lys Ser Pro Glu Asp Pro Ala His Pro Glu
    50                  55                  60

Asp Gln Asn Glu Gln Gly Ile Arg Val Phe Asp Pro Gly Tyr Ser Asn
65                  70                  75                  80

Thr Ala Val Ser Glu Ser Gln Val Thr Tyr Ile Asp Gly Leu Lys Gly
                85                  90                  95

Thr Ile Gln Tyr Arg Gly Tyr Asn Ile Glu Asp Ile Val Gly Lys Lys
            100                 105                 110

Lys Phe Ile Asp Thr Ala His Leu Leu Ile Trp Gly Glu Trp Pro Thr
            115                 120                 125

Pro Glu Gln Ala Lys Ser Leu Gln Glu Lys Leu Ser Ser Val Pro Val
130                 135                 140

Leu Asp Glu Ser Val Phe Lys Val Ile Gln Ala Phe Pro Pro Asn Ser
145                 150                 155                 160

Ser Ile Ile Gly Met Met Ile Ala Ala Leu Ser Ala Val Gln Ser Thr
                165                 170                 175

Gln Met Asp Arg Ile Pro Ala His Ala Ala Lys Asn Leu Tyr Leu Gly
            180                 185                 190

Asn Pro Lys Ala Val Asp Asp Glu Ile Val Arg Leu Met Gly Ser Leu
        195                 200                 205

Ser Met Ile Thr Ala Ala Val Tyr Cys His His Thr Gly Arg Glu Phe
    210                 215                 220

Thr Pro Pro Arg Pro Glu Leu Ser Tyr Ile Glu Asn Phe Leu Leu Met
225                 230                 235                 240

Met Gly His Val Glu Ser Ser Thr Gly Leu Pro Asn Pro Gln Tyr Val
                245                 250                 255

Asp Arg Ile Glu Arg Leu Trp Val Leu Ile Ala Asp His Glu Met Thr
            260                 265                 270

Cys Ser Thr Ala Ala Phe Leu Gln Thr Ala Ser Ser Leu Pro Asp Val
        275                 280                 285

Phe Ser Cys Met Ile Ser Ala Leu Ser Ala Leu Tyr Gly Pro Leu His
    290                 295                 300

Gly Gly Ala Ile Glu Ala Tyr Lys Asn Phe Glu Glu Ile Gly Ser
305                 310                 315                 320

Val Glu Asn Val Ala Ala Lys Ile Glu Arg Val Lys Ala Gly Lys Glu
                325                 330                 335

Arg Leu Tyr Gly Tyr Gly His Arg Ile Tyr Arg Val Thr Asp Pro Arg
            340                 345                 350

Phe Ile Phe Ile Arg Gln Ile Leu Asp Glu Leu Lys Glu Glu Ile Ala
        355                 360                 365

Arg Asn Pro Leu Leu Lys Val Ala Phe Glu Val Asp Arg Val Ala Ser
    370                 375                 380

Glu Asp Glu Tyr Phe Val Thr Arg Lys Leu Arg Pro Asn Ala Asp Leu
385                 390                 395                 400

Phe Ala Ala Leu Val Tyr Ser Ala Met Gly Phe Pro Thr Glu Phe Ile
                405                 410                 415

Leu Pro Leu Ser Leu Leu Ser Arg Thr Gln Gly Phe Met Ala His Trp
            420                 425                 430

Lys Glu Ala Met Ser Ser Thr Ala Arg Ile Trp Arg Pro Gly Gln Ile
        435                 440                 445

Tyr Thr Gly His Leu Asn Arg Glu Met Ala
    450                 455

<210> SEQ ID NO 32
<211> LENGTH: 458
<212> TYPE: PRT
<213> ORGANISM: Aspergillus niger

<400> SEQUENCE: 32

Met Pro Asp Ile Ala Ser Asn Gly Ala Arg Asn Gly Ala Ser Gln Asn
1               5                   10                  15

Ala Glu Thr Lys Pro Glu Pro Pro Val Leu His Val Val Asp Ser Arg

```
                    20                  25                  30
Thr Gly Lys Tyr Phe Pro Ile Pro Ile Val Arg Asn Ala Ile Asn Ala
                35                  40                  45

Ser Glu Phe Lys Lys Leu Lys Ser Pro Glu Asp Pro Ala His Pro Glu
 50                  55                  60

Asp Gln Asn Glu Gln Gly Ile Arg Val Phe Asp Pro Gly Tyr Ser Asn
 65                  70                  75                  80

Thr Ala Val Ser Glu Ser Gln Val Thr Tyr Ile Asp Gly Leu Lys Gly
                 85                  90                  95

Thr Ile Gln Tyr Arg Gly Tyr Asn Ile Glu Asp Ile Val Gly Lys Lys
                100                 105                 110

Lys Phe Ile Asp Thr Ala His Leu Leu Ile Trp Gly Glu Trp Pro Thr
                115                 120                 125

Pro Glu Gln Ala Lys Ser Leu Gln Glu Lys Leu Ser Ser Val Pro Val
                130                 135                 140

Leu Asp Glu Ser Val Phe Lys Val Ile Gln Ala Phe Pro Pro Asn Ser
145                 150                 155                 160

Ser Ile Ile Gly Met Met Ile Ala Ala Leu Ser Ala Val Gln Ser Thr
                165                 170                 175

Gln Met Asp Arg Ile Pro Ala His Ala Ala Lys Asn Leu Tyr Leu Gly
                180                 185                 190

Asn Pro Lys Ala Val Asp Asp Glu Ile Val Arg Leu Met Gly Ser Leu
                195                 200                 205

Ser Met Ile Thr Ala Ala Val Tyr Cys His His Thr Gly Arg Glu Phe
                210                 215                 220

Thr Pro Pro Arg Pro Glu Leu Ser Tyr Ile Glu Asn Phe Leu Leu Met
225                 230                 235                 240

Met Gly His Val Glu Ser Ser Thr Gly Leu Pro Asn Pro Gln Tyr Val
                245                 250                 255

Asp Arg Ile Glu Arg Leu Trp Val Leu Ile Ala Asp His Glu Met Thr
                260                 265                 270

Cys Ser Thr Ala Ala Phe Leu Gln Thr Ala Ser Ser Leu Pro Asp Val
                275                 280                 285

Phe Ser Cys Met Ile Ser Ala Leu Ser Ala Leu Tyr Gly Pro Leu His
                290                 295                 300

Gly Gly Ala Ile Glu Val Ala Tyr Lys Asn Phe Glu Glu Ile Gly Ser
305                 310                 315                 320

Val Glu Asn Val Ala Ala Lys Ile Glu Arg Val Lys Ala Gly Lys Glu
                325                 330                 335

Arg Leu Tyr Gly Tyr Gly His Arg Ile Tyr Arg Val Thr Asp Pro Arg
                340                 345                 350

Phe Ile Phe Ile Arg Gln Ile Leu Asp Glu Leu Lys Glu Glu Ile Ala
                355                 360                 365

Arg Asn Pro Leu Leu Lys Val Ala Phe Glu Val Asp Arg Val Ala Ser
                370                 375                 380

Glu Asp Glu Tyr Phe Val Thr Arg Lys Leu Arg Pro Asn Ala Asp Leu
385                 390                 395                 400

Phe Ala Ala Leu Val Tyr Ser Met Gly Phe Pro Thr Glu Phe Ile
                405                 410                 415

Leu Pro Leu Ser Leu Leu Ser Arg Thr Gln Gly Phe Leu Ala His Trp
                420                 425                 430

Lys Glu Ala Met Ser Ser Thr Ala Arg Ile Trp Arg Pro Gly Gln Ile
                435                 440                 445
```

Tyr Thr Gly His Leu Asn Arg Glu Met Ala
    450                 455

<210> SEQ ID NO 33
<211> LENGTH: 458
<212> TYPE: PRT
<213> ORGANISM: Zea mays

<400> SEQUENCE: 33

Met Pro Asp Ile Ala Pro Asn Val Ala Arg Asn Gly Ser Ser Lys His
1               5                   10                  15

Ala Glu Thr Lys Pro Glu Thr Pro Val Leu His Val Val Asp Ser Arg
            20                  25                  30

Thr Gly Asn Tyr Phe Pro Ile Pro Ile Val Arg Asn Ala Ile Asn Ala
        35                  40                  45

Ser Glu Phe Lys Lys Leu Lys Ser Pro Glu Asp Pro Ala His Pro Glu
    50                  55                  60

Asp Gln Asn Glu Gln Gly Ile Arg Val Phe Asp Pro Gly Tyr Ser Asn
65                  70                  75                  80

Thr Ala Val Ser Glu Ser Gln Val Thr Tyr Ile Asp Gly Leu Lys Gly
                85                  90                  95

Thr Ile Gln Tyr Arg Gly Tyr Asn Ile Glu Asp Ile Val Gly Lys Lys
            100                 105                 110

Lys Phe Ile Asp Thr Ala His Leu Leu Ile Trp Gly Glu Trp Pro Thr
        115                 120                 125

Pro Glu Gln Ala Lys Ser Leu Gln Glu Lys Leu Ser Ser Val Pro Ile
    130                 135                 140

Leu Asp Glu Ser Val Phe Lys Val Ile Gln Ala Phe Pro Pro Asn Ser
145                 150                 155                 160

Ser Ile Ile Gly Met Met Ile Ala Ala Leu Ser Ala Val Gln Ser Ser
                165                 170                 175

Gln Met Asp Arg Ile Pro Ala His Ala Ala Lys Asn Leu Tyr Leu Gly
            180                 185                 190

Asn Pro Gln Ala Val Asp Asp Glu Ile Val Arg Leu Met Gly Ser Leu
        195                 200                 205

Ser Met Ile Thr Ala Ala Val Tyr Cys His His Thr Gly Arg Glu Phe
    210                 215                 220

Thr Pro Pro Arg Pro Glu Leu Ser Tyr Ile Glu Asn Phe Leu Leu Met
225                 230                 235                 240

Met Gly His Val Glu Ser Ser Thr Gly Leu Pro Asn Pro Gln Tyr Val
                245                 250                 255

Asp Arg Ile Glu Arg Leu Trp Val Leu Ile Ala Asp His Glu Met Thr
            260                 265                 270

Cys Ser Thr Ala Ala Phe Leu Gln Thr Ala Ser Ser Leu Pro Asp Val
        275                 280                 285

Phe Ser Cys Met Ile Ser Ala Leu Ser Ala Leu Tyr Gly Pro Leu His
    290                 295                 300

Gly Gly Ala Ile Glu Val Ala Tyr Lys Asn Phe Glu Glu Ile Gly Ser
305                 310                 315                 320

Val Glu Asn Val Ala Ala Lys Ile Glu Arg Val Lys Ala Gly Lys Glu
                325                 330                 335

Arg Leu Tyr Gly Tyr Gly His Arg Ile Tyr Arg Val Thr Asp Pro Arg
            340                 345                 350

Phe Ile Phe Ile Arg Gln Ile Leu Asp Glu Leu Lys Glu Glu Ile Ala 355                 360                 365
Arg Asn Pro Leu Leu Lys Val Ala Phe Glu Val Asp Arg Val Ala Ser
            370                 375                 380

Glu Asp Glu Tyr Phe Val Thr Arg Lys Leu Arg Pro Asn Ala Asp Leu
385                 390                 395                 400

Phe Ala Ala Leu Val Tyr Ser Ala Met Gly Phe Pro Thr Glu Phe Ile
                405                 410                 415

Leu Pro Leu Ser Leu Leu Ser Arg Thr Gln Gly Phe Met Ala His Trp
            420                 425                 430

Lys Glu Ala Met Ser Ser Thr Ala Arg Ile Trp Arg Pro Gly Gln Ile
            435                 440                 445

Tyr Thr Gly His Leu Asn Arg Glu Met Ala
450                 455

<210> SEQ ID NO 34
<211> LENGTH: 458
<212> TYPE: PRT
<213> ORGANISM: Aspergillus kawachii

<400> SEQUENCE: 34

Met Pro Asp Ile Ala Pro Asn Val Ala Arg Asn Gly Ser Ala Lys Asn
1               5                   10                  15

Ala Glu Asn Lys Pro Glu Thr Pro Val Leu His Val Val Asp Ser Arg
            20                  25                  30

Thr Gly Asn Tyr Phe Pro Ile Pro Ile Val Arg Asn Ala Ile Asn Ala
        35                  40                  45

Ser Glu Phe Lys Lys Leu Lys Ser Pro Glu Asp Pro Ala His Pro Glu
    50                  55                  60

Asp Gln Asn Glu Gln Gly Ile Arg Val Phe Asp Pro Gly Tyr Ser Asn
65                  70                  75                  80

Thr Ala Val Ser Glu Ser Gln Val Thr Tyr Ile Asp Gly Leu Lys Gly
                85                  90                  95

Thr Ile Gln Tyr Arg Gly Tyr Asn Ile Glu Asp Ile Val Gly Lys Lys
            100                 105                 110

Lys Phe Ile Asp Thr Ala His Leu Leu Ile Trp Gly Glu Trp Pro Thr
        115                 120                 125

Pro Glu Gln Ala Arg Ser Leu Gln Glu Lys Leu Ser Ser Val Pro Ile
    130                 135                 140

Leu Asp Glu Ser Val Phe Lys Val Ile Gln Ala Phe Pro Pro Asn Ser
145                 150                 155                 160

Ser Ile Ile Gly Met Met Ile Ala Ala Leu Ser Ala Val Gln Ser Ser
                165                 170                 175

Gln Met Asp Arg Ile Pro Ala His Ala Ala Lys Asn Leu Tyr Leu Gly
            180                 185                 190

Asn Pro Gln Ala Val Asp Asp Glu Ile Val Arg Leu Met Gly Ser Leu
        195                 200                 205

Ser Met Ile Thr Ala Ala Val Tyr Cys His His Thr Gly Arg Glu Phe
    210                 215                 220

Thr Pro Pro Arg Leu Glu Leu Ser Tyr Ile Glu Asn Phe Leu Leu Met
225                 230                 235                 240

Met Gly His Val Glu Ser Ser Thr Gly Leu Pro Asn Pro Gln Tyr Val
                245                 250                 255

Asp Arg Ile Glu Arg Leu Trp Val Leu Ile Ala Asp His Glu Met Thr
            260                 265                 270

```
Cys Ser Thr Ala Ala Phe Leu Gln Thr Ala Ser Ser Leu Pro Asp Val
        275                 280                 285

Phe Ser Cys Met Ile Ser Ala Leu Ser Ala Leu Tyr Gly Pro Leu His
    290                 295                 300

Gly Gly Ala Ile Glu Val Ala Tyr Lys Asn Phe Glu Glu Ile Gly Ser
305                 310                 315                 320

Val Glu Asn Val Ala Ala Lys Ile Glu Arg Val Lys Ala Gly Lys Glu
                325                 330                 335

Arg Leu Tyr Gly Tyr Gly His Arg Ile Tyr Arg Val Thr Asp Pro Arg
            340                 345                 350

Phe Ile Phe Ile Arg Gln Ile Leu Asp Glu Leu Lys Glu Glu Ile Ala
        355                 360                 365

Arg Asn Pro Leu Leu Lys Val Ala Phe Glu Val Asp Arg Val Ala Ser
    370                 375                 380

Glu Asp Glu Tyr Phe Val Thr Arg Lys Leu Arg Pro Asn Ala Asp Leu
385                 390                 395                 400

Phe Ala Ala Leu Val Tyr Ser Ala Met Gly Phe Pro Thr Glu Phe Ile
                405                 410                 415

Leu Pro Leu Ser Leu Leu Ser Arg Thr Gln Gly Phe Met Ala His Trp
            420                 425                 430

Lys Glu Ala Met Ser Ser Thr Ala Arg Ile Trp Arg Pro Gly Gln Ile
        435                 440                 445

Tyr Thr Gly His Leu Ser Arg Glu Met Ala
    450                 455

<210> SEQ ID NO 35
<211> LENGTH: 447
<212> TYPE: PRT
<213> ORGANISM: Aspergillus oryzae

<400> SEQUENCE: 35

Met Thr Val Thr Gln Glu Ala Ser Pro Lys Arg Glu Ser Leu His Ile
1               5                   10                  15

Ile Asp Asp Arg Thr Gly Ser Tyr Tyr Ser Ile Pro Ile Val Asn Asn
            20                  25                  30

Ala Ile Asn Ala Ser Asp Phe Lys Lys Val Thr Ala Pro Glu Asp Lys
        35                  40                  45

Ala Tyr Pro Ala Asn Gln Thr Glu Asn Gly Leu Arg Val Tyr Asp Pro
    50                  55                  60

Gly Tyr Ser Asn Thr Ala Val Ser His Ser Lys Ile Thr Tyr Ile Asp
65                  70                  75                  80

Gly Leu Lys Gly Thr Ile Gln Tyr Arg Gly Tyr Ser Ile Asn Asp Ile
                85                  90                  95

Val Gly Arg Lys Thr Phe Ile Asp Thr Ala His Leu Leu Ile Trp Gly
            100                 105                 110

His Trp Pro Ser Ala Ala Glu Ala Glu Thr Leu Gln Gln Arg Leu Asp
        115                 120                 125

Gln Val Pro Val Pro Gln Asp Phe Val Phe Asn Val Ile Lys Ser Phe
    130                 135                 140

Pro Arg Asp Gly Ser Leu Met Gly Met Val Ile Ala Gly Leu Ser Ala
145                 150                 155                 160

Leu Gln Ser Ser Asp Met Asn Ala Ile Pro Ala His Val Gly Lys Thr
                165                 170                 175

Ile Tyr Leu Asn Asn Pro Glu Leu Ala Asp Gln Gln Ile Ile Arg Val
            180                 185                 190
```

Met Ala Asn Met Ser Met Leu Thr Ala Ala Tyr Cys His His Ile
        195                 200                 205

Gly Arg Asp Phe Thr Pro Pro Arg Ala Gly Leu Ser Tyr Ile Glu Asn
    210                 215                 220

Phe Leu Met Thr Gly His Val Glu Ala Ala Thr Gly Leu Pro Asn
225                 230                 235                 240

Pro Arg Tyr Val Asn Ala Ile Glu Arg Leu Trp Val Leu Ile Ala Asp
            245                 250                 255

His Glu Met Thr Cys Ser Thr Ala Ala Leu Leu Gln Thr Ala Ser Ala
        260                 265                 270

Leu Pro Asp Val Ile Ser Cys Met Val Ser Ala Ile Ser Ala Leu Tyr
    275                 280                 285

Gly Pro Leu His Gly Gly Ala Ile Glu Val Ala Tyr Lys Asn Ile Glu
290                 295                 300

Ser Ile Gly Ser Ile Ser Asn Val Pro Ala Lys Ile Ala Arg Val Lys
305                 310                 315                 320

Ala Gly Lys Glu Arg Leu Tyr Gly Tyr Gly His Arg Val Tyr Arg Val
            325                 330                 335

Thr Asp Pro Arg Phe Val Phe Ile Arg Glu Ile Leu Asn Glu Leu Ser
        340                 345                 350

Glu Glu Val Glu Lys Asp Pro Leu Leu Lys Val Ala Phe Glu Val Asp
    355                 360                 365

Arg Val Ala Ser Glu Asp Glu Tyr Phe Thr Ser Arg Asn Leu Arg Pro
370                 375                 380

Asn Ala Asp Leu Phe Ala Ala Phe Val Tyr Lys Ala Leu Gly Phe Pro
385                 390                 395                 400

Pro Glu Phe Ile Leu Pro Leu Ser Ile Leu Ser Arg Thr Gln Gly Phe
            405                 410                 415

Met Ala His Trp Arg Glu Ala Met Gly Asn Pro Pro Arg Ile Trp Arg
        420                 425                 430

Pro Gly Gln Ile Tyr Thr Gly Asp Leu Asn Lys Ser Met Asp Glu
    435                 440                 445

<210> SEQ ID NO 36
<211> LENGTH: 447
<212> TYPE: PRT
<213> ORGANISM: Aspergillus oryzae

<400> SEQUENCE: 36

Met Thr Val Thr Gln Glu Ala Ser Pro Lys Arg Glu Ser Leu His Ile
1               5                   10                  15

Ile Asp Asp Arg Thr Gly Ser Tyr Tyr Ser Ile Pro Ile Val Asn Asn
            20                  25                  30

Ala Ile Asn Ala Ser Asp Phe Lys Lys Val Thr Ala Pro Glu Asp Lys
        35                  40                  45

Ala Tyr Pro Ala Asn Gln Thr Glu Asn Gly Leu Arg Val Tyr Asp Pro
    50                  55                  60

Gly Tyr Ser Asn Thr Ala Val Ser His Ser Lys Ile Thr Tyr Ile Asp
65                  70                  75                  80

Gly Leu Lys Gly Thr Ile Gln Tyr Arg Gly Tyr Ser Ile Asn Asp Ile
                85                  90                  95

Val Gly Arg Lys Thr Phe Ile Asp Thr Ala His Leu Leu Ile Trp Gly
            100                 105                 110

His Trp Pro Ser Thr Ala Glu Ala Glu Thr Leu Gln Gln Arg Leu Asp

Gln Val Pro Val Pro Gln Asp Phe Val Phe Asn Val Ile Lys Ser Phe
              115                 120                 125

Pro Arg Asp Gly Ser Leu Met Gly Met Val Ile Ala Gly Leu Ser Ala
130                 135                 140

Leu Gln Ser Ser Asp Met Asn Ala Ile Pro Ala His Val Gly Lys Thr
145                 150                 155                 160

Ile Tyr Leu Asn Asn Pro Glu Leu Ala Asp Gln Gln Ile Ile Arg Val
              165                 170                 175

Met Ala Asn Met Ser Met Leu Thr Ala Ala Tyr Cys His His Ile
              180                 185                 190

Gly Arg Asp Phe Thr Pro Pro Arg Ala Gly Leu Ser Tyr Ile Glu Asn
195                 200                 205

Phe Leu Leu Met Thr Gly His Val Glu Ala Ala Thr Gly Leu Pro Asn
              210                 215                 220

Pro Arg Tyr Val Asn Ala Ile Glu Arg Leu Trp Val Leu Ile Ala Asp
225                 230                 235                 240

His Glu Met Thr Cys Ser Thr Ala Ala Leu Leu Gln Thr Ala Ser Ala
              245                 250                 255

Leu Pro Asp Val Ile Ser Cys Met Val Ser Ala Ile Ser Ala Leu Tyr
              260                 265                 270

Gly Pro Leu His Gly Gly Ala Ile Glu Val Ala Tyr Lys Asn Ile Glu
              275                 280                 285

Ser Ile Gly Ser Ile Ser Asn Val Pro Ala Lys Ile Ala Arg Val Lys
290                 295                 300

Ala Gly Lys Glu Arg Leu Tyr Gly Tyr Gly His Arg Val Tyr Arg Val
305                 310                 315                 320

Thr Asp Pro Arg Phe Val Phe Ile Arg Glu Ile Leu Asn Glu Leu Ser
              325                 330                 335

Glu Glu Val Glu Lys Asp Pro Leu Leu Lys Val Ala Phe Glu Val Asp
              340                 345                 350

Arg Val Ala Ser Glu Asp Glu Tyr Phe Thr Ser Arg Asn Leu Arg Pro
              355                 360                 365

Asn Ala Asp Leu Phe Ala Ala Phe Val Tyr Lys Ala Leu Gly Phe Pro
              370                 375                 380

Pro Glu Phe Ile Leu Pro Leu Ser Ile Leu Ser Arg Thr Gln Gly Phe
385                 390                 395                 400

Met Ala His Trp Arg Glu Ala Met Gly Asn Pro Pro Arg Ile Trp Arg
              405                 410                 415

Pro Gly Gln Ile Tyr Thr Gly Asp Leu Asn Lys Ser Met Asp Glu
              420                 425                 430

435                 440                 445

<210> SEQ ID NO 37
<211> LENGTH: 447
<212> TYPE: PRT
<213> ORGANISM: Aspergillus oryzae

<400> SEQUENCE: 37

Met Thr Val Thr Gln Glu Ala Ser Pro Lys Arg Glu Ser Leu His Ile
1               5                   10                  15

Ile Asp Asp Arg Thr Gly Ser Tyr Tyr Ser Ile Pro Ile Val Asn Asn
                20                  25                  30

Ala Ile Asn Ala Ser Asp Phe Lys Lys Val Thr Ala Pro Glu Asp Lys
            35                  40                  45

```
Ala Tyr Pro Ala Asn Gln Thr Glu Asn Gly Leu Arg Val Tyr Asp Pro
     50                  55                  60

Gly Tyr Ser Asn Thr Ala Val Ser His Ser Lys Ile Thr Tyr Ile Asp
 65                  70                  75                  80

Gly Leu Lys Gly Thr Ile Gln Tyr Arg Gly Tyr Ser Ile Asn Asp Ile
                 85                  90                  95

Val Gly Arg Lys Thr Phe Ile Asp Thr Ala His Leu Leu Ile Trp Gly
            100                 105                 110

His Trp Pro Ser Thr Ala Glu Ala Glu Thr Leu Gln Gln Arg Leu Asp
            115                 120                 125

Gln Val Pro Val Pro Gln Asp Phe Val Phe Asn Val Ile Lys Ser Phe
130                 135                 140

Pro Arg Asp Gly Ser Leu Met Gly Met Val Ile Ala Gly Leu Ser Ala
145                 150                 155                 160

Leu Gln Ser Ser Asp Met Asn Ala Ile Pro Ala His Val Gly Lys Thr
                165                 170                 175

Ile Tyr Leu Asn Asn Pro Glu Leu Ala Asp Gln Gln Ile Ile Arg Val
            180                 185                 190

Met Ala Asn Met Ser Met Leu Thr Ala Ala Tyr Cys His His Ile
            195                 200                 205

Gly Arg Asp Phe Thr Pro Pro Arg Ala Gly Leu Ser Tyr Ile Glu Asn
210                 215                 220

Phe Leu Leu Met Thr Gly His Val Glu Ala Ala Thr Gly Leu Pro Asn
225                 230                 235                 240

Pro Arg Tyr Val Asn Ala Ile Glu Arg Leu Trp Val Leu Ile Ala Asp
                245                 250                 255

His Glu Met Thr Cys Ser Thr Ala Ala Leu Leu Gln Thr Ala Ser Ala
            260                 265                 270

Leu Pro Asp Val Ile Ser Cys Met Val Ser Ala Ile Ser Ala Leu Tyr
            275                 280                 285

Gly Pro Leu His Gly Gly Ala Ile Glu Val Ala Tyr Lys Asn Ile Glu
            290                 295                 300

Ser Ile Gly Ser Ile Ser Asn Val Pro Ala Lys Ile Ala Arg Val Lys
305                 310                 315                 320

Ala Gly Lys Glu Arg Leu Tyr Gly Tyr Gly His Arg Val Tyr Arg Val
                325                 330                 335

Thr Asp Pro Arg Phe Val Phe Ile Arg Glu Ile Leu Asn Glu Leu Ser
            340                 345                 350

Glu Glu Val Glu Lys Asp Pro Leu Leu Lys Val Ala Phe Glu Val Asp
            355                 360                 365

Arg Val Ala Ser Glu Asp Glu Tyr Phe Thr Ser Arg Asn Leu Arg Pro
370                 375                 380

Asn Ala Asp Leu Phe Ala Ala Phe Val Tyr Lys Ala Leu Gly Phe Pro
385                 390                 395                 400

Pro Glu Phe Ile Leu Pro Leu Ser Ile Leu Ser Arg Thr Gln Gly Phe
                405                 410                 415

Met Ala His Trp Arg Glu Ala Met Gly Asn Pro Pro Arg Ile Trp Arg
            420                 425                 430

Pro Gly Gln Ile Tyr Thr Gly Asp Leu Asn Lys Ser Met Asp Glu
            435                 440                 445

<210> SEQ ID NO 38
<211> LENGTH: 466
<212> TYPE: PRT
```

-continued

<213> ORGANISM: Aspergillus flavus

<400> SEQUENCE: 38

Met Thr Val Thr Gln Glu Ala Ser Pro Lys Arg Glu Ser Leu His Ile
1               5                   10                  15

Ile Asp Asp Arg Thr Gly Ser Tyr Tyr Ser Ile Pro Ile Val Asn Asn
            20                  25                  30

Ala Ile Asn Ala Ser Asp Phe Lys Lys Val Thr Ala Pro Glu Asp Lys
        35                  40                  45

Ala Tyr Pro Ala Asn Gln Thr Glu Asn Gly Leu Arg Val Tyr Asp Pro
    50                  55                  60

Gly Tyr Ser Asn Thr Ala Val Ser His Ser Lys Ile Tyr Ile Asp
65                  70                  75                  80

Gly Leu Lys Gly Thr Ile Gln Tyr Arg Gly Tyr Ser Ile Asn Asp Ile
                85                  90                  95

Val Gly Arg Lys Thr Phe Ile Asp Thr Ala His Leu Leu Ile Trp Gly
            100                 105                 110

His Trp Pro Ser Thr Ala Glu Ala Glu Thr Leu Gln Gln Arg Leu Asp
        115                 120                 125

Gln Val Pro Val Pro Gln Asp Phe Val Phe Asn Val Ile Lys Ser Phe
    130                 135                 140

Pro Arg Asp Gly Ser Leu Met Gly Met Val Ile Ala Gly Leu Ser Ala
145                 150                 155                 160

Leu Gln Ser Ser Asp Met Asn Ala Ile Pro Ala His Val Gly Lys Thr
                165                 170                 175

Ile Tyr Leu Asn Asn Pro Glu Leu Ala Asp Gln Gln Ile Ile Arg Val
            180                 185                 190

Met Ala Asn Met Ser Met Leu Thr Ala Ala Tyr Cys His His Ile
        195                 200                 205

Gly Arg Asp Phe Thr Pro Pro Arg Ala Gly Leu Ser Tyr Ile Glu Asn
    210                 215                 220

Phe Leu Leu Met Thr Gly His Val Glu Ala Ala Thr Gly Leu Pro Asn
225                 230                 235                 240

Pro Arg Tyr Val Asn Ala Ile Glu Arg Leu Trp Val Leu Ile Ala Asp
                245                 250                 255

His Glu Met Thr Cys Ser Thr Ala Ala Leu Leu Gln Thr Ala Ser Ala
            260                 265                 270

Leu Pro Asp Val Ile Ser Cys Met Val Ser Ala Ile Ser Ala Leu Tyr
        275                 280                 285

Gly Pro Leu His Gly Gly Ala Ile Glu Val Ala Tyr Lys Asn Ile Glu
    290                 295                 300

Ser Ile Gly Ser Ile Ser Asn Val Pro Ala Lys Ile Ala Arg Val Lys
305                 310                 315                 320

Ala Gly Lys Glu Arg Leu Tyr Gly Tyr Gly His Arg Val Tyr Arg Val
                325                 330                 335

Thr Asp Pro Arg Phe Val Phe Ile Arg Glu Ile Leu Asn Glu Leu Ser
            340                 345                 350

Glu Glu Val Glu Lys Asp Pro Leu Leu Lys Val Ala Phe Glu Val Asp
        355                 360                 365

Arg Val Ala Ser Glu Asp Glu Tyr Phe Thr Ser Arg Asn Leu Arg Pro
    370                 375                 380

Asn Ala Asp Leu Phe Ala Ala Val Tyr Lys Ala Leu Gly Phe Pro
385                 390                 395                 400

```
Pro Glu Phe Ile Leu Pro Leu Ser Ile Leu Ser Arg Thr Gln Gly Phe
                405                 410                 415
Met Ala His Trp Arg Glu Ala Met Gly Met Pro Glu Ser Thr Leu Asn
            420                 425                 430
Ser Ser Arg Ser Ile Cys Pro Asp Thr Asn Ile Gly Asn Pro Pro Arg
        435                 440                 445
Ile Trp Arg Pro Gly Gln Ile Tyr Thr Gly Asp Leu Asn Lys Ser Met
450                 455                 460
Asp Glu
465

<210> SEQ ID NO 39
<211> LENGTH: 447
<212> TYPE: PRT
<213> ORGANISM: Aspergillus flavus

<400> SEQUENCE: 39

Met Thr Val Thr Gln Glu Ala Ser Pro Lys Arg Glu Ser Leu His Ile
1               5                   10                  15
Ile Asp Asp Arg Thr Gly Ser Tyr Tyr Ser Ile Pro Ile Val Asn Asn
            20                  25                  30
Ala Ile Asn Ala Ser Asp Phe Lys Lys Val Thr Ala Pro Glu Asp Lys
        35                  40                  45
Ala Tyr Pro Ala Asn Gln Thr Glu Asn Gly Leu Arg Val Tyr Asp Pro
    50                  55                  60
Gly Tyr Ser Asn Thr Ala Val Ser His Ser Lys Ile Thr Tyr Ile Asp
65                  70                  75                  80
Gly Leu Lys Gly Thr Ile Gln Tyr Arg Gly Tyr Ser Ile Asn Asp Ile
                85                  90                  95
Val Gly Arg Lys Thr Phe Ile Asp Thr Ala His Leu Leu Ile Trp Gly
            100                 105                 110
His Trp Pro Ser Thr Ala Glu Ala Glu Thr Leu Gln Gln Arg Leu Asp
        115                 120                 125
Gln Val Pro Val Pro Gln Asp Phe Val Phe Asn Val Ile Lys Ser Phe
    130                 135                 140
Pro Arg Asp Gly Ser Leu Met Gly Met Val Ile Ala Gly Leu Ser Ala
145                 150                 155                 160
Leu Gln Ser Ser Asp Met Asn Ala Ile Pro Ala His Val Gly Lys Thr
                165                 170                 175
Ile Tyr Leu Asn Asn Pro Glu Leu Ala Asp Gln Gln Ile Ile Arg Val
            180                 185                 190
Met Ala Asn Met Ser Met Leu Thr Ala Ala Ala Tyr Cys His His Ile
        195                 200                 205
Gly Arg Asp Phe Thr Pro Pro Arg Ala Gly Leu Ser Tyr Ile Glu Asn
    210                 215                 220
Phe Leu Leu Met Thr Gly His Val Glu Ala Ala Thr Gly Leu Pro Asn
225                 230                 235                 240
Pro Arg Tyr Val Asn Ala Ile Glu Arg Leu Trp Val Leu Ile Ala Asp
                245                 250                 255
His Glu Met Thr Cys Ser Thr Ala Ala Leu Leu Gln Thr Ala Ser Ala
            260                 265                 270
Leu Pro Asp Val Ile Ser Cys Met Val Ser Ala Ile Ser Ala Leu Tyr
        275                 280                 285
Gly Pro Leu His Gly Gly Ala Ile Glu Val Ala Tyr Lys Asn Ile Glu
    290                 295                 300
```

```
Ser Ile Gly Ser Ile Ser Asn Val Pro Ala Lys Ile Ala Arg Val Lys
305                 310                 315                 320

Ala Gly Lys Glu Arg Leu Tyr Gly Tyr Gly His Arg Val Tyr Arg Val
            325                 330                 335

Thr Asp Pro Arg Phe Val Phe Ile Arg Glu Ile Leu Asn Glu Leu Ser
        340                 345                 350

Glu Glu Val Glu Lys Asp Pro Leu Leu Lys Val Ala Phe Glu Val Asp
    355                 360                 365

Arg Val Ala Ser Glu Asp Glu Tyr Phe Thr Ser Arg Asn Leu Arg Pro
370                 375                 380

Asn Ala Asp Leu Phe Ala Ala Phe Val Tyr Lys Ala Leu Gly Phe Pro
385                 390                 395                 400

Pro Glu Phe Ile Leu Pro Leu Ser Ile Leu Ser Arg Thr Gln Gly Phe
                405                 410                 415

Met Ala His Trp Arg Glu Ala Met Gly Asn Pro Pro Arg Ile Trp Arg
            420                 425                 430

Pro Gly Gln Ile Tyr Thr Gly Asp Leu Asn Lys Ser Met Asp Glu
            435                 440                 445

<210> SEQ ID NO 40
<211> LENGTH: 463
<212> TYPE: PRT
<213> ORGANISM: Talaromyces marneffei

<400> SEQUENCE: 40

Met Ser Pro Ala Ala Ile Ile Ser Ser Asp Ala Ala Lys Ser Val
1               5                   10                  15

Asp Ala Lys Ala Ser Ala Lys Thr Ile Ser Arg Asn Phe Leu His Val
                20                  25                  30

Ile Asp Glu Arg Thr Gly Gln Tyr Tyr Gln Ile Pro Ile His His Asn
            35                  40                  45

Ala Ile Ser Ala Asn Glu Phe Lys Lys Ile Lys Ala Pro Asp Ser Glu
        50                  55                  60

Tyr Tyr Ala Asp Gln Asn Glu Asn Gly Ile Arg Val Phe Asp Pro Gly
65                  70                  75                  80

Phe Thr Asn Thr Ala Val Val Glu Ser Lys Val Thr Tyr Val Asp Gly
                85                  90                  95

Lys Arg Gly Lys Ile Gln Tyr Arg Gly Tyr Asp Leu Ala Asp Val Val
                100                 105                 110

Ala Asn Asn Lys Lys Phe Ile Asp Thr Ala His Leu Met Val Phe Gly
            115                 120                 125

Phe Trp Pro Thr Ala Glu Glu Gly Ala Gly Phe Gln Gln Lys Leu Phe
        130                 135                 140

Asp Ala Met His Ile Glu Gln Cys Val Ile Asp Thr Ile His Ala Phe
145                 150                 155                 160

Pro Arg Thr Ala Ser Thr Thr Leu Met Leu Thr Ala Gly Leu Ala Ala
                165                 170                 175

Val Gln Ala Thr Gln Met Asp Arg Ile Pro Ala His Met Ala Lys Asn
            180                 185                 190

Leu Tyr Leu Gly Asn Pro Thr Leu Val Asp Glu Gln Ile Val Arg Leu
        195                 200                 205

Met Gly Val Leu Pro Ile Val Ser Ala Val Ala Tyr Cys His His Thr
210                 215                 220

Gly Arg Glu Phe Lys Ser Pro Arg Ser Asp Leu Thr Tyr Ile Glu Asn
```

```
                    225                 230                 235                 240
            Phe Leu Tyr Met Cys Gly His Val Gln Glu Glu Thr Gly Leu Pro Asn
                            245                 250                 255
            Pro Arg Tyr Val Gln Asn Phe Glu Arg Leu Trp Ser Leu Val Ala Asp
                            260                 265                 270
            His Glu Met Thr Cys Ser Thr Ala Ala Val Leu Leu Thr Ala Ser Ser
                            275                 280                 285
            Leu Pro Asp Pro Ile Ser Cys Ile Ile Ser Gly Ile Gly Ala Ser Tyr
                290                 295                 300
            Gly Pro Leu His Gly Gly Ala Ile Glu Phe Ala Tyr Lys Asp Met Ala
            305                 310                 315                 320
            Asp Ile Gly Ser Val Asp Asn Cys Gln Thr Lys Ile Asp Arg Val Lys
                            325                 330                 335
            Ser Gly Lys Glu Arg Leu Phe Gly Tyr Gly His Arg Val Tyr Lys Val
                            340                 345                 350
            Thr Asp Pro Arg Ser Glu His Ile Gln Ala Val Leu Glu Thr Leu Lys
                            355                 360                 365
            Glu Glu Ile Asp Asn Asp Pro Leu Leu Lys Val Ala Phe Glu Leu Asn
                370                 375                 380
            Arg Ile Ala Gln Glu Asp Glu Tyr Phe Val Ser Arg Gly Leu Lys Pro
            385                 390                 395                 400
            Asn Ala Asp Leu Phe Ala Ala Phe Thr Tyr Gly Ala Met Gly Phe Pro
                            405                 410                 415
            Pro Asp Phe Ile Leu Thr Ile Ser Thr Ile Ser Arg Thr Gln Gly Leu
                            420                 425                 430
            Met Ala His Trp Lys Glu Ala Met Ser Gly Lys Pro Leu Ile Trp Arg
                            435                 440                 445
            Pro Thr Gln Val Tyr Thr Gly Lys Leu Asp Leu Lys Met Glu Val
                            450                 455                 460

<210> SEQ ID NO 41
<211> LENGTH: 458
<212> TYPE: PRT
<213> ORGANISM: Aspergillus acidus

<400> SEQUENCE: 41

Met Pro Asp Ile Ala Pro Asn Val Ala Arg Asn Gly Ser Ala Lys Asn
            1               5                   10                  15
            Ala Glu Asn Lys Pro Glu Thr Pro Val Leu His Val Val Asp Ser Arg
                            20                  25                  30
            Thr Gly Asn Tyr Phe Pro Ile Pro Ile Val Arg Asn Ala Ile Asn Ala
                            35                  40                  45
            Ser Glu Phe Lys Lys Leu Lys Ser Pro Glu Asp Pro Ala His Pro Glu
                50                  55                  60
            Asp Gln Asn Glu Gln Gly Ile Arg Val Phe Asp Pro Gly Tyr Ser Asn
            65                  70                  75                  80
            Thr Ala Val Ser Glu Ser Gln Val Thr Tyr Ile Asp Gly Leu Lys Gly
                            85                  90                  95
            Thr Ile Gln Tyr Arg Gly Tyr Asn Ile Glu Asp Ile Val Gly Lys Lys
                            100                 105                 110
            Lys Phe Ile Asp Thr Ala His Leu Leu Ile Trp Gly Glu Trp Pro Thr
                            115                 120                 125
            Pro Glu Gln Ala Lys Ser Leu Gln Glu Lys Leu Ser Ser Val Pro Ile
                130                 135                 140
```

```
Leu Asp Glu Ser Val Phe Lys Val Ile Gln Ala Phe Pro Pro Asn Ser
145                 150                 155                 160

Ser Ile Ile Gly Met Met Ile Ala Ala Leu Ser Ala Val Gln Ser Ser
            165                 170                 175

Gln Met Asp Arg Ile Pro Ala His Ala Ala Lys Asn Leu Tyr Leu Gly
        180                 185                 190

Asn Pro Gln Ala Val Asp Asp Glu Ile Val Arg Leu Met Gly Ser Leu
    195                 200                 205

Ser Met Ile Thr Ala Ala Val Tyr Cys His His Thr Gly Arg Glu Phe
210                 215                 220

Thr Pro Pro Arg Leu Glu Leu Ser Tyr Ile Glu Asn Phe Leu Leu Met
225                 230                 235                 240

Met Gly His Val Glu Ser Ser Thr Gly Leu Pro Asn Pro Gln Tyr Val
            245                 250                 255

Asp Arg Ile Glu Arg Leu Trp Val Leu Ile Ala Asp His Glu Met Thr
        260                 265                 270

Cys Ser Thr Ala Ala Phe Leu Gln Thr Ala Ser Ser Leu Pro Asp Val
    275                 280                 285

Phe Ser Cys Met Ile Ser Ala Leu Ser Ala Leu Tyr Gly Pro Leu His
290                 295                 300

Gly Gly Ala Ile Glu Val Ala Tyr Lys Asn Phe Glu Glu Ile Gly Ser
305                 310                 315                 320

Val Glu Asn Val Ala Ala Lys Ile Glu Arg Val Lys Ala Gly Lys Glu
            325                 330                 335

Arg Leu Tyr Gly Tyr Gly His Arg Ile Tyr Arg Val Thr Asp Pro Arg
        340                 345                 350

Phe Ile Phe Ile Arg Gln Ile Leu Asp Glu Leu Lys Glu Glu Ile Ala
    355                 360                 365

Arg Asn Pro Leu Leu Lys Val Ala Phe Glu Val Asp Arg Val Ala Ser
370                 375                 380

Glu Asp Glu Tyr Phe Val Thr Arg Lys Leu Arg Pro Asn Ala Asp Leu
385                 390                 395                 400

Phe Ala Ala Leu Val Tyr Ser Ala Met Gly Phe Pro Thr Glu Phe Ile
            405                 410                 415

Leu Pro Leu Ser Leu Leu Ser Arg Thr Gln Gly Phe Met Ala His Trp
        420                 425                 430

Lys Glu Ala Met Ser Ser Thr Ala Arg Ile Trp Arg Pro Gly Gln Ile
    435                 440                 445

Tyr Thr Gly His Leu Asn Arg Glu Met Ala
450                 455
```

<210> SEQ ID NO 42
<211> LENGTH: 458
<212> TYPE: PRT
<213> ORGANISM: Aspergillus carbonarius

<400> SEQUENCE: 42

```
Met Pro Asp Ile Ala Ser Asn Gly Ala Arg Asn Gly Thr Ser Ala His
1               5                   10                  15

Ala Glu Asp Lys Pro Asp Thr Pro Val Leu His Val Val Asp Ser Arg
            20                  25                  30

Thr Gly Lys Tyr His Ser Ile Pro Ile Val Arg Asn Ala Ile Asn Ala
        35                  40                  45

Ser Glu Phe Lys Lys Leu Lys Thr Pro Glu Asp Pro Glu His Pro Glu
    50                  55                  60
```

```
Asp Gln Asn Glu Gln Gly Ile Arg Val Phe Asp Pro Gly Tyr Ser Asn
 65                  70                  75                  80

Thr Ala Val Ser Glu Ser Lys Val Thr Tyr Ile Asp Gly Leu Lys Gly
                 85                  90                  95

Thr Ile Gln Tyr Arg Gly Tyr Arg Ile Glu Asp Ile Val Gly Lys Lys
            100                 105                 110

Lys Phe Ile Asp Thr Ala His Leu Leu Ile Trp Gly Asp Trp Pro Thr
        115                 120                 125

Pro Glu Gln Ala Gln Thr Leu His Glu Lys Leu Ala Ser Val Pro Val
    130                 135                 140

Ile Asn Glu Ser Val Phe Lys Val Ile Gln Ala Phe Pro Pro Asn Ala
145                 150                 155                 160

Ser Ile Ile Gly Met Met Ile Ala Ala Leu Ser Ala Val Gln Ser Ser
                165                 170                 175

Gln Met Asp Arg Ile Pro Ala His Ala Ala Lys Asn Leu Tyr Leu Gly
            180                 185                 190

Val Pro Lys Ala Val Asp Asp Glu Ile Ile Arg Leu Met Gly Thr Leu
        195                 200                 205

Ser Met Ile Thr Ala Ala Val Tyr Cys His His Ile Gly Arg Glu Phe
210                 215                 220

Thr Pro Pro Arg Pro Glu Leu Ser Tyr Ile Glu Asn Phe Leu Leu Met
225                 230                 235                 240

Met Gly His Val Asp Ala Ser Thr Gly Leu Pro Asn Pro Gln Tyr Val
                245                 250                 255

Asp Arg Ile Glu Arg Leu Trp Val Leu Ile Ala Asp His Glu Met Thr
            260                 265                 270

Cys Ser Thr Ala Ala Phe Leu Gln Thr Ala Ser Ser Leu Pro Asp Val
        275                 280                 285

Phe Ser Cys Met Ile Ser Ala Leu Ser Ala Leu Tyr Gly Pro Leu His
    290                 295                 300

Gly Gly Ala Ile Glu Val Ala Tyr Lys Asn Phe Glu Glu Ile Gly Thr
305                 310                 315                 320

Val Glu Asn Val Ala Ala Lys Ile Glu Arg Val Lys Ala Gly Lys Glu
                325                 330                 335

Arg Leu Tyr Gly Tyr Gly His Arg Ile Tyr Arg Val Thr Asp Pro Arg
            340                 345                 350

Phe Thr Phe Ile Ser Gln Ile Leu Asp Glu Leu Lys Glu Glu Ile Ala
        355                 360                 365

Arg Asn Pro Ile Leu Lys Val Ala Phe Glu Val Asp Arg Val Ala Ser
    370                 375                 380

Glu Asp Glu Tyr Phe Val Ser Arg Arg Leu Arg Pro Asn Ala Asp Leu
385                 390                 395                 400

Phe Ala Ala Leu Thr Tyr Ser Ala Met Gly Phe Pro Thr Glu Phe Ile
                405                 410                 415

Leu Pro Leu Ser Leu Leu Ser Arg Thr Gln Gly Phe Met Ala His Trp
            420                 425                 430

Lys Glu Ala Met Ser Gly Ser Ala Arg Ile Trp Arg Pro Gly Gln Ile
        435                 440                 445

Tyr Thr Gly His Leu Asn Arg Glu Met Glu
    450                 455

<210> SEQ ID NO 43
<211> LENGTH: 451
```

```
<212> TYPE: PRT
<213> ORGANISM: Aspergillus carbonarius

<400> SEQUENCE: 43
```

| | | | | | | | | | | | | | | |
|---|---|---|---|---|---|---|---|---|---|---|---|---|---|---|
|Met|Thr|Thr|Asn|Gly|Ile|Asn|Gly|Thr|Asn|Gly|Val|Asp|Ala|Val|Pro|
|1| | | |5| | | |10| | | |15| | |

Ser Leu His Val Val Asp Ser Arg Thr Gly Gln Tyr Tyr Glu Ile Pro
            20                  25                  30

Ile Val His Asn Ala Ile His Ala Ser Glu Phe Lys Arg Ile Lys Ala
            35                  40                  45

Pro Leu Asn Glu Asp Tyr Tyr Pro Asp Gln Thr Glu Asn Gly Ile Arg
 50                  55                  60

Val Phe Asp Pro Gly Phe Ser Asn Thr Ala Val Lys Glu Ser Lys Ile
 65                  70                  75                  80

Thr Tyr Ile Asp Gly Thr Lys Gly Ile Ile Gln Tyr Arg Gly Tyr Ser
            85                  90                  95

Ile Asp Asp Ile Ile Arg Gln Gly Lys Ser Phe Ile Asp Thr Val His
            100                 105                 110

Leu Leu Ile Trp Gly His Trp Pro Ser Pro Ile Glu Ala Lys Lys Leu
            115                 120                 125

Gln Ile Arg Ile Ser Asp Ala Met Thr Leu Asp Gly Ser Val Tyr Gln
130                 135                 140

Val Ile Arg Ser Phe Pro Pro Ser Gly Ser Ile Met Gly Met Ile Ile
145                 150                 155                 160

Ala Gly Leu Ser Ala Leu Gln Ser Thr Gln Met His Thr Val Pro Ala
            165                 170                 175

His Ala Ala Lys Asn Leu Tyr Leu Gly Asn Pro Glu Ala Val Asp Glu
            180                 185                 190

Gln Ile Ile Thr Val Leu Ala Ala Leu Pro Met Ile Ser Ala Ile Ala
            195                 200                 205

Tyr Cys His His Leu Asn Arg Pro Phe Thr Pro Pro Arg Arg Asp Leu
            210                 215                 220

Ser Tyr Ile Glu Asn Leu Phe Leu Met Thr Gly His Val Asp Pro Gln
225                 230                 235                 240

Thr Ser Leu Pro Asn Pro Arg Tyr Val Gly Tyr Phe Glu Arg Leu Trp
            245                 250                 255

Val Leu Ile Ala Asp His Glu Met Thr Cys Ser Thr Ala Ala Met Leu
            260                 265                 270

Gln Thr Ala Ser Ser Leu Pro Asp Ala Ile Ser Ser Leu Ile Ser Ala
            275                 280                 285

Ile Ser Ala Met Tyr Gly Pro Leu His Gly Gly Ala Ile Glu Val Ala
            290                 295                 300

Tyr Arg Asp Ile Ala Ala Ile Gly Ser Ile Pro Ala Cys Gln Glu Lys
305                 310                 315                 320

Ile Asp Arg Val Lys Ser Gly Lys Glu Arg Leu Tyr Gly Tyr Gly His
            325                 330                 335

Arg Val Tyr Arg Val Thr Asp Pro Arg Ala Val His Ile Gln Ala Val
            340                 345                 350

Leu Ala Glu Leu Gln Glu Glu Ile Ala Gln Asp Pro Leu Leu Lys Val
            355                 360                 365

Ala Phe Glu Leu Asn Arg Leu Ala Ala Asp Asp Glu Tyr Phe Val Lys
            370                 375                 380

Arg Lys Leu Lys Pro Asn Ala Asp Leu Phe Ala Ala Phe Thr Tyr Gly
385                 390                 395                 400

```
Ala Met Gly Phe Pro Glu Glu Phe Ile Leu Pro Ile Ser Ile Ile Ser
            405                 410                 415

Arg Thr Gln Gly Phe Leu Ala His Trp Lys Glu Ala Met Gly Gly Thr
        420                 425                 430

Ala Lys Ile Trp Arg Pro Gly Gln Val Tyr Val Gly Glu Val Asp Arg
        435                 440                 445

Lys Phe Glu
    450

<210> SEQ ID NO 44
<211> LENGTH: 462
<212> TYPE: PRT
<213> ORGANISM: Aspergillus brasiliensis

<400> SEQUENCE: 44

Met Pro Asp Ile Ala Ser Asn Gly Ala Arg Asn Gly Thr Ser Gln His
1               5                   10                  15

Ala Asp Lys Pro Glu Pro Val Leu His Val Val Asp Ser Arg Thr
            20                  25                  30

Gly Lys Tyr Phe Pro Ile Pro Ile Val Arg Asn Ala Ile Asn Ala Ser
        35                  40                  45

Glu Phe Lys Lys Leu Lys Ser Pro Glu Asp Pro Ala His Pro Glu Asp
50                  55                  60

Gln Asn Glu Gln Gly Ile Arg Val Phe Asp Pro Gly Tyr Ser Asn Thr
65                  70                  75                  80

Ala Val Ser Glu Ser Gln Ile Thr Tyr Ile Asp Gly Leu Lys Gly Thr
            85                  90                  95

Ile Gln Tyr Arg Gly Tyr Asn Ile Glu Asn Ile Val Gly Lys Lys Lys
        100                 105                 110

Phe Ile Asp Thr Ala His Leu Leu Ile Trp Gly Glu Trp Pro Thr Pro
        115                 120                 125

Glu Glu Ala Lys Ser Leu Gln Glu Lys Leu Ser Ser Val Pro Val Leu
    130                 135                 140

Asp Glu Ser Val Phe Lys Val Ile Gln Ala Phe Pro Leu Thr Ala Pro
145                 150                 155                 160

Ser Pro Asn Ser Ser Ile Ile Gly Met Met Ile Ala Ala Leu Ser Ala
                165                 170                 175

Val Gln Ser Ser Gln Met Asp Arg Ile Pro Ala His Ala Ala Lys Asn
            180                 185                 190

Leu Tyr Leu Gly Asn Pro Lys Ala Val Asp Asp Glu Ile Ile Arg Leu
        195                 200                 205

Met Gly Ser Leu Ser Met Ile Thr Ala Ala Val Tyr Cys His His Thr
    210                 215                 220

Gly Arg Glu Phe Thr Pro Pro Arg Pro Glu Leu Ser Tyr Ile Glu Asn
225                 230                 235                 240

Phe Leu Leu Met Met Gly His Val Glu Ser Thr Thr Gly Leu Pro Asn
                245                 250                 255

Pro Gln Tyr Val Asp Arg Ile Glu Arg Leu Trp Val Leu Ile Ala Asp
            260                 265                 270

His Glu Met Thr Cys Ser Thr Ala Ala Phe Leu Gln Thr Ala Ser Ser
        275                 280                 285

Leu Pro Asp Val Phe Ser Cys Met Ile Ser Ala Leu Ser Ala Leu Tyr
    290                 295                 300

Gly Pro Leu His Gly Gly Ala Ile Glu Val Ala Tyr Lys Asn Phe Glu
```

```
                305                 310                 315                 320
Glu Ile Gly Ser Val Glu Asn Val Ala Ala Lys Ile Glu Arg Val Lys
                325                 330                 335

Ala Gly Lys Glu Arg Leu Tyr Gly Tyr Gly His Arg Ile Tyr Arg Val
                340                 345                 350

Thr Asp Pro Arg Phe Ile Phe Ile Arg Gln Ile Leu Asp Glu Leu Lys
                355                 360                 365

Glu Glu Ile Ala Arg Asn Pro Leu Leu Lys Val Ala Phe Glu Val Asp
                370                 375                 380

Arg Val Ala Ser Glu Asp Glu Tyr Phe Val Ser Arg Lys Leu Arg Pro
385                 390                 395                 400

Asn Ala Asp Leu Phe Ala Ala Leu Val Tyr Ser Ala Met Gly Phe Pro
                405                 410                 415

Thr Glu Phe Ile Leu Pro Leu Ser Leu Leu Ser Arg Thr Gln Gly Phe
                420                 425                 430

Met Ala His Trp Lys Glu Ala Met Ser Ser Thr Ala Arg Ile Trp Arg
                435                 440                 445

Pro Gly Gln Ile Tyr Thr Gly His Leu Asn Arg Glu Met Ala
                450                 455                 460

<210> SEQ ID NO 45
<211> LENGTH: 458
<212> TYPE: PRT
<213> ORGANISM: Aspergillus tubingensis

<400> SEQUENCE: 45

Met Pro Asp Ile Ala Pro Asn Val Ala Arg Asn Gly Ser Ser Lys His
1               5                   10                  15

Ala Glu Thr Lys Pro Glu Thr Pro Val Leu His Val Val Asp Ser Arg
                20                  25                  30

Thr Gly Asn Tyr Phe Pro Ile Pro Ile Val Arg Asn Ala Ile Asn Ala
                35                  40                  45

Ser Glu Phe Lys Lys Leu Lys Ser Pro Glu Asp Pro Ala His Pro Glu
        50                  55                  60

Asp Gln Asn Glu Gln Gly Ile Arg Val Phe Asp Pro Gly Tyr Ser Asn
65                  70                  75                  80

Thr Ala Val Ser Glu Ser Gln Val Thr Tyr Ile Asp Gly Leu Lys Gly
                85                  90                  95

Thr Ile Gln Tyr Arg Gly Tyr Asn Ile Glu Asp Ile Val Gly Lys Lys
                100                 105                 110

Lys Phe Ile Asp Thr Ala His Leu Leu Ile Trp Gly Glu Trp Pro Ala
                115                 120                 125

Pro Glu Gln Ala Lys Ser Leu Gln Glu Lys Leu Ser Ser Val Pro Ile
        130                 135                 140

Leu Asp Glu Ser Val Phe Lys Val Ile Gln Ala Phe Pro Pro Asn Ser
145                 150                 155                 160

Ser Ile Ile Gly Met Met Ile Ala Ala Leu Ser Ala Val Gln Ser Ser
                165                 170                 175

Gln Met Asp Arg Ile Pro Ala His Ala Ala Lys Asn Leu Tyr Leu Gly
                180                 185                 190

Asn Pro Gln Ala Val Asp Asp Glu Ile Val Arg Leu Met Gly Ser Leu
                195                 200                 205

Ser Met Ile Thr Ala Ala Val Tyr Cys His His Thr Gly Arg Glu Phe
        210                 215                 220
```

```
Thr Pro Pro Arg Pro Glu Leu Ser Tyr Ile Glu Asn Phe Leu Leu Met
225                 230                 235                 240

Met Gly His Val Glu Ser Ser Thr Gly Leu Pro Asn Pro Gln Tyr Val
                245                 250                 255

Asp Arg Ile Glu Arg Leu Trp Val Leu Ile Ala Asp His Glu Met Thr
            260                 265                 270

Cys Ser Thr Ala Ala Phe Leu Gln Thr Ala Ser Ser Leu Pro Asp Val
        275                 280                 285

Phe Ser Cys Met Ile Ser Ala Leu Ser Ala Leu Tyr Gly Pro Leu His
    290                 295                 300

Gly Gly Ala Ile Glu Val Ala Tyr Lys Asn Phe Glu Glu Ile Gly Ser
305                 310                 315                 320

Val Glu Asn Val Ala Ala Lys Ile Glu Arg Val Lys Ala Gly Lys Glu
                325                 330                 335

Arg Leu Tyr Gly Tyr Gly His Arg Ile Tyr Arg Val Thr Asp Pro Arg
            340                 345                 350

Phe Ile Phe Ile Arg Gln Ile Leu Asp Glu Leu Lys Glu Glu Ile Ala
        355                 360                 365

Arg Asn Pro Leu Leu Lys Val Ala Phe Glu Val Asp Arg Val Ala Ser
370                 375                 380

Glu Asp Glu Tyr Phe Val Thr Arg Lys Leu Arg Pro Asn Ala Asp Leu
385                 390                 395                 400

Phe Ala Ala Leu Val Tyr Ser Ala Met Gly Phe Pro Thr Glu Phe Ile
                405                 410                 415

Leu Pro Leu Ser Leu Leu Ser Arg Thr Gln Gly Phe Met Ala His Trp
            420                 425                 430

Lys Glu Ala Met Ser Ser Thr Ala Arg Ile Trp Arg Pro Gly Gln Ile
        435                 440                 445

Tyr Thr Gly His Leu Asn Arg Glu Met Ala
    450                 455

<210> SEQ ID NO 46
<211> LENGTH: 457
<212> TYPE: PRT
<213> ORGANISM: Pestalotiopsis fici

<400> SEQUENCE: 46

Met Ser Pro Ala Val Ile Ser Gln Thr Asn Gly Ala Asn Gly Thr Asn
1               5                   10                  15

Gly Ala Lys Ala Gln Leu Gly Asp Val Leu His Ile Ile Asp Ser Arg
            20                  25                  30

Thr Gly Gln Tyr His Ala Ile Asn Ile His Gln Asn Ala Ile Asn Ala
        35                  40                  45

Ser Asp Leu Lys Val Leu Lys Ala Pro Lys Asp Ala Asn His Pro Glu
    50                  55                  60

Tyr Gln Asn Asp Gln Gly Ile Arg Val Tyr Asp Pro Gly Tyr Ser Asn
65                  70                  75                  80

Thr Leu Val Ser Glu Ser Lys Ile Thr Tyr Ile Asp Gly Leu Glu Gly
                85                  90                  95

Thr Ile Gln Tyr Arg Gly Tyr Ser Ile Asp Asp Ile Ile Gly Lys Lys
            100                 105                 110

Lys Phe Val Asp Val Ser His Leu Leu Ile Trp Gly Lys Trp Pro Ser
        115                 120                 125

Ala Asp Glu Ala Gln Thr Tyr Gln Gln Arg Leu Asn Asp Val Pro Leu
    130                 135                 140
```

```
Ile Asn Glu Thr Val Phe Asn Val Ile Arg Ser Phe Pro Lys Asp Gly
145                 150                 155                 160

Ser Ile Leu Gly Met Met Ile Ala Gly Leu Ser Ala Leu Gln Ser Ser
            165                 170                 175

Asp Met Ser Ala Val Pro Ala His Ala Ala Lys Asn Leu Tyr Leu Gly
        180                 185                 190

Gln Pro Lys Asn Val Asp Asp Gln Ile Ile Arg Val Met Ala Ser Leu
            195                 200                 205

Ser Met Ile Thr Ala Ala Tyr Cys His His Ser Asp Arg Thr Phe
210                 215                 220

Thr Pro Pro Arg Lys Asp Phe Ser Tyr Val Gly Asn Phe Leu Leu Met
225                 230                 235                 240

Thr Gly His Val Glu Glu Ser Thr Gly Val Pro Asn Pro Arg Tyr Val
            245                 250                 255

Asp Ala Ile Glu Arg Leu Trp Ala Thr Val Ala Asp His Glu Met Thr
        260                 265                 270

Cys Ser Thr Ala Ala Leu Leu Gln Thr Ala Ser Ala Leu Pro Asp Val
            275                 280                 285

Ile Ser Ser Leu Ile Ser Ala Leu Ser Ala Ser Tyr Gly Pro Leu His
        290                 295                 300

Gly Gly Ala Ile Glu Val Ala Tyr Lys Asn Ile Glu Glu Ile Gly Thr
305                 310                 315                 320

Val Glu Asp Val Pro Ala Lys Ile Glu Arg Val Lys Ala Gly Lys Glu
                325                 330                 335

Arg Leu Tyr Gly Tyr Gly His Arg Val Tyr Arg Val Thr Asp Pro Arg
            340                 345                 350

Phe Thr Tyr Ile Ser Asp Ile Leu Asp Glu Leu Ser Asp Glu Ile Glu
        355                 360                 365

Lys Asp Pro Leu Leu Arg Val Ala Phe Ala Leu Asp Arg Ala Ala Ala
370                 375                 380

Gln Asp Glu Tyr Phe Ile Ser Arg Lys Leu Arg Pro Asn Ala Asp Leu
385                 390                 395                 400

Phe Ala Ala Phe Ala Tyr Lys Ala Ile Gly Pro Ala Asn Phe Ile
                405                 410                 415

Leu Pro Ile Ser Ala Val Ser Arg Thr Gln Gly Phe Met Ala His Trp
            420                 425                 430

Lys Glu Ala Met Glu Gly Ala Pro Arg Ile Trp Arg Pro Gly Gln Lys
            435                 440                 445

Tyr Thr Gly Asn Leu Asn Gln Thr Glu
        450                 455

<210> SEQ ID NO 47
<211> LENGTH: 452
<212> TYPE: PRT
<213> ORGANISM: Neofusicoccum parvum

<400> SEQUENCE: 47

Met Ala Thr Thr Thr Ile Thr Ala Pro Ala Asn Gly Arg Val Ser Lys
1               5                   10                  15

Asp Ser Leu Thr Val Thr Asp Asn Arg Thr Gly Ser Thr Phe Thr Phe
            20                  25                  30

Pro Ile Thr His Asn Ala Val Asn Ala Ser Asn Phe Lys Gln Ile Lys
        35                  40                  45

Ala Pro Glu Asp Pro Asp Asn Ile Ala Asp Gln Asn Glu Gln Gly Leu
```

```
            50                  55                  60
Arg Val Phe Asp Pro Gly Phe Gly Asn Thr Cys Val Ser Glu Ser Lys
 65                  70                  75                  80

Ile Thr Phe Ile Asp Gly Leu Lys Gly Ile Ile Gln Tyr Arg Gly Tyr
                 85                  90                  95

Asp Ile Gly Asp Leu Ile Glu Ala Lys Lys Gly Phe Val Asp Thr Ala
            100                 105                 110

His Leu Leu Trp Phe Gly Thr Leu Pro Ser Pro Lys Glu Lys Gln Glu
            115                 120                 125

Leu Gln Asp Arg Leu Asn Ala Val Pro Leu Ile Asp Asp His Val Phe
130                 135                 140

Asn Thr Ile Arg Ser Phe Pro Lys Asn Gly Ser Pro Phe Gly Met Ile
145                 150                 155                 160

Ile Ala Gly Leu Met Ala Leu Gln Ser Ser Glu Met Asp Leu Ile Pro
                165                 170                 175

Ala His Ala Ala Lys Asn Ile Tyr Leu Gly Asn Leu Ser Leu Val Asp
            180                 185                 190

Ser Gln Leu Ile Arg Val Met Gln Ser Leu Ser Gln Ile Cys Ala Val
            195                 200                 205

Ala Tyr Cys His Gln Thr Gly Arg Thr Phe Thr Pro Pro Arg Ala Asp
            210                 215                 220

Leu Thr Phe Ile Glu Asn Phe Leu Leu Met Met Gly His Thr Glu Ala
225                 230                 235                 240

Ala Thr Gly Leu Pro Asn Pro Ala Tyr Val Ala Lys Phe Glu Arg Leu
                245                 250                 255

Trp Leu Leu Ile Ala Asp His Glu Met Thr Cys Ser Thr Ala Ala Met
            260                 265                 270

Leu Gln Thr Ala Ser Ala Met Pro Asp Ala Leu Ser Cys Leu Ala Ser
            275                 280                 285

Ala Thr Ser Ala Leu Tyr Gly Pro Leu His Gly Gly Ala Ile Glu Val
            290                 295                 300

Ala Tyr Lys Asn Ile Ala Glu Ile Gly Ser Val Asp Asn Ile Pro Pro
305                 310                 315                 320

Lys Ile Ala Arg Val Lys Ala Gly Lys Glu Arg Leu Tyr Gly Tyr Gly
                325                 330                 335

His Arg Val Tyr Arg Val Pro Asp Pro Arg Tyr Arg His Ile Lys Glu
            340                 345                 350

Val Leu Glu Asp Leu Thr Ala Glu Ile Glu Asp Asp Pro Leu Leu Lys
            355                 360                 365

Val Ala Phe Glu Leu Asp Arg Val Ala Arg Thr Asp Glu Tyr Phe Thr
370                 375                 380

Ser Arg Lys Leu Asn Pro Asn Ala Asp Leu Phe Ala Ala Leu Ala Tyr
385                 390                 395                 400

Asn Ala Met Gly Phe Glu Pro Glu Trp Ile Leu Pro Ile Ser Leu Met
                405                 410                 415

Ser Arg Ser Gln Gly Leu Leu Ala His Trp Lys Glu Ala Met Ser Gly
            420                 425                 430

Ser Ala Arg Ile Trp Arg Pro Gly Gln Ile Tyr Thr Gly Asp Leu Asn
            435                 440                 445

Lys Lys Ile Glu
            450

<210> SEQ ID NO 48
```

```
<211> LENGTH: 467
<212> TYPE: PRT
<213> ORGANISM: Eutypa lata

<400> SEQUENCE: 48
```

| | | | | | | | | | | | | | | | |
|---|---|---|---|---|---|---|---|---|---|---|---|---|---|---|---|
| Met | Ala | Thr | Ala | Ala | Pro | Thr | Ala | Thr | Lys | Ser | Thr | Ala | Ala | Asn | Asn |
| 1 | | | | 5 | | | | | 10 | | | | | 15 | |
| Pro | Met | Thr | Ser | Ser | Gln | Ser | Glu | Ile | Asn | Val | Ala | Val | Glu | Lys | Arg |
| | | | 20 | | | | | 25 | | | | | 30 | | |
| Asp | Val | Leu | His | Ala | Val | Asp | Gly | Arg | Thr | Gly | Leu | Tyr | Tyr | Ser | Ile |
| | | | 35 | | | | | 40 | | | | | 45 | | |
| Pro | Ile | Asn | Lys | Asn | Ala | Val | Asn | Ala | Gly | Asp | Phe | Lys | Lys | Ile | Lys |
| | 50 | | | | | 55 | | | | | 60 | | | | |
| Ser | Pro | Ala | Asp | Arg | Lys | His | Pro | Ala | Tyr | Gln | Asn | Glu | Leu | Gly | Leu |
| 65 | | | | | 70 | | | | | 75 | | | | | 80 |
| Arg | Ile | Tyr | Asp | Pro | Gly | Phe | Ser | Asn | Thr | Thr | Val | Ser | Glu | Ser | Lys |
| | | | | 85 | | | | | 90 | | | | | 95 | |
| Ile | Thr | Tyr | Ile | Asp | Gly | Ile | Glu | Gly | Thr | Ile | Gln | Tyr | Arg | Gly | Tyr |
| | | | 100 | | | | | 105 | | | | | 110 | | |
| Ser | Ile | His | Asp | Ile | Phe | Gly | Lys | Lys | Gly | Trp | Ile | Asp | Val | Ser | His |
| | | | 115 | | | | | 120 | | | | | 125 | | |
| Leu | Leu | Ile | Trp | Gly | Asn | Trp | Pro | Ser | Ser | Ala | Glu | Ala | Lys | Glu | Tyr |
| | 130 | | | | | 135 | | | | | 140 | | | | |
| Gln | Glu | Arg | Leu | Asn | Gly | Val | Pro | Leu | Leu | Asp | Gln | His | Val | Leu | Asp |
| 145 | | | | | 150 | | | | | 155 | | | | | 160 |
| Val | Ile | His | Ser | Phe | Pro | Lys | Asp | Gly | Val | Ile | Thr | Gly | Met | Met | Ile |
| | | | | 165 | | | | | 170 | | | | | 175 | |
| Ala | Gly | Leu | Ser | Ala | Leu | Gln | Ser | Cys | Asn | Leu | Asp | Ala | Val | Pro | Ala |
| | | | 180 | | | | | 185 | | | | | 190 | | |
| Tyr | Val | Gly | Asp | Asn | Leu | Tyr | Val | Gly | His | Pro | Asp | Arg | Val | Asp | Lys |
| | | | 195 | | | | | 200 | | | | | 205 | | |
| Gln | Ile | Ile | His | Leu | Leu | Gln | Ser | Phe | Ala | Met | Ile | Thr | Ala | Ala | Cys |
| | 210 | | | | | 215 | | | | | 220 | | | | |
| Tyr | Cys | His | Ser | Thr | Ser | Arg | Glu | Phe | Thr | Gln | Pro | Arg | Gln | Asp | Phe |
| 225 | | | | | 230 | | | | | 235 | | | | | 240 |
| Ser | Tyr | Val | Glu | Asn | Phe | Leu | Leu | Met | Val | Gly | His | Val | Asp | Ala | Thr |
| | | | | 245 | | | | | 250 | | | | | 255 | |
| Thr | Gly | Leu | Pro | Ser | Pro | Arg | His | Val | Asp | Ala | Leu | Glu | Arg | Leu | Trp |
| | | | 260 | | | | | 265 | | | | | 270 | | |
| Gly | Val | Val | Ala | Asp | His | Glu | Met | Thr | Cys | Ser | Thr | Ala | Ala | Phe | Leu |
| | | | 275 | | | | | 280 | | | | | 285 | | |
| His | Thr | Ala | Ser | Ser | Leu | Pro | Asp | Ile | Ile | Ser | Cys | Phe | Ile | Thr | Ala |
| | 290 | | | | | 295 | | | | | 300 | | | | |
| Ile | Cys | Ala | Ala | Thr | Gly | Pro | Leu | His | Gly | Gly | Ala | Ile | Ser | Val | Ala |
| 305 | | | | | 310 | | | | | 315 | | | | | 320 |
| His | Lys | His | Ile | Lys | Ala | Ile | Gly | Thr | Val | Ala | Asn | Val | Pro | Ala | Lys |
| | | | | 325 | | | | | 330 | | | | | 335 | |
| Ile | Glu | Arg | Val | Lys | Ser | Gly | Lys | Glu | Leu | Leu | Tyr | Gly | Tyr | Gly | His |
| | | | 340 | | | | | 345 | | | | | 350 | | |
| Arg | Val | Tyr | Arg | Thr | Thr | Asp | Pro | Arg | Tyr | Thr | Tyr | Ile | Asn | Gln | Val |
| | | | 355 | | | | | 360 | | | | | 365 | | |
| Leu | Asp | Gly | Leu | Thr | Glu | Glu | Val | Ala | Arg | Asp | Pro | Leu | Leu | Gln | Val |
| | 370 | | | | | 375 | | | | | 380 | | | | |
| Ala | Leu | Ala | Leu | Asp | Lys | Ala | Ala | Ser | Glu | Asp | Glu | Tyr | Phe | Thr | Ser |

```
                385                 390                 395                 400
Arg Lys Leu Phe Pro Asn Ala Asp Leu Phe Ala Ala Phe Ala Tyr Gln
                    405                 410                 415

Ala Leu Gly Phe Pro Pro Asp Phe Val Leu Pro Met Ser Cys Leu Ser
                    420                 425                 430

Arg Leu Gln Gly Phe Ala Ala His Trp Lys Glu Gly Leu Gln Gly Lys
                    435                 440                 445

Pro Lys Ile Trp Arg Pro Gly Gln Ile Tyr Thr Gly Asp Leu Glu Lys
                    450                 455                 460

Thr Met Gly
465

<210> SEQ ID NO 49
<211> LENGTH: 353
<212> TYPE: PRT
<213> ORGANISM: Aspergillus niger

<400> SEQUENCE: 49

Met Ser Lys Thr Arg Thr Pro Met Arg Asn Met Arg Ser Gln Phe Glu
1               5                   10                  15

Glu Arg Arg Ser Gln Pro Trp Thr Ser Arg Arg Ser Glu Pro Gln Glu
                20                  25                  30

Arg Glu Pro Thr Ala Gln Ile Arg Ser Arg Val Ala Ser Gly Glu Ile
            35                  40                  45

Asp Leu Glu Asp Val Leu His Arg Leu Val Ser Gly Ser Tyr Pro Thr
        50                  55                  60

Met Pro His Met Asp Gly Leu Ser His Lys Leu Thr Glu Ala Met Leu
65                  70                  75                  80

Ala Val Pro Asp Asp Val Gln Arg Thr Val Trp Thr His Pro His Pro
                85                  90                  95

Asp Met Ile Thr Ala Ser His Asp Ala Asn Met Phe Arg Lys Ser Pro
                100                 105                 110

Glu Asp Thr Asp Arg Val Met Ile Arg Thr Val Ala Ala Tyr Ala Val
            115                 120                 125

Val Ser Gly Leu Ala Asn Ser His Arg Lys Gly Leu Arg Phe Thr Pro
        130                 135                 140

Pro Thr Arg Gly Arg Ser Tyr Tyr Glu Lys Ser Phe Val Met Ala Gly
145                 150                 155                 160

Leu Val Pro Arg Thr Gly Arg Pro Gly Arg Val Lys Leu Ser Cys Phe
                165                 170                 175

Arg His Gln Arg Val Lys Gln Gly Arg Val Lys Val Phe Glu Tyr Gly
                180                 185                 190

His Arg Ser Tyr Lys Gly Ile Asn Pro Arg Val Pro Pro Ile Gln Ser
            195                 200                 205

Ile Leu Lys Asn Leu Asp Leu Ser Ala Asp Asn Pro Leu Lys Leu Ala
        210                 215                 220

Glu Arg Glu Phe Val Gln Leu Met Pro Thr Ser Lys Ser Arg Gly Tyr
225                 230                 235                 240

Ala Asp Thr Ser Asn Gly Phe Tyr Pro Lys Ile Ile Ser Met Ala Met
                245                 250                 255

Leu Ala Gln Arg Ile Met Gly Ile Met Thr His Trp Arg Glu Tyr Met
                260                 265                 270

Leu Met Arg Gly Lys Leu Leu Arg Pro Ser His Ile Tyr Thr Gly Glu
            275                 280                 285
```

```
Ala Glu Gly Gly Val Leu Pro Gly Ile Arg Thr Asp Arg Ala Ser Tyr
    290                 295                 300

Val Lys Val Ser Leu Ala Ser Ala Val Ala Ala Asp Val Leu Thr Ser
305                 310                 315                 320

Ala Glu Arg Gly Pro Tyr Met Asn Ile Thr Ser Leu Gly Ile Met Leu
                325                 330                 335

Val Pro Ser Ile Gly Pro Leu Leu Gly Leu Leu Ser Gln Gln Pro
                340                 345                 350

Gly
```

<210> SEQ ID NO 50
<211> LENGTH: 540
<212> TYPE: PRT
<213> ORGANISM: Aspergillus niger

<400> SEQUENCE: 50

```
Met Asp Gln Ser Leu Thr Val Tyr Leu Gly Val Ser Ile Arg Pro Phe
1               5                   10                  15

Glu Leu Phe Arg Pro Arg Leu His Gly Leu Gly Gln Met Ala Ala Ala
            20                  25                  30

Met Pro Asp Lys Val Gln Ile Cys Ala Ser Glu Pro Asp Lys Pro Gln
        35                  40                  45

Gln Asn Gln Asp Asn Ser Ser Asp Asn Pro Ser Gln Thr His Pro Ile
    50                  55                  60

Pro Phe Tyr Asn Met Ala Tyr Thr Leu Ala Ser Trp Leu Gly Arg Leu
65                  70                  75                  80

Phe Asp Ala Gly Lys Ser Leu Leu Pro Leu Gln Gly Asn Tyr Ile Asn
                85                  90                  95

Ala Leu Leu Glu Gln Glu Leu Pro Gly Glu Arg Glu Gly Thr Leu Thr
            100                 105                 110

Val Arg Asp Asn Arg Thr Gly Ser Lys Tyr Thr Ile Pro Ile Val Arg
        115                 120                 125

Asn Ser Val Pro Ala Met Gly Phe Arg Gln Ile Cys Val Asp Arg Ala
    130                 135                 140

Gly Lys Ser Pro Arg Gln Gln Phe Glu Asp Gly Leu Arg Leu Ile Asp
145                 150                 155                 160

Pro Gly Tyr Arg Asn Thr Ala Val Lys Met Ser Ser Ile Thr Tyr Ile
                165                 170                 175

Asn Gly Asn Glu Gly Val Ile Leu Tyr Arg Gly His Pro Leu Ala Ser
            180                 185                 190

Leu Ile Gly Lys Ser Tyr Glu Glu Ile Thr His Leu Leu Ile Trp Gly
        195                 200                 205

Ser Leu Pro Thr Pro Glu Gln Arg Leu Arg Phe Gln Arg Arg Ile Ala
    210                 215                 220

Glu Ala Met Met Val Val Pro Glu Asn Val Lys Gln Leu Val Ala Thr
225                 230                 235                 240

Phe Pro Arg Asn Thr Pro Pro Met Val Ile Leu Cys Ala Val Leu Thr
                245                 250                 255

Gly Tyr Leu Ala Asp Gln Pro Glu Leu Ile Pro Ala His Ala Gly Ala
            260                 265                 270

Asn Leu Tyr Asn Arg Arg Pro Glu Met Val Asp Glu Gln Ile Ile Arg
        275                 280                 285

Thr Leu Ala Val Thr Ala Ile Ala Gly Ser Ile Ala His Cys His Met
    290                 295                 300
```

```
Lys Gly Glu Glu Leu Arg Met Ala Asp Pro Asn Leu Ser Tyr Ile Glu
305                 310                 315                 320

Asn Ile Leu Trp Met Gly Arg Tyr Val Asp Asn Pro Ala Val Thr
            325                 330                 335

Arg Glu Lys Ala Ala Glu Ile Leu Thr Lys Ala Trp Ser Leu Tyr Ala
            340                 345                 350

Asp His Glu Met Thr Asn Ser Thr Ser Ala Phe Leu His Val Ser Ser
            355                 360                 365

Ser Leu Ala Asp Pro Leu Ser Ala Met Ala Ala Cys Cys Met Ser Gly
    370                 375                 380

Tyr Gly Leu Leu His Gly Gly Ala Ile Asp Ala Ala Tyr Arg Gly Met
385                 390                 395                 400

Arg Glu Ile Gly Gly Pro Gln Asn Val Pro Lys Leu Ile Glu Lys Val
            405                 410                 415

Ile Asn Lys Glu Cys Arg Leu Ser Gly Tyr Gly His Arg Ile Tyr Lys
            420                 425                 430

Gln Val Asp Pro Arg Ala Lys Tyr Val Arg Glu Met Leu Asp Glu Leu
            435                 440                 445

Thr Arg Asp Arg Asp Ile Arg Glu Met Asp Pro Val Leu Gln Val Ala
450                 455                 460

Met Glu Ile Asp Arg Ile Ala Ser Thr His Glu Tyr Phe Val Lys Arg
465                 470                 475                 480

Asn Leu Gln Ala Asn Ala Asp Leu Tyr Gly Ser Phe Val Tyr Thr Ala
                485                 490                 495

Leu Gly Ile Asp Ser Gln Phe Ala Thr Val Leu Ala Ala Thr Ala Arg
            500                 505                 510

Val Ser Gly Val Met Ala His Trp Lys Glu Gln Thr Glu Arg Ala Pro
            515                 520                 525

Asp Leu Trp Arg Pro Leu Gln Val Tyr Val Pro Asn
            530                 535                 540

<210> SEQ ID NO 51
<211> LENGTH: 1128
<212> TYPE: PRT
<213> ORGANISM: Aspergillus kawachii

<400> SEQUENCE: 51

Met Ser Ser Gly Ile Leu Tyr Val Lys Asp Ser Arg Thr Asp Val Gln
1               5                   10                  15

Tyr Glu Ile Pro Ile Arg Arg Asn Ala Val Ser Ala Val Asp Phe Lys
            20                  25                  30

Lys Ile Lys Gly Pro Gly Thr Gly Ala Asp Arg Ala Asp Gln Val Ala
        35                  40                  45

Gly Gly Leu Arg Val His Asp Pro Gly Leu Arg Asn Thr Thr Val Val
    50                  55                  60

Glu Thr Ala Ile Ser Phe Ser Asp His Glu Arg Ser Leu Leu Leu Phe
65                  70                  75                  80

Arg Gly Tyr Ser Leu Glu Gln Leu Trp Gln Ser Asp Phe Glu Asp Val
                85                  90                  95

Leu His Leu Leu Val Trp Gly Ser Tyr Pro Thr Val Pro Gln Arg Asn
            100                 105                 110

Asn Leu Ser His Arg Leu Thr Glu Ala Met Leu Ala Val Pro Asp Asp
        115                 120                 125

Val Gln Arg Thr Ile Trp Gly Leu Pro Gly Thr Ser Pro Leu Pro
    130                 135                 140
```

```
Leu Ile Val Ala Gly Leu Ser Ala Cys Leu Ala Ser His Pro Asp Met
145                 150                 155                 160

Ile Pro Ala Ser His Asp Ala Asn Met Tyr Arg Asn Asn Pro Glu Asp
                165                 170                 175

Thr Asp Arg Ala Ile Ile Gln Thr Val Ala Ala Tyr Ala Val Val Phe
            180                 185                 190

Gly Leu Val Asn Ser His Arg Lys Gly Leu Arg Phe Ser Pro Pro Ser
        195                 200                 205

Arg Gly Arg Ser Tyr Tyr Glu Asn Leu Phe Val Met Ala Gly Leu Val
    210                 215                 220

Asp Ser Arg Thr Gly Arg Pro Asp Arg Val Lys Leu Ser Cys Phe Arg
225                 230                 235                 240

Arg Phe Ser Ile Leu Asn Ser Asp His Gly Met Ala Leu Thr Val Phe
                245                 250                 255

Ser Ala Leu Ala Thr Ser Ser Leu Thr Asp Pro Ile Ser Cys Leu
                260                 265                 270

Ile Thr Ala Ile Gly Ser Ala Trp Gly Pro Leu His Phe Gly Ala Thr
            275                 280                 285

Glu Ser Ala Lys Arg Thr Leu Arg Glu Ile Gly Glu Ala Lys Asn Ile
290                 295                 300

Pro Gly Tyr Ile His Asn Val Lys Gln Gly His Val Lys Val Phe Gly
305                 310                 315                 320

Tyr Gly His Arg Ser Tyr Lys Gly Ile Asp Pro Arg Val Pro Pro Ile
                325                 330                 335

Arg Ser Ile Leu Lys Asp Leu Asp Met Ser Ala Asp Lys Leu Phe Lys
                340                 345                 350

Leu Ala Glu Arg Ile Glu Ser Ala Cys Ser Asn Asp Ala Tyr Phe Thr
                355                 360                 365

Glu Arg Gly Leu Tyr Val Asn Gly Asp Phe Tyr Gly His Phe Ile Phe
370                 375                 380

Thr Ala Ile Gly Phe Asp Pro Glu Ile Ile Pro Ala Ala Met Leu Ala
385                 390                 395                 400

Gln Arg Ile Met Gly Ile Met Ala His Trp Arg Glu Tyr Met Leu Thr
                405                 410                 415

Arg Gly Lys Leu Leu Arg Pro Ser His Ile Tyr Thr Gly Glu Ala Glu
                420                 425                 430

Glu Arg Leu Leu Pro Lys Phe Gln Gln Tyr Gln Ala Thr Leu Val Ala
                435                 440                 445

Ala Asn Gln Pro Ala Thr Glu Gly Thr Pro Leu Leu Ala Glu Gln Pro
                450                 455                 460

Ala Lys Lys Pro Tyr Ser Ile Phe Thr Pro Gly Gln Lys Arg Leu Ile
465                 470                 475                 480

Ile Val Thr Ala Ala Leu Ala Ser Ser Phe Ser Pro Leu Ser Ala Asn
                485                 490                 495

Ile Tyr Tyr Pro Ala Leu Asn Ser Ile Ala Ala Asp Leu His Val Thr
                500                 505                 510

Ser Ser Gln Ile Asn Leu Thr Ile Thr Thr Tyr Met Leu Cys Gln Gly
                515                 520                 525

Leu Ala Pro Ala Phe Met Gly Ser Phe Ala Asp Gln Ala Gly Arg Arg
                530                 535                 540

Pro Ala Tyr Ile Leu Cys Phe Ala Val Tyr Ile Thr Gly Asn Ile Ala
545                 550                 555                 560
```

```
Leu Ala Leu Gln His Ser Tyr Pro Ala Leu Leu Ile Leu Arg Ala Ile
                565                 570                 575

Gln Ser Cys Gly Ser Ser Gly Thr Val Ala Leu Ala Ser Ala Val Thr
            580                 585                 590

Ala Asp Val Ile Thr Ser Ala Glu Arg Gly Thr Tyr Met Gly Ile Thr
        595                 600                 605

Ser Leu Gly Ile Ile Leu Ala Pro Ser Val Gly Pro Leu Val Gly Gly
    610                 615                 620

Ile Leu Thr Pro Ala Ile Thr Ser Thr Pro Gly Gln Lys Ser Ser Arg
625                 630                 635                 640

Ile Ala Leu Pro Asn Pro Leu Thr Thr Leu Ser Leu Leu Ser His Arg
                645                 650                 655

Pro Thr Gly Leu Val Leu Leu Ser Asn Gly Leu Leu Phe Ala Ser Tyr
            660                 665                 670

Tyr Ala Val Thr Ala Gly Ile Pro Ser Gln Phe Lys Glu Thr Tyr His
        675                 680                 685

Leu Asn Asp Ser Val Ile Gly Leu Val Phe Val Pro Ala Gly Val Gly
    690                 695                 700

Ser Leu Leu Ser Thr Thr Phe Asn Gly Leu Leu Leu Asp Trp Asn Tyr
705                 710                 715                 720

Arg Arg Leu Arg Glu Gln Phe Arg Ser Pro Ile Leu Gln Ala His His
                725                 730                 735

His Gly Ala Phe Pro Ile Glu Arg Ala Arg Ile Gln Ile Cys Leu Pro
            740                 745                 750

Leu Thr Leu Leu Ala Ala Leu Ser Ile Leu Ser Tyr Ser Ala Leu Met
        755                 760                 765

Ser Leu Ala Thr Pro Thr Leu Ser His Ala Leu Val Leu Ile Phe Ala
    770                 775                 780

Ile Ser Phe Ser Ile Thr Ala Ala Tyr Asn Ile Met Asn Ile Leu Ile
785                 790                 795                 800

Val Asp Leu Tyr Tyr Ser Thr Pro Ala Thr Ala Met Ala Ala Asn Asn
                805                 810                 815

Leu Val Arg Cys Phe Leu Gly Ala Ala Ala Thr Gly Leu Val His Pro
            820                 825                 830

Ala Met Val Arg Trp Gly Thr Gly Trp Thr Thr Ile Met Asn Tyr His
        835                 840                 845

Leu Leu Ile Ser Leu Leu Ile Pro Leu Ile Thr Gln Ile Ile Asp
    850                 855                 860

Pro Leu Pro His Tyr Pro Gln Thr Leu His Leu Tyr Tyr Pro Asn Thr
865                 870                 875                 880

Pro Trp Ile Gln Pro Gly Asp Thr Leu Gln Ile Leu Asp Thr Lys Pro
                885                 890                 895

Leu Pro Ile Leu Ser Thr Gln His Pro Pro Leu His Gln Thr Tyr Thr
            900                 905                 910

Ile Leu Phe Leu Asp Leu Asp Val Leu Tyr Asn His Thr Thr Ala Thr
        915                 920                 925

Val Ile Leu His Trp Tyr Gln Pro Asp Leu Ile Pro Tyr Pro Asn Asn
    930                 935                 940

Thr Asn Ile Leu Leu Pro Asn Pro Gln Val Pro Thr Arg Lys Pro Ala
945                 950                 955                 960

Pro Tyr Ile Ala Pro Gln Pro Pro Thr Asn Ser His His Arg Tyr Leu
                965                 970                 975

Tyr Leu Leu Tyr Thr Gln Pro Pro Asn Tyr Thr Phe Pro Glu Cys Phe
```

```
                980                 985                 990
Glu His Ile Phe Pro Thr Ala Glu Ala Arg Ala Gly Phe Asp Met
                995                1000               1005

Lys Ile Phe Thr Asp Ala Ala Gly Leu Gly Thr Pro Val Ala Gly
       1010                1015               1020

Asn Trp Phe Tyr Val Arg Asn Glu Val Asp Leu Pro Thr Gly Ser
       1025                1030               1035

Gly Ser Gly Ser Lys Gly Gly Val Ala Thr Ser Thr Ser Met Asn
       1040                1045               1050

Thr Ala Thr Thr Thr Thr Thr Ser Met Arg Trp Val Glu Cys Asp
       1055                1060               1065

Leu Ser Ser Ser Ser Ser Ser Ser Ser Ser Ile Ser Thr Ser
       1070                1075               1080

Val Leu Thr Thr Ser Thr Ala Ile Val Ala Thr Thr Thr Thr Thr
       1085                1090               1095

His Arg Pro Thr Asp Ser Pro Thr Glu Thr Thr Leu Ala Met Ser
       1100                1105               1110

Asn Asn Ile Asp Glu Ser Gln Val Gln Ala Gln Ala Arg Leu Ser
       1115                1120               1125

<210> SEQ ID NO 52
<211> LENGTH: 433
<212> TYPE: PRT
<213> ORGANISM: Neosartorya fischeri

<400> SEQUENCE: 52

Met Ser Ser Gly Thr Leu Tyr Ile Arg Asp Ser Arg Thr Asn Ala Glu
 1               5                  10                  15

Tyr Glu Ile Pro Ile Arg Arg Asn Ala Val Ser Ala Met Asp Phe Lys
                20                  25                  30

Arg Ile Lys Ala Pro Ala Ala Gly Ala Asp Arg Ala Asp Gln Val Ala
            35                  40                  45

Ser Gly Leu Arg Val His Asp Pro Gly Leu Gln Asn Thr Thr Val Val
        50                  55                  60

Glu Thr Arg Ile Ser Phe Ser Asp His Glu Lys Gly Leu Leu Leu Phe
65                  70                  75                  80

Arg Gly Tyr Thr Leu Glu Gln Leu Trp Asp Ser Asp Phe Glu Asp Met
                85                  90                  95

Leu His Leu Leu Val Trp Gly Ser Tyr Pro Thr Ala Leu Gln Lys Lys
            100                 105                 110

Glu Leu Ser Arg Lys Leu Ser Glu Glu Met Thr Met Val Pro Lys Ser
        115                 120                 125

Val His Arg Thr Ile Glu Thr Leu Pro Arg Thr Thr Ser Pro Leu Pro
    130                 135                 140

Leu Met Leu Ala Gly Leu Ser Ala Cys Leu Ala Tyr Ala Pro Glu Ser
145                 150                 155                 160

Ile Pro Ala Ser Thr Lys Pro Asp Leu Tyr Gln Ser Asn Ser Asn Val
                165                 170                 175

Val Asp Arg Ala Ile Ile Arg Thr Val Ala Ala Tyr Ala Val Val Phe
            180                 185                 190

Gly Leu Val Asn Cys His Arg Arg Gly Ile Pro Phe Ala Gln Pro Ser
        195                 200                 205

Arg His Lys Ser Tyr Leu Glu Asn Leu Phe Gln Met Ala Gly Leu Val
    210                 215                 220
```

Asp Gln Thr Thr Gly Arg Pro Asp Pro Thr Lys Leu Ser Cys Phe Arg
225                 230                 235                 240

Arg Phe Ala Met Leu Asn Ala Asp His Gly Met Ala Leu Ser Val Phe
            245                 250                 255

Ser Ala Leu Val Thr Thr Ser Ser Leu Thr Asp Pro Ile Ser Cys Leu
        260                 265                 270

Ile Thr Ala Thr Gly Ala Ala Phe Gly Pro Leu His Phe Gly Ala Thr
        275                 280                 285

Glu Ser Ala Asn Leu Ala Leu Arg Glu Ile Gly Thr Pro Glu Lys Val
        290                 295                 300

Pro Lys Phe Ile Glu Glu Val Lys Gln Gly Lys Arg Arg Leu Phe Gly
305                 310                 315                 320

Tyr Gly His Arg Ser Tyr Lys Gly Leu Asp Pro Arg Val Ala Pro Ile
            325                 330                 335

Arg Ser Ile Leu Lys Asp Leu Asp Thr Ser Ser Asn Ser Leu Ile Lys
            340                 345                 350

Val Ala Glu Arg Ile Glu Gln Val Ala Ser Ala Asp Gly Tyr Phe Arg
        355                 360                 365

Ser Arg Gly Leu Tyr Pro Asn Ala Asp Phe Tyr Gly Asn Phe Val Phe
        370                 375                 380

Thr Gly Ile Gly Phe Glu Pro Glu Leu Ile Pro Ala Ala Met Met Ser
385                 390                 395                 400

Gln Arg Ile Met Gly Val Met Ala His Trp Arg Glu Tyr Met Cys Lys
            405                 410                 415

Ser Leu Gln Glu Ser Val Arg Tyr Arg Arg Val Ser Asp Leu Lys Tyr
            420                 425                 430

Val

<210> SEQ ID NO 53
<211> LENGTH: 433
<212> TYPE: PRT
<213> ORGANISM: Aspergillus fumigatus

<400> SEQUENCE: 53

Met Ser Phe Gly Thr Leu His Ile Arg Asp Ser Arg Thr Asn Ala Glu
1               5                   10                  15

Tyr Glu Ile Pro Ile Arg Arg Asn Ala Val Val Ala Met Asp Phe Lys
            20                  25                  30

Arg Ile Lys Ala Pro Ala Ala Gly Ala Asp Arg Ala Asp Gln Val Asp
        35                  40                  45

Ser Gly Leu Arg Val His Asp Pro Gly Leu Gln Asn Thr Thr Val Val
    50                  55                  60

Glu Thr Glu Ile Ser Phe Ser Asp His Trp Lys Arg Leu Leu Leu Tyr
65                  70                  75                  80

Arg Gly Tyr Thr Leu Glu Gln Leu Trp Asp Ser Asp Phe Glu Asp Met
            85                  90                  95

Leu His Leu Leu Val Trp Gly Ser Tyr Pro Thr Ala Leu Gln Lys Lys
            100                 105                 110

Glu Leu Ser Arg Lys Leu Ser Glu Glu Met Thr Met Val Pro Lys Ser
        115                 120                 125

Val His Arg Thr Ile Glu Thr Leu Pro Arg Thr Thr Ser Pro Leu Pro
    130                 135                 140

Leu Met Leu Val Gly Leu Ser Ala Cys Leu Ala Tyr Val Pro Glu Ser
145                 150                 155                 160

```
Ile Pro Ala Ser Thr Lys Pro Asp Leu Tyr Gln Ser Asn Ser Asn Val
            165                 170                 175

Leu Asp Arg Ala Ile Ile Arg Thr Val Ala Ala Tyr Ala Val Val Phe
        180                 185                 190

Gly Leu Val Asn Cys His Arg Arg Gly Ile Pro Phe Ala Gln Pro Ser
            195                 200                 205

Arg His Thr Ser Tyr Leu Glu Asn Leu Phe His Leu Ala Gly Leu Val
        210                 215                 220

Asp Gln Thr Thr Gly Arg Pro Asp Pro Thr Lys Leu Ser Cys Phe Gln
225                 230                 235                 240

Arg Phe Ala Met Leu Asn Ala Asp His Gly Met Ala Leu Ser Val Phe
                245                 250                 255

Ser Ala Leu Val Thr Ala Ser Ser Leu Thr Asp Pro Ile Ser Cys Leu
            260                 265                 270

Ile Thr Ala Thr Gly Ala Ala Phe Gly Pro Leu His Phe Gly Ala Thr
        275                 280                 285

Glu Ser Ala Asn Leu Ala Leu Arg Val Ile Gly Thr Pro Glu Asn Val
            290                 295                 300

Pro Asn Phe Ile Glu Glu Val Lys Gln Gly Lys Gln Arg Leu Phe Gly
305                 310                 315                 320

Tyr Gly His Arg Ser Tyr Lys Gly Val Asp Pro Arg Val Ala Pro Ile
                325                 330                 335

Arg Ser Ile Leu Lys Asp Leu Asp Met Ser Ser Asn Ser Leu Leu Lys
            340                 345                 350

Val Ala Glu Arg Ile Glu Gln Val Ala Ser Ala Asp Asp Tyr Phe Arg
        355                 360                 365

Asn Arg Gly Leu Tyr Pro Asn Ala Asp Phe Tyr Gly Asn Phe Val Phe
        370                 375                 380

Thr Glu Ile Gly Phe Glu Pro Asp Met Ile Pro Ala Ala Met Met Ala
385                 390                 395                 400

Gln Arg Ile Met Gly Val Met Ala His Trp Arg Glu Tyr Met Cys Lys
                405                 410                 415

Pro Leu Gln Gln Ser Val Arg Tyr Arg Arg Val Ser His Ile Asp Tyr
            420                 425                 430

Ile

<210> SEQ ID NO 54
<211> LENGTH: 426
<212> TYPE: PRT
<213> ORGANISM: Aspergillus flavus

<400> SEQUENCE: 54

Met Tyr Gln Lys Ser Leu Glu Pro Pro Met Ser Ser Gly Val Leu His
1               5                   10                  15

Ile Val Asp Ser Arg Thr Lys Gln Lys Tyr Glu Ile Pro Ile Arg Arg
            20                  25                  30

Asn Val Ile Ser Ala Ile Asp Leu Lys Ser Ile Lys Ala Pro Ala Ala
        35                  40                  45

Gly Thr Asp Arg Ala Asp His Val Ala Asp Gly Leu Arg Val His Asp
    50                  55                  60

Pro Gly Leu Gln Asn Thr Thr Val Ile Glu Ser Ala Ile Ser Tyr Ser
65                  70                  75                  80

Asp His Glu Arg Gly Val Leu Leu Phe His Gly Tyr Thr Leu Ser Gln
                85                  90                  95
```

```
Leu Trp Asp Ser Asp Phe Glu Asp Met Leu His Leu Leu Val Trp Gly
            100                 105                 110

Thr Tyr Pro Thr Met Gln Gln Lys Lys Asp Leu Asn Arg Lys Leu Thr
        115                 120                 125

Glu Gln Met Leu Ala Val Pro Asp Ser Val His Arg Thr Ile Arg Gly
130                 135                 140

Leu Pro Arg Thr Thr Ser Pro Leu Pro Leu Ile Leu Ala Gly Leu Ser
145                 150                 155                 160

Ala Tyr Leu Ala Cys Phe Pro Asp Thr Ile Pro Ala Ser Thr His Ala
                165                 170                 175

Ser Leu Tyr Gln Gly Asn Leu Arg Asn Val Asp His Ala Val Ile Arg
            180                 185                 190

Thr Val Ala Ala Tyr Gly Val Ile Phe Gly Leu Val Asn Ser His Arg
        195                 200                 205

Lys Gly Ile Asp Phe Gln Pro Pro Ser Gln Glu Asn Ser Tyr Cys Ala
210                 215                 220

Asn Leu Phe Ile Met Ala Gly Leu Leu Asp Arg His Ser Ser Arg Pro
225                 230                 235                 240

Asp Pro Thr Lys Leu Ser Cys Phe Arg Arg Phe Ala Met Leu Asn Ala
                245                 250                 255

Asp His Gly Met Ala Leu Thr Val Phe Ser Ala Leu Val Thr Ala Ser
            260                 265                 270

Ser Leu Thr Asp Pro Ile Ser Cys Leu Ile Ser Ala Val Ala Ala Ala
        275                 280                 285

Tyr Gly Pro Leu His Phe Gly Ala Thr Val Ser Ala Gln Arg Thr Leu
290                 295                 300

Arg Glu Ile Gly Ser Thr Asp Lys Val Pro Glu Phe Ile Glu Gly Val
305                 310                 315                 320

Lys Asn Arg Arg Thr Lys Leu Phe Gly Tyr Gly His Arg Ser Tyr Lys
                325                 330                 335

Gly Leu Asp Pro Arg Val Arg Pro Ile Gln Ser Ile Leu Lys Asp Leu
            340                 345                 350

Asp Leu Ser Lys Asn Asp Tyr Leu Lys Ile Thr Glu Arg Ile Glu Glu
        355                 360                 365

Ile Ala Ser Ala Asp Asp Tyr Phe Arg His Arg Gly Leu Tyr Pro Asn
370                 375                 380

Ala Asp Phe Tyr Gly Asn Phe Val Phe Thr Ala Ile Gly Phe Asp Pro
385                 390                 395                 400

Asp Ile Ile Pro Ala Ala Met Leu Thr Gln Arg Ile Ile Gly Ile Met
                405                 410                 415

Ala His Trp Arg Glu Tyr Met Cys Met Cys
            420                 425

<210> SEQ ID NO 55
<211> LENGTH: 510
<212> TYPE: PRT
<213> ORGANISM: Aspergillus oryzae

<400> SEQUENCE: 55

Met Ser Ser Gly Val Leu His Ile Val Asp Ser Arg Thr Lys Gln Lys
1               5                   10                  15

Tyr Glu Ile Pro Ile Arg Arg Asn Val Ile Ser Ala Ile Asp Leu Lys
            20                  25                  30

Ser Ile Lys Ala Pro Ala Ala Gly Thr Asp Arg Ala Asp His Val Ala
        35                  40                  45
```

```
Asp Gly Leu Arg Val His Asp Pro Gly Leu Gln Asn Thr Thr Val Ile
     50                  55                  60

Glu Ser Ala Ile Ser Tyr Ser Asp His Glu Arg Gly Val Leu Leu Phe
 65                  70                  75                  80

His Gly Tyr Thr Leu Ser Gln Leu Trp Asp Ser Asp Phe Glu Asp Met
                 85                  90                  95

Leu His Leu Leu Val Trp Gly Thr Tyr Pro Ser Met Gln Gln Lys Lys
                100                 105                 110

Asp Leu Asn Arg Lys Leu Thr Glu Gln Met Leu Ala Val Pro Asp Ser
            115                 120                 125

Val His Arg Thr Ile Arg Gly Leu Pro Arg Thr Thr Ser Pro Leu Pro
    130                 135                 140

Leu Ile Leu Ala Gly Leu Ser Ala Tyr Leu Ala Cys Phe Pro Asp Thr
145                 150                 155                 160

Ile Pro Ala Ser Thr His Ala Ser Leu Tyr Gln Gly Asn Leu Arg Asn
                165                 170                 175

Val Asp His Ala Val Ile Arg Thr Val Ala Ala Tyr Gly Val Ile Phe
            180                 185                 190

Gly Leu Val Asn Ser His Arg Lys Gly Ile Asp Phe Gln Pro Pro Ser
    195                 200                 205

Gln Glu Asn Ser Tyr Cys Ala Asn Leu Phe Ile Met Ala Gly Leu Leu
    210                 215                 220

Asp Arg His Ser Ser Arg Pro Asp Pro Thr Lys Leu Ser Cys Phe Arg
225                 230                 235                 240

Arg Phe Ala Met Leu Asn Ala Asp His Gly Met Ala Leu Thr Val Phe
                245                 250                 255

Ser Ala Leu Val Thr Ala Ser Ser Leu Thr Asp Pro Ile Ser Cys Leu
            260                 265                 270

Ile Ser Ala Val Ala Ala Ala Tyr Gly Pro Leu His Phe Gly Ala Thr
    275                 280                 285

Val Ser Ala Gln Arg Thr Leu Arg Glu Ile Gly Ser Thr Asp Lys Val
    290                 295                 300

Pro Glu Phe Ile Glu Gly Val Lys Asn Arg Arg Thr Lys Leu Phe Gly
305                 310                 315                 320

Tyr Gly His Arg Ser Tyr Lys Gly Leu Asp Pro Arg Val Arg Pro Ile
                325                 330                 335

Gln Ser Ile Leu Lys Asp Leu Asp Leu Ser Lys Asn Asp Tyr Leu Lys
            340                 345                 350

Ile Thr Glu Arg Ile Glu Glu Ile Ala Ser Ala Asp Asp Tyr Phe Arg
    355                 360                 365

His Arg Gly Leu Tyr Pro Asn Ala Asp Phe Tyr Gly Asn Phe Val Phe
    370                 375                 380

Thr Ala Ile Gly Phe Asp Pro Asp Ile Ile Pro Ala Ala Met Leu Thr
385                 390                 395                 400

Gln Arg Ile Ile Gly Ile Met Ala His Trp Arg Glu Tyr Met Cys Ser
                405                 410                 415

Asp Thr Ile Asp Leu Ser Asp Asn Trp Leu Gln Glu Phe Ile Ser Gly
            420                 425                 430

Gln Pro Ala Asp Leu Thr Gln Asp Arg Asn Phe Leu Asp Ala Leu Gly
    435                 440                 445

Leu Asn Ser Ala Asp Ser Thr Leu Thr Ala Ile Pro Ser Ser Thr Asn
    450                 455                 460
```

```
Asp Phe Thr Gly Ser Ala Lys Thr Ile Asp Val Ala Ser Ser Glu Leu
465                 470                 475                 480

Gln Asp Gln Leu Pro Leu Ala Ala Tyr Tyr Pro Pro Ala Ser Gly Phe
            485                 490                 495

Ser Ser Tyr Asn Tyr Thr Phe Phe His Gly Lys Arg Phe Cys
            500                 505                 510

<210> SEQ ID NO 56
<211> LENGTH: 425
<212> TYPE: PRT
<213> ORGANISM: Aspergillus nidulans

<400> SEQUENCE: 56

Met Ser Ser Gly Thr Leu Tyr Ile Arg Asp Ser Arg Thr Asp Ala Leu
1               5                   10                  15

Tyr Glu Ile Pro Ile Arg Arg Asn Ser Val Ser Ala Ala Asp Phe Lys
            20                  25                  30

Arg Ile Lys Ala Pro Gly Ile Gly Ala Asn Arg Ala Asp Gln Val Ser
        35                  40                  45

Gly Gly Leu Arg Val His Asp Pro Gly Leu Leu Asn Thr Thr Val Ile
    50                  55                  60

Glu Ser Ala Ile Ser Phe Ser Asp His Glu Arg Gly Leu Leu Leu Phe
65                  70                  75                  80

Arg Gly Tyr Ser Leu Glu Glu Leu Trp Lys Ser Asp Phe Glu Asp Met
                85                  90                  95

Leu His Leu Leu Val Trp Gly Ser Tyr Pro Thr Pro Pro Gln Lys Glu
            100                 105                 110

Gln Leu Arg Ser Lys Leu Ala Ala Gln Met Leu Ala Val Pro Glu Thr
        115                 120                 125

Val Gln Thr Ala Val Gln Ser Leu Pro Asn Thr Thr Pro Pro Leu Ala
    130                 135                 140

Leu Ile Leu Thr Gly Leu Ser Thr Tyr Leu Ser Cys Ile Pro Glu Thr
145                 150                 155                 160

Ile Pro Ala Ser Thr Asp Ala His Gln Tyr Arg Ala Asn Arg Glu Asn
                165                 170                 175

Val Asp Asn Ala Val Leu Arg Thr Val Ala Ala Tyr Ala Val Val Phe
            180                 185                 190

Gly Ile Val Ala Ser His Arg Lys Ser Ile Pro Phe Thr Pro Pro Ser
        195                 200                 205

Pro Asp Arg Thr Tyr Cys Glu Asn Leu Phe Thr Met Ala Gly Leu Val
    210                 215                 220

Asp Pro Val Ala Gly Met Pro Asp Pro Val Lys Leu Ser Cys Phe Arg
225                 230                 235                 240

Arg Phe Ala Met Leu Asn Ala Asp His Gly Met Ala Leu Thr Val Phe
                245                 250                 255

Ser Ala Leu Val Thr Ala Ser Ser Leu Thr Asp Pro Val Ser Cys Leu
            260                 265                 270

Ile Thr Ser Val Ala Ser Ala Trp Gly Pro Leu His Phe Gly Ala Thr
        275                 280                 285

Glu Ser Ala Gln Arg Ala Leu Asp Ile Gly Thr Glu Ala Gly Ile
    290                 295                 300

Pro Ala Phe Leu Asp Glu Val Lys Gln Gly Arg Lys Arg Leu Phe Gly
305                 310                 315                 320

Tyr Gly His Arg Ser Tyr Lys Arg Ile Asp Pro Arg Val Arg Phe Val
                325                 330                 335
```

-continued

```
Gln Ser Ile Leu His Asp Leu Pro Ser Thr Arg Leu Leu Lys Leu Ala
            340                 345                 350

Glu Ala Ile Glu Cys Ala Ala Ser Ala Asp Asp Tyr Phe Arg Ser Arg
            355                 360                 365

Gly Leu Tyr Pro Asn Ala Asp Phe Tyr Gly Asn Phe Val Phe Thr Gly
            370                 375                 380

Ile Gly Phe Glu Val Glu Met Ile Pro Ala Ala Met Leu Ala Gln Arg
385                 390                 395                 400

Ile Met Gly Ile Met Ala His Trp Arg Glu Tyr Met Arg Glu Phe Cys
            405                 410                 415

Ala His Thr Thr Arg Ala Met Gln Arg
            420                 425

<210> SEQ ID NO 57
<211> LENGTH: 928
<212> TYPE: PRT
<213> ORGANISM: Aspergillus nidulans

<400> SEQUENCE: 57

Met Ser Ser Gly Thr Leu Tyr Ile Arg Asp Ser Arg Thr Asp Ala Leu
1               5                   10                  15

Tyr Glu Ile Pro Ile Arg Arg Asn Ser Val Ser Ala Ala Asp Phe Lys
            20                  25                  30

Arg Ile Lys Ala Pro Gly Ile Gly Ala Asn Arg Ala Asp Gln Val Ser
            35                  40                  45

Gly Gly Leu Arg Val His Asp Pro Gly Leu Leu Asn Thr Thr Val Ile
        50                  55                  60

Glu Ser Ala Ile Ser Phe Ser Asp His Glu Arg Gly Leu Leu Leu Phe
65                  70                  75                  80

Arg Gly Tyr Ser Leu Glu Glu Leu Trp Lys Ser Asp Phe Glu Asp Met
                85                  90                  95

Leu His Leu Leu Val Trp Gly Ser Tyr Pro Thr Pro Pro Gln Lys Glu
            100                 105                 110

Gln Leu Arg Ser Lys Leu Ala Ala Gln Met Leu Ala Val Pro Glu Thr
            115                 120                 125

Val Gln Thr Ala Val Gln Ser Leu Pro Asn Thr Thr Pro Pro Leu Ala
        130                 135                 140

Leu Ile Leu Thr Gly Leu Ser Thr Tyr Leu Ser Cys Ile Pro Glu Thr
145                 150                 155                 160

Ile Pro Ala Ser Thr Asp Ala His Gln Tyr Arg Ala Asn Arg Glu Asn
                165                 170                 175

Val Asp Asn Ala Val Leu Arg Thr Val Ala Ala Tyr Ala Val Val Phe
            180                 185                 190

Gly Ile Val Ala Ser His Arg Lys Ser Ile Pro Phe Thr Pro Pro Ser
        195                 200                 205

Pro Asp Arg Thr Tyr Cys Glu Asn Leu Phe Thr Met Ala Gly Leu Val
    210                 215                 220

Asp Pro Val Ala Gly Met Pro Asp Pro Val Lys Leu Ser Cys Phe Arg
225                 230                 235                 240

Arg Phe Ala Met Leu Asn Ala Asp His Gly Met Ala Leu Thr Val Phe
                245                 250                 255

Ser Ala Leu Val Thr Ala Ser Ser Leu Thr Asp Pro Val Ser Cys Leu
            260                 265                 270

Ile Thr Ser Val Ala Ser Ala Trp Gly Pro Leu His Phe Gly Ala Thr
```

-continued

```
            275                 280                 285
Glu Ser Ala Gln Arg Ala Leu Ala Asp Ile Gly Thr Glu Ala Gly Ile
290                 295                 300

Pro Ala Phe Leu Asp Glu Val Lys Gln Gly Arg Lys Arg Leu Phe Gly
305                 310                 315                 320

Tyr Gly His Arg Ser Tyr Lys Arg Ile Asp Pro Arg Val Arg Phe Val
                325                 330                 335

Gln Ser Ile Leu His Asp Leu Pro Ser Thr Arg Leu Leu Lys Leu Ala
            340                 345                 350

Glu Ala Ile Glu Cys Ala Ala Ser Ala Asp Asp Tyr Phe Arg Ser Arg
        355                 360                 365

Gly Leu Tyr Pro Asn Ala Asp Phe Tyr Gly Asn Phe Val Phe Thr Gly
    370                 375                 380

Ile Gly Phe Glu Val Glu Met Ile Pro Ala Ala Met Leu Ala Gln Arg
385                 390                 395                 400

Ile Met Gly Ile Met Ala His Trp Arg Glu Tyr Met His Pro Ile Ala
                405                 410                 415

Cys Pro Thr Arg Lys Ser Tyr Val Leu Pro Met Arg Leu Ala Thr Arg
            420                 425                 430

Ser Ser Ser Ile Asn Thr Ser Leu Leu Phe Thr Ser Asn His Glu Thr
        435                 440                 445

Ser Arg Arg Ile His Asp His Ala His Arg Asn Arg Asn Asn Pro Ser
    450                 455                 460

Pro Leu Thr Asn Cys His Thr Arg Ile Thr Thr Thr Ala Asn Thr Asn
465                 470                 475                 480

Thr Ile Ile Ile Ala Leu Ile Phe Glu Leu Gly Leu Lys His Ser Pro
                485                 490                 495

Gln Ile Glu Pro Tyr Asn His Leu Lys Tyr Leu Leu His Thr Phe Pro
            500                 505                 510

Lys Ala Ala His Asn Thr His Arg Ile Pro Cys Val His Leu Leu Pro
        515                 520                 525

Pro Leu Val Lys His Leu Leu Ser Ser Pro Lys Arg Pro Arg Gly Gly
    530                 535                 540

Ser Ala Arg Leu Leu Ile Ala Asn Gln Pro His Asn His Tyr Ile His
545                 550                 555                 560

Gly Leu Arg Ala Val Gln Ser Ser Gly Ile Ser Gly Thr Val Ala Leu
                565                 570                 575

Ser Ala Ala Val Ala Ala Asp Ile Val Asp Ser His Glu Arg Gly Ala
            580                 585                 590

Tyr Met Gly Leu Thr Ser Leu Gly Asn Ile Leu Ala Pro Ser Leu Gly
        595                 600                 605

Pro Val Leu Gly Gly Leu Ile Thr Ser His Cys Gly Trp Arg Gly Val
    610                 615                 620

Phe Cys Phe Leu Ala Gly Gly Val Val Leu Val Leu Gly
625                 630                 635                 640

Phe Phe Leu Pro Glu Thr Arg Lys Ala Arg Val Asn Thr Leu Glu Val
                645                 650                 655

Gly Ser Val Glu Arg Gly Gln Ala Glu Gly Ala Ala Pro Asp Asn Gln
            660                 665                 670

Gln Ser Lys Arg Arg Lys Lys Pro Gly Leu Pro Asn Pro Leu Thr Pro
        675                 680                 685

Leu Arg Leu Leu Ala His Phe Pro Thr Ser Leu Val Leu Leu Ser Asn
    690                 695                 700
```

```
Gly Leu Val Phe Ala Ser Tyr Tyr Ala Val Thr Ala Gly Ile Pro Ser
705                 710                 715                 720

Gln Phe Ala Arg Ile Tyr Gly Leu Ser Asp Met Glu Val Gly Leu Val
            725                 730                 735

Phe Leu Pro Ala Gly Val Gly Ser Leu Val Ser Ala Thr Phe Asn Gly
        740                 745                 750

Ala Leu Val Asp Trp Asn Tyr Arg Arg Val Arg Lys Met Tyr Glu Asp
    755                 760                 765

Thr Lys Val Thr Ala Glu Gly Asp Asn Glu Val Ser Gly Ala Ala Glu
770                 775                 780

Gly Thr Gln Ser Asp Trp Glu Phe Pro Val Glu Arg Ala Arg Leu Gln
785                 790                 795                 800

Val Gly Gly Pro Met Thr Leu Phe Cys Ser Leu Val Ile Phe Ile Tyr
                805                 810                 815

Gly Leu Val Leu Asp Arg His Pro Pro Leu Ala Leu Ser Leu Ala Met
            820                 825                 830

Ile Phe Leu Val Ser Phe Ser Ile Thr Ala Ser Tyr Asn Val Met Asn
        835                 840                 845

Val Leu Leu Val Asp Leu Tyr Tyr Ser Thr Pro Ala Thr Val Met Ala
    850                 855                 860

Thr Asn Asn Phe Val Arg Cys Phe Leu Gly Ala Val Ser Thr Ala Leu
865                 870                 875                 880

Val Thr Pro Met Ile Glu Arg Phe Gly Gly Arg Thr Tyr Gly Met
                885                 890                 895

Val Ala Ala Leu Ile Val Gly Val Cys Cys Pro Val Leu Gly Thr Val
            900                 905                 910

Tyr Val Asn Gly Val Gln Trp Arg Val Gln Arg Glu Ser Lys Phe Arg
        915                 920                 925

<210> SEQ ID NO 58
<211> LENGTH: 441
<212> TYPE: PRT
<213> ORGANISM: Penicillium roqueforti

<400> SEQUENCE: 58

Met Ser Thr Gly Ile Leu Phe Ile Arg Asp Ser Arg Thr Asn Ala Asn
1               5                   10                  15

Tyr Glu Ile Pro Ile Asn Arg Asn Ala Val Arg Ala Thr Asp Leu Gln
            20                  25                  30

Arg Ile Arg Ala Pro Ser Leu Asn Ser Asn Arg Ala Asp Gln Val Ala
        35                  40                  45

His Gly Leu Arg Val Tyr Asp Pro Gly Leu Gln Asn Thr Ala Val Thr
    50                  55                  60

Glu Ser Pro Ile Ser Phe Ser Asp His Glu Arg Gly Leu Leu Leu Tyr
65                  70                  75                  80

Arg Gly Tyr Thr Leu Asp Gln Leu Trp Gly Cys Asp Phe Glu Glu Met
            85                  90                  95

Phe His Leu Leu Leu Trp Gly Thr Tyr Pro Thr Ala Ser Gln Phe Glu
            100                 105                 110

Glu Leu Arg Arg Gln Leu Ala Gln Tyr Met Gln Val Val Pro Asp Ile
        115                 120                 125

Val Arg Gln Thr Ile Val Asn Leu Pro Lys Glu Thr Ser Pro Leu Pro
    130                 135                 140

Leu Val Leu Ala Gly Leu Ser Ala Tyr Leu Ala Cys Thr Pro Asp Val
```

```
                    145                 150                 155                 160
Ile Pro Ala Thr Thr Asn Pro Thr Ile Tyr Gln Arg Asp Ile Lys Arg
                165                 170                 175

Ala Asp Gln Ile Ile Leu Arg Thr Val Ala Ala Tyr Ala Val Val Phe
            180                 185                 190

Gly Ala Val Arg Ser His Arg Leu Gly Ile Pro Trp Lys Ser Pro Ser
            195                 200                 205

Ile His Gln Thr Tyr Tyr Glu Asn Leu Phe Ala Met Ala Gly Leu Val
        210                 215                 220

Asp Pro Lys Thr Asn Arg Pro Asp Pro Thr Arg Val Ser Cys Phe Arg
225                 230                 235                 240

Arg Phe Gly Asn Leu Asn Ala Glu His Gly Met Ala Leu Thr Val Phe
                245                 250                 255

Ser Thr Val Val Thr Ala Ser Ser Leu Thr Asp Pro Val Ser Cys Leu
                260                 265                 270

Ile Ala Thr Val Ala Ala His Gly Pro Leu His Phe Gly Ala Thr
            275                 280                 285

Glu Ser Ala Gln Leu Ala Leu Arg Asn Ile Gly Glu Pro Lys Asn Val
        290                 295                 300

Pro Ala Phe Ile Glu Asp Ile Lys Ser Gly Lys Gln Lys Leu Phe Gly
305                 310                 315                 320

Tyr Gly His Arg Thr Tyr Lys Gly Met Asp Pro Arg Val Arg Pro Ile
                325                 330                 335

Gln Ser Ile Leu Lys Asp Met Thr Asp Val Asn Gln Pro Leu Leu Lys
                340                 345                 350

Val Ala Glu Ala Ile Glu Glu Ala Ala Ser Lys Asp Glu Phe Phe Ser
            355                 360                 365

Thr Arg Gly Leu Tyr Pro Asn Ala Asp Phe Tyr Gly Asn Phe Val Phe
        370                 375                 380

Thr Gly Ile Gly Phe Glu Pro Asp Met Ile Pro Ala Ala Met Leu Ala
385                 390                 395                 400

His Arg Ile Ile Gly Ile Met Ala His Trp Arg Glu Tyr Met Val Asn
                405                 410                 415

Arg Gly Lys Leu Phe Arg Pro Ile His Leu Tyr Thr Gly His Ala Glu
                420                 425                 430

Pro Thr Ser Gly Pro Arg Pro Lys Ile
        435                 440

<210> SEQ ID NO 59
<211> LENGTH: 469
<212> TYPE: PRT
<213> ORGANISM: Penicillium chrysogenum

<400> SEQUENCE: 59

Met Cys Leu Cys Arg Gln Val Ser Gly Glu Thr Thr Tyr Phe Val Pro
1               5                   10                  15

Ser Gly Thr Leu Cys Ser Arg Arg Ile Leu Leu Lys Met Ser Thr Gly
            20                  25                  30

Thr Leu Phe Ile Arg Asp Ser Arg Thr Asn Val Asn Tyr Glu Ile Pro
        35                  40                  45

Ile Asn Arg Asn Ala Val Arg Ala Thr Asp Leu Gln Gly Ile Arg Ala
    50                  55                  60

Ser Ser Leu Asn Ser Asn Arg Ala Asp Gln Val Ala His Gly Leu Arg
65                  70                  75                  80
```

```
Val Tyr Asp Pro Gly Leu Gln Asn Thr Ala Val Thr Gln Ser Thr Ile
                85                  90                  95

Ser Phe Ser Asp His Glu His Gly Leu Leu Tyr Arg Gly Tyr Thr
            100                 105                 110

Leu Glu Gln Leu Trp Gly Cys Glu Phe Glu Glu Met Phe His Leu Leu
            115                 120                 125

Leu Arg Gly Thr Tyr Pro Thr Ala His Gln Cys Glu Glu Leu Arg Gln
            130                 135                 140

Arg Leu Ala Gln Tyr Met Gln Glu Val Pro Asp Ile Val Arg Gln Thr
145                 150                 155                 160

Ile Phe Asn Leu Pro Arg Lys Thr Ser Pro Leu Pro Leu Ile Leu Ala
                165                 170                 175

Gly Leu Ser Ala Tyr Leu Ala Cys Ile Pro Asp Val Ile Pro Ala Thr
            180                 185                 190

Ala Asn Ala Thr Ile Tyr Gln Thr His Ile Lys Arg Ala Asp Gln Val
            195                 200                 205

Ile Leu Gln Thr Val Ala Ala Tyr Ala Val Phe Gly Ala Val Arg
            210                 215                 220

Ser His Arg Leu Gly Ile Pro Trp Arg Ser Pro Ser Leu His Gln Thr
225                 230                 235                 240

Tyr Tyr Glu Asn Leu Phe Thr Met Ala Gly Leu Val Asp Pro Glu Thr
                245                 250                 255

Asn Arg Pro Asp Pro Thr Arg Ile Ser Cys Phe Arg Arg Phe Gly Asn
                260                 265                 270

Leu Asn Ala Glu His Gly Met Ala Leu Ser Val Phe Thr Thr Leu Val
            275                 280                 285

Thr Ala Ser Ser Leu Thr Asp Pro Val Ser Cys Leu Ile Ser Ser Val
290                 295                 300

Ala Ala Ala His Gly Pro Leu His Phe Gly Ala Thr Glu Ser Ala Gln
305                 310                 315                 320

Arg Ala Leu His Asn Val Gly Glu Pro Ser Asn Val Pro Ala Phe Ile
                325                 330                 335

Glu Glu Ile Lys Ala Gly Lys Gln Lys Leu Phe Gly Tyr Gly His Arg
            340                 345                 350

Thr Tyr Lys Gly Met Asp Pro Arg Val Arg Pro Ile Gln Ser Ile Leu
            355                 360                 365

Lys Asp Leu Thr Asp Val His Gln Pro Leu Leu Lys Val Ala Glu Ala
            370                 375                 380

Ile Glu Glu Ala Ala Ala Lys Asp Glu Tyr Phe Ser Thr Arg Gly Leu
385                 390                 395                 400

Tyr Pro Asn Ala Asp Phe Tyr Gly Asn Phe Val Phe Thr Gly Ile Gly
                405                 410                 415

Phe Glu Pro Glu Met Ile Pro Ala Ala Met Leu Ala His Arg Ile Met
            420                 425                 430

Gly Ile Met Ala His Trp Arg Glu Tyr Met Val Thr Arg Gly Lys Leu
            435                 440                 445

Phe Arg Pro Ile His Leu Tyr Thr Gly Gln Ala Glu Pro Thr Pro Gly
            450                 455                 460

Pro Arg Pro Lys Ile
465

<210> SEQ ID NO 60
<211> LENGTH: 441
<212> TYPE: PRT
```

<213> ORGANISM: Bipolaris zeicola

<400> SEQUENCE: 60

```
Met Ser Asn Gly Phe Leu Leu Val Lys Asp Ser Arg Thr Thr Leu Glu
1               5                   10                  15

Tyr Arg Val Pro Ile Gln Arg Asn Ser Val Leu Ala Thr Ala Phe Lys
            20                  25                  30

Asp Ile Lys Ala Pro Ser Ser Gly Asn Arg Ala Asp Lys Val Gly
        35                  40                  45

Ser Gly Leu Arg Val His Asp Pro Gly Leu Leu Asn Thr Thr Val Val
    50                  55                  60

Glu Thr Gly Val Ser Phe Ala Asp Gly Glu Arg Asp Leu Leu Leu Phe
65                  70                  75                  80

Arg Gly Tyr Ser Leu Glu Gln Leu Trp Gln Ser Asp Tyr Glu Asp Met
                85                  90                  95

Leu His Leu Met Val Trp Ala Lys Tyr Pro Thr Pro Val Gln Lys Glu
            100                 105                 110

Ser Leu Arg Arg Leu Leu Ile Ala Ala Met Leu Glu Val Pro Lys Asn
        115                 120                 125

Val Phe Glu Ile Val Ser Ala Phe Pro Ser Ser Pro Pro Met Pro
130                 135                 140

Met Val Val Ala Gly Leu Ala Ala Tyr Leu Gly Ser Asn Pro Ala Met
145                 150                 155                 160

Ile Pro Ala Ser Ser Gly Gly Asn Ile Tyr Gln Gly Asn Ile Glu Lys
                165                 170                 175

Thr Asp Glu Ala Ile Ile Asn Thr Ile Ala Ala Tyr Ala Val Ile Val
            180                 185                 190

Gly Met Ala Ala Cys His Arg Lys Gly Ile Glu Phe Thr Ala Pro Ser
        195                 200                 205

Leu Asp Tyr Ser Phe Val Glu Asn Leu Phe His Met Ser Gly Met Val
    210                 215                 220

Asp Asp Leu Thr Gly Arg Pro Asp Ala Met Lys Val Ser Cys Phe Arg
225                 230                 235                 240

Arg Phe Ala Ala Leu Asn Met Asp His Gly Met Ala Leu Ala Val Phe
                245                 250                 255

Ser Thr Met Val Thr Ala Ser Ser Leu Thr Asp Pro Val Ser Cys Leu
            260                 265                 270

Ile Ala Ser Leu Ala Ala Ala Tyr Gly Pro Leu His Phe Gly Ala Thr
        275                 280                 285

Glu Ala Ala His Leu Ser Leu Arg Ser Ile Gly Asp Lys Ser Lys Val
    290                 295                 300

Pro Glu Phe Ile Ser Glu Val Lys Gln Gly Lys Arg Lys Leu Phe Gly
305                 310                 315                 320

Tyr Gly His Arg Thr Tyr Lys Gly Thr Asp Pro Arg Val Arg Pro Ile
                325                 330                 335

Lys Glu Leu Ile Glu Asp Ser Gly Ala Asn Ser Asp Arg Leu Ile Glu
            340                 345                 350

Ile Ala Arg Glu Ile Glu Arg Leu Ala Ser Asn Asp Asp Tyr Phe Thr
        355                 360                 365

Ser Arg Gly Leu His Pro Asn Ala Asp Phe Tyr Gly Asn Phe Val Phe
    370                 375                 380

Thr Ala Val Gly Phe Gln Ser Asp Phe Ile Pro Ile Ala Met Ile Ser
385                 390                 395                 400
```

```
Gln Arg Leu Ile Gly Ile Met Ala His Trp Arg Glu Ala Met Val Arg
                405                 410                 415

Gly Ile Lys Leu Phe Arg Pro Ser His Ile Tyr Thr Gly Asp Thr Glu
            420                 425                 430

Pro Val Tyr Thr Ala Ser Ala Lys Leu
            435                 440

<210> SEQ ID NO 61
<211> LENGTH: 441
<212> TYPE: PRT
<213> ORGANISM: Bipolaris oryzae

<400> SEQUENCE: 61

Met Ser Asn Gly Phe Leu Val Arg Asp Ser Arg Thr Thr Leu Glu
1               5                   10                  15

Tyr Arg Val Pro Ile Gln Arg Asn Ser Ile Leu Ala Thr Ala Phe Lys
                20                  25                  30

Asp Ile Lys Ala Pro Ser Ser Ala Ser Arg Ala Asp Lys Val Gly
            35                  40                  45

Ser Gly Leu Arg Val His Asp Pro Gly Leu Leu Asn Thr Thr Val Val
    50                  55                  60

Glu Thr Gly Val Ser Phe Ala Asp Gly Glu Arg Asp Leu Leu Leu Phe
65                  70                  75                  80

Arg Gly Tyr Ser Leu Glu Gln Leu Trp Gln Ser Asp Tyr Glu Asp Met
                85                  90                  95

Leu His Leu Met Val Trp Asp Lys Tyr Pro Thr Pro Val Gln Lys Glu
            100                 105                 110

Ser Leu Arg Arg Ala Leu Ile Thr Ala Met Leu Glu Val Pro Lys Thr
    115                 120                 125

Val Phe Glu Ile Val Ser Thr Phe Pro Ser Ala Ser Pro Pro Met Pro
130                 135                 140

Met Val Val Ala Gly Leu Ala Ala Tyr Leu Gly Gly Asn Pro Asp Met
145                 150                 155                 160

Ile Pro Ala Ser Ser Gly Gly Asn Ile Tyr Gln Gly Asn Ile Glu Lys
                165                 170                 175

Thr Asp Lys Ala Val Ile Lys Thr Ile Ala Ala Tyr Ala Val Val Val
            180                 185                 190

Gly Met Ala Ala Cys His Arg Lys Gly Ile Glu Phe Thr Ala Pro Ser
    195                 200                 205

Leu Asp Tyr Asn Phe Ile Glu Asn Leu Phe His Met Ser Gly Met Val
210                 215                 220

Asp Asp Leu Thr Gly Arg Pro Asp Ala Ile Lys Val Ser Cys Phe Arg
225                 230                 235                 240

Arg Phe Ala Ala Leu Asn Met Asp His Gly Met Ala Leu Ala Val Phe
                245                 250                 255

Ser Thr Met Val Thr Ala Ser Ser Leu Thr Asp Pro Ile Ser Cys Leu
            260                 265                 270

Ile Ala Ser Leu Ala Ala Ala Tyr Gly Pro Leu His Phe Gly Ala Thr
    275                 280                 285

Glu Ala Ala His Leu Asn Leu Arg Ser Ile Gly Asp Lys Ser Lys Val
290                 295                 300

Pro Glu Phe Ile Ser Glu Val Lys Gln Gly Lys Arg Lys Leu Phe Gly
305                 310                 315                 320

Tyr Gly His Arg Thr Tyr Lys Gly Thr Asp Pro Arg Val Lys Pro Ile
                325                 330                 335
```

```
Lys Glu Leu Ile Glu Asp Ser Gly Ala Asn Ser Asp Pro Leu Ile Glu
            340                 345                 350

Ile Ala Lys Glu Ile Glu Arg Leu Ala Ser Asn Asp Tyr Phe Thr
        355                 360                 365

Ser Arg Gly Leu His Pro Asn Ala Asp Phe Tyr Gly Asn Phe Val Phe
    370                 375                 380

Thr Ala Val Gly Phe Gln Ser Asp Phe Ile Pro Ile Ala Met Ile Ser
385                 390                 395                 400

Gln Arg Leu Ile Gly Ile Met Ala His Trp Arg Glu Ala Met Val Arg
                405                 410                 415

Gly Ile Lys Leu Phe Arg Pro Ser His Ile Tyr Thr Gly Asp Thr Glu
            420                 425                 430

Pro Val Tyr Thr Ala Ser Ala Lys Leu
            435                 440
```

<210> SEQ ID NO 62
<211> LENGTH: 454
<212> TYPE: PRT
<213> ORGANISM: Aspergillus clavatus

<400> SEQUENCE: 62

```
Met Tyr Ala Met Ile Leu Leu Cys Tyr Ala Ile Phe Gly Val Pro Gln
1               5                   10                  15

Leu Pro Met Asp Ile Asn Arg Ala Glu Trp Leu Cys Asn Leu Leu Tyr
            20                  25                  30

Gln Ile Cys Pro Gly Phe Ala Val Lys Ser Cys Thr Met Ser Ser Gly
        35                  40                  45

Val Leu Phe Ile Lys Asp Ser Arg Thr Asn Ile Gln Tyr Glu Ile Pro
50                  55                  60

Ile Arg Arg Asn Ala Ile Ala Ala Val Asp Phe Lys Arg Ile Lys Ala
65                  70                  75                  80

Pro Ser Ala Gly Thr Asp Arg Ala Asp Gln Val Ala Ser Gly Leu Arg
                85                  90                  95

Val His Asp Pro Gly Leu Leu Asn Thr Thr Val Val Glu Thr Glu Ile
            100                 105                 110

Ser Phe Ser Asp His Glu Arg Gly Leu Leu Leu Phe Arg Gly Tyr Thr
        115                 120                 125

Leu Gln Gln Leu Trp Asp Ser Glu Phe Glu Asp Met Leu His Leu Leu
    130                 135                 140

Val Trp Gly Thr Tyr Pro Thr Leu Arg Gln Arg Lys Glu Leu Ser Arg
145                 150                 155                 160

Lys Leu Val Asp Cys Met Leu Ala Val Pro Lys Thr Val His Glu Val
                165                 170                 175

Ile Arg Thr Leu Pro Ser Thr Ser Pro Leu Pro Leu Ile Met Ala
            180                 185                 190

Gly Leu Ser Ala Tyr Leu Ala Cys Ile Pro Gly Thr Ile Pro Ala Ser
        195                 200                 205

Thr Asn Pro Asp Leu Tyr Gln Gly Asn Met Glu Glu Val Asp Arg Ala
    210                 215                 220

Ile Val Arg Thr Val Ala Ala Tyr Ala Val Phe Gly Leu Val Asn
225                 230                 235                 240

Cys His Arg Lys Gly Ile Pro Phe Thr Pro Ser His Glu Gln Leu
                245                 250                 255

Tyr Phe Glu Asn Leu Phe Ser Met Ala Gly Leu Val Asp Pro Ala Thr
```

```
                  260                 265                 270
Asn Ser Ala Asp Ala Thr Lys Leu Ser Cys Phe Arg Arg Phe Ala Met
                275                 280                 285
Leu Asn Ala Asp His Gly Met Ala Leu Ser Val Phe Ser Ala Leu Val
                290                 295                 300
Thr Ala Ser Ser Leu Pro Asp Pro Ile Ser Cys Leu Ile Thr Ser Ile
305                 310                 315                 320
Gly Ala Ala Phe Gly Pro Leu His Phe Ala Ala Thr Glu Ser Ala Gln
                325                 330                 335
Leu Ala Leu Arg Glu Ile Gly Thr Pro Asp Lys Val Pro Glu Phe Ile
                340                 345                 350
Glu Glu Val Lys Arg Gly Gln Arg Arg Leu Phe Gly Tyr Gly His Arg
                355                 360                 365
Ser Tyr Lys Gly Thr Asp Pro Arg Val Ala Pro Ile Lys Ser Ile Leu
                370                 375                 380
Lys Asp Leu Asp Thr Ser Asp Asn Pro Phe Leu Lys Ile Ala Glu Gln
385                 390                 395                 400
Ile Glu Arg Val Ala Ser Ala Asp Asp Phe Phe Ser Lys Arg Gly Leu
                    405                 410                 415
His Pro Asn Ala Asp Phe Tyr Gly Asn Phe Val Phe Thr Ala Ile Asp
                420                 425                 430
Asp Ser Arg Arg Asp Asp Gly Ala Ala Asp Tyr Arg Gly His Gly Thr
                435                 440                 445
Leu Glu Gly Val Tyr Val
    450

<210> SEQ ID NO 63
<211> LENGTH: 441
<212> TYPE: PRT
<213> ORGANISM: Bipolaris victoriae

<400> SEQUENCE: 63

Met Ser Asn Gly Phe Leu Leu Val Lys Asp Ser Arg Thr Thr Leu Glu
1               5

Thr Asp Lys Ala Ile Ile Asn Thr Ile Ala Ala Tyr Ala Val Ile Val
            180                 185                 190

Gly Met Ala Ala Cys His Arg Lys Gly Ile Glu Phe Thr Ala Pro Ser
        195                 200                 205

Leu Asp Tyr Ser Phe Val Glu Asn Leu Phe His Met Ser Gly Met Val
    210                 215                 220

Asp Asp Leu Thr Gly Arg Pro Asp Ala Met Lys Val Ser Cys Phe Arg
225                 230                 235                 240

Arg Phe Ala Ala Leu Asn Met Asp His Gly Met Ala Leu Ala Val Phe
                245                 250                 255

Ser Thr Met Val Thr Ala Ser Ser Leu Thr Asp Pro Val Ser Cys Leu
        260                 265                 270

Ile Ala Ser Leu Ala Ala Ala Tyr Gly Pro Leu His Phe Gly Ala Thr
            275                 280                 285

Glu Ala Ala His Leu Ser Leu Arg Ser Ile Gly Asp Lys Ser Lys Val
        290                 295                 300

Pro Glu Phe Ile Ser Glu Val Lys Gln Gly Lys Arg Lys Leu Phe Gly
305                 310                 315                 320

Tyr Gly His Arg Thr Tyr Lys Gly Thr Asp Pro Arg Val Arg Pro Ile
                325                 330                 335

Lys Glu Leu Ile Glu Asp Ser Gly Ala Asn Ser Asp Pro Leu Ile Glu
            340                 345                 350

Ile Ala Arg Glu Ile Glu Arg Leu Ala Ser Asn Asp Tyr Phe Thr
        355                 360                 365

Ser Arg Gly Leu His Pro Asn Ala Asp Phe Tyr Gly Asn Phe Val Phe
    370                 375                 380

Thr Ala Val Gly Phe His Ser Asp Phe Ile Pro Ile Ala Met Ile Ser
385                 390                 395                 400

Gln Arg Leu Ile Gly Ile Met Ala His Trp Arg Glu Ala Met Val Arg
                405                 410                 415

Gly Ile Lys Leu Phe Arg Pro Ser His Ile Tyr Thr Gly Asp Thr Glu
            420                 425                 430

Pro Val Tyr Thr Ala Ser Ala Lys Leu
        435                 440

<210> SEQ ID NO 64
<211> LENGTH: 978
<212> TYPE: PRT
<213> ORGANISM: Aspergillus ruber

<400> SEQUENCE: 64

Met Ala Gly Met Leu Asn Ile Thr Asp Ser Arg Thr Asn Ala Gln His
1               5                   10                  15

Gln Ile Ser Ile Arg His Asn Ala Ile Leu Ala Ser Asp Leu Lys Lys
            20                  25                  30

Thr Thr Gly Leu Arg Val His Asp Pro Gly Leu Gln Asn Thr Thr Val
        35                  40                  45

Val Glu Thr Gly Ile Thr Val Ser His His Asp Thr Gly Leu Leu Leu
    50                  55                  60

Phe Arg Gly Tyr Lys Leu Gln Asp Leu Trp Asp Ile Asn Ser Asp Phe
65                  70                  75                  80

Glu Asp Ile Leu His Leu Leu Val Trp Gly Val Tyr Pro Ser Ser Glu
                85                  90                  95

Gln Arg Lys Thr Leu Ser Arg Gln Leu Ala Thr Ala Met Leu Glu Val
            100                 105                 110

```
Pro Asp Val Val Phe Gln Thr Ile Arg Ala Leu Pro Lys Thr Thr Ser
        115                 120                 125

Pro Leu Pro Leu Leu Met Ala Gly Leu Ser Ala Ser Leu Ser Cys Arg
    130                 135                 140

Pro Glu Met Ile Pro Ala Ser Thr Asn Pro His Leu Tyr Arg Asp Pro
145                 150                 155                 160

Lys Ile Ala Asp His Ala Ile Ile Tyr Thr Ile Ala Thr Tyr Ala Val
                165                 170                 175

Ala Phe Gly Ile Ile Arg Cys His Arg Gln Gly Ile Thr Phe Thr Ser
            180                 185                 190

Pro Ser Val Asp Asn Ser Tyr Leu Glu Asn Leu Phe Ile Met Ala Gly
        195                 200                 205

Leu Val Asp Pro Ser Thr Gly Arg Pro Asp Pro Val Arg Leu Ser Cys
    210                 215                 220

Tyr Arg His Phe Gly Ile Phe Asn Ser Asp His Gly Met Ala Leu Ser
225                 230                 235                 240

Val Phe Ser Ala Leu Val Thr Ala Ser Ser Gln Thr Asp Pro Ile Ser
                245                 250                 255

Cys Leu Ile Thr Ala Thr Gly Ala Ala Tyr Gly Pro Leu His Phe Gly
            260                 265                 270

Ala Thr Glu Ser Ala Lys Arg Ala Leu Leu His Ile Gly Thr Ile Asp
        275                 280                 285

Asn Val Pro Ser Phe Ile Glu Gly Val Lys Gln Gly Lys Gln Lys Leu
    290                 295                 300

Phe Gly Tyr Gly His Arg Ser Tyr Lys Gly Met Asp Pro Arg Val Gln
305                 310                 315                 320

Pro Met Arg Lys Leu Val Cys Asp Leu Lys Leu Asp Ser Ala Ser Asn
                325                 330                 335

Pro Leu Leu Lys Ile Ala Glu Arg Ile Glu Gln Val Ala Ser Glu Asp
            340                 345                 350

Glu Trp Phe Ala Arg Arg Gly Leu Tyr Pro Asn Ala Asp Phe Tyr Gly
        355                 360                 365

His Phe Val Leu Ser Gly Cys Gly Phe Glu Thr Asp Ile Ile Pro Ala
    370                 375                 380

Ala Met Leu Ala Gln Arg Val Val Gly Ile Met Ala His Trp Arg Glu
385                 390                 395                 400

Tyr Met Leu Thr Gly Gly Lys Leu Phe Arg Pro Ser His Ile Tyr Thr
                405                 410                 415

Gly Glu Glu Glu Gly Lys Leu Lys Leu His Leu Gly Gln Gln Val Lys
            420                 425                 430

Met Ser Glu Glu Asn Glu Asn Thr Pro Leu Leu Leu Pro Tyr Ser Val
        435                 440                 445

Phe Thr Pro Ser Gln Lys Arg Leu Leu Ile Leu Thr Ala Ala Leu Ala
    450                 455                 460

Ser Ser Phe Ser Pro Phe Ser Ala Asn Ile Tyr Tyr Pro Ser Leu Asn
465                 470                 475                 480

Ser Ile Ala Arg Asp Leu His Val Ser Ser Gln Ile Asn Leu Thr
                485                 490                 495

Ile Thr Thr Tyr Met Ile Cys Gln Gly Leu Ala Pro Ala Phe Met Gly
            500                 505                 510

Ser Leu Ala Asp Gln Ala Gly Arg Arg Pro Ala Tyr Leu Leu Cys Phe
        515                 520                 525
```

```
Ile Ile Tyr Ile Ala Gly Asn Ile Ala Leu Ala Leu Gln His Ser Tyr
            530                 535                 540

Pro Ala Leu Leu Ile Leu Arg Ala Val Gln Ser Cys Gly Ser Ser Gly
545                 550                 555                 560

Thr Val Ala Leu Ala Ser Ala Val Ala Ala Asp Val Ile Thr Ser Ala
                565                 570                 575

Glu Arg Gly Met Tyr Met Gly Ile Ala Ser Leu Gly Asn Ile Leu Ala
                580                 585                 590

Pro Ser Leu Gly Pro Ile Leu Gly Gly Pro Arg Pro Lys Ile Thr
            595                 600                 605

Phe Pro Asn Pro Leu Gly Thr Leu Arg Leu Leu Phe His Arg Pro Thr
610                 615                 620

Gly Phe Val Leu Leu Ala Asn Gly Ile Ile Tyr Ala Ser Tyr Tyr Ser
625                 630                 635                 640

Val Thr Ala Gly Leu Pro Ala Gln Phe His Glu Leu Tyr Asn Leu Gln
                645                 650                 655

Asp Leu Gly Ile Gly Leu Ser Phe Ile Pro Ala Gly Leu Gly Ser Leu
            660                 665                 670

Phe Ser Ala Thr Val Asn Gly Met Leu Val Asp Trp Asn Tyr His Arg
        675                 680                 685

Val Lys Met Lys Met Gly Leu Pro Val Thr Arg Asp Gln Lys Gln Asp
690                 695                 700

His Gly Asp Phe Pro Ile Glu Gln Thr Arg Leu Gln Ile Gly Leu Pro
705                 710                 715                 720

Met Met Val Phe Leu Ser Phe Phe Ala Thr Val Ser Leu Thr Leu Val
                725                 730                 735

Phe Leu Ile Ser Leu Phe Ile Thr Ala Ala Tyr Asn Val Leu Asn Val
            740                 745                 750

Leu Ile Val Asp Leu Tyr Tyr Thr Thr Pro Ala Thr Ala Met Ala Ala
        755                 760                 765

Asn Asn Leu Val Arg Cys Phe Leu Gly Ala Ala Ala Thr Ala Val Val
770                 775                 780

His Pro Leu Ser Ser Gln Trp Gly Ile Gly Trp Thr Tyr Ser Ala Asn
785                 790                 795                 800

Ile Met Met Leu Ser Thr Leu Leu Pro Leu Val Ser Ala Leu His
                805                 810                 815

Gly His Leu Tyr Met Arg Tyr Pro Asp Ser Arg Trp Ile Thr Pro Gly
            820                 825                 830

Asp Thr Leu Pro Ile Ala Glu Thr Lys Pro Ile Pro Ile Leu Gln Thr
            835                 840                 845

Thr Leu Pro Cys Thr Ser Pro Tyr Leu Leu Thr Ile Asp Pro Asp
850                 855                 860

Val Gln Tyr Gly Thr Thr Ser Thr Ile Val Leu His Trp Leu Gln Ser
865                 870                 875                 880

Leu Arg Ala Asp Cys Gln Thr Gly Phe Leu Tyr Glu Asn Pro Lys Ser
                885                 890                 895

Glu Glu Thr Ala Val Tyr Ile Pro Pro Gln Pro Pro Lys Arg Ser His
                900                 905                 910

His Arg Tyr Ile Phe Leu Leu Phe Gln Gln Pro Glu Asp Tyr Asn Leu
            915                 920                 925

Pro Glu Cys Tyr Gln His Ile Leu Pro Ala Thr Lys Glu Ala Arg Val
930                 935                 940

Gly Phe Asn Pro Lys Glu Phe Val Glu Val Leu Gly Leu Gly Gly Pro
```

```
                      945                 950                 955                 960
Leu Ala Gly Asn Trp Phe Tyr Val Glu Asn Gly Gly Asp Ala Arg Asn
                  965                 970                 975

Glu Leu

<210> SEQ ID NO 65
<211> LENGTH: 420
<212> TYPE: PRT
<213> ORGANISM: Bipolaris maydis

<400> SEQUENCE: 65

Met Ser Asn Gly Phe Leu Phe Val Arg Asp Ser Arg Thr Thr Gln Glu
1               5                   10                  15

Tyr Arg Val Pro Ile Gln Arg Asn Ala Ile Leu Ala Thr Ala Phe Lys
            20                  25                  30

Asp Ile Lys Ala Pro Ser Ser Gly Asn Arg Ala Asp Lys Leu Asp
        35                  40                  45

Ser Gly Leu Arg Val His Asp Pro Gly Leu Leu Asn Thr Thr Val Val
50                  55                  60

Glu Thr Gly Val Ser Phe Ala Asp Gly Glu Arg Asp Leu Leu Leu Phe
65                  70                  75                  80

Arg Gly Tyr Ser Leu Glu Gln Leu Trp Gln Ser Asp Tyr Glu Asp Met
                85                  90                  95

Leu His Leu Leu Val Trp Ala Lys Tyr Pro Thr Pro Val Gln Lys Glu
            100                 105                 110

Ser Leu Arg Arg Ala Leu Ile Ala Ala Met Leu Glu Val Pro Lys Thr
        115                 120                 125

Val Phe Glu Val Val Ser Ala Phe Pro Ser Ala Ser Pro Pro Met Pro
130                 135                 140

Met Val Val Ala Gly Leu Ala Ala Tyr Leu Gly Ser Asn Pro Asp Met
145                 150                 155                 160

Ile Pro Ala Ser Asn Gly Gly Asn Ile Tyr Gln Gly Asp Ile Glu Lys
                165                 170                 175

Thr Asp Lys Ala Ile Val Lys Thr Ile Ala Ala Tyr Ala Val Val Val
            180                 185                 190

Gly Met Ala Ala Cys His Arg Lys Gly Ile Glu Phe Thr Ala Pro Leu
        195                 200                 205

Leu Asp Tyr Asn Phe Ile Glu Asn Leu Phe His Met Ser Gly Met Val
    210                 215                 220

Asp Asp Leu Thr Gly Arg Pro Asp Ala Met Lys Val Ser Cys Phe Arg
225                 230                 235                 240

Arg Phe Ala Ala Leu Asn Met Asp His Gly Met Ala Leu Ala Val Phe
                245                 250                 255

Ser Thr Met Val Thr Ala Ser Ser Leu Thr Asp Pro Ile Ser Cys Leu
            260                 265                 270

Val Ala Ser Leu Ala Ala Ala Tyr Gly Pro Leu His Phe Gly Ala Thr
        275                 280                 285

Glu Ala Ala His Leu Asn Leu Arg Ser Ile Gly Asp Lys Ser Lys Val
    290                 295                 300

Pro Glu Phe Ile Ser Glu Val Lys Gln Gly Lys Arg Lys Leu Phe Gly
305                 310                 315                 320

Tyr Gly His Arg Thr Tyr Lys Gly Thr Asp Pro Arg Val Arg Pro Ile
                325                 330                 335

Lys Glu Leu Ile Glu Asp Ser Gly Ala Asn Ser Asp Pro Leu Ile Glu
```

```
            340                 345                 350
Ile Ala Arg Glu Val Glu Arg Leu Ala Ser Asn Asp Asp Tyr Phe Thr
                355                 360                 365

Ser Arg Gly Leu His Pro Asn Ala Asp Phe Tyr Gly Asn Phe Val Phe
    370                 375                 380

Thr Ala Val Gly Phe Gln Ser Asp Phe Ile Pro Ile Ala Met Ile Ser
385                 390                 395                 400

Gln Arg Leu Ile Gly Ile Met Ala His Trp Arg Glu Ala Met Gly Glu
                405                 410                 415

Ser Ser Asp Thr
            420

<210> SEQ ID NO 66
<211> LENGTH: 443
<212> TYPE: PRT
<213> ORGANISM: Talaromyces stipitatus

<400> SEQUENCE: 66

Met Ser Asp Gly Thr Leu Phe Val Glu Asp Ser Arg Ser Gly Lys Lys
1               5                   10                  15

Tyr Glu Ile Pro Ile Arg His Asn Thr Val Leu Ala Thr Asp Leu Lys
                20                  25                  30

Arg Ile Lys Ala Ser Ser Thr Ala Ala Asn Arg Ala Asp Lys Val Ala
            35                  40                  45

Asp Gly Leu Arg Leu Tyr Asp Pro Gly Leu Glu Asn Thr Thr Val Val
        50                  55                  60

Glu Thr Ser Met Thr Tyr Ala Asp Ala Asp Arg Gly Leu Leu Met Phe
65                  70                  75                  80

Arg Gly Tyr Ala Leu Glu Gln Leu Trp Glu Ser Glu Phe Glu Asp Met
                85                  90                  95

Leu His Leu Met Val Trp Gly Lys Tyr Pro Thr Pro Ser Gln Ser Ala
                100                 105                 110

Ser Leu Arg Lys Asp Leu Ala Ser Leu Met Gly Asp Ile Pro Lys Thr
            115                 120                 125

Val Phe Glu Val Ile Glu Lys Phe Pro Arg Asp Cys Pro Pro Met Pro
        130                 135                 140

Met Leu Val Ala Gly Leu Ala Ala Tyr Leu Ser Asp Asp Leu Asp Ser
145                 150                 155                 160

Ile Pro Thr Phe Asn Gly Gly Asn Ile Phe His Gly Asn Val Glu Lys
                165                 170                 175

Thr Asp Glu Ala Ile Leu Lys Thr Val Ala Ala Phe Ala Ser Val Val
            180                 185                 190

Gly Ile Ala Gly Ser His Arg Arg Gly Ile Ala Phe Thr Pro Pro Ser
        195                 200                 205

Leu Asp Lys Gly Tyr Leu Asp Asn Leu Phe Lys Met Met Gly Ile Val
    210                 215                 220

Asp Pro Thr Thr Asn Lys Pro Ser Pro Glu Lys Leu Asp Cys Phe Arg
225                 230                 235                 240

Arg Phe Thr Ile Ile Asn Thr Asp His Gly Met Ala Leu Ser Ala Phe
                245                 250                 255

Ala His Leu Val Ala Thr Ser Ala Leu Ala Asp Pro Ile Ser Gly Leu
            260                 265                 270

Ile Gly Ser Leu Val Ala Ala Tyr Gly Pro Leu His Phe Gly Ala Pro
        275                 280                 285
```

```
Glu Ala Ala Tyr Lys Thr Ile Lys Ser Ile Gly Gly Pro Gln Asn Val
    290                 295                 300

Pro Ser Phe Leu Asp Glu Val Lys Ser Gly Lys Arg Arg Leu Phe Gly
305                 310                 315                 320

Tyr Gly His Arg Thr Tyr Arg Thr Val Asp Pro Arg Leu Ala Pro Ile
                325                 330                 335

Lys Ser Ala Leu Gln Thr Leu Asn Val Glu Thr Asp Ile Pro Leu Glu
                340                 345                 350

Thr Ala Tyr Glu Ile Asp Arg Leu Ala Ser Asn Asp Asp Tyr Phe Leu
            355                 360                 365

Lys Arg Gly Leu His Ala Asn Ala Asp Phe Tyr Thr Pro Tyr Cys Phe
370                 375                 380

Ile Lys Ile Gly Phe His Pro Glu Glu Phe Pro Ile Ala Met Phe Ala
385                 390                 395                 400

Gln Arg Ile Ile Gly Ile Met Ala His Trp Arg Glu Ala Met Leu Arg
                405                 410                 415

Lys Val Lys Leu Phe Arg Pro Thr His Ile Tyr Thr Gly Glu Thr Glu
                420                 425                 430

Pro Val Glu His Ile Lys Ile Pro Ser Lys Leu
                435                 440

<210> SEQ ID NO 67
<211> LENGTH: 438
<212> TYPE: PRT
<213> ORGANISM: Talaromyces stipitatus

<400> SEQUENCE: 67

Met Ser Asp Gly Thr Leu Phe Ile Gln Asp Ser Arg Thr Ser Lys Gln
1               5                   10                  15

Tyr Thr Ile Ser Val Thr Ser Asp Thr Ile Thr Ala Val Asp Phe Gln
                20                  25                  30

Lys Ile Thr Ser Pro Thr Gly Lys Leu Ala Leu Tyr Asp Pro Gly Leu
            35                  40                  45

Gln Asn Thr Ile Ile Lys Lys Thr Gln Ile Thr Gly Arg Asp Pro Val
50                  55                  60

Thr Gly Ile Thr Leu Phe Arg Gly Leu Ser Ala Lys Glu Ile Trp Asn
65                  70                  75                  80

Arg His Ala Asp Phe Glu Asp His Phe His Leu Leu Val Phe Gly Lys
                85                  90                  95

Tyr Pro Ser Pro Glu Glu Ser Glu Ala Leu Arg Arg Arg Leu Ala Val
                100                 105                 110

Gln Met Thr Val Val Pro Glu Thr Val Ile Lys Ala Val Gln Ala Phe
            115                 120                 125

Pro Arg Thr Ser His Pro Leu Pro Met Ile Ile Ala Gly Leu Ala Ala
130                 135                 140

Phe Ile Ser Ala Asp Pro Ser Ser Leu Pro Ala Ile Arg Gly Gly Asn
145                 150                 155                 160

Ile Tyr His Gly Asn Arg Ala Leu Cys Asp Glu Gly Val Ile Arg Ala
                165                 170                 175

Thr Ala Ala Tyr Ala Val Val Met Gly Leu Ile Asn Ser His Arg Lys
                180                 185                 190

Gln Leu Pro Tyr Val Pro Ala Asp Pro Gln Lys Ser Phe Tyr Glu Asn
            195                 200                 205

Val Phe Ala Met Met Arg Cys Pro Val His His Asn Tyr Leu Val Thr
210                 215                 220
```

```
Phe Arg Glu Gly Met Val Leu Asn Ser Asp Asn Gly Met Thr Gln Ser
225                 230                 235                 240

Ser Val Val Leu Leu Ser Thr Ala Ser Ser Leu Pro Asp Pro Ile Ser
                245                 250                 255

Cys Leu Ile Ser Ala Ile Thr Ala Ala Tyr Gly Pro Leu His Tyr Gly
                260                 265                 270

Ala Gln Glu Ala Gly Ser Thr Thr Leu Lys Ser Ile Gly Ser Leu Asp
            275                 280                 285

Lys Val Pro Glu Phe Leu Glu Gln Val Lys Arg Arg Glu Arg Arg Leu
            290                 295                 300

Phe Gly Phe Gly His Arg Leu His Lys Arg Glu Asp Pro Arg Leu Ala
305                 310                 315                 320

Ser Val Lys Arg Trp Leu Lys Met Met Asp Tyr Thr Pro Asp Gln Glu
                325                 330                 335

Pro Leu Leu Glu Leu Ala Gln Glu Ile Asp Arg Leu Ala Ser Ser Asp
                340                 345                 350

Glu Tyr Phe Ile Lys Arg Asn Leu Arg Ala Asn Ala Asp Phe Tyr Thr
            355                 360                 365

His Phe Leu Phe Lys Ala Trp Gly Phe Asp Trp Asp Met Leu Cys Ala
370                 375                 380

Ala Asn Met Phe His Arg Ile Ile Gly Leu Met Ala His Trp Arg Glu
385                 390                 395                 400

Ala Met Asp Gln Pro Ile Lys Ile Phe Arg Ala Thr Asp Leu Tyr Val
                405                 410                 415

Gly Pro Val Val Ile Gln Glu Asp Asn Arg Thr Val Leu Glu Glu Pro
            420                 425                 430

Lys Ile Gln Ser Arg Leu
            435

<210> SEQ ID NO 68
<211> LENGTH: 221
<212> TYPE: PRT
<213> ORGANISM: Aspergillus terreus

<400> SEQUENCE: 68

Met Ala Gly Leu Leu Asn Gln Pro Ser Ala Thr Pro Asp Gly Val Lys
1               5                   10                  15

Ile Ser Cys Phe Arg Arg Phe Ala Leu Leu Asn Ala Asp His Gly Met
                20                  25                  30

Ala Leu Ser Val Phe Ser Ala Leu Val Thr Ala Ser Ser Leu Pro Asp
            35                  40                  45

Pro Leu Ser Ser Val Leu Ser Ala Val Ala Ala Tyr Gly Pro Leu
            50                  55                  60

His Phe Gly Ala Thr Glu Thr Ala His Arg Thr Leu Arg Glu Ile Gly
65                  70                  75                  80

Ser Pro Asp Asn Val Pro Ser Phe Ile Glu Glu Val Lys Asn Gly Arg
                85                  90                  95

Arg Lys Leu Phe Gly Tyr Gly His Arg Ala Tyr Lys Gly Val Asp Pro
                100                 105                 110

Arg Val Gln Pro Ile Gln Ser Ile Leu Lys Asp Leu Asp Met Ser Ser
            115                 120                 125

Asn Gly Leu Leu Lys Ile Ala Glu Arg Ile Glu Gln Thr Ala Ser Thr
            130                 135                 140

Asp Asp Tyr Phe Leu Lys Arg Gly Leu Tyr Pro Asn Ala Asp Phe Tyr
```

```
145                 150                 155                 160
Gly Asn Phe Val Phe Thr Gly Ile Gly Phe Glu Pro Asp Met Ile Pro
                165                 170                 175

Ala Ala Met Leu Ala Gln Arg Ile Ile Gly Ile Met Ala His Trp Arg
            180                 185                 190

Glu Tyr Met Leu Asn Arg Gly Lys Leu Leu Arg Pro Ser His Ile Tyr
        195                 200                 205

Thr Gly Asp Val Lys Ala Ala Glu Ile Ser Ser Lys Leu
    210                 215                 220

<210> SEQ ID NO 69
<211> LENGTH: 253
<212> TYPE: PRT
<213> ORGANISM: Penicillium digitatum

<400> SEQUENCE: 69

Met Cys Ser Lys Ala Thr Ser Pro Leu Pro Leu Ile Leu Ala Gly Leu
1               5                   10                  15

Ser Ala His Leu Ala Cys Leu Pro Asp Val Ile Pro Ala Thr Thr Asn
            20                  25                  30

Pro Thr Ile Tyr Gln Thr Asp Ile Lys Arg Ala Asp Gln Ile Ile Leu
        35                  40                  45

Gln Thr Val Ala Gly Tyr Ala Val Val Phe Gly Ala Val Arg Ser His
    50                  55                  60

Arg Leu Gly Leu Pro Trp Arg Ser Pro Ser Leu His Gln Thr Tyr Tyr
65                  70                  75                  80

Glu Asn Leu Phe Thr Met Ala Gly Leu Val Asp Pro Gly Thr Asn Tyr
                85                  90                  95

Pro Asp Leu Arg Gly Ile Ser Cys Phe Arg Arg Phe Gly Asn Leu Asn
            100                 105                 110

Ala Glu His Gly Met Ala Leu Thr Ala Phe Ser Ser Ile Val Thr Ala
        115                 120                 125

Ser Ser Leu Thr Asp Pro Val Ser Cys Leu Ile Ser Ala Leu Ala Ala
    130                 135                 140

Ala His Gly Pro Leu His Phe Gly Ala Thr Glu Ser Ala Gln Arg Ala
145                 150                 155                 160

Leu Arg Asp Ile Gly Glu Pro Lys Asn Val Pro Ala Phe Ile Glu Glu
                165                 170                 175

Val Lys Ala Gly Lys Gln Lys Leu Phe Gly Tyr Gly His Arg Thr Tyr
            180                 185                 190

Lys Gly Met Asp Pro Arg Val Arg Pro Ile Gln Ser Ile Leu Lys Asp
        195                 200                 205

Leu Ile His Ile Asn Gln Pro Leu Leu Lys Val Ala Glu Ala Ile Glu
    210                 215                 220

Asp Ala Ala Ala Lys Asp Tyr Phe Val Ser Arg Gly Leu Tyr Pro
225                 230                 235                 240

Asn Ala Asp Phe Tyr Gly Asn Phe Val Phe Thr Gly Met
                245                 250

<210> SEQ ID NO 70
<211> LENGTH: 493
<212> TYPE: PRT
<213> ORGANISM: Colletotrichum graminicola

<400> SEQUENCE: 70

Met Gly Val Ile Phe Tyr Gly Leu Lys His Leu Arg Pro Phe Phe Ser
```

```
1               5                   10                  15
Leu Leu Gly Leu Val Lys Arg Ser Met Val Met Val Asn Lys Ala Ile
                20                  25                  30
Gln Lys Ser Pro Arg Ile Val His Trp Val Leu Gly Arg His Asp Ile
                35                  40                  45
Asp Ser Pro Cys Ser Thr Leu Thr Val Leu Asp Asn Arg Thr Lys Arg
        50                  55                  60
Arg Tyr Glu Ile Pro Ile Arg Arg Asn Ala Val Ser Ala Leu Glu Phe
65                  70                  75                  80
Gln Lys Ile Thr Thr Ala His Cys Gly Ile Glu Ser Val Gly Gln Val
                85                  90                  95
Asp Phe Gly Leu Arg Val Leu Asp Pro Gly Tyr Arg Asn Thr Ala Cys
            100                 105                 110
Val Glu Ser Asn Ile Thr Phe Val Asp Gly Lys Arg Gly Tyr Ile Gln
            115                 120                 125
Leu Arg Gly Tyr Pro Ile Glu Tyr Leu Val Glu Asn His Asp Tyr Glu
        130                 135                 140
Glu Val Ile His Leu Leu Ile Trp Gly Arg Leu Pro Asp Ala Val Glu
145                 150                 155                 160
Lys Lys Glu Leu Gln Arg Arg Ile Ala Ala Gly Cys Ala Pro Pro Glu
                165                 170                 175
His Val Val Gln Val Ile Thr Ser Phe Pro Arg Asp Ser Leu Thr Ser
            180                 185                 190
Thr Met Val Met Ala Gly Met Ala Ala Tyr Ala Ser Cys Asp Glu Gly
            195                 200                 205
Ala Val Ser Thr Leu Gln Ser Gly Cys Pro Ala Tyr Leu Gly Gln Pro
        210                 215                 220
Asp Lys Val Asp Ala Ala Leu Ile Ser Thr Ile Ser Ala Leu Ala Thr
225                 230                 235                 240
Val Val Ala Leu Thr Tyr Cys His Lys Arg Gly Lys Arg Leu Ala Pro
                245                 250                 255
Val Asp Pro Glu Ala Ser Phe Thr Ala Asn Val Leu Gly Met Met Gly
            260                 265                 270
Phe Gln Glu Gly Met Ser Gly Lys Pro Asp Ala Glu Met Val Gln Cys
            275                 280                 285
Phe Glu Lys Leu Trp Ile Leu Tyr Ala Asp Gln Glu Met Thr Asn Ser
        290                 295                 300
Thr Ser Ala Phe Leu His Ala Ala Ser Thr Leu Val Asp Pro Leu Ser
305                 310                 315                 320
Cys Cys Ile Ser Gly Ile Val Ser Gly Tyr Gly Pro Leu His Gly Gly
                325                 330                 335
Ala Ile Asp Leu Ala Tyr Lys Ala Phe Gln Asp Val Lys Thr Pro Glu
            340                 345                 350
Asn Val Pro Ala Leu Ile Ala Asp Val Lys Ala Lys Gln Arg Leu
            355                 360                 365
Phe Gly Tyr Gly His Arg Val Tyr Lys Val Val Asp Pro Arg Ala Lys
        370                 375                 380
Phe Ile Arg Ala Met Ile Asn Gln Tyr Arg Asp Lys Val Glu Ser Asn
385                 390                 395                 400
Pro Leu Leu Ser Val Ala Met Glu Ile Asp Arg Val Ala Ser Thr Asp
                405                 410                 415
Glu Tyr Phe Thr Ser Arg Ser Leu Lys Ala Asn Ala Asp Leu Tyr Gly
            420                 425                 430
```

```
Cys Phe Leu Tyr Thr Ala Phe Gly Phe Glu Pro Asp Ile Ile Val Ala
            435                 440                 445

Met Ala Ser Leu Ser Arg Ile Pro Gly Val Leu Ala His Trp Arg Glu
450                 455                 460

Ala Met Leu Glu Lys Gly Pro Leu Leu Trp Arg Pro Gln Gln Val Phe
465                 470                 475                 480

Thr Gly Ala Leu Ala Asp Glu Tyr Tyr Cys Ala Thr Arg
            485                 490

<210> SEQ ID NO 71
<211> LENGTH: 450
<212> TYPE: PRT
<213> ORGANISM: Auricularia delicata

<400> SEQUENCE: 71

Met Gly Arg Trp Ala Leu Asn Lys Ala Gly Ala Thr Ser Leu Gly Glu
1               5                   10                  15

Ser Ser Gly Ser Leu Thr Val Ile Asp Asn Arg Thr Gln Arg Thr Tyr
            20                  25                  30

Glu Val Glu Ile Lys His Asn Ala Ile Lys Ala Thr Asp Leu Arg Arg
        35                  40                  45

Ile Thr Ala Ala Gly Val Ala Ala Asp Pro Val Asp Gln Val Glu Ser
50                  55                  60

Gly Leu Arg Val Leu Asp Lys Gly Tyr Leu Asn Thr Ala Cys Met Glu
65                  70                  75                  80

Ser Ser Val Thr Leu Ile Asp Gly Lys Arg Gly Tyr Ile Gln Tyr Arg
            85                  90                  95

Asp Lys Ser Ile Asp Glu Leu Val Arg Asn Asn Asp Tyr Glu Glu Val
        100                 105                 110

Ala His Leu Leu Ile Trp Gly Arg Leu Pro Ser Leu Glu Glu Lys Thr
    115                 120                 125

Arg Leu Arg Arg Gly Leu Ala Ala Met Val Pro Pro Gln Ser Val
    130                 135                 140

Ile Asp Val Ile Gln Ala Phe Pro Arg Asp Ser Leu Thr Phe Pro Met
145                 150                 155                 160

Leu Leu Ala Gly Leu Ser Ala Phe Ala Ala Val Asp Lys Gly Thr Gln
            165                 170                 175

Gln Val His Glu Ser Gly Arg Pro Val Tyr Leu Gly Asn Thr Pro Ala
        180                 185                 190

Val Asp Ala Ala Ile Val Arg Ser Leu Ala Ala Leu Thr Thr Val
    195                 200                 205

Ala Leu Val His Cys His Lys Arg Gly Ile Ala Phe Thr Pro Ala Asp
    210                 215                 220

Pro Glu Gly Thr Leu Ile Gly Asn Leu Leu Leu Met Met Gly Phe Lys
225                 230                 235                 240

Lys Asp Gly Arg Pro Asp Pro Lys Ile Glu Lys Cys Leu Glu Lys Leu
            245                 250                 255

Trp Ile Leu Tyr Ala Asp His Glu Met Thr Asn Ser Thr Ala Ser Phe
        260                 265                 270

Leu His Ala Ala Ser Thr Leu Thr Asp Pro Ile Ser Cys Leu Ile Ala
    275                 280                 285

Gly Val Val Ser Gly Tyr Gly Pro Leu His Gly Gly Ala Ile Asp Leu
    290                 295                 300

Ala Tyr Lys Gly Phe Glu Glu Val Gly Thr Pro Glu Arg Val Pro Glu
```

-continued

```
            305                 310                 315                 320
Leu Ile Ala Asp Val Lys Ala Lys Lys Gln Arg Leu Phe Gly Tyr Gly
                    325                 330                 335

His Arg Val Tyr Lys Thr Val Asp Pro Arg Thr Arg Tyr Ile Arg Asp
                340                 345                 350

Met Met Asp Asp His Trp Ala Glu Met Ser Ala Asn Pro Leu Leu Arg
            355                 360                 365

Val Ala Leu Glu Ile Asp Arg Val Ala Gly Gln Asp Pro Tyr Phe Thr
        370                 375                 380

Ser Arg Asn Leu Lys Val Asn Ala Asp Leu Tyr Gly Cys Phe Leu Tyr
385                 390                 395                 400

Thr Ala Phe Gly Phe Asp Thr Asp Ile Ile Thr Ala Val Ala Ala Val
                    405                 410                 415

Ser Arg Ile Ala Gly Val Leu Ala His Trp Arg Glu Ala Met His Gln
                420                 425                 430

Gln Pro Met Leu Trp Arg Pro Met Gln Val Phe Thr Gly Ser Met Ala
            435                 440                 445

Gln Ala
    450

<210> SEQ ID NO 72
<211> LENGTH: 447
<212> TYPE: PRT
<213> ORGANISM: Aspergillus oryzae

<400> SEQUENCE: 72

Met Thr Val Thr Gln Glu Ala Ser Pro Lys Arg Glu Ser Leu His Ile
1               5                   10                  15

Ile Asp Asp Arg Thr Gly Ser Tyr Tyr Ser Ile Pro Ile Val Asn Asn
                20                  25                  30

Ala Ile Asn Ala Ser Asp Phe Lys Lys Val Thr Ala Pro Glu Asp Lys
            35                  40                  45

Ala Tyr Pro Ala Asn Gln Thr Glu Asn Gly Leu Arg Val Tyr Asp Pro
        50                  55                  60

Gly Tyr Ser Asn Thr Ala Val Ser His Ser Lys Ile Tyr Ile Asp
65                  70                  75                  80

Gly Leu Lys Gly Thr Ile Gln Tyr Arg Gly Tyr Ser Ile Asn Asp Ile
                85                  90                  95

Val Gly Arg Lys Thr Phe Ile Asp Thr Ala His Leu Leu Ile Trp Gly
            100                 105                 110

His Trp Pro Ser Thr Ala Glu Ala Glu Thr Leu Gln Gln Arg Leu Asp
        115                 120                 125

Gln Val Pro Val Pro Gln Asp Phe Val Phe Asn Val Ile Lys Ser Phe
    130                 135                 140

Pro Arg Asp Gly Ser Leu Met Gly Met Val Ile Ala Gly Leu Ser Ala
145                 150                 155                 160

Leu Gln Ser Ser Asp Met Asn Ala Ile Pro Ala His Val Gly Lys Thr
                165                 170                 175

Ile Tyr Leu Asn Asn Pro Glu Leu Ala Asp Gln Gln Ile Ile Arg Val
            180                 185                 190

Met Ala Asn Met Ser Met Leu Thr Ala Ala Ala Tyr Cys His His Ile
        195                 200                 205

Gly Arg Asp Phe Thr Pro Pro Arg Ala Gly Leu Ser Tyr Ile Glu Asn
    210                 215                 220
```

```
Phe Leu Leu Met Thr Gly His Val Glu Ala Ala Thr Gly Leu Pro Asn
225                 230                 235                 240

Pro Arg Tyr Val Asn Ala Ile Glu Arg Leu Trp Val Leu Ile Ala Asp
            245                 250                 255

His Glu Met Thr Cys Ser Thr Ala Ala Leu Leu Gln Thr Ala Ser Ala
                260                 265                 270

Leu Pro Asp Val Ile Ser Cys Met Val Ser Ala Ile Ser Ala Leu Tyr
            275                 280                 285

Gly Pro Leu His Gly Gly Ala Ile Glu Val Ala Tyr Lys Asn Ile Glu
        290                 295                 300

Ser Ile Gly Ser Ile Ser Asn Val Pro Ala Lys Ile Ala Arg Val Lys
305                 310                 315                 320

Ala Gly Lys Glu Arg Leu Tyr Gly Tyr Gly His Arg Val Tyr Arg Val
                325                 330                 335

Thr Asp Pro Arg Phe Val Phe Ile Arg Glu Ile Leu Asn Glu Leu Ser
            340                 345                 350

Glu Glu Val Glu Lys Asp Pro Leu Leu Lys Val Ala Phe Glu Val Asp
        355                 360                 365

Arg Val Ala Ser Glu Asp Glu Tyr Phe Thr Ser Arg Asn Leu Arg Pro
370                 375                 380

Asn Ala Asp Leu Phe Ala Ala Phe Val Tyr Lys Ala Leu Gly Phe Pro
385                 390                 395                 400

Pro Glu Phe Ile Leu Pro Leu Ser Ile Leu Ser Arg Thr Gln Gly Phe
                405                 410                 415

Met Ala His Trp Arg Glu Ala Met Gly Asn Pro Pro Arg Ile Trp Arg
            420                 425                 430

Pro Gly Gln Ile Tyr Thr Gly Asp Leu Asn Lys Ser Met Asp Glu
        435                 440                 445

<210> SEQ ID NO 73
<211> LENGTH: 447
<212> TYPE: PRT
<213> ORGANISM: Aspergillus oryzae

<400> SEQUENCE: 73

Met Thr Val Thr Gln Glu Ala Ser Pro Lys Arg Glu Ser Leu His Ile
1               5                   10                  15

Ile Asp Asp Arg Thr Gly Ser Tyr Tyr Ser Ile Pro Ile Val Asn Asn
            20                  25                  30

Ala Ile Asn Ala Ser Asp Phe Lys Lys Val Thr Ala Pro Glu Asp Lys
        35                  40                  45

Ala Tyr Pro Ala Asn Gln Thr Glu Asn Gly Leu Arg Val Tyr Asp Pro
    50                  55                  60

Gly Tyr Ser Asn Thr Ala Val Ser His Ser Lys Ile Thr Tyr Ile Asp
65                  70                  75                  80

Gly Leu Lys Gly Thr Ile Gln Tyr Arg Gly Tyr Ser Ile Asn Asp Ile
                85                  90                  95

Val Gly Arg Lys Thr Phe Ile Asp Thr Ala His Leu Leu Ile Trp Gly
            100                 105                 110

His Trp Pro Ser Ala Ala Glu Ala Glu Thr Leu Gln Gln Arg Leu Asp
        115                 120                 125

Gln Val Pro Val Pro Gln Asp Phe Val Phe Asn Val Ile Lys Ser Phe
    130                 135                 140

Pro Arg Asp Gly Ser Leu Met Gly Met Val Ile Ala Gly Leu Ser Ala
145                 150                 155                 160
```

```
Leu Gln Ser Ser Asp Met Asn Ala Ile Pro Ala His Val Gly Lys Thr
                165                 170                 175

Ile Tyr Leu Asn Asn Pro Glu Leu Ala Asp Gln Gln Ile Ile Arg Val
            180                 185                 190

Met Ala Asn Met Ser Met Leu Thr Ala Ala Tyr Cys His His Ile
            195                 200                 205

Gly Arg Asp Phe Thr Pro Pro Arg Ala Gly Leu Ser Tyr Ile Glu Asn
        210                 215                 220

Phe Leu Leu Met Thr Gly His Val Glu Ala Ala Thr Gly Leu Pro Asn
225                 230                 235                 240

Pro Arg Tyr Val Asn Ala Ile Glu Arg Leu Trp Val Leu Ile Ala Asp
                245                 250                 255

His Glu Met Thr Cys Ser Thr Ala Ala Leu Leu Gln Thr Ala Ser Ala
            260                 265                 270

Leu Pro Asp Val Ile Ser Cys Met Val Ser Ala Ile Ser Ala Leu Tyr
        275                 280                 285

Gly Pro Leu His Gly Gly Ala Ile Glu Val Ala Tyr Lys Asn Ile Glu
    290                 295                 300

Ser Ile Gly Ser Ile Ser Asn Val Pro Ala Lys Ile Ala Arg Val Lys
305                 310                 315                 320

Ala Gly Lys Glu Arg Leu Tyr Gly Tyr Gly His Arg Val Tyr Arg Val
                325                 330                 335

Thr Asp Pro Arg Phe Val Phe Ile Arg Glu Ile Leu Asn Glu Leu Ser
            340                 345                 350

Glu Glu Val Glu Lys Asp Pro Leu Leu Lys Val Ala Phe Glu Val Asp
        355                 360                 365

Arg Val Ala Ser Glu Asp Glu Tyr Phe Thr Ser Arg Asn Leu Arg Pro
    370                 375                 380

Asn Ala Asp Leu Phe Ala Ala Phe Val Tyr Lys Ala Leu Gly Phe Pro
385                 390                 395                 400

Pro Glu Phe Ile Leu Pro Leu Ser Ile Leu Ser Arg Thr Gln Gly Phe
                405                 410                 415

Met Ala His Trp Arg Glu Ala Met Gly Asn Pro Pro Arg Ile Trp Arg
            420                 425                 430

Pro Gly Gln Ile Tyr Thr Gly Asp Leu Asn Lys Ser Met Asp Glu
        435                 440                 445
```

<210> SEQ ID NO 74
<211> LENGTH: 458
<212> TYPE: PRT
<213> ORGANISM: Aspergillus kawachii

<400> SEQUENCE: 74

```
Met Pro Asp Ile Ala Pro Asn Val Ala Arg Asn Gly Ser Ala Lys Asn
1               5                   10                  15

Ala Glu Asn Lys Pro Glu Thr Pro Val Leu His Val Val Asp Ser Arg
            20                  25                  30

Thr Gly Asn Tyr Phe Pro Ile Pro Ile Val Arg Asn Ala Ile Asn Ala
        35                  40                  45

Ser Glu Phe Lys Lys Leu Lys Ser Pro Glu Asp Pro Ala His Pro Glu
    50                  55                  60

Asp Gln Asn Glu Gln Gly Ile Arg Val Phe Asp Pro Gly Tyr Ser Asn
65                  70                  75                  80

Thr Ala Val Ser Glu Ser Gln Val Thr Tyr Ile Asp Gly Leu Lys Gly
```

```
                        85                  90                  95
Thr Ile Gln Tyr Arg Gly Tyr Asn Ile Glu Asp Ile Val Gly Lys Lys
                100                 105                 110

Lys Phe Ile Asp Thr Ala His Leu Leu Ile Trp Gly Glu Trp Pro Thr
            115                 120                 125

Pro Glu Gln Ala Arg Ser Leu Gln Glu Lys Leu Ser Ser Val Pro Ile
        130                 135                 140

Leu Asp Glu Ser Val Phe Lys Val Ile Gln Ala Phe Pro Pro Asn Ser
145                 150                 155                 160

Ser Ile Ile Gly Met Met Ile Ala Ala Leu Ser Ala Val Gln Ser Ser
                165                 170                 175

Gln Met Asp Arg Ile Pro Ala His Ala Ala Lys Asn Leu Tyr Leu Gly
            180                 185                 190

Asn Pro Gln Ala Val Asp Asp Glu Ile Val Arg Leu Met Gly Ser Leu
        195                 200                 205

Ser Met Ile Thr Ala Ala Val Tyr Cys His His Thr Gly Arg Glu Phe
    210                 215                 220

Thr Pro Pro Arg Leu Glu Leu Ser Tyr Ile Glu Asn Phe Leu Leu Met
225                 230                 235                 240

Met Gly His Val Glu Ser Ser Thr Gly Leu Pro Asn Pro Gln Tyr Val
                245                 250                 255

Asp Arg Ile Glu Arg Leu Trp Val Leu Ile Ala Asp His Glu Met Thr
            260                 265                 270

Cys Ser Thr Ala Ala Phe Leu Gln Thr Ala Ser Ser Leu Pro Asp Val
        275                 280                 285

Phe Ser Cys Met Ile Ser Ala Leu Ser Ala Leu Tyr Gly Pro Leu His
    290                 295                 300

Gly Gly Ala Ile Glu Val Ala Tyr Lys Asn Phe Glu Glu Ile Gly Ser
305                 310                 315                 320

Val Glu Asn Val Ala Ala Lys Ile Glu Arg Val Lys Ala Gly Lys Glu
                325                 330                 335

Arg Leu Tyr Gly Tyr Gly His Arg Ile Tyr Arg Val Thr Asp Pro Arg
            340                 345                 350

Phe Ile Phe Ile Arg Gln Ile Leu Asp Glu Leu Lys Glu Glu Ile Ala
        355                 360                 365

Arg Asn Pro Leu Leu Lys Val Ala Phe Glu Val Asp Arg Val Ala Ser
    370                 375                 380

Glu Asp Glu Tyr Phe Val Thr Arg Lys Leu Arg Pro Asn Ala Asp Leu
385                 390                 395                 400

Phe Ala Ala Leu Val Tyr Ser Ala Met Gly Phe Pro Thr Glu Phe Ile
                405                 410                 415

Leu Pro Leu Ser Leu Leu Ser Arg Thr Gln Gly Phe Met Ala His Trp
            420                 425                 430

Lys Glu Ala Met Ser Ser Thr Ala Arg Ile Trp Arg Pro Gly Gln Ile
        435                 440                 445

Tyr Thr Gly His Leu Ser Arg Glu Met Ala
    450                 455

<210> SEQ ID NO 75
<211> LENGTH: 458
<212> TYPE: PRT
<213> ORGANISM: Zea mays

<400> SEQUENCE: 75
```

```
Met Pro Asp Ile Ala Pro Asn Val Ala Arg Asn Gly Ser Ser Lys His
1               5                   10                  15

Ala Glu Thr Lys Pro Glu Thr Pro Val Leu His Val Val Asp Ser Arg
            20                  25                  30

Thr Gly Asn Tyr Phe Pro Ile Pro Ile Val Arg Asn Ala Ile Asn Ala
                35                  40                  45

Ser Glu Phe Lys Lys Leu Lys Ser Pro Glu Asp Pro Ala His Pro Glu
    50                  55                  60

Asp Gln Asn Glu Gln Gly Ile Arg Val Phe Pro Gly Tyr Ser Asn
65                  70                  75                  80

Thr Ala Val Ser Glu Ser Gln Val Thr Tyr Ile Asp Gly Leu Lys Gly
                85                  90                  95

Thr Ile Gln Tyr Arg Gly Tyr Asn Ile Glu Asp Ile Val Gly Lys Lys
            100                 105                 110

Lys Phe Ile Asp Thr Ala His Leu Leu Ile Trp Gly Glu Trp Pro Thr
                115                 120                 125

Pro Glu Gln Ala Lys Ser Leu Gln Glu Lys Leu Ser Ser Val Pro Ile
    130                 135                 140

Leu Asp Glu Ser Val Phe Lys Val Ile Gln Ala Phe Pro Pro Asn Ser
145                 150                 155                 160

Ser Ile Ile Gly Met Met Ile Ala Ala Leu Ser Ala Val Gln Ser Ser
                165                 170                 175

Gln Met Asp Arg Ile Pro Ala His Ala Ala Lys Asn Leu Tyr Leu Gly
            180                 185                 190

Asn Pro Gln Ala Val Asp Asp Glu Ile Val Arg Leu Met Gly Ser Leu
    195                 200                 205

Ser Met Ile Thr Ala Ala Val Tyr Cys His His Thr Gly Arg Glu Phe
210                 215                 220

Thr Pro Pro Arg Pro Glu Leu Ser Tyr Ile Glu Asn Phe Leu Leu Met
225                 230                 235                 240

Met Gly His Val Glu Ser Ser Thr Gly Leu Pro Asn Pro Gln Tyr Val
                245                 250                 255

Asp Arg Ile Glu Arg Leu Trp Val Leu Ile Ala Asp His Glu Met Thr
            260                 265                 270

Cys Ser Thr Ala Ala Phe Leu Gln Thr Ala Ser Ser Leu Pro Asp Val
    275                 280                 285

Phe Ser Cys Met Ile Ser Ala Leu Ser Ala Leu Tyr Gly Pro Leu His
    290                 295                 300

Gly Gly Ala Ile Glu Val Ala Tyr Lys Asn Phe Glu Glu Ile Gly Ser
305                 310                 315                 320

Val Glu Asn Val Ala Ala Lys Ile Glu Arg Val Lys Ala Gly Lys Glu
                325                 330                 335

Arg Leu Tyr Gly Tyr Gly His Arg Ile Tyr Arg Val Thr Asp Pro Arg
            340                 345                 350

Phe Ile Phe Ile Arg Gln Ile Leu Asp Glu Leu Lys Glu Glu Ile Ala
    355                 360                 365

Arg Asn Pro Leu Leu Lys Val Ala Phe Glu Val Asp Arg Val Ala Ser
    370                 375                 380

Glu Asp Glu Tyr Phe Val Thr Arg Lys Leu Arg Pro Asn Ala Asp Leu
385                 390                 395                 400

Phe Ala Ala Leu Val Tyr Ser Ala Met Gly Phe Pro Thr Glu Phe Ile
                405                 410                 415

Leu Pro Leu Ser Leu Leu Ser Arg Thr Gln Gly Phe Met Ala His Trp
```

```
                420             425             430
Lys Glu Ala Met Ser Ser Thr Ala Arg Ile Trp Arg Pro Gly Gln Ile
                435                 440                 445
Tyr Thr Gly His Leu Asn Arg Glu Met Ala
    450                 455

<210> SEQ ID NO 76
<211> LENGTH: 458
<212> TYPE: PRT
<213> ORGANISM: Aspergillus niger

<400> SEQUENCE: 76

Met Pro Asp Ile Ala Ser Asn Gly Ala Arg Asn Gly Ala Ser Gln Asn
1               5                   10                  15
Ala Glu Thr Lys Pro Glu Pro Val Leu His Val Val Asp Ser Arg
            20                  25                  30
Thr Gly Lys Tyr Phe Pro Ile Pro Ile Val Arg Asn Ala Ile Asn Ala
            35                  40                  45
Ser Glu Phe Lys Lys Leu Lys Ser Pro Glu Asp Pro Ala His Pro Glu
    50                  55                  60
Asp Gln Asn Glu Gln Gly Ile Arg Val Phe Asp Pro Gly Tyr Ser Asn
65                  70                  75                  80
Thr Ala Val Ser Glu Ser Gln Val Thr Tyr Ile Asp Gly Leu Lys Gly
                85                  90                  95
Thr Ile Gln Tyr Arg Gly Tyr Asn Ile Glu Asp Ile Val Gly Lys Lys
            100                 105                 110
Lys Phe Ile Asp Thr Ala His Leu Leu Ile Trp Gly Glu Trp Pro Thr
        115                 120                 125
Pro Glu Gln Ala Lys Ser Leu Gln Glu Lys Leu Ser Ser Val Pro Val
    130                 135                 140
Leu Asp Glu Ser Val Phe Lys Val Ile Gln Ala Phe Pro Pro Asn Ser
145                 150                 155                 160
Ser Ile Ile Gly Met Met Ile Ala Ala Leu Ser Ala Val Gln Ser Thr
                165                 170                 175
Gln Met Asp Arg Ile Pro Ala His Ala Ala Lys Asn Leu Tyr Leu Gly
            180                 185                 190
Asn Pro Lys Ala Val Asp Asp Glu Ile Val Arg Leu Met Gly Ser Leu
        195                 200                 205
Ser Met Ile Thr Ala Ala Val Tyr Cys His His Thr Gly Arg Glu Phe
    210                 215                 220
Thr Pro Pro Arg Pro Glu Leu Ser Tyr Ile Glu Asn Phe Leu Leu Met
225                 230                 235                 240
Met Gly His Val Glu Ser Ser Thr Gly Leu Pro Asn Pro Gln Tyr Val
                245                 250                 255
Asp Arg Ile Glu Arg Leu Trp Val Leu Ile Ala Asp His Glu Met Thr
            260                 265                 270
Cys Ser Thr Ala Ala Phe Leu Gln Thr Ala Ser Ser Leu Pro Asp Val
        275                 280                 285
Phe Ser Cys Met Ile Ser Ala Leu Ser Ala Leu Tyr Gly Pro Leu His
    290                 295                 300
Gly Gly Ala Ile Glu Val Ala Tyr Lys Asn Phe Glu Glu Ile Gly Ser
305                 310                 315                 320
Val Glu Asn Val Ala Ala Lys Ile Glu Arg Val Lys Ala Gly Lys Glu
                325                 330                 335
```

```
Arg Leu Tyr Gly Tyr Gly His Arg Ile Tyr Arg Val Thr Asp Pro Arg
                340                 345                 350

Phe Ile Phe Ile Arg Gln Ile Leu Asp Glu Leu Lys Glu Glu Ile Ala
        355                 360                 365

Arg Asn Pro Leu Leu Lys Val Ala Phe Glu Val Asp Arg Val Ala Ser
    370                 375                 380

Glu Asp Glu Tyr Phe Val Thr Arg Lys Leu Arg Pro Asn Ala Asp Leu
385                 390                 395                 400

Phe Ala Ala Leu Val Tyr Ser Ala Met Gly Phe Pro Thr Glu Phe Ile
                405                 410                 415

Leu Pro Leu Ser Leu Leu Ser Arg Thr Gln Gly Phe Met Ala His Trp
            420                 425                 430

Lys Glu Ala Met Ser Ser Thr Ala Arg Ile Trp Arg Pro Gly Gln Ile
        435                 440                 445

Tyr Thr Gly His Leu Asn Arg Glu Met Ala
    450                 455

<210> SEQ ID NO 77
<211> LENGTH: 495
<212> TYPE: PRT
<213> ORGANISM: Aspergillus niger

<400> SEQUENCE: 77

Met Pro Asp Ile Ala Ser Asn Gly Ala Arg Asn Gly Ala Ser Gln Asn
1               5                   10                  15

Ala Glu Thr Lys Pro Glu Pro Pro Val Leu His Val Val Asp Ser Arg
                20                  25                  30

Thr Gly Lys Tyr Phe Pro Ile Pro Ile Val Arg Asn Ala Ile Asn Ala
            35                  40                  45

Ser Glu Phe Lys Lys Leu Lys Ser Pro Glu Asp Pro Ala His Pro Glu
    50                  55                  60

Asp Gln Asn Glu Gln Gly Ile Arg Val Phe Asp Pro Gly Tyr Ser Asn
65                  70                  75                  80

Thr Ala Val Ser Glu Ser Gln Val Thr Tyr Ile Asp Gly Leu Lys Gly
                85                  90                  95

Thr Ile Gln Tyr Arg Gly Tyr Asn Ile Glu Asp Ile Val Gly Lys Lys
            100                 105                 110

Lys Phe Ile Asp Thr Ala His Leu Leu Ile Trp Gly Trp Pro Thr
            115                 120                 125

Pro Glu Gln Ala Lys Ser Leu Gln Glu Lys Leu Ser Ser Val Pro Val
    130                 135                 140

Leu Asp Glu Ser Val Phe Lys Val Ile Gln Ala Phe Pro Pro Asn Ser
145                 150                 155                 160

Ser Ile Ile Gly Met Met Ile Ala Ala Leu Ser Ala Val Gln Ser Thr
                165                 170                 175

Gln Met Asp Arg Ile Pro Ala His Ala Ala Lys Asn Leu Tyr Leu Gly
            180                 185                 190

Asn Pro Lys Ala Val Asp Asp Glu Ile Val Arg Leu Met Gly Ser Leu
        195                 200                 205

Ser Met Ile Thr Ala Ala Val Tyr Cys His His Thr Gly Arg Glu Phe
    210                 215                 220

Thr Pro Pro Arg Pro Glu Leu Ser Tyr Ile Glu Asn Phe Leu Leu Met
225                 230                 235                 240

Met Gly His Val Glu Ser Ser Thr Gly Leu Pro Asn Pro Gln Tyr Val
                245                 250                 255
```

```
Asp Arg Ile Glu Arg Leu Trp Val Leu Ile Ala Asp His Glu Met Thr
            260                 265                 270

Cys Ser Thr Ala Ala Phe Leu Gln Thr Ala Ser Ser Leu Pro Asp Val
            275                 280                 285

Phe Ser Cys Met Ile Ser Ala Leu Ser Ala Leu Tyr Gly Pro Leu His
            290                 295                 300

Gly Gly Ala Ile Glu Val Ala Tyr Lys Asn Phe Glu Glu Ile Gly Ser
305                 310                 315                 320

Val Glu Asn Val Ala Ala Lys Ile Glu Arg Val Lys Ala Gly Lys Glu
                325                 330                 335

Arg Leu Tyr Gly Tyr Gly His Arg Ile Tyr Arg Val Thr Asp Pro Arg
            340                 345                 350

Phe Ile Phe Ile Arg Gln Ile Leu Asp Glu Leu Lys Glu Glu Ile Ala
            355                 360                 365

Arg Asn Pro Leu Leu Lys Val Ala Phe Glu Val Asp Arg Val Ala Ser
        370                 375                 380

Glu Asp Glu Tyr Phe Val Thr Arg Lys Leu Arg Pro Asn Ala Asp Leu
385                 390                 395                 400

Phe Ala Ala Leu Val Tyr Ser Ala Met Gly Phe Pro Thr Glu Phe Ile
                405                 410                 415

Leu Pro Leu Ser Leu Leu Ser Arg Thr Gln Gly Phe Met Ala His Trp
            420                 425                 430

Lys Glu Ala Met Ser Ser Thr Ala Arg Ile Trp Arg Pro Gly Gln Ile
            435                 440                 445

Tyr Thr Gly His Leu Asn Arg Glu Met Ala Ile Ser Lys Ala Arg Thr
            450                 455                 460

Lys Thr His Ala Ser Arg Gln Thr Thr Trp Ala Arg Arg Asn Val
465                 470                 475                 480

Ser Gly Leu Arg Leu Met Lys Ile Ala Asn Arg Met Ala Asn Gly
                485                 490                 495

<210> SEQ ID NO 78
<211> LENGTH: 458
<212> TYPE: PRT
<213> ORGANISM: Aspergillus niger

<400> SEQUENCE: 78

Met Pro Asp Ile Ala Ser Asn Gly Ala Arg Asn Gly Ala Ser Gln Asn
1               5                   10                  15

Ala Glu Thr Lys Pro Glu Pro Val Leu His Val Val Asp Ser Arg
            20                  25                  30

Thr Gly Lys Tyr Phe Pro Ile Pro Ile Val Arg Asn Ala Ile Asn Ala
            35                  40                  45

Ser Glu Phe Lys Lys Leu Lys Ser Pro Glu Asp Pro Ala His Pro Glu
    50                  55                  60

Asp Gln Asn Glu Gln Gly Ile Arg Val Phe Asp Pro Gly Tyr Ser Asn
65                  70                  75                  80

Thr Ala Val Ser Glu Ser Gln Val Thr Tyr Ile Asp Gly Leu Lys Gly
                85                  90                  95

Thr Ile Gln Tyr Arg Gly Tyr Asn Ile Glu Asp Ile Val Gly Lys Lys
            100                 105                 110

Lys Phe Ile Asp Thr Ala His Leu Leu Ile Trp Gly Glu Trp Pro Thr
            115                 120                 125

Pro Glu Gln Ala Lys Ser Leu Gln Glu Lys Leu Ser Ser Val Pro Val
```

```
                130                 135                 140
Leu Asp Glu Ser Val Phe Lys Val Ile Gln Ala Phe Pro Pro Asn Ser
145                 150                 155                 160

Ser Ile Ile Gly Met Met Ile Ala Ala Leu Ser Ala Val Gln Ser Thr
                165                 170                 175

Gln Met Asp Arg Ile Pro Ala His Ala Ala Lys Asn Leu Tyr Leu Gly
            180                 185                 190

Asn Pro Lys Ala Val Asp Asp Glu Ile Val Arg Leu Met Gly Ser Leu
        195                 200                 205

Ser Met Ile Thr Ala Ala Val Tyr Cys His His Thr Gly Arg Glu Phe
    210                 215                 220

Thr Pro Pro Arg Pro Glu Leu Ser Tyr Ile Glu Asn Phe Leu Leu Met
225                 230                 235                 240

Met Gly His Val Glu Ser Ser Thr Gly Leu Pro Asn Pro Gln Tyr Val
                245                 250                 255

Asp Arg Ile Glu Arg Leu Trp Val Leu Ile Ala Asp His Glu Met Thr
            260                 265                 270

Cys Ser Thr Ala Ala Phe Leu Gln Thr Ala Ser Ser Leu Pro Asp Val
        275                 280                 285

Phe Ser Cys Met Ile Ser Ala Leu Ser Ala Leu Tyr Gly Pro Leu His
    290                 295                 300

Gly Gly Ala Ile Glu Val Ala Tyr Lys Asn Phe Glu Glu Ile Gly Ser
305                 310                 315                 320

Val Glu Asn Val Ala Ala Lys Ile Glu Arg Val Lys Ala Gly Lys Glu
                325                 330                 335

Arg Leu Tyr Gly Tyr Gly His Arg Ile Tyr Arg Val Thr Asp Pro Arg
            340                 345                 350

Phe Ile Phe Ile Arg Gln Ile Leu Asp Glu Leu Lys Glu Glu Ile Ala
        355                 360                 365

Arg Asn Pro Leu Leu Lys Val Ala Phe Glu Val Asp Arg Val Ala Ser
    370                 375                 380

Glu Asp Glu Tyr Phe Val Thr Arg Lys Leu Arg Pro Asn Ala Asp Leu
385                 390                 395                 400

Phe Ala Ala Leu Val Tyr Ser Ala Met Gly Phe Pro Thr Glu Phe Ile
                405                 410                 415

Leu Pro Leu Ser Leu Leu Ser Arg Thr Gln Gly Phe Leu Ala His Trp
            420                 425                 430

Lys Glu Ala Met Ser Ser Thr Ala Arg Ile Trp Arg Pro Gly Gln Ile
        435                 440                 445

Tyr Thr Gly His Leu Asn Arg Glu Met Ala
    450                 455

<210> SEQ ID NO 79
<211> LENGTH: 463
<212> TYPE: PRT
<213> ORGANISM: Talaromyces marneffei

<400> SEQUENCE: 79

Met Ser Pro Ala Ala Ile Ile Ser Ser Asp Ala Ala Lys Ser Val
1               5                   10                  15

Asp Ala Lys Ala Ser Ala Lys Thr Ile Ser Arg Asn Phe Leu His Val
            20                  25                  30

Ile Asp Glu Arg Thr Gly Gln Tyr Tyr Gln Ile Pro Ile His His Asn
        35                  40                  45
```

-continued

```
Ala Ile Ser Ala Asn Glu Phe Lys Lys Ile Lys Ala Pro Asp Ser Glu
    50                  55                  60

Tyr Tyr Ala Asp Gln Asn Glu Asn Gly Ile Arg Val Phe Asp Pro Gly
65                  70                  75                  80

Phe Thr Asn Thr Ala Val Val Glu Ser Lys Val Thr Tyr Val Asp Gly
                85                  90                  95

Lys Arg Gly Lys Ile Gln Tyr Arg Gly Tyr Asp Leu Ala Asp Val Val
            100                 105                 110

Ala Asn Asn Lys Lys Phe Ile Asp Thr Ala His Leu Met Val Phe Gly
            115                 120                 125

Phe Trp Pro Thr Ala Glu Glu Gly Ala Gly Phe Gln Gln Lys Leu Phe
130                 135                 140

Asp Ala Met His Ile Glu Gln Cys Val Ile Asp Thr Ile His Ala Phe
145                 150                 155                 160

Pro Arg Thr Ala Ser Thr Thr Leu Met Leu Thr Ala Gly Leu Ala Ala
                165                 170                 175

Val Gln Ala Thr Gln Met Asp Arg Ile Pro Ala His Met Ala Lys Asn
            180                 185                 190

Leu Tyr Leu Gly Asn Pro Thr Leu Val Asp Glu Gln Ile Val Arg Leu
            195                 200                 205

Met Gly Val Leu Pro Ile Val Ser Ala Val Ala Tyr Cys His His Thr
            210                 215                 220

Gly Arg Glu Phe Lys Ser Pro Arg Ser Asp Leu Thr Tyr Ile Glu Asn
225                 230                 235                 240

Phe Leu Tyr Met Cys Gly His Val Gln Glu Glu Thr Gly Leu Pro Asn
                245                 250                 255

Pro Arg Tyr Val Gln Asn Phe Glu Arg Leu Trp Ser Leu Val Ala Asp
            260                 265                 270

His Glu Met Thr Cys Ser Thr Ala Ala Val Leu Leu Thr Ala Ser Ser
            275                 280                 285

Leu Pro Asp Pro Ile Ser Cys Ile Ile Ser Gly Ile Gly Ala Ser Tyr
            290                 295                 300

Gly Pro Leu His Gly Gly Ala Ile Glu Phe Ala Tyr Lys Asp Met Ala
305                 310                 315                 320

Asp Ile Gly Ser Val Asp Asn Cys Gln Thr Lys Ile Asp Arg Val Lys
                325                 330                 335

Ser Gly Lys Glu Arg Leu Phe Gly Tyr Gly His Arg Val Tyr Lys Val
            340                 345                 350

Thr Asp Pro Arg Ser Glu His Ile Gln Ala Val Leu Glu Thr Leu Lys
            355                 360                 365

Glu Glu Ile Asp Asn Asp Pro Leu Leu Lys Val Ala Phe Glu Leu Asn
370                 375                 380

Arg Ile Ala Gln Glu Asp Glu Tyr Phe Val Ser Arg Gly Leu Lys Pro
385                 390                 395                 400

Asn Ala Asp Leu Phe Ala Ala Phe Thr Tyr Gly Ala Met Gly Phe Pro
                405                 410                 415

Pro Asp Phe Ile Leu Thr Ile Ser Thr Ile Ser Arg Thr Gln Gly Leu
            420                 425                 430

Met Ala His Trp Lys Glu Ala Met Ser Gly Lys Pro Leu Ile Trp Arg
            435                 440                 445

Pro Thr Gln Val Tyr Thr Gly Lys Leu Asp Leu Lys Met Glu Val
450                 455                 460
```

```
<210> SEQ ID NO 80
<211> LENGTH: 466
<212> TYPE: PRT
<213> ORGANISM: Aspergillus flavus

<400> SEQUENCE: 80

Met Thr Val Thr Gln Glu Ala Ser Pro Lys Arg Glu Ser Leu His Ile
1               5                   10                  15

Ile Asp Asp Arg Thr Gly Ser Tyr Tyr Ser Ile Pro Ile Val Asn Asn
            20                  25                  30

Ala Ile Asn Ala Ser Asp Phe Lys Lys Val Thr Ala Pro Glu Asp Lys
        35                  40                  45

Ala Tyr Pro Ala Asn Gln Thr Glu Asn Gly Leu Arg Val Tyr Asp Pro
    50                  55                  60

Gly Tyr Ser Asn Thr Ala Val Ser His Ser Lys Ile Thr Tyr Ile Asp
65                  70                  75                  80

Gly Leu Lys Gly Thr Ile Gln Tyr Arg Gly Tyr Ser Ile Asn Asp Ile
                85                  90                  95

Val Gly Arg Lys Thr Phe Ile Asp Thr Ala His Leu Leu Ile Trp Gly
            100                 105                 110

His Trp Pro Ser Thr Ala Glu Ala Glu Thr Leu Gln Gln Arg Leu Asp
        115                 120                 125

Gln Val Pro Val Pro Gln Asp Phe Val Phe Asn Val Ile Lys Ser Phe
    130                 135                 140

Pro Arg Asp Gly Ser Leu Met Gly Met Val Ile Ala Gly Leu Ser Ala
145                 150                 155                 160

Leu Gln Ser Ser Asp Met Asn Ala Ile Pro Ala His Val Gly Lys Thr
                165                 170                 175

Ile Tyr Leu Asn Asn Pro Glu Leu Ala Asp Gln Gln Ile Ile Arg Val
            180                 185                 190

Met Ala Asn Met Ser Met Leu Thr Ala Ala Tyr Cys His His Ile
            195                 200                 205

Gly Arg Asp Phe Thr Pro Pro Arg Ala Gly Leu Ser Tyr Ile Glu Asn
            210                 215                 220

Phe Leu Leu Met Thr Gly His Val Glu Ala Ala Thr Gly Leu Pro Asn
225                 230                 235                 240

Pro Arg Tyr Val Asn Ala Ile Glu Arg Leu Trp Val Leu Ile Ala Asp
            245                 250                 255

His Glu Met Thr Cys Ser Thr Ala Ala Leu Leu Gln Thr Ala Ser Ala
            260                 265                 270

Leu Pro Asp Val Ile Ser Cys Met Val Ser Ala Ile Ser Ala Leu Tyr
        275                 280                 285

Gly Pro Leu His Gly Gly Ala Ile Glu Val Ala Tyr Lys Asn Ile Glu
    290                 295                 300

Ser Ile Gly Ser Ile Ser Asn Val Pro Ala Lys Ile Ala Arg Val Lys
305                 310                 315                 320

Ala Gly Lys Glu Arg Leu Tyr Gly Tyr Gly His Arg Val Tyr Arg Val
                325                 330                 335

Thr Asp Pro Arg Phe Val Phe Ile Arg Glu Ile Leu Asn Glu Leu Ser
            340                 345                 350

Glu Glu Val Glu Lys Asp Pro Leu Leu Lys Val Ala Phe Glu Val Asp
        355                 360                 365

Arg Val Ala Ser Glu Asp Glu Tyr Phe Thr Ser Arg Asn Leu Arg Pro
    370                 375                 380
```

```
Asn Ala Asp Leu Phe Ala Ala Phe Val Tyr Lys Ala Leu Gly Phe Pro
385                 390                 395                 400

Pro Glu Phe Ile Leu Pro Leu Ser Ile Leu Ser Arg Thr Gln Gly Phe
            405                 410                 415

Met Ala His Trp Arg Glu Ala Met Gly Met Pro Glu Ser Thr Leu Asn
        420                 425                 430

Ser Ser Arg Ser Ile Cys Pro Asp Thr Asn Ile Gly Asn Pro Pro Arg
    435                 440                 445

Ile Trp Arg Pro Gly Gln Ile Tyr Thr Gly Asp Leu Asn Lys Ser Met
450                 455                 460

Asp Glu
465

<210> SEQ ID NO 81
<211> LENGTH: 467
<212> TYPE: PRT
<213> ORGANISM: Eutypa lata

<400> SEQUENCE: 81

Met Gly Gly Ser Trp Thr Gln Met Leu Ser Pro Thr Phe Leu Val His
1               5                   10                  15

Met Val Ala Lys Leu Leu Gly Gln Thr Gln Met Gly Glu Ala Asp Gly
            20                  25                  30

Ser Leu Thr Ile Thr Asp Asn Arg Thr Gly Arg Gln Tyr Thr Ile Pro
        35                  40                  45

Ile Asn Arg Asn Thr Val Lys Ala Thr Asp Phe Arg Arg Ile Thr Ala
    50                  55                  60

Ala Gly Leu Gly Ala Asp Pro Ala Glu Met Val Glu Ser Gly Leu Lys
65                  70                  75                  80

Val Phe Asp Arg Gly Tyr Leu Asn Thr Ala Cys Met Glu Ser Asn Ile
                85                  90                  95

Thr Phe Ile Asp Gly Lys Arg Gly Tyr Ile Gln Tyr Arg Asp Tyr Ser
            100                 105                 110

Ile Asp His Leu Phe Arg Asn Asn Asp Phe Glu Glu Val Ala His Leu
        115                 120                 125

Val Met Phe Gly Lys Leu Pro Ser Pro Ser Glu Lys Met Thr Phe Arg
    130                 135                 140

Arg Ala Leu Ala Lys Gly Met Glu Ala Pro Gln Asn Val Ile Asn Val
145                 150                 155                 160

Ile Arg Ala Phe Pro Lys Asp Ser Leu Thr Phe Pro Met Ile Leu Ala
                165                 170                 175

Gly Leu Ser Ala Tyr Ala Gly Val Asp Pro Gly Thr Glu Lys Thr His
            180                 185                 190

His Glu Gly Arg Ala Tyr Tyr Leu Gly Asn Met Lys Glu Val Asp Ala
        195                 200                 205

Ala Ile Ile Arg Thr Leu Ser Ala Leu Ala Thr Val Ile Ala Ile Thr
    210                 215                 220

Tyr Cys His Lys Arg Gly Arg Glu Phe Thr Pro Ala Asp Pro Asn Gly
225                 230                 235                 240

Ser Phe Val Ala Asn Thr Leu Leu Met Met Gly Phe Thr Lys Asp Gly
                245                 250                 255

Lys Ala Asp Pro Glu Val Glu Ala Cys Phe Glu Arg Leu Trp Ile Leu
            260                 265                 270

Tyr Ala Asp His Glu Met Thr Asn Ser Thr Ala Ala Val Leu His Ala
        275                 280                 285
```

```
Ala Ser Thr Leu Thr Asp Pro Ile Ser Ser Leu Val Ser Gly Ile Val
        290                 295                 300

Ser Ala Tyr Gly Pro Leu His Gly Gly Ala Ile Asp Leu Ala Tyr Lys
305                 310                 315                 320

Gly Phe Glu Glu Val Gly Thr Val Asp Asn Val Ser Gln Leu Ile Thr
                325                 330                 335

Asp Val Lys Gly Lys Lys Gln Arg Leu Phe Gly Tyr Gly His Arg Ile
            340                 345                 350

Tyr Lys Thr Val Asp Pro Arg Ser Lys Phe Ile Arg Glu Met Ile Ala
        355                 360                 365

Glu Lys Gln Glu Leu Val Asp Ser Asn Pro Leu Leu Arg Ile Ala Phe
    370                 375                 380

Glu Ile Asp Arg Ile Ala Asn Glu Asp Pro Tyr Phe Thr Ser Arg Asn
385                 390                 395                 400

Leu Lys Ala Asn Ala Asp Leu Tyr Gly Cys Phe Leu Tyr Thr Ala Leu
                405                 410                 415

Gly Phe Glu Thr Asp Ile Ile Ile Ala Met Ala Cys Leu Ser Arg Thr
            420                 425                 430

Pro Gly Ala Met Ala His Trp Arg Glu Ser Met Gln Gln Gly Pro Met
        435                 440                 445

Leu Trp Arg Pro Leu Gln Val Phe Thr Gly Asn Val Thr Ala Pro Ser
    450                 455                 460

Ala Arg Ser
465

<210> SEQ ID NO 82
<211> LENGTH: 467
<212> TYPE: PRT
<213> ORGANISM: Eutypa lata

<400> SEQUENCE: 82

Met Ala Thr Ala Ala Pro Thr Ala Thr Lys Ser Thr Ala Ala Asn Asn
1               5                   10                  15

Pro Met Thr Ser Ser Gln Ser Glu Ile Asn Val Ala Val Glu Lys Arg
            20                  25                  30

Asp Val Leu His Ala Val Asp Gly Arg Thr Gly Leu Tyr Tyr Ser Ile
        35                  40                  45

Pro Ile Asn Lys Asn Ala Val Asn Ala Gly Asp Phe Lys Lys Ile Lys
    50                  55                  60

Ser Pro Ala Asp Arg Lys His Pro Ala Tyr Gln Asn Glu Leu Gly Leu
65                  70                  75                  80

Arg Ile Tyr Asp Pro Gly Phe Ser Asn Thr Thr Val Ser Glu Ser Lys
                85                  90                  95

Ile Thr Tyr Ile Asp Gly Ile Glu Gly Thr Ile Gln Tyr Arg Gly Tyr
            100                 105                 110

Ser Ile His Asp Ile Phe Gly Lys Gly Trp Ile Asp Val Ser His
        115                 120                 125

Leu Leu Ile Trp Gly Asn Trp Pro Ser Ala Glu Ala Lys Glu Tyr
    130                 135                 140

Gln Glu Arg Leu Asn Gly Val Pro Leu Leu Asp Gln His Val Leu Asp
145                 150                 155                 160

Val Ile His Ser Phe Pro Lys Asp Gly Val Ile Thr Gly Met Met Ile
                165                 170                 175

Ala Gly Leu Ser Ala Leu Gln Ser Cys Asn Leu Asp Ala Val Pro Ala
```

-continued

```
                180                 185                 190
Tyr Val Gly Asp Asn Leu Tyr Val Gly His Pro Asp Arg Val Asp Lys
            195                 200                 205

Gln Ile Ile His Leu Leu Gln Ser Phe Ala Met Ile Thr Ala Ala Cys
        210                 215                 220

Tyr Cys His Ser Thr Ser Arg Glu Phe Thr Gln Pro Arg Gln Asp Phe
225                 230                 235                 240

Ser Tyr Val Glu Asn Phe Leu Leu Met Val Gly His Val Asp Ala Thr
                245                 250                 255

Thr Gly Leu Pro Ser Pro Arg His Val Asp Ala Leu Glu Arg Leu Trp
            260                 265                 270

Gly Val Val Ala Asp His Glu Met Thr Cys Ser Thr Ala Ala Phe Leu
        275                 280                 285

His Thr Ala Ser Ser Leu Pro Asp Ile Ile Ser Cys Phe Ile Thr Ala
    290                 295                 300

Ile Cys Ala Ala Thr Gly Pro Leu His Gly Gly Ala Ile Ser Val Ala
305                 310                 315                 320

His Lys His Ile Lys Ala Ile Gly Thr Val Ala Asn Val Pro Ala Lys
                325                 330                 335

Ile Glu Arg Val Lys Ser Gly Lys Glu Leu Leu Tyr Gly Tyr Gly His
            340                 345                 350

Arg Val Tyr Arg Thr Thr Asp Pro Arg Tyr Thr Tyr Ile Asn Gln Val
        355                 360                 365

Leu Asp Gly Leu Thr Glu Glu Val Ala Arg Asp Pro Leu Leu Gln Val
    370                 375                 380

Ala Leu Ala Leu Asp Lys Ala Ala Ser Glu Asp Glu Tyr Phe Thr Ser
385                 390                 395                 400

Arg Lys Leu Phe Pro Asn Ala Asp Leu Phe Ala Ala Phe Ala Tyr Gln
                405                 410                 415

Ala Leu Gly Phe Pro Pro Asp Phe Val Leu Pro Met Ser Cys Leu Ser
            420                 425                 430

Arg Leu Gln Gly Phe Ala Ala His Trp Lys Glu Gly Leu Gln Gly Lys
        435                 440                 445

Pro Lys Ile Trp Arg Pro Gly Gln Ile Tyr Thr Gly Asp Leu Glu Lys
    450                 455                 460

Thr Met Gly
465

<210> SEQ ID NO 83
<211> LENGTH: 452
<212> TYPE: PRT
<213> ORGANISM: Neofusicoccum parvum

<400> SEQUENCE: 83

Met Ala Thr Thr Thr Ile Thr Ala Pro Ala Asn Gly Arg Val Ser Lys
1               5                   10                  15

Asp Ser Leu Thr Val Thr Asp Asn Arg Thr Gly Ser Thr Phe Thr Phe
            20                  25                  30

Pro Ile Thr His Asn Ala Val Asn Ala Ser Asn Phe Lys Gln Ile Lys
        35                  40                  45

Ala Pro Glu Asp Pro Asp Asn Ile Ala Asp Gln Asn Glu Gln Gly Leu
    50                  55                  60

Arg Val Phe Asp Pro Gly Phe Gly Asn Thr Cys Val Ser Glu Ser Lys
65                  70                  75                  80
```

Ile Thr Phe Ile Asp Gly Leu Lys Gly Ile Gln Tyr Arg Gly Tyr
            85                  90                  95

Asp Ile Gly Asp Leu Ile Glu Ala Lys Lys Gly Phe Val Asp Thr Ala
        100                 105                 110

His Leu Leu Trp Phe Gly Thr Leu Pro Ser Pro Lys Glu Lys Gln Glu
        115                 120                 125

Leu Gln Asp Arg Leu Asn Ala Val Pro Leu Ile Asp Asp His Val Phe
130                 135                 140

Asn Thr Ile Arg Ser Phe Pro Lys Asn Gly Ser Pro Phe Gly Met Ile
145                 150                 155                 160

Ile Ala Gly Leu Met Ala Leu Gln Ser Ser Glu Met Asp Leu Ile Pro
                165                 170                 175

Ala His Ala Ala Lys Asn Ile Tyr Leu Gly Asn Leu Ser Leu Val Asp
                180                 185                 190

Ser Gln Leu Ile Arg Val Met Gln Ser Leu Ser Gln Ile Cys Ala Val
            195                 200                 205

Ala Tyr Cys His Gln Thr Gly Arg Thr Phe Thr Pro Pro Arg Ala Asp
        210                 215                 220

Leu Thr Phe Ile Glu Asn Phe Leu Leu Met Met Gly His Thr Glu Ala
225                 230                 235                 240

Ala Thr Gly Leu Pro Asn Pro Ala Tyr Val Ala Lys Phe Glu Arg Leu
                245                 250                 255

Trp Leu Leu Ile Ala Asp His Glu Met Thr Cys Ser Thr Ala Ala Met
                260                 265                 270

Leu Gln Thr Ala Ser Ala Met Pro Asp Ala Leu Ser Cys Leu Ala Ser
            275                 280                 285

Ala Thr Ser Ala Leu Tyr Gly Pro Leu His Gly Gly Ala Ile Glu Val
        290                 295                 300

Ala Tyr Lys Asn Ile Ala Glu Ile Gly Ser Val Asp Asn Ile Pro Pro
305                 310                 315                 320

Lys Ile Ala Arg Val Lys Ala Gly Lys Glu Arg Leu Tyr Gly Tyr Gly
                325                 330                 335

His Arg Val Tyr Arg Val Pro Asp Pro Arg Tyr Arg His Ile Lys Glu
                340                 345                 350

Val Leu Glu Asp Leu Thr Ala Glu Ile Glu Asp Pro Leu Leu Lys
            355                 360                 365

Val Ala Phe Glu Leu Asp Arg Val Ala Arg Thr Asp Glu Tyr Phe Thr
        370                 375                 380

Ser Arg Lys Leu Asn Pro Asn Ala Asp Leu Phe Ala Ala Leu Ala Tyr
385                 390                 395                 400

Asn Ala Met Gly Phe Glu Pro Glu Trp Ile Leu Pro Ile Ser Leu Met
                405                 410                 415

Ser Arg Ser Gln Gly Leu Leu Ala His Trp Lys Glu Ala Met Ser Gly
            420                 425                 430

Ser Ala Arg Ile Trp Arg Pro Gly Gln Ile Tyr Thr Gly Asp Leu Asn
        435                 440                 445

Lys Lys Ile Glu
    450

<210> SEQ ID NO 84
<211> LENGTH: 472
<212> TYPE: PRT
<213> ORGANISM: Aspergillus niger

<400> SEQUENCE: 84

```
Met Ala Tyr Thr Leu Ala Ser Trp Leu Gly Arg Leu Phe Asp Ala Gly
1               5                   10                  15

Lys Ser Leu Leu Pro Leu Gln Gly Asn Tyr Ile Asn Ala Leu Leu Glu
            20                  25                  30

Gln Glu Leu Pro Gly Glu Arg Glu Gly Thr Leu Thr Val Arg Asp Asn
        35                  40                  45

Arg Thr Gly Ser Lys Tyr Thr Ile Pro Ile Val Arg Asn Ser Val Pro
    50                  55                  60

Ala Met Gly Phe Arg Gln Ile Cys Val Asp Arg Ala Gly Lys Ser Pro
65              70                  75                  80

Arg Gln Gln Phe Glu Asp Gly Leu Arg Leu Ile Asp Pro Gly Tyr Arg
                85                  90                  95

Asn Thr Ala Val Lys Met Ser Ser Ile Thr Tyr Ile Asn Gly Asn Glu
            100                 105                 110

Gly Val Ile Leu Tyr Arg Gly His Pro Leu Ala Ser Leu Ile Gly Lys
        115                 120                 125

Ser Tyr Glu Glu Ile Thr His Leu Leu Ile Trp Gly Ser Leu Pro Thr
    130                 135                 140

Pro Glu Gln Arg Leu Arg Phe Gln Arg Ile Ala Glu Ala Met Met
145                 150                 155                 160

Val Val Pro Glu Asn Val Lys Gln Leu Val Ala Thr Phe Pro Arg Asn
                165                 170                 175

Thr Pro Pro Met Val Ile Leu Cys Ala Val Leu Thr Gly Tyr Leu Ala
            180                 185                 190

Asp Gln Pro Glu Leu Ile Pro Ala His Ala Gly Ala Asn Leu Tyr Asn
                195                 200                 205

Arg Arg Pro Glu Met Val Asp Glu Gln Ile Ile Arg Thr Leu Ala Val
    210                 215                 220

Thr Ala Ile Ala Gly Ser Ile Ala His Cys His Met Lys Gly Glu Glu
225                 230                 235                 240

Leu Arg Met Ala Asp Pro Asn Leu Ser Tyr Ile Glu Asn Ile Leu Trp
                245                 250                 255

Met Gly Arg Tyr Val Asp Asn Asn Pro Ala Val Thr Arg Glu Lys Ala
            260                 265                 270

Ala Glu Ile Leu Thr Lys Ala Trp Ser Leu Tyr Ala Asp His Glu Met
        275                 280                 285

Thr Asn Ser Thr Ser Ala Phe Leu His Val Ser Ser Leu Ala Asp
    290                 295                 300

Pro Leu Ser Ala Met Ala Ala Cys Cys Met Ser Gly Tyr Gly Leu Leu
305                 310                 315                 320

His Gly Gly Ala Ile Asp Ala Ala Tyr Arg Gly Met Arg Glu Ile Gly
                325                 330                 335

Gly Pro Gln Asn Val Pro Lys Leu Ile Glu Lys Val Ile Asn Lys Glu
            340                 345                 350

Cys Arg Leu Ser Gly Tyr Gly His Arg Ile Tyr Lys Gln Val Asp Pro
        355                 360                 365

Arg Ala Lys Tyr Val Arg Glu Met Leu Asp Glu Leu Thr Arg Asp Arg
    370                 375                 380

Asp Ile Arg Glu Met Asp Pro Val Leu Gln Val Ala Met Glu Ile Asp
385                 390                 395                 400

Arg Ile Ala Ser Thr His Glu Tyr Phe Val Lys Arg Asn Leu Gln Ala
                405                 410                 415
```

```
Asn Ala Asp Leu Tyr Gly Ser Phe Val Tyr Thr Ala Leu Gly Ile Asp
            420                 425                 430

Ser Gln Phe Ala Thr Val Leu Ala Ala Thr Ala Arg Val Ser Gly Val
        435                 440                 445

Met Ala His Trp Lys Glu Gln Thr Glu Arg Ala Pro Asp Leu Trp Arg
450                 455                 460

Pro Leu Gln Val Tyr Val Pro Asn
465             470

<210> SEQ ID NO 85
<211> LENGTH: 472
<212> TYPE: PRT
<213> ORGANISM: Aspergillus kawachii

<400> SEQUENCE: 85

Met Ala Tyr Thr Leu Ala Ser Trp Leu Gly Arg Leu Phe Asp Ala Gly
1               5                   10                  15

Lys Ser Leu Leu Pro Leu Gln Gly Asn Tyr Ile Asn Ala Leu Leu Glu
            20                  25                  30

Gln Glu Leu Pro Gly Glu Arg Glu Gly Thr Leu Thr Val Arg Asp Asn
        35                  40                  45

Arg Thr Gly Ser Lys Tyr Thr Ile Pro Ile Val Arg Asn Ser Val Pro
    50                  55                  60

Ala Met Gly Phe Arg Gln Ile Cys Val Asp Arg Ala Gly Lys Ser Pro
65                  70                  75                  80

Arg Gln Gln Phe Glu Asp Gly Leu Arg Leu Ile Asp Pro Gly Tyr Arg
                85                  90                  95

Asn Thr Ala Val Lys Met Ser Ser Ile Thr Tyr Ile Asn Gly Asn Glu
            100                 105                 110

Gly Val Ile Leu Tyr Arg Gly His Pro Leu Ala Ser Leu Ile Gly Lys
        115                 120                 125

Ser Tyr Glu Glu Ile Thr His Leu Leu Ile Trp Gly Ser Leu Pro Thr
    130                 135                 140

Pro Glu Glu Arg Leu Arg Phe Gln Arg Arg Ile Ala Glu Ala Met Met
145                 150                 155                 160

Val Val Pro Glu Asn Val Lys Gln Leu Val Ala Thr Phe Pro Arg Asn
                165                 170                 175

Thr Pro Pro Met Val Ile Leu Cys Ala Val Leu Thr Gly Tyr Leu Ala
            180                 185                 190

Asp Gln Pro Glu Leu Ile Pro Ala His Ala Gly Ala Asn Leu Tyr Asn
        195                 200                 205

Arg Arg Pro Glu Met Val Asp Glu Gln Ile Ile Arg Thr Leu Ala Val
    210                 215                 220

Thr Ala Ile Ala Gly Ser Ile Ala His Cys His Met Lys Gly Glu Glu
225                 230                 235                 240

Leu Arg Ala Ala Asp Pro Asn Leu Ser Tyr Ile Glu Asn Ile Leu Trp
                245                 250                 255

Met Gly Arg Tyr Val Asp Asn Asn Ala Ala Ile Thr Arg Glu Lys Ala
            260                 265                 270

Ala Glu Ile Leu Thr Lys Ala Trp Ser Leu Tyr Ala Asp His Glu Met
        275                 280                 285

Thr Asn Ser Thr Ser Ala Phe Leu His Val Ser Ser Leu Ala Asp
    290                 295                 300

Pro Leu Ser Ala Met Ala Ala Cys Cys Met Ser Gly Tyr Gly Leu Leu
305                 310                 315                 320
```

```
His Gly Gly Ala Ile Asp Ala Ala Tyr Arg Gly Met Arg Glu Ile Gly
                325                 330                 335

Gly Pro Glu Asn Val Pro Lys Leu Ile Glu Lys Val Ile Asn Lys Glu
            340                 345                 350

Cys Arg Leu Ser Gly Tyr Gly His Arg Ile Tyr Lys Gln Val Asp Pro
            355                 360                 365

Arg Ala Lys Tyr Val Arg Glu Met Leu Asp Glu Leu Thr Arg Asp Arg
    370                 375                 380

Asp Ile Arg Glu Met Asp Pro Val Leu Gln Val Ala Met Glu Ile Asp
385                 390                 395                 400

Arg Ile Ala Ser Thr His Glu Tyr Phe Val Lys Arg Asn Leu Gln Ala
                405                 410                 415

Asn Ala Asp Leu Tyr Gly Ser Phe Val Tyr Thr Ala Leu Gly Ile Asp
            420                 425                 430

Ser Gln Phe Ala Thr Val Leu Ala Ala Thr Ala Arg Val Ser Gly Val
            435                 440                 445

Met Ala His Trp Lys Glu Gln Thr Glu Arg Ala Pro Asp Leu Trp Arg
    450                 455                 460

Pro Leu Gln Val Tyr Val Pro Asn
465                 470

<210> SEQ ID NO 86
<211> LENGTH: 152
<212> TYPE: PRT
<213> ORGANISM: Aspergillus niger

<400> SEQUENCE: 86

Met Pro His Met Asp Gly Leu Ser His Lys Leu Thr Glu Ala Met Leu
1               5                   10                  15

Ala Val Pro Asp Asp Val Gln Arg Thr Val Trp Thr His Pro Ile Cys
            20                  25                  30

Gln Glu Asn Phe Glu Arg Ser Trp Lys Ser Gly Asn Ile Pro Gly Tyr
        35                  40                  45

Ser Gln Arg Val Lys Gln Gly Arg Val Lys Val Phe Glu Tyr Gly His
    50                  55                  60

Arg Ser Tyr Lys Gly Ile Asn Pro Arg Val Pro Pro Ile Gln Ser Ile
65              70                  75                  80

Leu Lys Asn Leu Asp Leu Ser Ala Asp Asn Pro Leu Lys Leu Ala Glu
            85                  90                  95

Arg Leu Glu Arg Val Cys Pro Thr Asp Ala Tyr Phe Lys Glu Gln Gly
            100                 105                 110

Leu Tyr Val Asn Asp Ala Asp Thr Ser Asn Gly Phe Tyr Pro Lys Ile
        115                 120                 125

Ile Ser Met Ala Met Leu Ala Gln Arg Ile Met Gly Ile Met Thr His
    130                 135                 140

Trp Arg Glu Tyr Met Cys Lys Gln
145                 150
```